United States Patent
Steemers et al.

(10) Patent No.: US 11,981,891 B2
(45) Date of Patent: May 14, 2024

(54) HIGH-THROUGHPUT SINGLE-CELL SEQUENCING WITH REDUCED AMPLIFICATION BIAS

(71) Applicants: Illumina, Inc., San Diego, CA (US); University of Washington, Seattle, WA (US)

(72) Inventors: Frank J. Steemers, San Diego, CA (US); Jay Shendure, Seattle, WA (US); Yi Yin, Seattle, WA (US)

(73) Assignees: Illumina, Inc., San Diego, CA (US); University of Washington, Seattle, WA (US)

( * ) Notice: Subject to any disclaimer, the term of this patent is extended or adjusted under 35 U.S.C. 154(b) by 0 days.

(21) Appl. No.: 16/415,969

(22) Filed: May 17, 2019

(65) Prior Publication Data

US 2019/0382753 A1 Dec. 19, 2019

Related U.S. Application Data

(60) Provisional application No. 62/821,864, filed on Mar. 21, 2019, provisional application No. 62/673,023, filed on May 17, 2018.

(51) Int. Cl.
| | |
|---|---|
| *C12N 15/10* | (2006.01) |
| *C12N 9/12* | (2006.01) |
| *C40B 40/06* | (2006.01) |
| *C40B 50/06* | (2006.01) |
| *C40B 50/10* | (2006.01) |
| *B82Y 5/00* | (2011.01) |

(52) U.S. Cl.
CPC ....... *C12N 15/1003* (2013.01); *C12N 9/1247* (2013.01); *C40B 40/06* (2013.01); *C40B 50/06* (2013.01); *C40B 50/10* (2013.01); *B82Y 5/00* (2013.01)

(58) Field of Classification Search
CPC .... C07H 21/04; C12Q 1/6806; C12Q 1/6844; C12Q 1/6846; C12Q 1/6855; C12Q 1/6865; C12Q 2531/101; C12Q 2535/122; C12Q 2563/159; C12Q 2563/179; C12N 15/1003; C12N 15/1065; C12N 15/1082; C12N 15/1093; C12N 9/1247; C40B 40/06; C40B 40/02; C40B 40/08; C40B 50/06; C40B 50/10
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,130,238 A | 7/1992 | Malek et al. | |
| 5,185,243 A | 2/1993 | Ullman et al. | |
| 5,223,414 A | 6/1993 | Zarling et al. | |
| 5,455,166 A | 10/1995 | Walker | |
| 5,573,907 A | 11/1996 | Carrino et al. | |
| 5,679,524 A | 10/1997 | Nikiforov et al. | |
| 6,172,218 B1 | 1/2001 | Brenner | |
| 6,210,891 B1 | 4/2001 | Nyren et al. | |
| 6,214,587 B1 | 4/2001 | Dattagupta et al. | |
| 6,245,974 B1 | 6/2001 | Michalowski et al. | |
| 6,258,568 B1 | 7/2001 | Nyren | |
| 6,274,320 B1 | 8/2001 | Rothberg et al. | |
| 6,306,597 B1 | 10/2001 | Macevicz | |
| 6,514,706 B1 * | 2/2003 | Von Kalle et al. | 435/6 |
| 6,969,488 B2 | 11/2005 | Bridgham et al. | |
| 7,001,792 B2 | 2/2006 | Sauer et al. | |
| 7,057,026 B2 | 6/2006 | Barnes et al. | |
| 7,115,400 B1 | 10/2006 | Adessi et al. | |
| 7,211,414 B2 | 5/2007 | Hardin et al. | |
| 7,315,019 B2 | 1/2008 | Turner et al. | |
| 7,329,492 B2 | 2/2008 | Hardin et al. | |
| 7,399,590 B2 | 7/2008 | Piepenburg et al. | |
| 7,405,281 B2 | 7/2008 | Xu et al. | |
| 7,427,673 B2 | 9/2008 | Balasubramanian et al. | |
| 7,582,420 B2 | 9/2009 | Oliphant et al. | |
| 7,611,869 B2 | 11/2009 | Fan | |
| 7,741,463 B2 | 6/2010 | Gormley et al. | |
| 7,829,284 B2 | 11/2010 | Kong et al. | |
| 7,910,354 B2 | 3/2011 | Drmanac et al. | |

(Continued)

FOREIGN PATENT DOCUMENTS

| | | |
|---|---|---|
| CN | 103890191 A | 6/2014 |
| CN | 105339503 A | 2/2016 |

(Continued)

OTHER PUBLICATIONS

Gabriel et al. ("Linear Amplification Mediated PCR—Localization of Genetic Elements and Characterization of Unknown Flanking DNA" J. Vis. Exp. (88), e51543, doi:10.3791/51543 (2014) (Year: 2014).*
Gravina et al. "Single-cell, locus-specific bisulfite sequencing (SLBS) for direct detection of epimutations in DNA methylation patterns" Nucleic Acids Research, 2015, vol. 43, No. 14 e93, doi: 10.1093/nar/gkv366 (Year: 2015).*
Reuter et al. "Simul-seq: combined DNA and RNA sequencing for whole-genome and transcriptome profiling" Nat Methods, Nov. 2016, 13(11): 953-958. doi:10.1038/nmeth.4028 (Year: 2016).*
Vitak et al. "Sequencing thousands of single-cell genomes with combinatorial indexing" Nature Methods, vol. 14, No. 3, Mar. 2017, published online Jan. 30, 2017; doi:10.1038/nmeth.4154 (Year: 2017).*
International Search Report and Written Opinion for International Application No. PCT/US2019/032966, dated Sep. 20, 2019, 13 pages.

(Continued)

*Primary Examiner* — Sahana S Kaup
(74) *Attorney, Agent, or Firm* — Mueting Raasch Group

(57) ABSTRACT

Provided herein are methods for preparing a sequencing library that includes nucleic acids from a plurality of single cells. In one embodiment, the methods include linear amplification of the nucleic acids. In one embodiment, the sequencing library includes whole genome nucleic acids from the plurality of single cells. In one embodiment, the nucleic acids include three index sequences. Also provided herein are compositions, such as compositions that include the nucleic acids having three index sequences.

24 Claims, 23 Drawing Sheets

Specification includes a Sequence Listing.

(56) References Cited

U.S. PATENT DOCUMENTS

| | | |
|---|---|---|
| 8,003,354 B2 | 8/2011 | Shen et al. |
| 8,053,192 B2 | 11/2011 | Bignell et al. |
| 8,563,477 B2 | 10/2013 | Smith et al. |
| 8,778,848 B2 | 7/2014 | Lin et al. |
| 8,778,849 B2 | 7/2014 | Bowen et al. |
| 8,895,249 B2 | 11/2014 | Shen et al. |
| 8,951,781 B2 | 2/2015 | Reed et al. |
| 9,079,148 B2 | 7/2015 | Rigatti et al. |
| 9,169,513 B2 | 10/2015 | Shen et al. |
| 9,309,502 B2 | 4/2016 | Piepenburg et al. |
| 9,359,642 B2 | 6/2016 | Yin et al. |
| 10,900,065 B2 | 1/2021 | Seelig et al. |
| 11,168,355 B2 | 11/2021 | Seelig et al. |
| 11,427,856 B2 | 8/2022 | Seelig et al. |
| 2005/0079516 A1 | 4/2005 | Maniotis et al. |
| 2005/0100900 A1 | 5/2005 | Mayer et al. |
| 2006/0188901 A2 | 8/2006 | Barnes et al. |
| 2006/0240439 A1 | 10/2006 | Smith et al. |
| 2006/0281109 A1 | 12/2006 | Ost et al. |
| 2007/0099208 A1 | 5/2007 | Drmanac et al. |
| 2007/0166705 A1 | 7/2007 | Milton et al. |
| 2008/0009420 A1 | 1/2008 | Schroth et al. |
| 2008/0108082 A1 | 5/2008 | Rank et al. |
| 2009/0005252 A1 | 1/2009 | Drmanac et al. |
| 2009/0011943 A1 | 1/2009 | Drmanac et al. |
| 2009/0026082 A1 | 1/2009 | Rothberg et al. |
| 2009/0047680 A1 | 2/2009 | Lok |
| 2009/0118488 A1 | 5/2009 | Drmanac et al. |
| 2009/0127589 A1 | 5/2009 | Rothberg et al. |
| 2009/0155781 A1 | 6/2009 | Drmanac et al. |
| 2009/0264299 A1 | 10/2009 | Drmanac et al. |
| 2010/0111768 A1 | 5/2010 | Banerjee et al. |
| 2010/0120098 A1 | 5/2010 | Grunenwald et al. |
| 2010/0137143 A1 | 6/2010 | Rothberg et al. |
| 2010/0282617 A1 | 11/2010 | Rothberg et al. |
| 2011/0287435 A1 | 11/2011 | Grunenwald et al. |
| 2012/0094849 A1 | 4/2012 | Rava et al. |
| 2012/0208705 A1 | 8/2012 | Steemers et al. |
| 2012/0208724 A1 | 8/2012 | Steemers et al. |
| 2012/0270305 A1 | 10/2012 | Reed et al. |
| 2013/0079232 A1 | 3/2013 | Kain et al. |
| 2013/0184796 A1 | 7/2013 | Marzano et al. |
| 2013/0196860 A1 | 8/2013 | Grunenwald et al. |
| 2013/0260372 A1 | 10/2013 | Buermann et al. |
| 2013/0338042 A1 | 12/2013 | Shen et al. |
| 2014/0194313 A1 | 7/2014 | Craighead et al. |
| 2014/0194324 A1 | 7/2014 | Gormley et al. |
| 2014/0200146 A1 | 7/2014 | Xie et al. |
| 2014/0243224 A1 | 8/2014 | Barnard et al. |
| 2014/0274740 A1 | 9/2014 | Srinivasan et al. |
| 2015/0329891 A1 | 11/2015 | Tan et al. |
| 2016/0060691 A1 | 3/2016 | Giresi et al. |
| 2016/0061517 A1 | 3/2016 | Seitter et al. |
| 2017/0342483 A1* | 11/2017 | Arezi et al. .......... C12Q 1/6874 |
| 2018/0023119 A1 | 1/2018 | Adey et al. |
| 2018/0273933 A1* | 9/2018 | Gunderson et al. ........... C12N 15/1065 |
| 2018/0340172 A1* | 11/2018 | Belhocine et al. ........... C12N 15/1065 |
| 2018/0355348 A1 | 12/2018 | Adey et al. |
| 2019/0040382 A1 | 2/2019 | Steemers et al. |
| 2019/0071656 A1 | 3/2019 | Chang et al. |
| 2019/0382753 A1 | 12/2019 | Steemers et al. |

FOREIGN PATENT DOCUMENTS

| | | | |
|---|---|---|---|
| EP | | 320308 B1 | 11/1993 |
| EP | | 336731 B1 | 5/1994 |
| EP | | 439182 B1 | 4/1996 |
| JP | | H08239400 A | 9/1996 |
| JP | | 2007526743 A | 9/2007 |
| JP | | 2010535513 A | 11/2010 |
| JP | | 2015519084 A | 7/2015 |
| JP | | 2016508715 A | 3/2016 |
| JP | | 2016518860 A | 6/2016 |
| JP | | 2017-506877 A | 3/2017 |
| JP | | 2020-523011 A1 | 6/2020 |
| KR | | 20170107423 A | 9/2017 |
| RU | | 2529784 C2 | 9/2013 |
| RU | | 2571855 C2 | 12/2014 |
| WO | | 8703910 A1 | 7/1987 |
| WO | | 8909835 A1 | 10/1989 |
| WO | | 8912696 A1 | 12/1989 |
| WO | | 9001069 A1 | 2/1990 |
| WO | | 9106678 A1 | 5/1991 |
| WO | | 9523875 A1 | 9/1995 |
| WO | | 9844151 A1 | 10/1998 |
| WO | | 0018957 A1 | 4/2000 |
| WO | | 0246456 A1 | 6/2002 |
| WO | | 2004018497 A2 | 3/2004 |
| WO | | 2004108951 A1 | 12/2004 |
| WO | | 2005065814 A1 | 7/2005 |
| WO | | 2006064199 A1 | 6/2006 |
| WO | | 2007010251 A2 | 1/2007 |
| WO | | 2007123744 A2 | 11/2007 |
| WO | | 2012061832 A1 | 5/2012 |
| WO | | 2013188582 A1 | 12/2013 |
| WO | | 2014142850 A1 | 9/2014 |
| WO | | 2014145820 A2 | 9/2014 |
| WO | | 2014189957 A2 | 11/2014 |
| WO | | 2015002813 A1 | 1/2015 |
| WO | | 2015026853 A2 | 2/2015 |
| WO | | 2015106941 A1 | 7/2015 |
| WO | WO 2015/103339 A1 | | 7/2015 |
| WO | WO 2015/104302 A1 | | 7/2015 |
| WO | | 2016003814 A1 | 1/2016 |
| WO | WO 2016/061517 A2 | | 4/2016 |
| WO | | 2016066586 A1 | 5/2016 |
| WO | | 2016083823 A1 | 6/2016 |
| WO | WO 2016/130704 A2 | | 8/2016 |
| WO | | 2018018008 A1 | 1/2018 |
| WO | WO 2018/226708 A1 | | 12/2018 |
| WO | | 2019222688 A1 | 11/2019 |

OTHER PUBLICATIONS

Cao et al., "Comprehensive Single-cell transcriptional profiling of a multicellular organism," *Science*, 2017; 357:661-667.

Cao et al., "The single-cell transcriptional landscape of mammalian organogenesis," *Nature*, 2019; 566(7745):496-502.

Chen et al., "Single-cell whole-genome analyses by Linear Amplification via Transposon Insertion (LIANTI)," *Science*, 2017; 356:189-194.

Cusanovich et al., "Multiplex single cell profiling of chromatin accessibility by combinatorial cellular indexing," *Science*, 2015; 348:910-914.

Drmanac et al., "Human genome sequencing using unchained base reads on self-assembling DNA nanoarrays," *Science*, 2010; 327(5961):78-81.

Eberwine et al., "Analysis of gene expression in single live neurons," *Proceedings of the National Academy of Sciences*, 1992; 89:3010-3014.

Hashimshony et al., "CEL-Seq: single-cell RNA-Seq by multiplexed linear amplification," *Cell Rep*, 2012; 2:666-673.

Lizardi et al., "Mutation detection and single-molecule counting using isothermal rolling-circle amplification," *Nature Genetics*, 1998; 19:225-232.

Ramani et al., "Massively multiplex single-cell Hi-C," *Nat. Methods*, 2017; 14:263-266.

Sos et al., "Characterization of chromatin accessibility with a transposome hypersensitive sites sequencing (THS-seq) assay," *Genome Biol*, 2016; 17:20; 15 pages.

Vitak et al., "Sequencing thousands of single-cell genomes with combinatorial indexing," *Nat. Methods*, 2017; 14:302-308.

Yin et al., "High-throughput mapping of meiotic crossover and chromosome mis-segregation events in interspecific hyprid mice," *bioRxiv*, posted Jun. 4, 2018; 19 pages. Retrieved from the Internet: <URL:https://doi.org/10.1101/338053>.

(56) References Cited

OTHER PUBLICATIONS

International Search Report and Written Opinion for PCT/US2018/036078 dated Sep. 18, 2018, 14 pages.
Adey and Shendure, "Ultra-low-input, tagmentation-based whole-genome bisulfite sequencing," *Genome Res.*, Mar. 30, 2012; 22:1139-43.
Amini et al., "Haplotype-resolved whole-genome sequencing by contiguity-preserving transposition and combinatorial indexing," *Nature Genetics*, Dec. 2014;46(12):1343-1349.
Amini et al., "Supplementary Information for Haplotype-resolved whole-genome sequencing by contiguity-preserving transposition and combinatorial indexing," *Nature Genetics*, Dec. 2014;46(12):1343-1349. 15 pgs.
Angermueller et al. "Parallel single-cell sequencing links transcriptional and epigenetic heterogeneity," *Nat Methods.*, Mar. 2016; 13(3):229-232.
Clark et al., "Single-cell epigenomics: powerful new methods for understanding gene regulation and cell identity," *Genome Biol.*, Apr. 18, 2016; 17(72):1-10.
Devarajan, "Nonnegative Matrix Factorization: An Analytical and Interpretive Tool in Computational Biology," *PLoS Comput Biol.*, Jul. 25, 2008; 4(7):e1000029.
Diep et al., "Library-free Methylation Sequencing with Bisulfite Padlock Probes," *Nat. Methods.*, Sep. 30, 2012; 9(3):270-272.
Farlik et al., "Single-Cell DNA Methylome Sequencing and Bioinformatic Inference of Epigenomic Cell-State Dynamics," *Cell Reports*, Mar. 3, 2015; 10:1386-1397.
Farlik et al., "DNA Methylation Dynamics of Human Hematopoietic Stem Cell Differentiation," *Cell Stem Cell.*, Dec. 1, 2016; 19(6):808-822.
Frommer et al., "A genomic sequencing protocol that yields a positive display of 5-methylcytosine residues in individual DNA strands," *Proc. Natl. Acad. Sci. USA*, Mar. 1, 1992; 89(5):1827-1831.
Grothues et al., "PCR amplification of megabase DNA with tagged random primers (T-PCR)," *Nucleic Acids Res.*, Mar. 11, 1993; 21(5):1321-2.
Harvey and Cheng, "Methods for Characterization of Alternative RNA Splicing," In: Feng Y., Zhang L. (eds) Long Non-Coding RNAs. Methods in Molecular Biology, vol. 1402, 2016, 229-241. https://doi.org/10.1007/978-1-4939-3378-5_18.
Hu et al., "Simultaneous profiling of transcriptome and DNA methylome from a single cell," *Genome Biol.*, 2016; 17:88, 1-11.
Jamieson et al., "Exploring nonlinear feature space dimension reduction and data representation in breast CADx with Laplacian eigenmaps and t-SNE," *Med. Phys.*, Jan. 2010; 37(1):339-351.
Krueger and Andrews et al., "Bismark: a flexible aligner and methylation caller for Bisulfite-Seq applications," Jun. 1, 2011; 27(11):1571-1572.
Lister et al., "Global Epigenomic Reconfiguration During Mammalian Brian Development," *Science*, Aug. 9, 2013, Epub Jul. 4, 2013; 341(6146):1237905.
Mulqueen et al., "Highly scalable generation of DNA methylation profiles in single cells," Nat. Biotechnol, 2018; 36:428-431.
Olek et al., "A modified and improved method for bisulphite based cytosine methylation analysis," *Nucleic Acids Res.*, Dec. 15, 1996; 24(24):5064-6.
Pollen et al., "Low-coverage single-cell mRNA sequencing reveals cellular heterogeneity and activated signaling pathways in developing cerebral cortex," *Nat. Biotechnol.*, Oct. 2014, Epub Aug. 3, 2014; 32(10):1053-1058.
Ruiz et al., "Identification of a specific reprogramming-associated epigenetic signature in human induced pluripotent stem cells," *Proc Natl Acad Sci USA*, Oct. 2, 2012, Epub Sep. 18, 2012; 109(40):16196-201. (2012).
Smallwood et al., "Single-cell genome-wide bisulfite sequencing for assessing epigenetic heterogeneity," *Nature Methods*, Aug. 1, 2014; 11(8):817-822.
Svensson et al., "Power analysis of single-cell RNA-sequencing experiments," *Nat. Methods*, Apr. 2017, Epub Mar. 6, 2017; 14(4):381-387.
Vester and Wengel, "LNA (Locked Nucleic Acid): High-Affinity Targeting of Complementary RNA and DNA," *Biochemistry*, Oct. 26, 2004; 43(42):13233-41.
Vitak et al., "Construction of thousands of single cell genome sequencing libraries using combinatorial indexing," *BioRxiv*, Jul. 23, 2016; 18 pgs.
Wang et al., "Tagmentation-based whole-genome bisulfite sequencing," *Nature Protocols*, 2013;8(10):2202-2032.
Zerbino et al., "The Ensemble Regulatory Build," *Genome Biol.*, Mar. 24, 2015; 16:56.
European Search Report for EP Appl. No. 19803332.6 dated Jan. 25, 2022, 7 pages.
Zilionis et al. "Single-cell barcoding and sequencing using droplet microfluidics", Nature Protocols, Nature Publishing Group, GB, vol. 12, No. 1, Dec. 18, 2016, pp. 44-73.
Masser et al., "Focused, high accuracy 5-methylcytosine quantitation with base resolution by benchtop next-generation sequencing," Epigenetics & Chromatin, 2013, vol. 6, No. 33, pp. 1-12.
Adey et al., "In vitro, long-range sequence information for de novo genome assembly via transposase contiguity," Genome Res., Oct. 2014; 24:2041-2049.
Adey et al., "Rapid, low-input, low-bias construction of shotgun fragment libraries by high-density in vitro transposition," Genome Biol., 2010; 11:R1 19, 1-17.
Adey et al., "The haplotype-resolved genome and epigenome of the aneuploid HeLa cancer cell line," Nature, Aug. 2013; 5007461:207-211.
Alberts et al., Molecular Biology of the Cell, 4th ed., New York: Garland Science; 2002. Available online at <ncbi.nlm.nih.gov/books/NBK26834/#630>, obtained on Oct. 10, 2019; excerpt from section title "Nucleosomes Are the Basic Unit of Eucaryotic Chromosome Structure". 1 pg.
Arrigoni et al., Standardizing Chromatin Research: A Simple and Universal Method for ChIP-Seq, Nucleic Acids Reasearch, 2015, 44(7), 1-13. (Year: 2015).
Bailey et al., "Genomic analyses identify molecular subtypes of pancreatic cancer," Nature, Mar. 2016; 531(7592):47-52.
Baslan et al., "Optimizing sparse sequencing of single cells for highly multiplex copy number profiling," Genome Res., Apr. 2015; 25:714-724.
Beitel et al., "Strain- and plasmid-level deconvolution of a synthetic metagenome by sequencing proximity ligation products," PeerJ, May 2014; 2:e415.
Bentley et al., "Accurate whole genome sequencing using reversible terminator chemistry," Nature, Nov. 2008; 456(7218):53-59.
Boeke et al., "Transcription and reverse transcription of retrotransposons," Annu Rev Microbial., 1989; 43:403-34.
Borrell et al., The Action of Triton X-100 and Sodium Dodecyl Sulphate on Lipid Layers. Effect on Monolayers and Liposomes, Journal of Microencapsulation, 1990, 7(2), 255-259 (Year: 1990).
Brown et al., "Retroviral integration: structure of the initial covalent product and its precursor, and a role for the viral IN protein," Proc Natl Acad Sci USA, Apr. 1989; 86(8):2525-9.
Buenrostro et al., Transposition of Native Chromatin for Fast and Sensitive Epigenomic Profiling of Open Chromatin, DNA-Binding Proteins and Nucelosome Position, Nature Methods, 2013, 10(12), 1213-1218. (Year: 2013).
Burton et al., "Species-level deconvolution of metagenome assemblies with Hi-C-based contact probability maps," G3 (Bethesda). May 2014; 4(7):1339-46.
Cai et al. "Single-Cell, Genome-wide Sequencing Identifies Clonal Somatic Copy-Number Variation in the Human Brain," Cell Rep., Sep. 2014; 8:1280-1289.
Callaway, "'Platinum' genome takes on disease," Nat. News, Nov. 2014; 515(7527):323.
Clyde, "Barcoding the nucleus", Nature Reviews Genetics, published online Feb. 13, 2017, doi:10.1038/nrg.2017.11.
Cockroft et al., "A single-molecule nanopore device detects DNA polymerase activity with single-nucleotide resolution," J Am. Chem. Soc., Jan. 2008; 130(3):818-820.

(56) References Cited

OTHER PUBLICATIONS

Colegio et al., "In vitro transposition system for efficient generation of random mutants of Campylobacterjejuni," J Bacterial., Apr. 2001; 183(7):2384-8.
Craig, "Transposon Tn7," Curr Top Microbial. Immunol., 1996; 204:27-48.
Craig, "V(D)J recombination and transposition: closer than expected," Science, Mar. 1996; 271(5255):1512.
Cusanovich et al., Supplementary Materials, Multiplex Single-Cell Profiling of Chromatin Accessibility by Combinatorial Cellular Indexing, Science, 2015, 1-34. (Year: 2015).
De Kouchkovsky et al., "Acute myeloid leukemia: a comprehensive review and 2016 update," Blood Cancer J, Jul. 2016; 6(7):e441.
Deamer et al., "Characterization of nucleic acids by nanopore analysis," Acc. Chem. Res., Oct. 2002; 35(10):817-825.
Deamer et al., "Nanopores and nucleic acids: prospects for ultrapid sequencing," Trends Biotechnol., Apr. 2000; 18(4):147-151.
Dean et al., "Comprehensive human genome amplification using multiple displacement amplification," Proc. Natl. Acad Sci. USA, Apr. 2002; 99(8):5261-66.
Devine et al., "Efficient integration of artificial transposons into plasmid targets in vitro: a useful tool for DNA mapping, sequencing and genetic analysis," Nucleic Acids Res., Sep. 1994; 22(18):3765-72.
Dolezel et al., "Nuclear DNA Content and Genome Size of Trout and Human," Cytometry Part A, 2003, vol. 51A, pp. 127-128.
Eirew et al., "Dynamics of genomic clones in breast cancer patient xenografts at single-cell resolution," Nature, Feb. 2015; 518:422-6.
Forbes et al. "COSMIC: Exploring the world's knowledge of somatic mutations in human cancer," Nucleic Acids Res., Jan. 2015; 43:D805-D811.
Gao et al., "Punctuated copy number evolution and clonal stasis in triple-negative breast cancer," Nat. Genet., Oct. 2016; 48(10):1119-1130.
Garvin et al., "Interactive analysis and quality assessment of single-cell copy-number variations," bioRxiv, Nov. 2014; 1-32. doi:10.1101/011346.
Gawad et al., "Dissecting the clonal origins of childhood acute lymphoblastic leukemia by single-cell genomics," Proc. Natl. Acad Sci. USA., Dec. 2014; 111(50):17947-52.
Gawad et al., "Single-cell genome sequencing: current state of the science," Nat. Rev. Genet., Jan. 2016; 17:175-88.
Gloor, "Gene targeting in *Drosophila*," Methods Mal. Biol., 2004; 260:97-114.
Goldenberger et al., A Simple "Universal" DNA Extraction Procedure Using SDS and Proteinase K Is Compatible with Direct PCR Amplification, PCR Methods and Applications, 1995, 4, 368-370. (Year: 1995).
Goryshin et al., "Tn5 in vitro transposition," J Biol. Chem., Mar. 1998; 273(13):7367-74.
Goryshin et al., "Tn5/IS50 target recognition," Proc. Natl. Acad Sci. USA, Sep. 1998; 95(18)10716-10721.
Gravina et al., "Single-cell, locus-specific bisulfite sequencing (SLBS) for direct detection of epimutations in DNA methylation patterns," Nucleic Acids Research, 2015, vol. 43, No. 14, e93, pp. 1-7.
Ha et al., "Integrative analysis of genome-wide loss of heterozygosity and monoallelic expression at nucleotide resolution reveals disrupted pathways in triple-negative breast cancer," Genome Research, Oct. 2012; 22(10):1995-2007.
Healy, "Nanopore-based single-molecule DNA analysis," Nanomedicine (Land)., Aug. 2007; 2( 4):459-481.
Hoffman et al., "Formaldehyde Crosslinking: A Tool for the Study of Chomatin Complexes," J Biol. Chem., Oct. 2015; 290(44):26404-26411.
Ichikawa, "In vitro transposition of transposon Tn3," J Biol. Chem., Nov. 1990; 265(31):18829-32.
Illumina® Safety Data Sheet, LP#-TSB, Tagment Stop Buffer, Issued Nov. 12, 2018, Revised Jan. 22, 2020, Revision No. 4.2.
Illumina® Safety Data Sheet, NX#-TD, Tagment DNA Buffer, Issued Jun. 5, 2018, Revised Jan. 22, 2020, Revision No. 2.4.
Illumina® Safety Data Sheet, NX#-TDE1 Tagment DNA Enzyme 1, Issued Jan. 15, 2018, Revised Jan. 22, 2020, Revision No. 1.1.
International Preliminary Report on Patentability in PCT/US2017/043381, dated Jan. 22, 2019, 8 pages.
International Preliminary Report on Patentability in PCT/US2018/036078, dated Dec. 10, 2019, 7 pages.
International Search Report and Written Opinion for International Application No. PCT/US2017/043381, dated Nov. 15, 2017, 17 pages.
Kawashima et al., Efficient Extraction of Proteins From Formalin-Fixed Paraffin-Embedded Tissues Requires Higher Concentration of Tris(hydroxymethyl)aminomethane, Clinical Proteomics, 2014, 11(4), 1-6. (Year: 2014).
Kirby et al., "Cryptic plasmids of *Mycobacterium avium*: Tn552 to the rescue," Mal. Microbial., Jan. 2002; 431:173-86.
Kleckner et al., "TnI0 and ISI0 transposition and chromosome rearrangements: mechanism and regulation in vivo and in vitro," Curr Top Microbial Immunol., 1996; 204:49-82.
Knouse et al., "Assessment of megabase-scale somatic copy number variation using single cell sequencing," Genome Res., Jan. 2016; doi:10.1101/gr.198937.115.
Knouse et al., "Single cell sequencing reveals low levels of aneuploidy across mammalian tissues," Proc Natl Acad Sci USA, Sep. 2014; 11137:13409-13414.
Korlach, J. et al. "Selective aluminum passivation for targeted immobilization of single DNA polymerase molecules in zero-mode waveguide nanostructures." Proc. Natl. Acad Sci. USA, Jan. 2008; 1054:1176-1181.
Krishnaswami et al., Using Nuclei for RNA-Seq to Capture the Transcriptome of Postmortem Neurons, Nature Protocol, 2016, 113, 499-524. Year: 2016.
Kumagai et al., "Epigenetic regulation and molecular characterization of C/EBPalpha in pancreatic cancer cells," Int. J Cancer, Feb. 2009; 1244:827-833.
Kustatscher et al., Chromatin Enrichment for Proteomics, Nature Protocols, 2014, 99, 2090-2099. Year: 2014.
Lage et al., "Whole genome analysis of genetic alterations in small DNA samples using hyperbranched strand displacement amplification and array-CGH," Genome Res., Feb. 2003; 132:294-307.
Lampe et al., "A purified mariner transposase is sufficient to mediate transposition in vitro," The EMBO Journal, 1996; 1519:5470-9.
Langmead et al., "Fast gapped-read alignment with Bowtie 2," Nat Methods, Mar. 2012; 9:357-359.
Levene et al. "Zero-mode waveguides for single-molecule analysis at high concentrations," Science, Jan. 2003; 2995607:682-686.
Li et al., "DNA molecules and configurations in a solid-state nanopore microscope," Nature Materials, Aug. 2003; 2:611-615.
Lundquist et al. "Parallel confocal detection of single molecules in real time," Opt. Lett., May 2008; 339:1026-1028.
Macosko et al., "Highly Parallel Genome-wide Expression Profiling ofIndividual Cells Using Nanoliter Droplets," Cell, May 2015; 1615:1202-1214.
McConnell et al., "Mosaic Copy Number Variation in Human Neurons," Science, Nov. 2013; 3426158:632-637.
Metzker, "Emerging technologies in DNA sequencing," Genome Res., Dec. 2005; 1512:1767-1776.
Mirkovitch et al., "Organization of the higher-order chromatin loop: specific DNA attachment sites on nuclear scaffold," Cell, Nov. 1984; 391:223-232.
Mizuuchi, "In vitro transposition of bacteriophage Mu: a biochemical approach to a novel replication reaction," Cell, Dec. 1983; 353 Pt 2:785-94.
Nagano et al., "Single-cell Hi-C reveals cell-to-cell variability in chromosome structure," Nature, Oct. 2013; 502:59-64.
Navin et al., "Tumour evolution inferred by single-cell sequencing," Nature, Apr. 2011; 4727341:90-94.
Nextera, Nextera XT Library Prep: Tips and Troubleshooting, Illumina, 2015, 1-6. (Year: 2015).
Nickerson et al., The Nuclear Matrix Revealed by Eluting Chromatin From a Cross-linked Nucleus, Proc. Natl. Acad. Sci., 1997, 94, 4446-4450. Year: 1997.

(56) References Cited

OTHER PUBLICATIONS

Ohtsubo et al., "Bacterial insertion sequences," Curr. Top. Microbial. Immunol., 1996; 204:1-26.
Olshen et al., "Circular binary segmentation for the analysis of array-based DNA copy number data," Biostatistics, Oct. 2004; 54:557-572.
Perkins, "Integrating cell-signalling pathways with NF-kappaB and IKK function," Nat. Rev. Mal. Cell Biol., Jan. 2007; 81:49-62.
Plasterk, "The Tel/mariner transposon family," Curr Topics Microbial. Immunol., 1996; 204:125-43.
Rehen et al., "Chromosomal variation in neurons of the developing and adult mammalian nervous system," Proc. Natl. Acad Sci. USA., Nov. 2001; 9823:13361-6.
Ronaghi et al., "A sequencing method based on real-time pyrophosphate," Science, Jul. 1998; 2815375:363, 365.
Ronaghi et al., "Real-time DNA sequencing using detection of pyrophosphate release," Analytical Biochemistry, Nov. 1996; 2421:84-9.
Ronaghi, "Pyrosequencing sheds light on DNA sequencing," Genome Res., Jan. 2001; 111:3-11.
Rosenkrantz et al., "Investigating somatic aneuploidy in the brain: why we need a new model," Chromosoma, Jun. 2017; 1263:337-350.
Ruparel et al., "Design and synthesis of a 3'-O-allyl photocleavable fluorescent nucleotide as a reversible terminator for DNA sequencing by synthesis," Proc. Natl. Acad Sci. USA, Apr. 2005; 102(17):5932-7.
Savilahti et al., "The phage Mu transpososome core: DNA requirements for assembly and function," EMBO J, Oct. 1995; 1419:4893-4903.
Shalek, "Baring cellular souls," Science Translational Medicine, Feb. 15, 2017, vol. 9, Issue 377.
Sigma-Aldrich, "Detergents and Solubilization Reagents," Biofiles for Life Science Research, 2008, vol. 3, No. 3, pp. 1-36.
Soni et al., "Progress toward ultrafast DNA sequencing using solid-state nanopores," Clin. Chem., Nov. 2007; 5311:1996-2001.
Stahley et al., "Desmosomes in acquired disease," Cell Tissue Res., Jun. 2015; 3603:439-56.
Stergachis et al., "Developmental fate and cellular maturity encoded in human regulatory DNA landscapes," Cell, Aug. 2013; 1544:888-903.
The ENCODE Project Consortium, "An integrated encyclopedia of DNA elements in the human genome," Nature, Sep. 2012; 4897414:57-74.
Tomschik et al., "Fast, long-range, reversible conformational fluctuations in nucleosomes revealed by single-pair fluorescence resonance energy transfer," Proc. Natl. Acad Sci. USA., Mar. 1, 2005; 1029:3278-3283.
Vitak et al., "SCI-seq: Sequencing thousands of single-cell genomes with combinatorial indexing," Nature Methods, doi:10.1038/nmeth.4154; 41 pages.
Waddell et al., "Whole genomes redefine the mutational landscape of pancreatic cancer," Nature, Feb. 2015; 5187540:495-501.
Walker et al., "Strand displacement amplification—an isothermal, in vitro DNA amplification technique," Nucl. Acids Res., Apr. 1992; 20(7):1691-96.
White et al., "The Impact of Detergents on the Tissue Decellularization Process: A ToF-SIMS Study," Acta Biomaterialia, 2017, 50, 207-219. Year: 2017.
Wilson et al., "New transposon delivery plasmids for insertional mutagenesis in Bacillus anthracis," J Microbial. Methods, Dec. 2007; 713:332-5.
Wilson et al., Improved Immunodetection of Nuclear Antigens After Sodium Dodecyl Sulfate Treatment of Formaldehyde-Fixed Cells, Journal of Histochemistry & Cytochemistry, 1999, 478, 1095-1100. Year: 1999.
Zhang et al., "A Novel Mechanism of Transposon-Mediated Gene Activation," PLoS Genet., Oct. 2009; 510: el000689.
Zong et al., "Genome-Wide Detection of Single Nucleotide and Copy Number Variations of a Single Human Cell," Science, 2012; 3386114: 1622-1626.
Jackson et al., "Evaluating bias-reducing protocols for RNA sequencing library preparation," 2014, *Genomics*, 15(569): 9 pages.
Oyola et al., "Optimizing illumina next-generation sequencing library preparation for extremely at-biased genomes," 2012, *Genomics*, 13(1): 12 pages.

\* cited by examiner

HIGH-THROUGHPUT SINGLE-CELL SEQUENCING WITH REDUCED AMPLIFICATION BIAS

CROSS-REFERENCE TO RELATED APPLICATIONS

This application claims the benefit of U.S. Provisional Application Ser. No. 62/673,023, filed May 17, 2018, and U.S. Provisional Application Ser. No. 62/821,864, filed Mar. 21, 2019, each of which is incorporated by reference herein in its entirety.

GOVERNMENT FUNDING

This invention was made with government support under Grant No. DP1 HG007811, awarded by the National Institutes of Health. The government has certain rights in the invention.

SEQUENCE LISTING

This application contains a Sequence Listing electronically submitted via EFS-Web to the United States Patent and Trademark Office as an ASCII text file entitled "IP-1695-US_ST25.txt" having a size of 65.8 kilobytes and created on Jul. 25, 2019. The information contained in the Sequence Listing is incorporated by reference herein.

FIELD

Embodiments of the present disclosure relate to sequencing nucleic acids. In particular, embodiments of the methods and compositions provided herein relate to producing indexed single-cell sequencing libraries and obtaining sequence data therefrom for characterizing rare events including crossover and chromosome mis-segregation events. In some embodiments, the methods relate to resolving cancer heterogeneity at the single cell level.

BACKGROUND

Contemporary single cell genome sequencing technologies have two major limitations. First, most methods require compartmentalizing individual cells, which can limit throughput. Second, most amplification methods are PCR-based and thus suffer from exponential amplification biases. To resolve the first issue, we and colleagues developed single cell combinatorial indexing ('sci-'), wherein one performs several rounds of split-pool molecular barcoding to uniquely tag the nucleic acid contents of single cells, thereby enabling exponential gains in throughput with each successive round of indexing. Sci-methods have been successfully developed to profile chromatin accessibility (sci-ATAC-seq), transcriptomes (sci-RNA-seq), genomes (sci-DNA-seq), methylomes (sci-MET), chromosome conformation (sci-Hi-C) in large numbers of single cells (Cao et al., 2017, Science 357:661-667; Cusanovich et al., 2015, Science, 348:910-914; Mulqueen et al., 2018, Nat. Biotechnol. 36:428-431; Ramani et al., 2017, Nat. Methods 14:263-266; Vitak et al., 2017, Nat. Methods 14:302-308). To resolve the second issue, linear amplification via T7-based transcription provides a potential solution that has previously been deployed in the context of single cell assays (Eberwine et al., 1992; Proceedings of the National Academy of Sciences 89:3010-3014; Hashimshony et al., 2012, Cell Rep. 2:666-673; Sos et al., 2016, Genome Biolol., 17:20). For example, recently, Chen et al. developed Linear Amplification via Transposon Insertion ("LIANTI"), which uses Tn5 transposon to fragment the genome and simultaneously insert a T7 RNA promoter for in vitro transcription (IVT). RNA copies generated from the DNA template cannot serve as template for further amplification; therefore, all copies derive directly from the original DNA template. By avoiding exponential amplification, LIANTI maintains uniformity and minimizes sequence errors. However, the method is low-throughput because it requires serial library preparation from each single cell (Chen et al., 2017, Science 356:189-194).

SUMMARY OF THE APPLICATION

Described herein are methods that integrate single cell combinatorial indexing and linear amplification to minimize amplification biases while at the same time enabling exponential gains in throughput. With multiple rounds of molecular barcoding, the methods improve the throughput to at least thousands and potentially millions of cells per experiment, while retaining the advantages of linear amplification. The inventors demonstrate the generalizability of the methods through proof-of-concept demonstrations of single cell whole genome sequencing ("sci-L3-WGS"), targeted genome sequencing ("sci-L3-target-seq"), and a co-assay of the genome and transcriptome ("sci-L3-RNA/DNA"). As a further demonstration, single cell whole genome sequencing is applied to map an unprecedented number of meiotic crossover and rare chromosome mis-segregation events in premature and mature male germ cells from infertile, interspecific (B6×Spretus) F1 male mice, as well as fertile, intraspecific (B6×Cast) F1 male mice.

Definitions

Terms used herein will be understood to take on their ordinary meaning in the relevant art unless specified otherwise. Several terms used herein and their meanings are set forth herein.

As used herein, the terms "organism," "subject," are used interchangeably and refer to microbes (e.g., prokaryotic or eukaryotic) animals and plants. An example of an animal is a mammal, such as a human.

As used herein, the term "cell type" is intended to identify cells based on morphology, phenotype, developmental origin or other known or recognizable distinguishing cellular characteristic. A variety of different cell types can be obtained from a single organism (or from the same species of organism). Exemplary cell types include, but are not limited to, gametes (including female gametes, e.g., ova or egg cells, and male gametes, e.g., sperm), ovary epithelial, ovary fibroblast, testicular, urinary bladder, immune cells, B cells, T cells, natural killer cells, dendritic cells, cancer cells, eukaryotic cells, stem cells, blood cells, muscle cells, fat cells, skin cells, nerve cells, bone cells, pancreatic cells, endothelial cells, pancreatic epithelial, pancreatic alpha, pancreatic beta, pancreatic endothelial, bone marrow lymphoblast, bone marrow B lymphoblast, bone marrow macrophage, bone marrow erythroblast, bone marrow dendritic, bone marrow adipocyte, bone marrow osteocyte, bone marrow chondrocyte, promyeloblast, bone marrow megakaryoblast, bladder, brain B lymphocyte, brain glial, neuron, brain astrocyte, neuroectoderm, brain macrophage, brain microglia, brain epithelial, cortical neuron, brain fibroblast, breast epithelial, colon epithelial, colon B lymphocyte, mammary epithelial, mammary myoepithelial, mammary fibroblast, colon enterocyte, cervix epithelial, breast duct epithelial, tongue epithelial, tonsil dendritic, tonsil B lymphocyte, peripheral blood lymphoblast, peripheral blood T lymphoblast, peripheral blood cutaneous T lymphocyte, peripheral blood natural killer, peripheral blood B lymphoblast, peripheral blood monocyte, peripheral blood myeloblast, peripheral blood monoblast, peripheral blood promyeloblast, peripheral blood macrophage, peripheral blood basophil, liver endothelial, liver mast, liver epithelial, liver B lymphocyte, spleen endothelial, spleen epithelial, spleen B lymphocyte, liver hepatocyte, liver, fibroblast, lung epithelial, bronchus epithelial, lung fibroblast, lung B lymphocyte, lung Schwann, lung squamous, lung macrophage, lung osteoblast, neuroendocrine, lung alveolar, stomach epithelial, and stomach fibroblast.

As used herein, the term "tissue" is intended to mean a collection or aggregation of cells that act together to perform one or more specific functions in an organism. The cells can optionally be morphologically similar. Exemplary tissues include, but are not limited to, epididymidis, eye, muscle, skin, tendon, vein, artery, blood, heart, spleen, lymph node, bone, bone marrow, lung, bronchi, trachea, gut, small intestine, large intestine, colon, rectum, salivary gland, tongue, gall bladder, appendix, liver, pancreas, brain, stomach, skin, kidney, ureter, bladder, urethra, gonad, testicle, ovary, uterus, fallopian tube, thymus, pituitary, thyroid, adrenal, or parathyroid. Tissue can be derived from any of a variety of organs of a human or other organism. A tissue can be a healthy tissue or an unhealthy tissue. Examples of unhealthy tissues include, but are not limited to, malignancies in reproductive tissue, lung, breast, colorectum, prostate, nasopharynx, stomach, testes, skin, nervous system, bone, ovary, liver, hematologic tissues, pancreas, uterus, kidney, lymphoid tissues, etc. The malignancies may be of a variety of histological subtypes, for example, carcinoma, adenocarcinoma, sarcoma, fibroadenocarcinoma, neuroendocrine, or undifferentiated.

As used herein, the term "nucleosome" refers to the basic repeating unit of chromatin. The human genome consists of several meters of DNA compacted within the nucleus of a cell having an average diameter of ~10 µm. In the eukaryote nucleus, DNA is packaged into a nucleoprotein complex known as chromatin. The nucleosome (the basic repeating unit of chromatin) typically includes ~146 base pairs of DNA wrapped approximately 1.7 times around a core histone octamer. The histone octamer consists of two copies of each of the histones H2A, H2B, H3 and H4. Nucleosomes are regularly spaced along the DNA in the manner of beads on a string.

As used herein, the term "compartment" is intended to mean an area or volume that separates or isolates something from other things. Exemplary compartments include, but are not limited to, vials, tubes, wells, droplets, boluses, beads, vessels, surface features, or areas or volumes separated by physical forces such as fluid flow, magnetism, electrical current or the like. In one embodiment, a compartment is a well of a multi-well plate, such as a 96- or 384-well plate. As used herein, a droplet may include a hydrogel bead, which is a bead for encapsulating one or more nuclei or cell, and includes a hydrogel composition or droplet-based microfluidics. In some embodiments, the droplet is a homogeneous droplet of hydrogel material or is a hollow droplet having a polymer hydrogel shell. Whether homogenous or hollow, a droplet may be capable of encapsulating one or more nuclei or cells.

As used herein, a "transposome complex" refers to an integration enzyme and a nucleic acid including an integration recognition site. A "transposome complex" is a functional complex formed by a transposase and a transposase recognition site that is capable of catalyzing a transposition reaction (see, for instance, Gunderson et al., WO 2016/130704). Examples of integration enzymes include, but are not limited to, an integrase or a transposase. Examples of integration recognition sites include, but are not limited to, a transposase recognition site.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of adenine, uracil, cytosine or guanine. Useful non-native bases that can be included in a nucleic acid are known in the art. Examples of non-native bases include a locked nucleic acid (LNA), a bridged nucleic acid (BNA), and pseudo-complementary bases (Trilink Biotechnologies, San Diego, CA). LNA and BNA bases can be incorporated into a DNA oligonucleotide and increase oligonucleotide hybridization strength and specificity. LNA and BNA bases and the uses of such bases are known to the person skilled in the art and are routine.

As used herein, the term "target," when used in reference to a nucleic acid, is intended as a semantic identifier for the nucleic acid in the context of a method or composition set forth herein and does not necessarily limit the structure or function of the nucleic acid beyond what is otherwise explicitly indicated. A target nucleic acid may be essentially any nucleic acid of known or unknown sequence. It may be, for example, a fragment of genomic DNA (e.g., chromosomal DNA), extra-chromosomal DNA such as a plasmid, cell-free DNA, RNA (e.g., RNA or non-coding RNA), proteins (e.g. cellular or cell surface proteins), or cDNA. Sequencing may result in determination of the sequence of the whole, or a part of the target molecule. The targets can be derived from a primary nucleic acid sample, such as a nucleus. In one embodiment, the targets can be processed into templates suitable for amplification by the placement of universal sequences at one or both ends of each target fragment. The targets can also be obtained from a primary RNA sample by reverse transcription into cDNA. In one embodiment, target is used in reference to a subset of DNA, RNA, or proteins present in the cell. Targeted sequencing uses selection and isolation of genes or regions or proteins of interest, typically by either PCR amplification (e.g., region-specific primers) or hybridization-based capture method (e.g., use of a capture probe) or antibodies. Targeted enrichment can occur at various stages of the method. For instance, a targeted RNA representation can be obtained using target specific primers in the reverse transcription step or hybridization-based enrichment of a subset out of a more complex library. An example is exome sequencing or the L1000 assay (Subramanian et al., 2017, Cell, 171; 1, 437-

1452). Targeted sequencing can include any of the enrichment processes known to one of ordinary skill in the art.

As used herein, the term "universal," when used to describe a nucleotide sequence, refers to a region of sequence that is common to two or more nucleic acid molecules where the molecules also have regions of sequence that differ from each other. A universal sequence that is present in different members of a collection of molecules can allow capture of multiple different nucleic acids using a population of universal capture nucleic acids, e.g., capture oligonucleotides that are complementary to a portion of the universal sequence, e.g., a universal capture sequence. Non-limiting examples of universal capture sequences include sequences that are identical to or complementary to P5 and P7 primers. Similarly, a universal sequence present in different members of a collection of molecules can allow the replication (e.g., sequencing) or amplification of multiple different nucleic acids using a population of universal primers that are complementary to a portion of the universal sequence, e.g., a universal anchor sequence. Non-limiting examples of universal anchor sequences include sequences that are identical to or complementary to spacer sequences, such as sp1 and sp2. In one embodiment universal anchor sequences are used as a site to which a universal primer (e.g., a sequencing primer for read 1 or read 2) anneals for sequencing. A capture oligonucleotide or a universal primer therefore includes a sequence that can hybridize specifically to a universal sequence.

The terms "P5" and "P7" may be used when referring to a universal capture sequence or a capture oligonucleotide. The terms "P5'" (P5 prime) and "P7'" (P7 prime) refer to the complement of P5 and P7, respectively. It will be understood that any suitable universal capture sequence or a capture oligonucleotide can be used in the methods presented herein, and that the use of P5 and P7 are exemplary embodiments only. Uses of capture oligonucleotides such as P5 and P7 or their complements on flowcells are known in the art, as exemplified by the disclosures of WO 2007/010251, WO 2006/064199, WO 2005/065814, WO 2015/106941, WO 1998/044151, and WO 2000/018957. For example, any suitable forward amplification primer, whether immobilized or in solution, can be useful in the methods presented herein for hybridization to a complementary sequence and amplification of a sequence. Similarly, any suitable reverse amplification primer, whether immobilized or in solution, can be useful in the methods presented herein for hybridization to a complementary sequence and amplification of a sequence. One of skill in the art will understand how to design and use primer sequences that are suitable for capture and/or amplification of nucleic acids as presented herein.

As used herein, the term "primer" and its derivatives refer generally to any nucleic acid that can hybridize to a target sequence of interest. Typically, the primer functions as a substrate onto which nucleotides can be polymerized by a polymerase or to which a nucleotide sequence such as an index can be ligated; in some embodiments, however, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In some embodiments, the primer is a single-stranded oligonucleotide or polynucleotide. The terms "polynucleotide" and "oligonucleotide" are used interchangeably herein to refer to a polymeric form of nucleotides of any length, and may include ribonucleotides, deoxyribonucleotides, analogs thereof, or mixtures thereof. The terms should be understood to include, as equivalents, analogs of either DNA, RNA, cDNA or antibody-oligo conjugates made from nucleotide analogs and to be applicable to single stranded (such as sense or antisense) and double stranded polynucleotides. The term as used herein also encompasses cDNA, that is complementary or copy DNA produced from a RNA template, for example by the action of reverse transcriptase. This term refers only to the primary structure of the molecule. Thus, the term includes triple-, double- and single-stranded deoxyribonucleic acid ("DNA"), as well as triple-, double- and single-stranded ribonucleic acid ("RNA").

As used herein, the term "adapter" and its derivatives, e.g., universal adapter, refers generally to any linear oligonucleotide which can be ligated to a nucleic acid molecule of the disclosure. In some embodiments, the adapter is substantially non-complementary to the 3' end or the 5' end of any target sequence present in the sample. In some embodiments, suitable adapter lengths are in the range of about 10-100 nucleotides, about 12-60 nucleotides, or about 15-50 nucleotides in length. Generally, the adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. In some embodiments, the adapter can include a barcode (also referred to herein as a tag or index) to assist with downstream error correction, identification, or sequencing. The terms "adaptor" and "adapter" are used interchangeably.

As used herein, the term "each," when used in reference to a collection of items, is intended to identify an individual item in the collection but does not necessarily refer to every item in the collection unless the context clearly dictates otherwise.

As used herein, the term "transport" refers to movement of a molecule through a fluid. The term can include passive transport such as movement of molecules along their concentration gradient (e.g. passive diffusion). The term can also include active transport whereby molecules can move along their concentration gradient or against their concentration gradient. Thus, transport can include applying energy to move one or more molecules in a desired direction or to a desired location such as an amplification site.

As used herein, "amplify", "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodiments, such amplification can include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction can include any of the amplification processes known to one of ordinary skill in the art. In some embodiments, the amplification reaction includes polymerase chain reaction (PCR).

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more target sequences flanked by a universal sequence, or to amplify an amplified target sequence ligated to one or more adapters. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{2+}$ or $Mn^{2+}$ and can also include various modifiers of ionic strength.

As used herein, "re-amplification" and their derivatives refer generally to any process whereby at least a portion of an amplified nucleic acid molecule is further amplified via any suitable amplification process (referred to in some embodiments as a "secondary" amplification), thereby producing a reamplified nucleic acid molecule. The secondary amplification need not be identical to the original amplification process whereby the amplified nucleic acid molecule was produced; nor need the reamplified nucleic acid molecule be completely identical or completely complementary to the amplified nucleic acid molecule; all that is required is that the reamplified nucleic acid molecule include at least a portion of the amplified nucleic acid molecule or its complement. For example, the re-amplification can involve the use of different amplification conditions and/or different primers, including different target-specific primers than the primary amplification.

As used herein, the term "polymerase chain reaction" ("PCR") refers to the method of Mullis U.S. Pat. Nos. 4,683,195 and 4,683,202, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double stranded polynucleotide of interest. The mixture is denatured at a higher temperature first and the primers are then annealed to complementary sequences within the polynucleotide of interest molecule. Following annealing, the primers are extended with a polymerase to form a new pair of complementary strands. The steps of denaturation, primer annealing and polymerase extension can be repeated many times (referred to as thermocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as PCR. Because the desired amplified segments of the polynucleotide of interest become the predominant nucleic acid sequences (in terms of concentration) in the mixture, they are said to be "PCR amplified". In a modification to the method discussed above, the target nucleic acid molecules can be PCR amplified using a plurality of different primer pairs, in some cases, one or more primer pairs per target nucleic acid molecule of interest, thereby forming a multiplex PCR reaction.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher. It is also possible to detect the amplified target sequences by several different methodologies (e.g., gel electrophoresis followed by densitometry, quantitation with a bioanalyzer or quantitative PCR, hybridization with a labeled probe; incorporation of biotinylated primers followed by avidin-enzyme conjugate detection; incorporation of $^{32}$P-labeled deoxynucleotide triphosphates into the amplified target sequence).

As used herein, "amplified target sequences" and its derivatives, refers generally to a nucleic acid sequence produced by the amplifying the target sequences using target-specific primers and the methods provided herein. The amplified target sequences may be either of the same sense (i.e. the positive strand) or antisense (i.e., the negative strand) with respect to the target sequences.

As used herein, the terms "ligating", "ligation" and their derivatives refer generally to the process for covalently linking two or more molecules together, for example covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, the ligation can include forming a covalent bond between a 5' phosphate group of one nucleic acid and a 3' hydroxyl group of a second nucleic acid thereby forming a ligated nucleic acid molecule. Generally, for the purposes of this disclosure, an amplified target sequence can be ligated to an adapter to generate an adapter-ligated amplified target sequence.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but are not limited to, T4 DNA ligase, T4 RNA ligase, and E. coli DNA ligase.

As used herein, "ligation conditions" and its derivatives, generally refers to conditions suitable for ligating two molecules to each other. In some embodiments, the ligation conditions are suitable for sealing nicks or gaps between nucleic acids. As used herein, the term nick or gap is consistent with the use of the term in the art. Typically, a nick or gap can be ligated in the presence of an enzyme, such as ligase at an appropriate temperature and pH. In some embodiments, T4 DNA ligase can join a nick between nucleic acids at a temperature of about 70-72° C.

The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "capacity," when used in reference to a site and nucleic acid material, means the maximum amount of nucleic acid material that can occupy the site. For example, the term can refer to the total number of nucleic acid molecules that can occupy the site in a particular condition. Other measures can be used as well including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

As used herein, the term "capture agent" refers to a material, chemical, molecule, or moiety thereof that is capable of attaching, retaining or binding to a target molecule (e.g., a target nucleic acid). Exemplary capture agents include, without limitation, a capture nucleic acid (also referred to herein as a capture oligonucleotide) that is complementary to at least a portion of a target nucleic acid, a member of a receptor-ligand binding pair (e.g. avidin, streptavidin, biotin, lectin, carbohydrate, nucleic acid binding protein, epitope, antibody, etc.) capable of binding to a target nucleic acid (or linking moiety attached thereto), or a chemical reagent capable of forming a covalent bond with a target nucleic acid (or linking moiety attached thereto).

As used herein, the term "reporter moiety" can refer to any identifiable tag, label, indices, barcodes, or group that enables to determine the composition, identity, and/or the source of an analyte that is investigated. In some embodiments, a reporter moiety may include an antibody that specifically binds to a protein. In some embodiments, the antibody may include a detectable label. In some embodiments, the reporter can include an antibody or affinity reagent labeled with a nucleic acid tag. The nucleic acid tag can be detectable, for example, via a proximity ligation assay (PLA) or proximity extension assay (PEA) or sequencing-based readout (Shahi et al. Scientific Reports volume 7, Article number: 44447, 2017) or CITE-seq (Stoeckius et al. Nature Methods 14:865-868, 2017).

As used herein, the term "clonal population" refers to a population of nucleic acids that is homogeneous with respect to a particular nucleotide sequence. The homogenous sequence is typically at least 10 nucleotides long, but can be even longer including for example, at least 50, 100, 250, 500 or 1000 nucleotides long. A clonal population can be derived from a single target nucleic acid or template nucleic acid. Typically, all of the nucleic acids in a clonal population will have the same nucleotide sequence. It will be understood that a small number of mutations (e.g. due to amplification artifacts) can occur in a clonal population without departing from clonality.

As used herein, the term "unique molecular identifier" or "UMI" refers to a molecular tag, either random, non-random, or semi-random, that may be attached to a nucleic acid molecule. When incorporated into a nucleic acid molecule, a UMI can be used to correct for subsequent amplification bias by directly counting unique molecular identifiers (UMIs) that are sequenced after amplification.

As used herein, "providing" in the context of a composition, an article, a nucleic acid, or a nucleus means making the composition, article, nucleic acid, or nucleus, purchasing the composition, article, nucleic acid, or nucleus, or otherwise obtaining the compound, composition, article, or nucleus.

The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

BRIEF DESCRIPTION OF THE FIGURES

The following detailed description of illustrative embodiments of the present disclosure may be best understood when read in conjunction with the following drawings

Figure 1A:
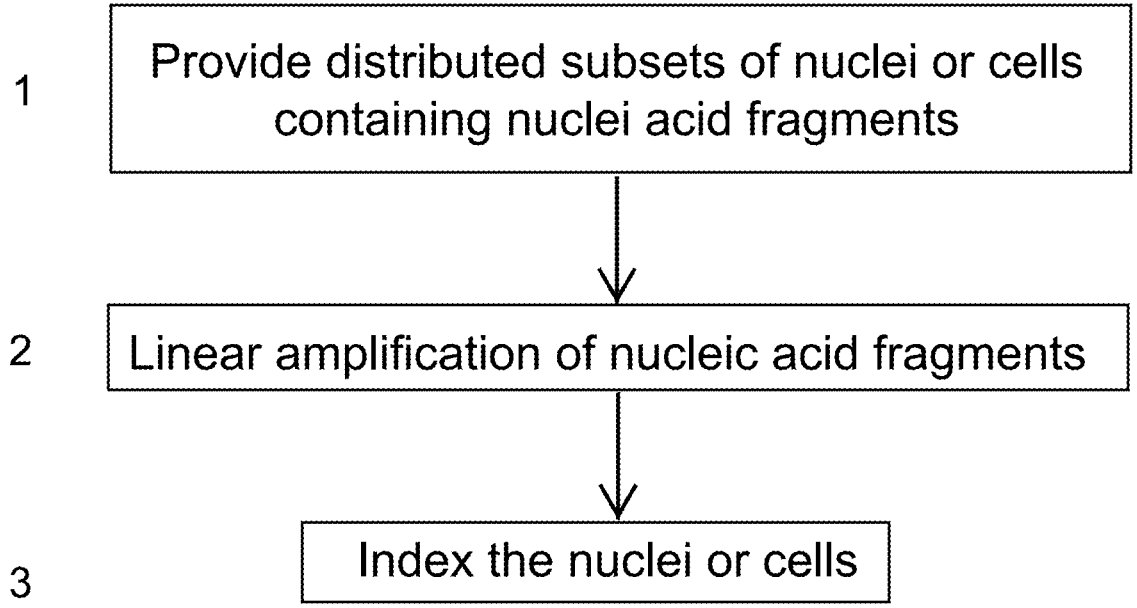
FIG. 1A-B shows general block diagrams of general illustrative methods for single-cell combinatorial indexing according to the present disclosure.

FIG. 10A-G shows meiotic crossover and uniparental chromosome distributions at the chromosome scale. (A) After normalizing for chromosome size, the number of haploid cells with at least one crossover on each chromosome negatively correlates with chromosome size (r=−0.87, p=2e-6). (B6×Spret) cross is shown. See FIG. 14C for (B6×Cast) cross. (B) Same as (A) for M2 cells (r=−0.91, p=8e-8). See FIG. 14D for (B6×Cast) cross. (C) Distribution of crossover (CO) counts per chromosome per haploid cell (mean=0.62 for (B6×Spret) and mean=0.58 for (B6×Cast)). (D) Same as (C) for M2 cells (mean=0.92 for (B6×Spret) and mean=1.03 for (B6×Cast)). (E) For chromosomes with at least two crossovers, crossover distance for all chromosomes. The distribution of expected numbers is generated by randomly placing 2 crossovers per chromosome. (B6×Spret) cross is shown. See FIG. 14E for (B6×Cast) cross. (F) Number (top) and chromosome distribution (bottom) of UPD and LOH events in Patski cells. (G) Mitochondrial copy number (normalized) broken down for M2 cells that segregated the majority of chromosomes reductionally vs. equationally. (B6×Spret) cross.

FIG. 11A-E shows sci-L3-WGS of the intraspecific hybrid mouse male germline also reveals numerous examples of non-independent equational segregation. (A-B) Number of reductionally (red) and equationally (blue) segregated chromosomes for artificial "2C" cells from barcode group 1, which derive from doublets of two random 1C cells. Each column represents one single 2C cell (19 chromosomes per cell, distributed as indicated by colors). (A) expected distribution of reductional vs. equational segregation based on the binomial distribution and assuming the probability of equational segregation p equals 0.5. (B) Observed data in 2C cells, which matches the expected distribution shown in (A). (C-E) Number of reductionally (red, pink, black) and equationally (blue, green) segregated chromosomes for non-1C cells from barcode group 2, which are a mixture of both artificial doublets of two random 1C nuclei and real 2C secondary spermatocytes. Each column represents one single non-1C cell (19 chromosomes per cell, distributed as indicated by colors). (C) All non-1C cells from barcode group 2. (D) Non-1C cells with biased chromosome segregation only, i.e., with at least 15 chromosomes segregated either equationally or reductionally. Black bar depicts Meiosis I nondisjunction (NDJ, 2 out of 2,185 chromosomes in total) where we observed 0 or 4 copies of the chromatids. (E) Same as (D) but further broken down by the number of chromosomes with or without crossovers (abbreviated as "CO"). Cells are sorted first by the number of equationally segregated chromosomes (light green and blue, in descending order) and then by the number of observed equationally segregated chromosomes without crossover (blue, in descending order).

FIG. 12A-C shows fitted finite mixture model with three binomial distributions (top) compared to observed data (bottom) from sci-L3-WGS of mouse male germline. See Example 2 for details of mixture modeling. (A) Mixture modeling of non-1C cells from barcode group 1 in (B6×Cast) hybrid. (B) Mixture modeling of non-1C cells from barcode group 2 in (B6×Cast) hybrid. (C) Mixture modeling of 2C cells from (B6×Spret) cross.

FIG. 13A-I shows meiotic crossover and uniparental chromosome distributions at the chromosome scale. (A) Number of crossovers normalized by chromosome size (cM/Mb) negatively correlates with chromosome size in haploid cells (r=−0.66, p=0.002). (B6×Spret) cross is shown. See FIG. 14A for (B6×Cast) cross. (B) Same as (A) for M2 cells (r=−0.83, p=1e-5). (B6×Spret) cross is shown. See FIG. 14B for (B6×Cast) cross. (C) Distribution of crossover (CO) frequency per chromosome per haploid cell. See FIG. 10C for distribution of counts. (D) Same as (C) for M2 cells. See FIG. 10D for distribution of counts. (E) For chromosomes with at least two crossovers, distance (Mb) between crossovers for chromosomes 1, 2, 12, and 13. See FIG. 10E for all chromosomes. (B6×Spret) cross is shown. See FIG. 14E for (B6×Cast) cross. The distribution of expected counts is generated by randomly placing 2 crossovers per chromosome. Box plot shows that the (B6×Cast) cross has stronger crossover interference than (B6×Spret) cross (p=5e-91). (F) Histograms of uniparental chromosome numbers per haploid (median=8, mean=8.1), M2 cell (median=1, mean=1.1), or other diploid/4C (median=0, mean=0.4) cell. (B6×Spret) cross is shown. See FIG. 14F for (B6×Cast) cross. (G) Uniparental chromosome distributions for haploid (r=−0.87, p=2e-6), M2 cell (r=−0.75, p=2e-4), and other diploid/4C (r=−0.68, p=0.001) cells. (B6×Spret) cross is shown. See FIG. 14G for (B6×Cast) cross. (H) Chromosome distribution of reverse segregation events in (B6×Spret) (left) and (B6×Cast) (right) crosses. (I) Number of mitochondrial reads per cell, normalized by read depth, for haploid, M2 cell, and other diploid/4C diploid cells. (B6×Spret) cross.

FIG. 14A-G shows chromosome distributions for meiotic crossover and UPD, (B6×Cast). (A) Number of crossovers normalized by chromosome size (cM/Mb) negatively correlates with chromosome size in haploid cells (r=−0.65, p=0.003). (B6×Cast) cross. (B) Same as (A) in M2 cells (r=−0.9, p=2e-7). (B6×Cast) cross. (C) After normalizing for chromosome size, the number of haploid cells with at least one crossover on each chromosome negatively correlates with chromosome size (r=−0.85, p=5e-6). (B6×Cast) cross. (D) Same as (C) for M2 cells (r=−0.94, p=3e-9). (B6×Cast) cross. (E) For chromosomes with at least two crossovers, crossover distance for all chromosomes. The distribution of expected numbers is generated by randomly placing 2 crossovers per chromosome. (B6×Cast) cross. (F) Uniparental chromosome numbers per haploid (median=8, mean=8.9) and M2 cell (median=0, mean=0.54) cells. (B6×Cast) cross. (G) Uniparental chromosome distribution (correlation with chromosome size shown in parentheses), haploid (r=−0.8, p=4e-5) and M2 cell (r=−0.45, p=0.05). (B6× Cast) cross.

Figure 15:
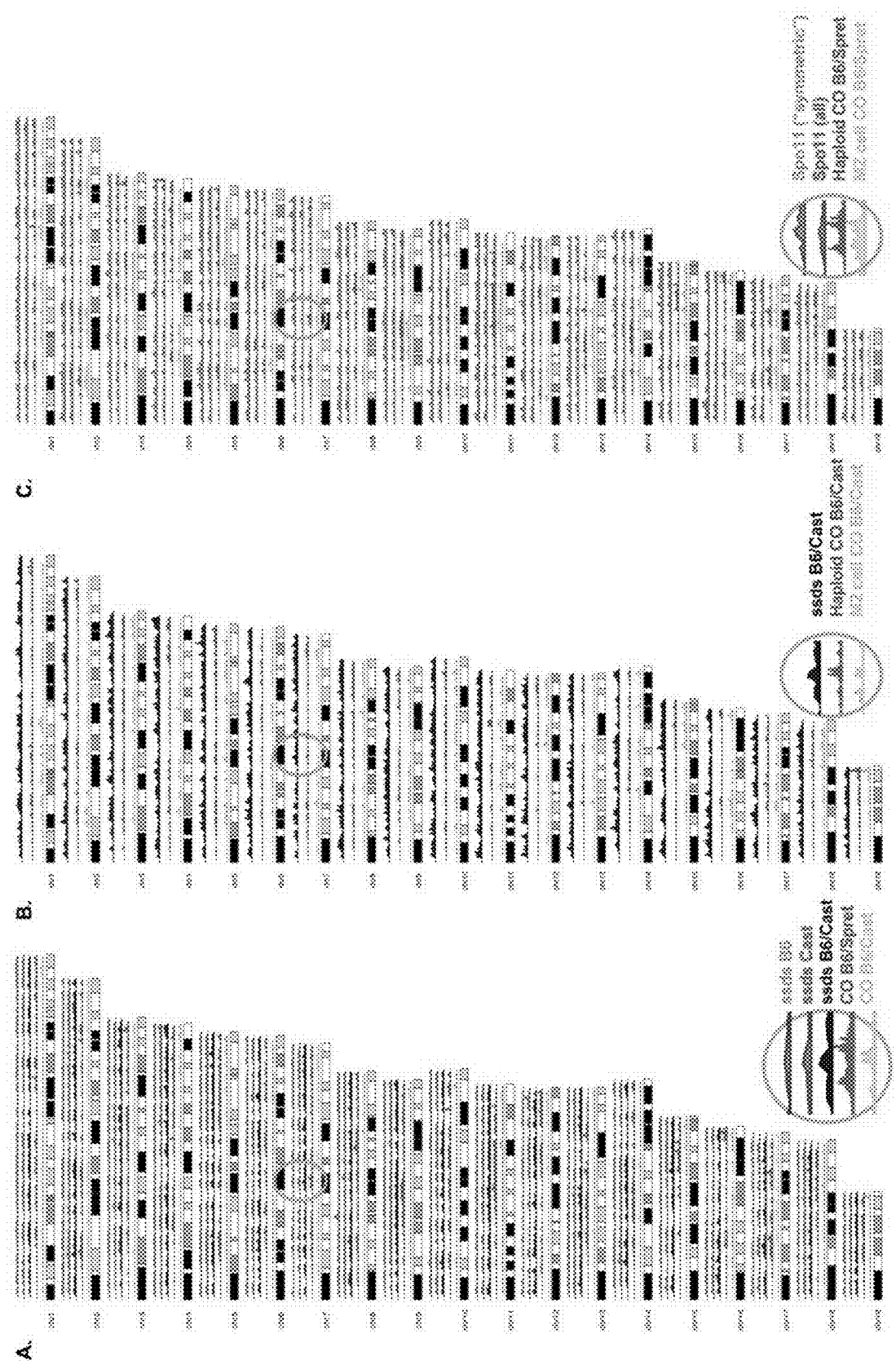

FIG. 15A-C shows crossover break point pileup profile. (A) Top to bottom: meiotic DSB hotspot by SSDS map for B6, Cast and (B6×Cast) F1 hybrid, crossover map in (B6× Spret) and (B6×Cast) generated in this study). See (B) and (C) for breakdown of haploid vs. M2 cell as well as Spo11-oligo map. (B) Top to bottom: 1) meiotic DSB hotspot map by SSDS for (B6×Cast) F1 hybrid, 2) haploid crossover map in (B6×Cast), and 3) M2 cell crossover map in (B6× Cast). (C) Top to bottom: 1) meiotic DSB hotspot by Spo11-oligo map with "symmetric" hotspots, 2) meiotic DSB hotspot by Spo11-oligo map with all hotspots: PRDM9 motifs are not considered. 3) haploid crossover map in (B6×Spret), and 4) M2 cell crossover map in (B6×Spret).

FIG. 16A-F shows meiotic crossover hotness and explanatory genomic features. (A) Marginal inclusion probability for features associated with crossover hotness by BMA. The x-axis ranks models by posterior probability, where grey boxes depict features not included in each model (vertical line, 20 top models are shown) and orange color scale depicts posterior probability of the models. The combined dataset from both the (B6×Spret) and (B6×Cast) crosses is shown here. See FIG. 15 for the two crosses analyzed separately. (B) Distribution of sizes for breakpoint resolution (log normal distribution). Left: (B6×Spret), median of 150 kb. Right: (B6×Cast), median of 250 kb. (C-D) Positions of the rightmost crossover of each chromosome. Length of the chromosome is indicated by the rightmost SNP (black bar) rather than the extent of the red line. (C) M2 cell. Crossovers in the (B6×Cast) (left) cross prefer the centromere-distal end of the chromosome, while crossovers in the (B6×Spret) cross (right) prefer the middle region of each chromosome arm. After accounting for inter-chromosome variability, we estimate that crossovers in the (B6×Spret) cross are on average 5.5 Mb more centromere-proximal. See FIG. 20A which is similar but for 1C cells. (D) Comparing 1C and M2 cells, (B6×Spret) cross. After accounting for inter-chromosome variability, we estimate that crossovers in M2 cells (right) are on average 9.4 Mb more centromere-proximal than in 1Cs (left) in the (B6× Spret) cross. The same trend is observed to a lesser extent in the (B6×Cast) cross (see FIG. 20B). (E) AUC of 0.73 quantifies expected accuracy in predicting if a region drawn from the mouse genome comes from B6×Spret crossover tracts or an equal number of randomly sampled tracts. Left: all 76 features. Right: a subset of 25 features from BMA with MIP>0.5. (F) AUC of 0.85 quantifies expected accuracy in predicting if a region drawn from the mouse genome comes from B6×Cast crossover tracts or an equal numbers of randomly sampled tracts. Left: all 69 features. Right: a subset of 25 features from BMA with MIP>0.5.

Figure 17:
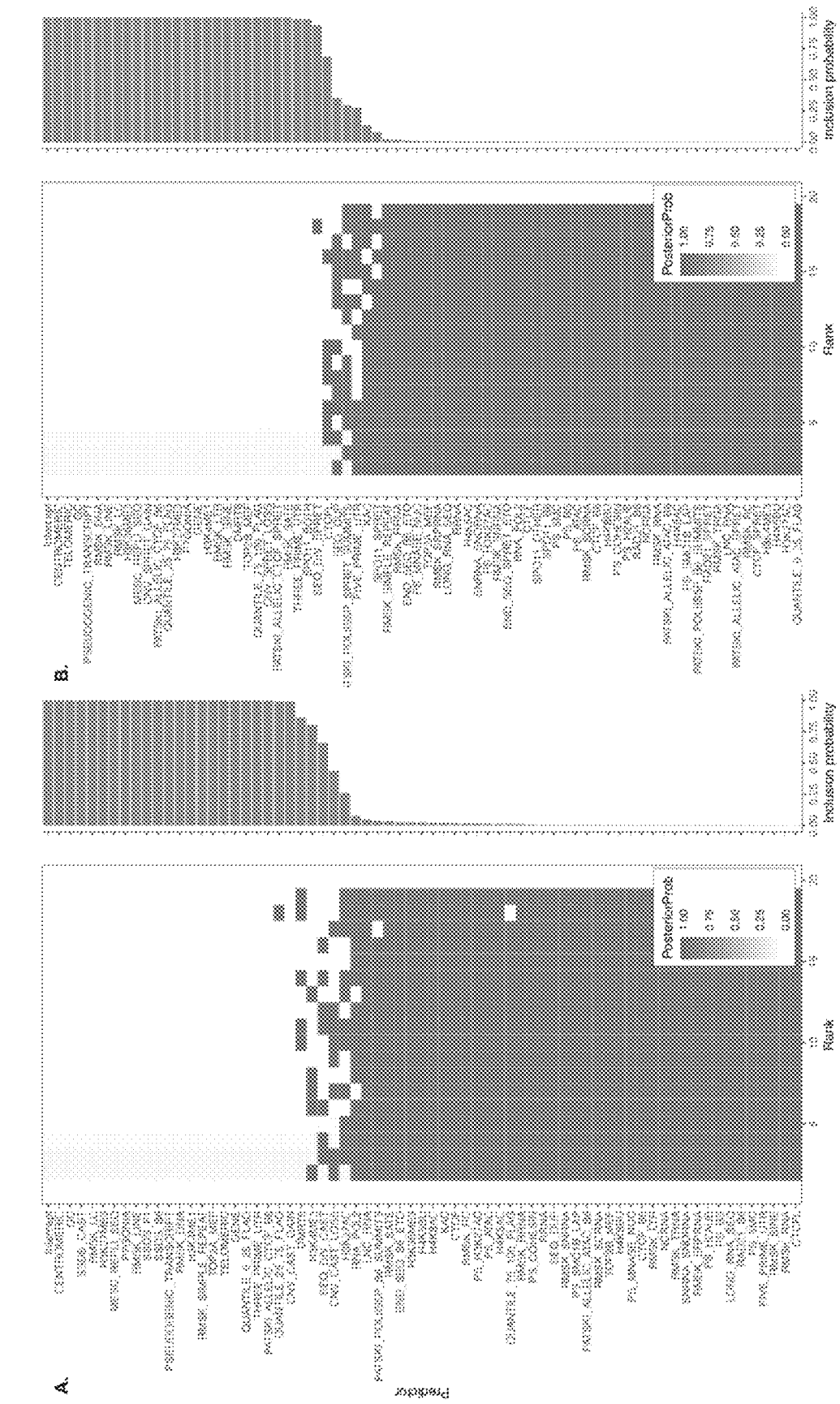

FIG. 17A-B shows marginal inclusion probability for features associated with crossover hotness by BMA. The x-axis ranks models by posterior probability. (A) (B6×Cast) cross. (B) (B6×Spret) cross.

Figure 18:
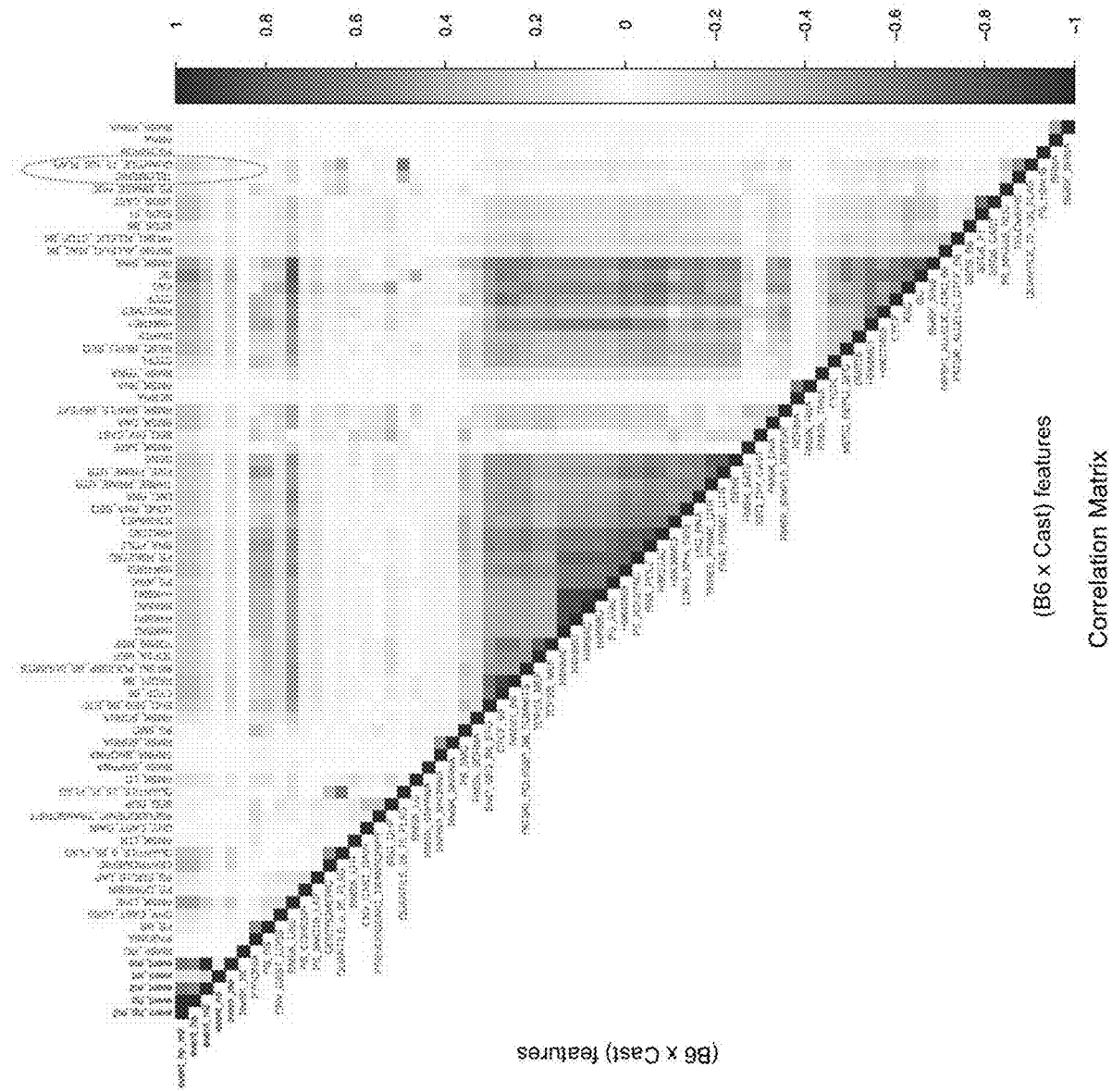

FIG. 18 shows correlation matrix for both crossover events and genomic features in the (B6×Cast) cross. Here we show all possible pairwise correlations between various crossover pileup tracks and genomic features, calculated on 100 kb windows. The crossover pileup tracks are the first five columns or rows ("event" prefix; red text labels), while the remainder are the same genomic features used in modeling (blue text labels). The crossover pileup tracks suffixed by "hp_m2", "hp", "m2", "mt" and "me" are from haploids and M2 cells, haploids, M2 cells, M2 cells that have biased equational segregation and M2 cells that have biased reductional segregation, respectively. Blue squares depict positive correlation and red squares depict negative correlation. Features are ordered by hierarchical clustering. The open ovals highlight the features "telomeric" and "quantile_75_100", which show different trends in the two crosses as described in the text.

Figure 19:
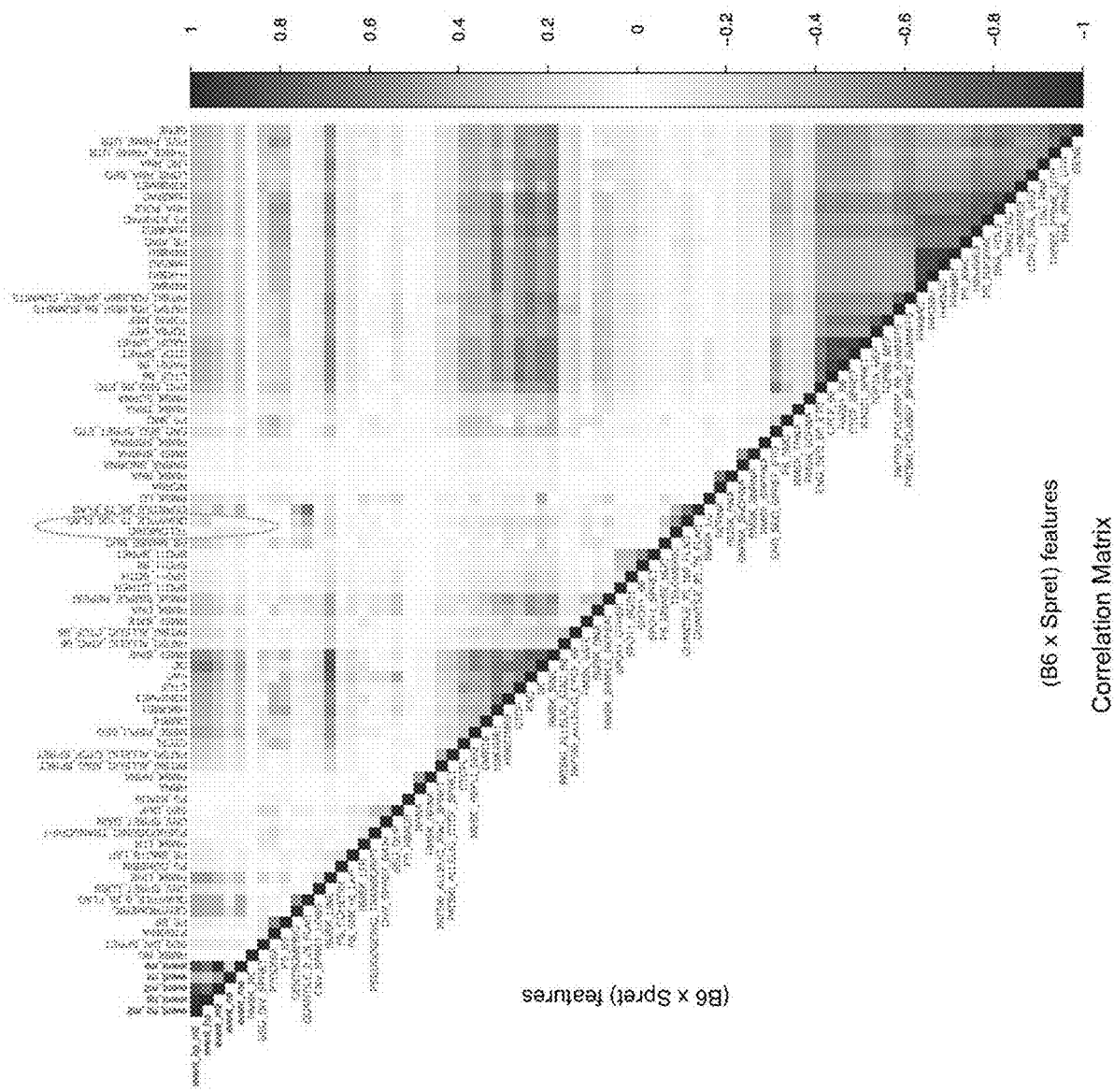

FIG. 19 shows correlation matrix for both crossover events and genomic features in the (B6×Spret) cross. Same format as described in FIG. 18 legend.

FIG. 20A-E shows positions of the rightmost crossover on each chromosome. (A) Haploid cells. In both crosses, crossovers prefer the centromere-distal end of the chromosome. (B) Comparing haploid and M2 cells (B6×Cast cross). After accounting for inter-chromosome variability, we estimate that crossovers in M2 cells are on average 5.2 Mb more centromere-proximal than in haploids in the (B6×Cast) cross. (C) Comparing M2 cells with biased chromosome segregations. After accounting for inter-chromosome variability, we estimate that crossovers in M2 cells with biased equational segregation are on average 13.7 Mb more centromere-distal than those in M2 cells with biased reductional segregation in the (B6×Cast) cross. (D) Same as in (C) in the (B6×Spret) cross. Crossovers are on average 8.7 Mb more centromere-distal. (E) A model for effects of positions of crossover on proper chromosome segregation. Crossovers closer to the centromere (in the middle two quartiles rather than in the last quartile) may facilitate reductional segregation by having stronger arm cohesion; however, crossovers near the end of the chromosome arm may facilitate MII segregation by having stronger CEN cohesion.

Figure 21:
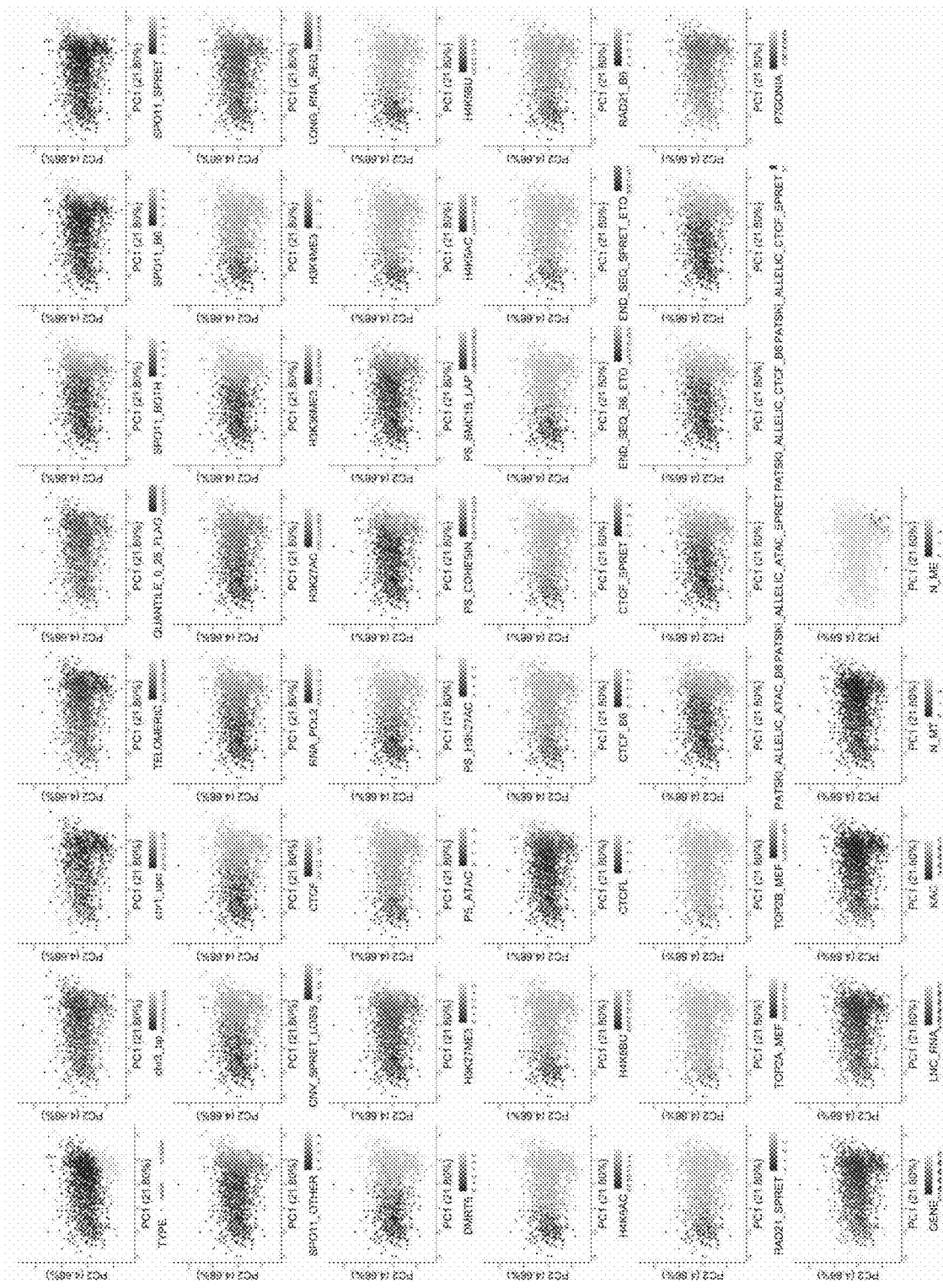

FIG. 21 shows principal components analysis of features distinguishing crossover hotspots in the B6×Spret cross. Note that "chr3_bp (breakpoints)" and "chr1_upc (uniparental chromosomes)" are representative of features that were included for all chromosomes. We show 44 out of 115 total features. Other than the 36 other chromosome breakpoints and UPC features omitted, 35 other features are not shown due to the lack of an obvious trend.

Figure 22:
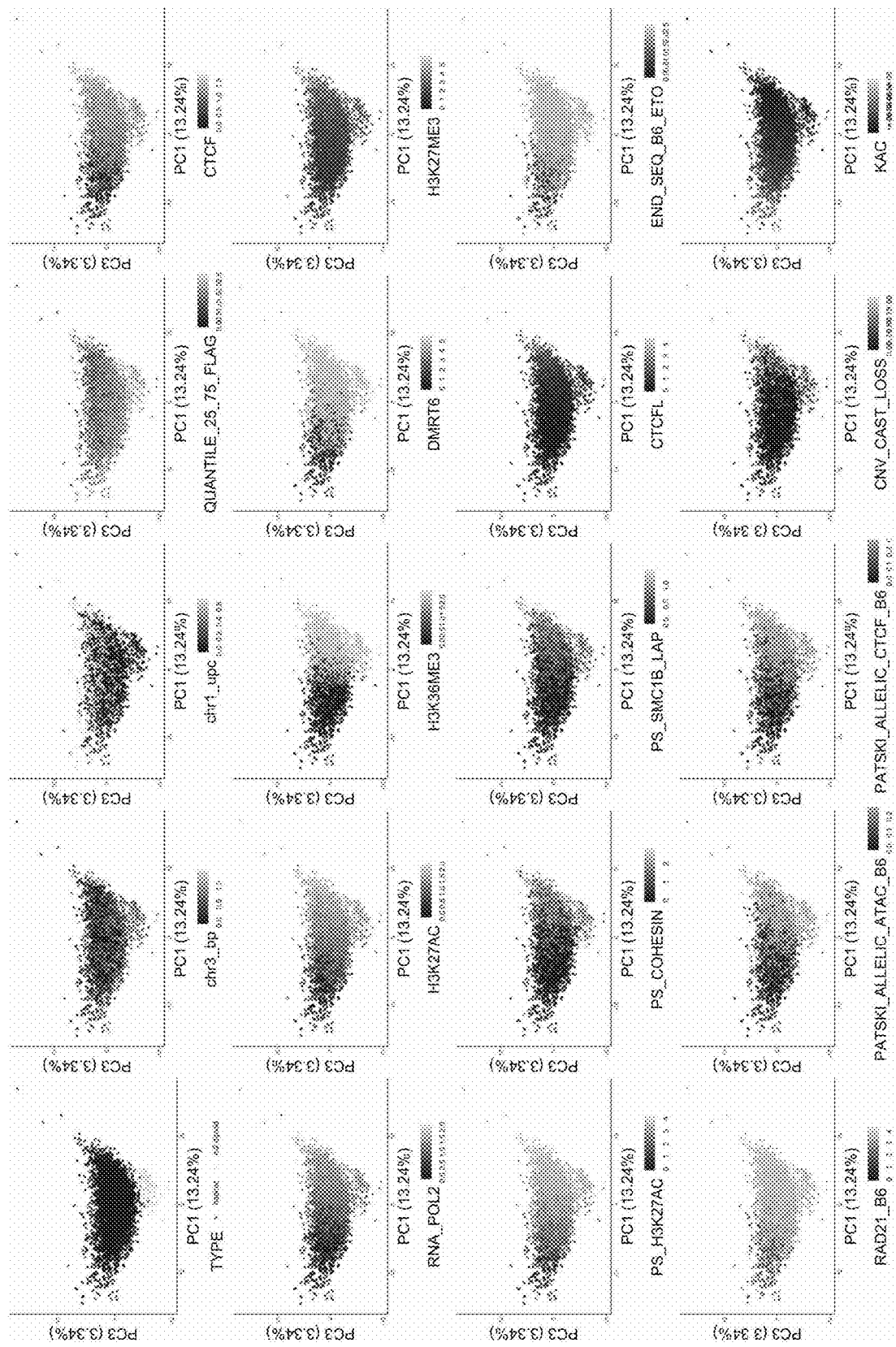

FIG. 22 shows principal components analysis of features distinguishing crossover hotspots for the B6×Cast cross. Note that "chr3 by (break points)" and "chr1_upc (uniparental chromosomes)" are representative of features that were included for all chromosomes. We show 19 out of 108 total features. Other than the 36 other chromosome breakpoints and UPC features omitted, 53 other features are not shown due to the lack of an obvious trend.

Figure 23:
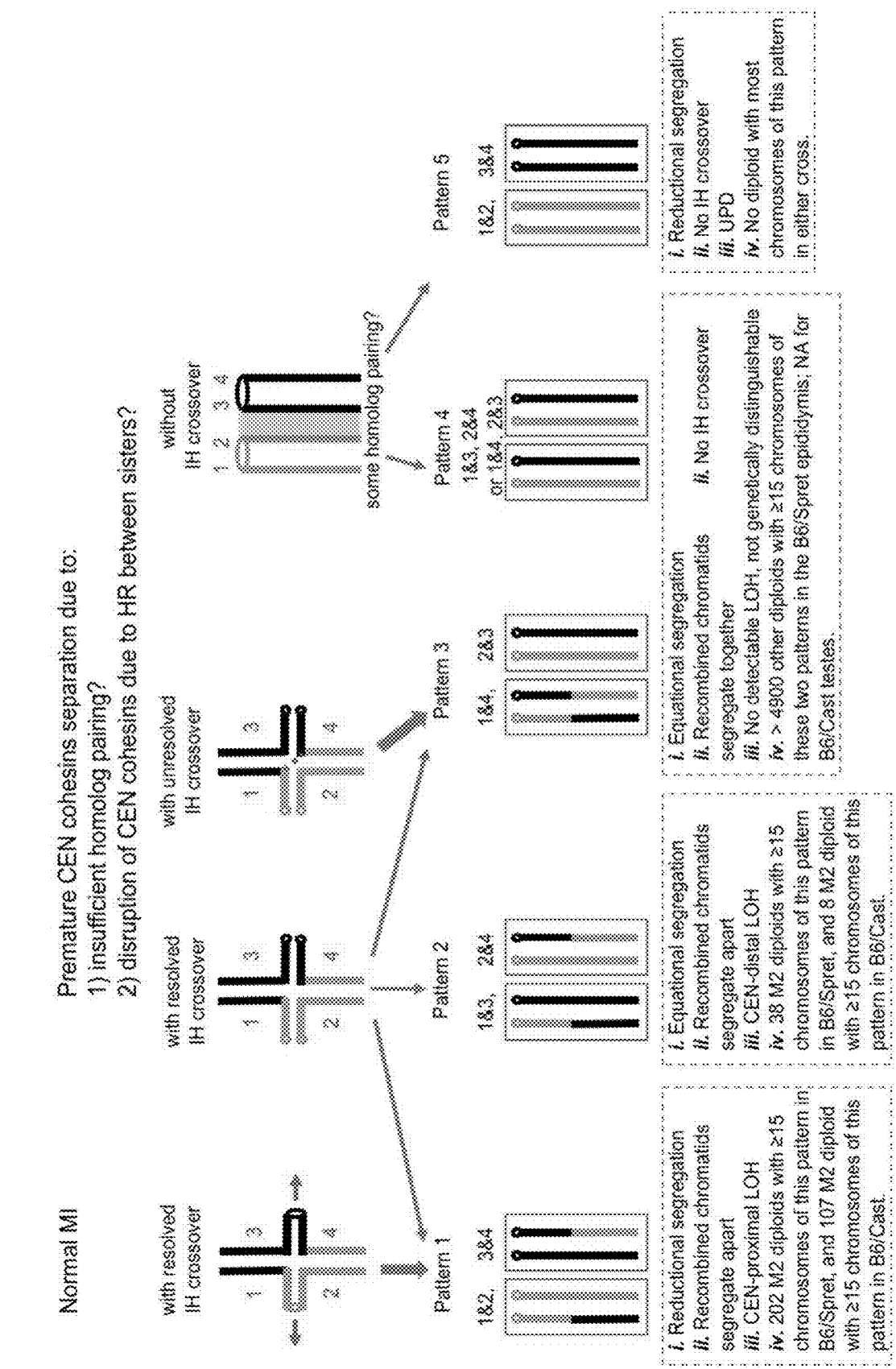

FIG. 23 shows a model for relationship between meiotic crossover and chromosome mis-segregation. "MI": meiosis I, "CEN": centromere (oval or round circles), "IH": interhomolog. The following detailed description of illustrative embodiments of the present disclosure may be best understood when read in conjunction with the following drawings.

Schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

The method provided herein can be used to produce single cell combinatorial indexing (sci) sequencing libraries of a plurality of single cells or nuclei, including, for instance, whole genomes (sci-WGS), transcriptomes (sci-RNA), co-assay of genome and transcriptome (sci-DNA/RNA) and/or methylomes (sci-MET). In one embodiment, the method can be used for targeted sequencing of a specific region or regions of interest. For instance, a primer that hybridizes to a specific region (e.g., coding region, non-coding region, etc.), a guide RNA, or a nucleotide sequence inserted by a guide RNA can be used to selectively enrich for a targeted sequence. In one embodiment, information for individual gene edits, DNA, edit, or marker for the edit, gene signature, perturbation, and/or functional read (RNA, DNA, protein or combination) from cells or nuclei can be collected and analyzed (Perturb-seq). In other embodiments, the method can be used for evaluating chromatin accessibility (sci-ATAC), chromatin conformation (Hi-C), and other single cell combinatorial indexing methods.

Figure 1B:
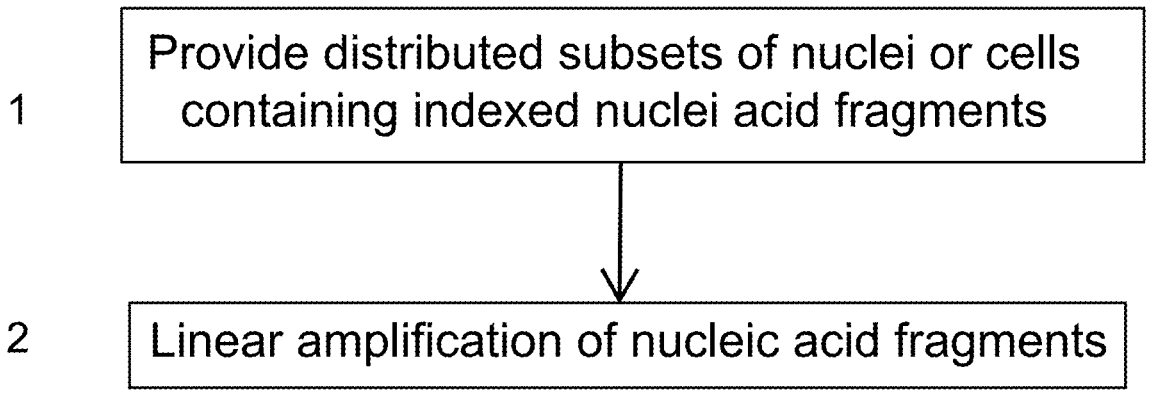

The method includes providing isolated nuclei or cells, distributing subsets of the nuclei or cells into compartments, processing the nuclei or cells so they include nucleic acid fragments, adding a compartment specific index to the nucleic acid fragments, and amplifying the nucleic acid fragments by linear amplification. These steps can occur in different orders and can be combined in different ways. Three embodiments are shown in FIGS. 1A and 1B. In one embodiment, the method includes providing distributed subsets of isolated nuclei or cells that contain nucleic acid fragments (FIG. 1A, block 1, and FIG. 1B, block 1). As shown in FIG. 1AB, amplifying the nucleic acid fragments by linear amplification (FIG. 1A, block 2) is followed by adding an index to the amplified nucleic acid fragments (FIG. 1A, block 3). As shown in FIG. 1B, the nucleic acid fragments in the distributed nuclei or cells include an index, and the nucleic acid fragments are amplified by linear amplification (FIG. 1B, block 2). The steps of providing isolated nuclei or cells, distributing subsets of the isolated nuclei or cells, processing the isolated nuclei or cells to include nucleic acid fragments, adding a compartment specific index, and amplifying the nucleic acid fragments by linear amplification are described herein.

Providing Isolated Nuclei or Cells

The method provided herein includes providing cells or isolated nuclei from a plurality of cells. The cells and nuclei can be from any sample, e.g., any organism(s), and from any cell type or any tissue of the organism(s). In one embodiment, the cells can be germ cells, e.g., sperm cells or egg cells. In one embodiment, tissue may be reproductive tissue, e.g., epididymis. In one embodiment, the cells or nuclei can be from cancer or a diseased tissue. The method can further include dissociating cells, and/or isolating the nuclei. Methods for isolating nuclei from cells are known to the person skilled in the art and are routine. The number of nuclei or cells can be at least two. The upper limit is dependent on the practical limitations of equipment (e.g., multi-well plates) used in other steps of the method as described herein. The number of nuclei or cells that can be used is not intended to be limiting, and can number in the billions. For instance, in one embodiment the number of nuclei or cells can be no greater than 100,000,000, no greater than 10,000,000, no greater than 1,000,000,000, no greater than 100,000,000, no greater than 10,000,000, no greater than 1,000,000, no greater than 100,000, no greater than 10,000, no greater than 1,000, no greater than 500, or no greater than 50. One or more samples can be provided. For instance, a sample can be one cell type or tissue from one organism. Using the indexing methods described herein, multiple samples, e.g., different cell types from one organism, one cell type or tissue from two or more organisms, or different cell type or tissue from two or more organisms, can be separately indexed with a first index to identify the sample and then combined. The skilled person will recognize that in some embodiments the nucleic acid molecules in each nucleus represent the entire genetic complement of an organism (also referred to as the whole genome of an organism) and are genomic DNA molecules which include both intron and exon sequences, as well as non-coding regulatory sequences such as promoter and enhancer sequences.

Nuclei isolation can be accomplished by incubating the cells in cell lysis buffer for at least 1 to 20 minutes, such as 5, 10, or 15 minutes. Optionally, the cells can be exposed to an external force to aid in lysis, such as movement through a pipette. An example of a cell lysis buffer includes 10 mM Tris-HCl, pH 7.4, 10 mM NaCl, 3 mM MgCl2, 0.1% IGEPAL CA-630, and 1% SUPERase In RNase Inhibitor. The skilled person will recognize these levels of the components can be altered somewhat without reducing the usefulness of the cell lysis buffer for isolating nuclei. The skilled person will recognize that RNAse inhibitors, BSA, and/or surfactants can be useful in buffers used for the isolation of nuclei, and that other additives can be added to the buffer for other downstream single-cell combinatorial indexing applications.

In one embodiment, nuclei are isolated from individual cells that are adherent or in suspension. Methods for isolating nuclei from individual cells are known to the person of ordinary skill in the art. In one embodiment, nuclei are isolated from cells present in a tissue. The method for obtaining isolated nuclei typically includes preparing the tissue and isolating the nuclei from the prepared tissue. In one embodiment all steps are done on ice.

Tissue preparation can include snap freezing the tissue in liquid nitrogen, and then subjecting the tissue to either mincing or a blunt force to reduce the size of the tissue to pieces of 1 mm or less in diameter. Optionally, cold proteases and/or other enzymes for breaking down cell-cell connections can be used. Mincing can be accomplished with a blade to cut the tissue to small pieces. Applying a blunt force can be accomplished by smashing the tissue with a hammer or similar object, and the resulting composition of smashed tissue is referred to as a powder.

Conventional tissue nuclei extraction techniques normally incubate tissues with tissue specific enzyme (e.g., trypsin) at high temperature (e.g., 37° C.) for 30 minutes to several hours, and then lyse the cells with cell lysis buffer for nuclei extraction. The nuclei isolation method described herein and in U.S. Prov. Pat. App. No. 62/680,259 has several advantages: (1) No artificial enzymes are introduced, and all steps are done on ice. This reduces potential perturbation to cell states (e.g., transcriptome state, chromatin state, or methylation state). (2) This has been validated across most tissue types including brain, lung, kidney, spleen, heart, cerebellum, and disease samples such as tumor tissues. Compared with conventional tissue nuclei extraction techniques that use different enzymes for different tissue types, the new technique can potentially reduce bias when comparing cell states from different tissues. (3) The method also reduces cost and increases efficiency by removing the enzyme treatment step. (4) Compared with other nuclei extraction techniques (e.g., Dounce tissue grinder), the technique is more robust for different tissue types (e.g., the Dounce method needs optimizing Dounce cycles for different tissues) and enables processing large pieces of samples in high throughput (e.g., the Dounce method is limited to the size of the grinder).

The isolated nuclei or cells can include nucleosomes, can be nucleosome-free, or can be subjected to conditions that deplete the nuclei of nucleosomes, generating nucleosome-depleted nuclei. Nucleosome-depleted nuclei are useful in methods for determining the DNA sequence of the whole genome of a cell, or a fraction thereof.

In one embodiment, the conditions used for nucleosome-depletion maintain the integrity of the isolated nuclei. Typically, nucleosome-depletion methods are used on a pellet or suspension of single cells, thus in those embodiments where an adherent cell culture or tissue is used as a source of the cells, the source is treated to obtain a pellet or suspension of single cells.

Methods for nucleosome-depletion are known and routine and include, but are not limited to, enzymatic treatment and chemical treatment. In one embodiment, the conditions for nucleosome-depletion include a chemical treatment with a chaotropic agent capable of disrupting nucleic acid-protein interactions. An example of a useful chaotropic agent includes, but is not limited to, 3,5-lithium diiodosalicylic acid. Conditions for using 3,5-lithium diiodosalicylic acid include adding it to a pellet of cells and incubating on ice.

In a preferred embodiment, the conditions include a chemical treatment with a detergent capable of disrupting nucleic acid-protein interactions. An example of a useful detergent includes, but is not limited to, sodium dodecyl sulfate (SDS). Conditions for using SDS include adding it to a pellet of cells and incubating at an elevated temperature such as 42° C., and then adding a nonionic detergent such as Triton™ X-100 and incubating at an elevated temperature such as 42° C.

In some embodiments, when a detergent such as SDS is used, the nuclei are exposed to a cross-linking agent prior to the depletion of nucleosomes (WO 2018/018008). In one embodiment, the nuclei are exposed to the cross-linking agent while inside cells, and in another embodiment, isolated nuclei are exposed to the cross-linking agent. A useful example of a cross-linking agent includes, but is not limited to, formaldehyde (Hoffman et al., 2015, J. Biol. Chem., 290:26404-26411). Treatment of cells with formaldehyde can include adding formaldehyde to a suspension of cells and incubating at room temperature. In one embodiment, after the formaldehyde treatment, the nuclei can be exposed to glycine and a nonionic, non-denaturing detergent non-ionic, non-denaturing detergent such as Igepal®.

During the process of depleting nucleosomes in the isolated nuclei, the integrity of the isolated nuclei is maintained. Whether nuclei remain intact after exposure to conditions for depleting nucleosomes can be determined by visualizing the status of the nuclei by routine methods such as phase-contrast imaging. In one embodiment, the number of nuclei intact after nucleosome-depletion can be 1 to 1,000, 1,000 to 10,000, 10,000 to 100,000, 100,000 to 1,000,000, 1,000,000 to 10,000,000, or 10,000,000 to 100,000,000.

Manipulation of the nuclei or cells, including providing, pooling, and distributing steps described herein, can include the use of a nuclei buffer. An example of a nuclei buffer includes 10 mM Tris-HCl, pH 7.4, 10 mM NaCl, 3 mM MgCl2, 1% SUPERase In RNase Inhibitor (20 U/µt, Ambion) and 1% BSA (20 mg/ml, NEB). The skilled person will recognize these levels of the components can be altered somewhat without reducing the usefulness of the nuclei buffer in which to suspend nuclei. The skilled person will also recognize various components can be substituted without reducing the usefulness of the nuclei buffer in which to suspend nuclei.

In one embodiment, the cells (including the cells from which nuclei are isolated) have been exposed to different predetermined conditions. For instance, subsets of cells to can be exposed to different predetermined conditions. Different conditions can include, for instance, different culture conditions (e.g., different media, different environmental conditions), different doses of an agent, different agents, or combinations of agents. Agents are described herein. The nuclei or cells of each subset of cells and/or sample or samples are indexed with one or more index sequences, pooled, and analyzed by massively multiplex single-nuclei or single-cell sequencing methods. Essentially any single-nuclei or single-cell sequencing method can be used including, but not limited to, single-nuclei transcriptome sequencing (U.S. Prov. Pat. App. No. 62/680,259 and Gunderson et al. (WO2016/130704)), whole genome sequencing of single-nuclei (U.S. Pat. Appl. Pub. No. US 2018/0023119), or single-nuclei sequencing of transposon accessible chromatin (U.S. Pat. No. 10,059,989), sci-HiC (Raman et al., Nature Methods, 2017, 14:263-266), DRUG-seq (Ye et al., Nature Commun., 9, article number 4307), Perturb-seq (Dixit et al., Cell, 2016, 167(7):1853-1866.e17), or any combination of analytes from DNA, RNA and proteins, for example sci-CAR (Cao et al., Science, 2018, 361(6409): 1380-1385). Droplet-based single cell analysis can also be applied after initial split-and-pool indexing (examples include 10× genomics Chromium™ system or Biorad ddseq system), including the use of an index as a sample index. The nuclear hashing is used to demultiplex and identify individual cells or nuclei from different conditions.

In one embodiment, each subset of cells is exposed to an agent or pertubation. An agent can be essentially anything that causes a change to a cell. For example, an agent can alter the transcriptome of a cell, alter the chromatin structure of a cell, alter the activity of a protein in the cell, alter the DNA of a cell, alter the DNA editing of a cell, or cause other changes. Examples of agents include, but are not limited to, a compound such as a protein (including an antibody), a non-ribosomal protein, a polyketide, an organic molecule (including an organic molecule of 900 Daltons or less), an inorganic molecule, an RNA or RNAi molecule, a carbohydrate, a glycoprotein, a nucleic acid, or a combination thereof. In one embodiment, an agent causes a genetic perturbation, for instance a DNA editing protein and/or guide RNA such as CRISPR or Talen. In one embodiment, an agent is a therapeutic drug. In one embodiment, the cell can be a wild-type cell, and in another embodiment, the cell can be genetically modified to include a genetic perturbation, for instance, gene knock-in or gene knock-out (Szlachta et al., Nat Commun., 2018, 9:4275). Subsets of cells can be exposed to the same agent, but different variables can be altered across the compartments of a multi-well device, permitting multiple variables to be tested in a single experiment. For instance, different dosages, different duration of exposure, and different cell types can be tested in a single plate. In one embodiment, the cells can express a protein having a known activity, and the effect of an agent on the activity evaluated under different conditions. The use of index sequences to label nuclei acid fragments permits later identification of the nucleic acids originating from a specific subset of nuclei or cells, e.g., from one well of a multi-well plate.

Distributing Subsets

The method provided herein includes distributing subsets of the nuclei, e.g., nucleosome-depleted nuclei, or cells into a plurality of compartments. The method can include multiple distribution steps, where a population of isolated nuclei or cells (also referred to herein as a pool) is split into subsets. Typically, a distribution of subsets of isolated nuclei or cells from a pool to a plurality of compartments occurs before the addition of an index to the nucleic acid fragments present in the subsets of isolated nuclei or cells. Accordingly, the method includes at least one "split and pool" step of taking pooled isolated nuclei or cells and distributing them, where the number of "split and pool" steps can depend on the number of different indexes that are added to the nucleic acid fragments. After indexing the subsets can be pooled, split into subsets, indexed, and pooled again as needed until a sufficient number of indexes are added to the nucleic acid fragments.

The number of nuclei or cells present in a subset, and therefore in each compartment, can be at least 1. In one embodiment, the number of nuclei or cells present in a subset is no greater than 100,000,000, no greater than 10,000,000, no greater than 1,000,000, no greater than 100,000, no greater than 10,000, no greater than 4,000, no greater than 3,000, no greater than 2,000, or no greater than 1,000, no greater than 500, or no greater than 50. In one embodiment, the number of nuclei or cells present in a subset can be 1 to 1,000, 1,000 to 10,000, 10,000 to 100,000, 100,000 to 1,000,000, 1,000,000 to 10,000,000, or 10,000,000 to 100,000,000. In one embodiment, the number of nuclei or cells present in each subset is approximately equal. The number of nuclei present in a subset, and therefore in each compartment, is based in part on the desire to reduce index collisions, which is the presence of two nuclei having the same transposase index ending up in the same compartment in this step of the method. Methods for distributing nuclei or cells into subsets are known to the person skilled in the art and are routine. Examples include, but are not limited to, fluorescence-activated cell sorting (FACS) cytometry and simple dilution. Optionally, nuclei of different ploidies can be gated and enriched by staining, e.g., DAPI (4',6-diamidino-2-phenylindole) staining.

The number of compartments in the distribution steps (and subsequent addition of an index) can depend on the format used. For instance, the number of compartments can be from 2 to 96 compartments (when a 96-well plate is used), from 2 to 384 compartments (when a 384-well plate is used), or from 2 to 1536 compartments (when a 1536-well plate is used). In one embodiment, each compartment can be a droplet. When the type of compartment used is a droplet that contains two or more nuclei or cells, any number of droplets can be used, such as at least 10,000, at least 100,000, at least 1,000,000, or at least 10,000,000 droplets. In one embodiment, the number of compartments is 24.

Processing to Yield Nucleic Acid Fragments

In one embodiment, processing isolated nuclei or cells can be used to fragment DNA nucleic acids, e.g., chromosomes and/or plasmids, in isolated nuclei or cells into nucleic acid fragments. Processing is typically necessary when the target nucleic acids to be sequenced are derived from DNA present in the nuclei or cells; however, in some embodiments processing is optional when the target nucleic acids to be sequenced are derived from RNA (e.g., mRNA and/or non-coding RNA) present in the nuclei or cells, as RNA molecules often do not need to be fragmented. Processing nucleic acids in nuclei or cells typically adds a nucleotide sequence to one or both ends of the nucleic acid fragments generated by the processing, and the nucleotide sequence can, and typically does, include one or more universal sequences. A universal sequence can be used as, for instance, a "landing pad" in a subsequent step to anneal a nucleotide sequence that can be used as a primer for addition of another nucleotide sequence, such as an index, to a nucleic acid fragment by a subsequent step of ligation, primer extension, or amplification. The nucleotide sequence of such a primer can optionally include an index sequence. Processing nucleic acids in nuclei or cells can add one or more unique molecular identifiers to one or both ends of the nuclei acid fragments generated by the processing.

There are several points in the method at which the processing of nucleic acids into nucleic acid fragments can occur. For instance, in one embodiment isolated nuclei or cells can be processed before distributing subsets of isolated nuclei or cells. In embodiments such as this the processing typically includes addition of a universal sequence and/or universal molecular identifier to the nucleic acid fragments, but not a compartment specific index, as adding a compartment specific index when all isolated nuclei or cells are combined would typically serve no purpose. In another embodiment, the isolated nuclei or cells can be processed after distribution of subsets into different compartments (e.g., FIG. 1A and FIG. 1B). In one aspect of this embodiment, the processing does not add an index, (FIG. 1A, block 1), and in another aspect of this embodiment, the processing can include addition of a compartment specific index (FIG. 1B, block 1). The processing at any point in the method can include addition of a universal sequence and/or universal molecular identifier to one or both ends of the nucleic acid fragments.

Various methods for processing nucleic acids in nuclei or cells into nucleic acid fragments are known. Examples include CRISPR and Talen like enzymes, and enzymes that unwind DNA (e.g. Helicases) that can make single stranded regions to which DNA fragments can hybridize and initiate extension or amplification. For example, helicase-based amplification can be used (Vincent et al., 2004, EMBO Rep., 5(8):795-800). In one embodiment, the extension or amplification is initiated with a random primer. In one embodiment, a transposome complex is used. The transposome complex is a transposase bound to a transposase recognition site and can insert the transposase recognition site into a target nucleic acid within a nucleus in a process sometimes termed "tagmentation." In some such insertion events, one strand of the transposase recognition site may be transferred into the target nucleic acid. Such a strand is referred to as a "transferred strand." In one embodiment, a transposome complex includes a dimeric transposase having two subunits, and two non-contiguous transposon sequences. In another embodiment, a transposase includes a dimeric transposase having two subunits, and a contiguous transposon sequence. In one embodiment, the 5' end of one or both strands of the transposase recognition site may be phosphorylated.

Some embodiments can include the use of a hyperactive Tn5 transposase and a Tn5-type transposase recognition site (Goryshin and Reznikoff, *J. Biol. Chem.*, 273:7367 (1998)), or MuA transposase and a Mu transposase recognition site comprising R1 and R2 end sequences (Mizuuchi, K., *Cell*, 35: 785, 1983; Savilahti, H, et al., *EMBO J.*, 14: 4893, 1995). Tn5 Mosaic End (ME) sequences can also be used as optimized by a skilled artisan.

More examples of transposition systems that can be used with certain embodiments of the compositions and methods provided herein include *Staphylococcus aureus* Tn552 (Colegio et al., *J. Bacteriol.*, 183: 2384-8, 2001; Kirby C et al., *Mol. Microbiol.*, 43: 173-86, 2002), Ty1 (Devine & Boeke, *Nucleic Acids Res.*, 22: 3765-72, 1994 and International Publication WO 95/23875), Transposon Tn7 (Craig, N L, *Science*. 271: 1512, 1996; Craig, N L, Review in: *Curr*

Top Microbiol Immunol., 204:27-48, 1996), Tn/O and IS10 (Kleckner N, et al., *Curr Top Microbiol Immunol.*, 204:49-82, 1996), Mariner transposase (Lampe D J, et al., *EMBO J.*, 15: 5470-9, 1996), Tc1 (Plasterk R H, *Curr. Topics Microbiol. Immunol.*, 204: 125-43, 1996), P Element (Gloor, G B, *Methods Mol. Biol.*, 260: 97-114, 2004), Tn3 (Ichikawa & Ohtsubo, *J Biol. Chem.* 265:18829-32, 1990), bacterial insertion sequences (Ohtsubo & Sekine, *Curr. Top. Microbiol. Immunol.* 204: 1-26, 1996), retroviruses (Brown, et al., *Proc Natl Acad Sci USA*, 86:2525-9, 1989), and retrotransposon of yeast (Boeke & Corces, *Annu Rev Microbiol.* 43:403-34, 1989). More examples include IS5, Tn10, Tn903, IS911, and engineered versions of transposase family enzymes (Zhang et al., (2009) *PLoS Genet.* 5:e1000689. Epub 2009 Oct. 16; Wilson C. et al (2007) *J. Microbiol. Methods* 71:332-5).

Other examples of integrases that may be used with the methods and compositions provided herein include retroviral integrases and integrase recognition sequences for such retroviral integrases, such as integrases from HIV-1, HIV-2, SIV, PFV-1, RSV.

Transposon sequences useful with the methods and compositions described herein are provided in U.S. Patent Application Pub. No. 2012/0208705, U.S. Patent Application Pub. No. 2012/0208724 and Int. Patent Application Pub. No. WO 2012/061832. In some embodiments, a transposon sequence includes a first transposase recognition site, and a second transposase recognition site. In those embodiments where a transposome complex is used to introduce an index sequence, the index sequence can be present between the transposase recognition sites or in the transposon.

Some transposome complexes useful herein include a transposase having two transposon sequences. In some such embodiments, the two transposon sequences are not linked to one another, in other words, the transposon sequences are non-contiguous with one another. Examples of such transposomes are known in the art (see, for instance, U.S. Patent Application Pub. No. 2010/0120098).

In some embodiments, a transposome complex includes a transposon sequence nucleic acid that binds two transposase subunits to form a "looped complex" or a "looped transposome." In one example, a transposome includes a dimeric transposase and a transposon sequence. Looped complexes can ensure that transposons are inserted into target DNA while maintaining ordering information of the original target DNA and without fragmenting the target DNA. As will be appreciated, looped structures may insert desired nucleic acid sequences, such as indexes, into a target nucleic acid, while maintaining physical connectivity of the target nucleic acid. In some embodiments, the transposon sequence of a looped transposome complex can include a fragmentation site such that the transposon sequence can be fragmented to create a transposome complex comprising two transposon sequences. Such transposome complexes are useful to ensuring that neighboring target DNA fragments, in which the transposons insert, receive code combinations that can be unambiguously assembled at a later stage of the assay.

In one embodiment, fragmenting nucleic acids is accomplished by using a fragmentation site present in the nucleic acids. Typically, fragmentation sites are introduced into target nucleic acids by using a transposome complex. In one embodiment, after nucleic acids are fragmented the transposase remains attached to the nucleic acid fragments, such that nucleic acid fragments derived from the same genomic DNA molecule remain physically linked (Adey et al., 2014, Genome Res., 24:2041-2049). For instance, a looped transposome complex can include a fragmentation site. A fragmentation site can be used to cleave the physical, but not the informational association between index sequences that have been inserted into a target nucleic acid. Cleavage may be by biochemical, chemical or other means. In some embodiments, a fragmentation site can include a nucleotide or nucleotide sequence that may be fragmented by various means. Examples of fragmentation sites include, but are not limited to, a restriction endonuclease site, at least one ribonucleotide cleavable with an RNAse, nucleotide analogues cleavable in the presence of a certain chemical agent, a diol linkage cleavable by treatment with periodate, a disulfide group cleavable with a chemical reducing agent, a cleavable moiety that may be subject to photochemical cleavage, and a peptide cleavable by a peptidase enzyme or other suitable means (see, for instance, U.S. Patent Application Pub. No. 2012/0208705, U.S. Patent Application Pub. No. 2012/0208724 and WO 2012/061832).

A transposome complex can optionally include at least one index sequence, and can be referred to as a transposase index. The index sequence is present as part of the transposon sequence. In one embodiment, the index sequence can be present on a transferred strand, the strand of the transposase recognition site that is transferred into the target nucleic acid.

A transposome complex can optionally include at least one nucleotide sequence that can be used by a linear amplification mediator. Examples of such nucleotide sequences include, but are not limited do, a RNA polymerase when the nucleic acid fragments include a phage promoter, such as T7 RNA polymerase for use with a T7 promoter, and a linear amplification primer. Examples of a linear amplification primer include a single primer or linear amplification mediator for use in a PCR type of amplification. Other embodiments of nucleotide sequence that can be used by linear amplification mediators are sequences that are recognized by a strand-displacing polymerase. The mediator can contain a nicking site to initiate replication. In some cases, the nicking site is regenerated for additional amplification.

Adding a Compartment Specific Index

An index sequence, also referred to as a tag or barcode, is useful as a marker characteristic of the compartment in which a particular nucleic acid was present. Accordingly, an index is a nucleic acid sequence tag which is attached to each of the target nucleic acids present in a particular compartment, the presence of which is indicative of, or is used to identify, the compartment in which a population of isolated nuclei or cells were present at a particular stage of the method. Addition of an index to nucleic acid fragments is accomplished with subsets of isolated nuclei or cells distributed to different compartments.

An index sequence can be any suitable number of nucleotides in length, e.g., 1, 2, 3, 4, 5, 6, 7, 8, 9, 10, 11, 12, 13, 14, 15, 16, 17, 18, 19, 20, or more. A four nucleotide tag gives a possibility of multiplexing 256 samples on the same array, and a six base tag enables 4096 samples to be processed on the same array.

In one embodiment, addition of an index is achieved during the processing of nucleic acids into nucleic acid fragments. For instance, a transposome complex that includes an index can be used. In other embodiments, an index is added after nucleic acid fragments containing a nucleotide sequence at one or both ends are generated by the processing. Methods for adding an index include, but are not limited to, ligation, extension (including extension using reverse transcriptase), hybridization, adsorption, specific or non-specific interactions of a primer, or amplification. The nucleotide sequence that is added to one or both ends of the nucleic acid fragments can also include one or more universal sequences and/or unique molecular identifiers. A universal sequence can be used as, for instance, a "landing pad" in a subsequent step to anneal a nucleotide sequence that can be used as a primer for addition of another nucleotide sequence, such as another index and/or another universal sequence, to a nucleic acid fragment.

For instance, in embodiments that include use of nucleic acid fragments that are derived from mRNA various methods can be used to add an index to mRNA in one or two steps. For example, an index can be added using the types of methods used to produce cDNA. A primer with a polyT sequence at the 3' end can be annealed to mRNA molecules and extended using a reverse transcriptase. Exposing the isolated nuclei or cells to these components under conditions suitable for reverse transcription results in a one step addition of the index to result in a population of indexed nuclei or cells, where each nucleus or contains indexed nucleic acid fragments. Alternatively, the primer with a polyT sequence includes a universal sequence instead of an index, and the index is added by a subsequent step of ligation, primer extension, amplification. The indexed nucleic acid fragments can, and typically do, include on the synthesized strand the index sequence indicative of the particular compartment.

In embodiments that include use of nucleic acid fragments that derived from non-coding RNA various methods can be used to add an index to the non-coding RNA in one or two steps. For example, an index can be added using a first primer that includes a random sequence and a template-switch primer, where either primer can include an index. A reverse transcriptase having a terminal transferase activity to result in addition of non-template nucleotides to the 3' end of the synthesized strand can be used, and the template-switch primer includes nucleotides that anneal with the non-template nucleotides added by the reverse transcriptase. An example of a useful reverse transcriptase enzyme is a Moloney murine leukemia virus reverse transcriptase. In a particular embodiment, the SMARTer™ reagent available from Takara Bio USA, Inc. (Cat. No. 634926 is used for the use of template-switching to add an index to non-coding RNA, and mRNA if desired. Alternatively, the first primer and/or the template-switch primer can include a universal sequence instead of an index, and the index is added by a subsequent step of ligation, primer extension, or amplification. The indexed nucleic acid fragments can, and typically do, include on the synthesized strand the index sequence indicative of the particular compartment. Other embodiments include 5' or 3' profiling of RNA or full-length RNA profiling.

Other methods can be used for the addition of an index to a nucleic acid fragment, and how an index is added is not intended to be limiting. For instance, in one embodiment the incorporation of an index sequence includes ligating a primer to one or both ends of the nucleic acid fragments. The ligation of the ligation primer can be aided by the presence of a universal sequence at the ends of the nucleic acid fragments. A non-limiting example of a primer is a hairpin ligation duplex. The ligation duplex can be ligated to one end or preferably both ends of nucleic acid fragments. In one embodiment, a primer such as a hairpin ligation duplex can contain a nucleotide sequence that is recognized by a linear amplification mediator. An example of a hairpin adapter containing such nucleotides is described in Example 1, FIG. 2. An assay scheme such as the one described in Example 1 that introduces an amplification mediator that only requires successful ligation at one of the two ends of the barcoded molecules to generate amplification products of that molecule is desirable as it has the advantage of increased efficiency of template conversion. For instance, if a single ligation event has 50% efficiency, this modification renders a 75% success rate at the ligation step of amplifying the molecule instead of 25% (Example 1, FIG. 2).

In another embodiment the incorporation of an index sequence includes use of single stranded nucleic acid fragments and synthesis of the second DNA strand. In one embodiment, the second DNA strand is produced using a primer that include sequences complementary to nucleotides present at the ends of the single stranded nucleic acid fragments.

In another embodiment, the incorporation of an index occurs in one, two, three, or more rounds of split and pool barcoding resulting in single, dual, triple or multiple indexed single cell libraries.

Figure 3:
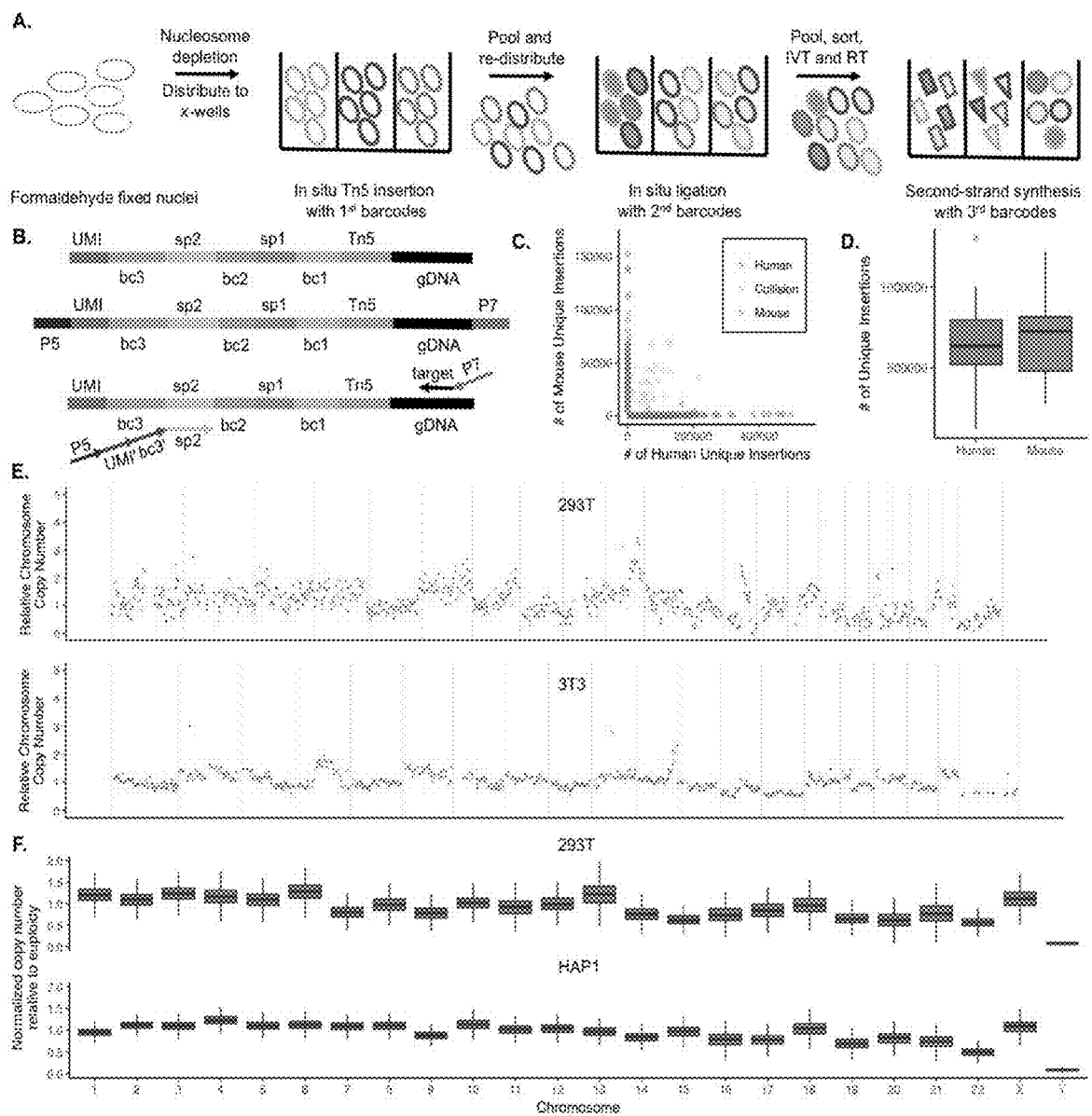
FIG. 3A-F shows sci-L3-WGS enables high-throughput, single cell, linear whole genome amplification. (A) Schematic of the sci-L3-WGS workflow with three levels of indexing. (B) Top: barcode structure of the resulting amplified DNA duplex that is compatible with various library preparation methods. bc, barcode; sp, spacer; gDNA, genomic DNA. Middle: example library structure for sci-L3-WGS. The P5 and P7 sequencing adaptors are added by A-tailing and ligation. Note that having P7 on the UMI end and P5 on the gDNA end are equally possible due to symmetry of ligation. Bottom: example library structure for sci-L3-target-seq. The P5 and P7 sequencing adaptors are added by priming from spacer 2 (sp2) and targeted loci of interest in the genome, respectively. Note that a new third round of barcode bc3' is also added by PCR corresponding to each bc3 in the WGS library, and new UMI' are added outside of bc3'. (C) Scatter plot of numbers of unique Tn5 insertion sites from human and mouse cells at low sequencing depth, 24 bc1×64 bc2×6 bc3 sci-L3-WGS, 100 to 300 cells sorted per well. Blue, inferred mouse cells (percentage of mouse reads >95%, with median of 98.7%, n=315); red, inferred human cells (percentage of human reads >95%, with median of 99.8%, n=719); grey, inferred collisions (n=48, 4%). (D) Box plots showing the number of unique Tn5 insertion sites per cell at an average of 2.4M raw reads per cell and 1.78× depth. Depth is defined as the ratio between the number of unique IVT transcripts to the number of unique Tn5 insertion sites. Thick horizontal lines, medians; upper and lower box edges, first and third quartiles, respectively; whiskers, 1.5 times the interquartile range; circles, outliers). See also FIG. 5 and Example 2, "Methods and molecular design of sci-L3-WGS and sci-L3-target-seq" section, for characterization of libraries made with improved versions of the protocol. (E) Example chromosome copy number variation (CNV) plots for individual cells. Upper, HEK293T cell, 2.6M raw reads, 2.4M unique molecules, 1.3M unique Tn5 insertion sites with MAPQ >1. Lower, 3T3 cell, 2.7M raw reads, 2.4M unique molecules, 1.2M unique Tn5 insertion sites with MAPQ >1. (F) Box plots for copy number variation across 822 293T cells or 1,453 HAP1 cells. Y-axis depicts reads fraction per chromosome normalized by chromosome length such that a euploid chromosome without segmental copy gain or loss is expected to have a value of 1.

In another embodiment, the incorporation of indices and nucleotide sequences that can be used by an amplification mediator is designed unidirectional, allowing targeted single cell sequencing libraries to be prepared (See Example 1, FIG. 3b).

Linear Amplification of Nucleic Acid Fragments

The method provided herein includes linear amplification of the nucleic acid fragments. Most amplification methods are PCR-based and thus suffer from exponential amplification bias. Linear amplification as used herein can reduce or eliminate exponential amplification bias, thereby leading to better uniformity and reduced sequence errors. In all single cell genomics methods that utilize whole genome amplification, the amplification products are contained by a compartment (e.g. well or droplet) and either directly or indirectly a barcode is attached to the amplified products. As such, only a single cell is present per compartment restricting throughput and increasing cost. The unique aspect of this invention is that multiple single cell libraries can be amplified without exponential amplification bias in a single compartment. Libraries from single cells can be assigned based on unique barcode or barcodes for each unique single cell.

In one embodiment, linear amplification is achieved by adding a phage promoter to one or both ends of the nucleic acid fragments. When placed upstream of a nucleic acid fragment, a phage promoter can be used to drive transcription using the corresponding phage RNA polymerase by in vitro transcription producing single stranded RNAs. The RNA copies generated from the DNA template cannot serve as template for further amplification; therefore, all copies derive directly from the original DNA template and exponential amplification is avoided. In one embodiment, subsequent steps can include reverse transcription of the RNA copies to obtain single stranded DNA, and then second strand synthesis to convert the single stranded DNA copies into double stranded molecules. Second strand synthesis typically requires the use of a primer, and this primer can be used to introduce one or more of an index, a universal sequence, and/or a universal molecular identifier.

Other methods of linear amplification can be used. For instance, PCR amplification can be used with one primer, or two primers with one in excess. In some embodiments linear PCR can be used for amplification of flanking sequences adjacent to transposon insertion sites (Xianbo et al. AMB Express, 2017, 7:195). Linked linear amplification (Reyes et al., Clin. Chem., 2001, 47(1):31-40), linear extension and linear extension and ligation, strand-displacement amplification (SDA) (Walker et al., Nucl. Acids Res., 1992, 20(7): 1691-1696), and rolling circle amplification (Ali et al., Chem. Soc. Rev., 2014, 43:3324-3341) can also be used in some embodiments. In some embodiments an index, universal sequence, and/or unique molecular identifier can be added to nucleic acid fragments during the linear amplification.

Typically, linear amplification includes introducing to the isolated nuclei or cells a linear amplification mediator. Examples of linear amplification mediators include a RNA polymerase when the nucleic acid fragments include a phage promoter, such as T7 RNA polymerase for use with a T7 promoter, and a linear amplification primer. Examples of a linear amplification primer include a single primer or linear amplification mediator for use in a PCR type of amplification. Other embodiments of amplification mediators are a strand-displacing polymerase that recognizes a nucleotide sequence. The mediator can contain a nicking site to initiate replication. In some cases, the nicking site is regenerated for additional amplification. The mediator can contain a unique barcode or primer allowing the barcode to be copied during amplification or labeling of the amplification products.

Addition of Universal Sequences for Immobilization

In one embodiment, the addition of nucleotides during the processing and/or indexing steps add universal sequences useful in the immobilizing and sequencing the fragments. In another embodiment, the indexed nucleic acid fragments can be further processed to add universal sequences useful in immobilizing and sequencing the nucleic acid fragments. The skilled person will recognize that in embodiments where the compartment is a droplet sequences for immobilizing nucleic acid fragments are optional. In one embodiment, the incorporation of universal sequences useful in immobilizing and sequencing the fragments includes ligating identical universal adapters (also referred to as 'mismatched adaptors,' the general features of which are described in Gormley et al., U.S. Pat. No. 7,741,463, and Bignell et al., U.S. Pat. No. 8,053,192,) to the 5' and 3' ends of the indexed nucleic acid fragments. In one embodiment, the universal adaptor includes all sequences necessary for sequencing, including sequences for immobilizing the indexed nucleic acid fragments on an array.

In one embodiment, blunt-ended ligation can be used. In another embodiment, the nucleic acid fragments are prepared with single overhanging nucleotides by, for example, activity of certain types of DNA polymerase such as Taq polymerase or Klenow exo minus polymerase which has a non-template-dependent terminal transferase activity that adds a single deoxynucleotide, for example, deoxyadenosine (A) to the 3' ends of the indexed nucleic acid fragments. In some cases, the overhanging nucleotide is more than one base. Such enzymes can be used to add a single nucleotide 'A' to the blunt ended 3' terminus of each strand of the nucleic acid fragments. Thus, an 'A' could be added to the 3' terminus of each strand of the double-stranded target fragments by reaction with Taq or Klenow exo minus polymerase, while the additional sequences to be added to each end of the nucleic acid fragment can include a compatible 'T' overhang present on the 3' terminus of each region of double stranded nucleic acid to be added. This end modification also prevents self-ligation of the nucleic acids such that there is a bias towards formation of the indexed nucleic acid fragments flanked by the sequences that are added in this embodiment.

In another embodiment, when the universal adapter ligated to the indexed nucleic acid fragments does not include all sequences necessary for sequencing, then an amplification step, such as PCR, can be used to further modify the universal adapters present in each indexed nucleic acid fragment prior to immobilizing and sequencing. For instance, an initial primer extension reaction can be carried out using a universal anchor sequence complementary to a universal sequence present in the indexed nucleic acid fragment, in which extension products complementary to both strands of each individual indexed nucleic acid fragment are formed. Typically, the PCR adds additional universal sequences, such as a universal capture sequence.

After the universal adapters are added, either by a single step method of ligating a universal adaptor including all sequences necessary for sequencing, or by a two-step method of ligating a universal adapter and then an amplification to further modify the universal adapter, the final index fragments will include a universal capture sequence and an anchor sequence. The result of adding universal adapters to each end is a plurality or library of indexed nucleic acid fragments.

The resulting indexed nucleic acid fragments collectively provide a library of nucleic acids that can be immobilized and then sequenced. The term library, also referred to herein as a sequencing library, refers to the collection of nucleic acid fragments from single nuclei or cells containing known universal sequences at their 3' and 5' ends.

The indexed nucleic acid fragments can be subjected to conditions that select for a predetermined size range, such as from 150 to 400 nucleotides in length, such as from 150 to 300 nucleotides. The resulting indexed nucleic acid fragments are pooled, and optionally can be subjected to a clean-up process to enhance the purity to the DNA molecules by removing at least a portion of unincorporated universal adapters or primers. Any suitable clean-up process may be used, such as electrophoresis, size exclusion chromatography, or the like. In some embodiments, solid phase reversible immobilization paramagnetic beads may be employed to separate the desired DNA molecules from unattached universal adapters or primers, and to select nucleic acids based on size. Solid phase reversible immobilization paramagnetic beads are commercially available from Beckman Coulter (Agencourt AMPure XP), Thermofisher (MagJet), Omega Biotek (Mag-Bind), Promega Beads (Promega), and Kapa Biosystems (Kapa Pure Beads).

Figure 2:
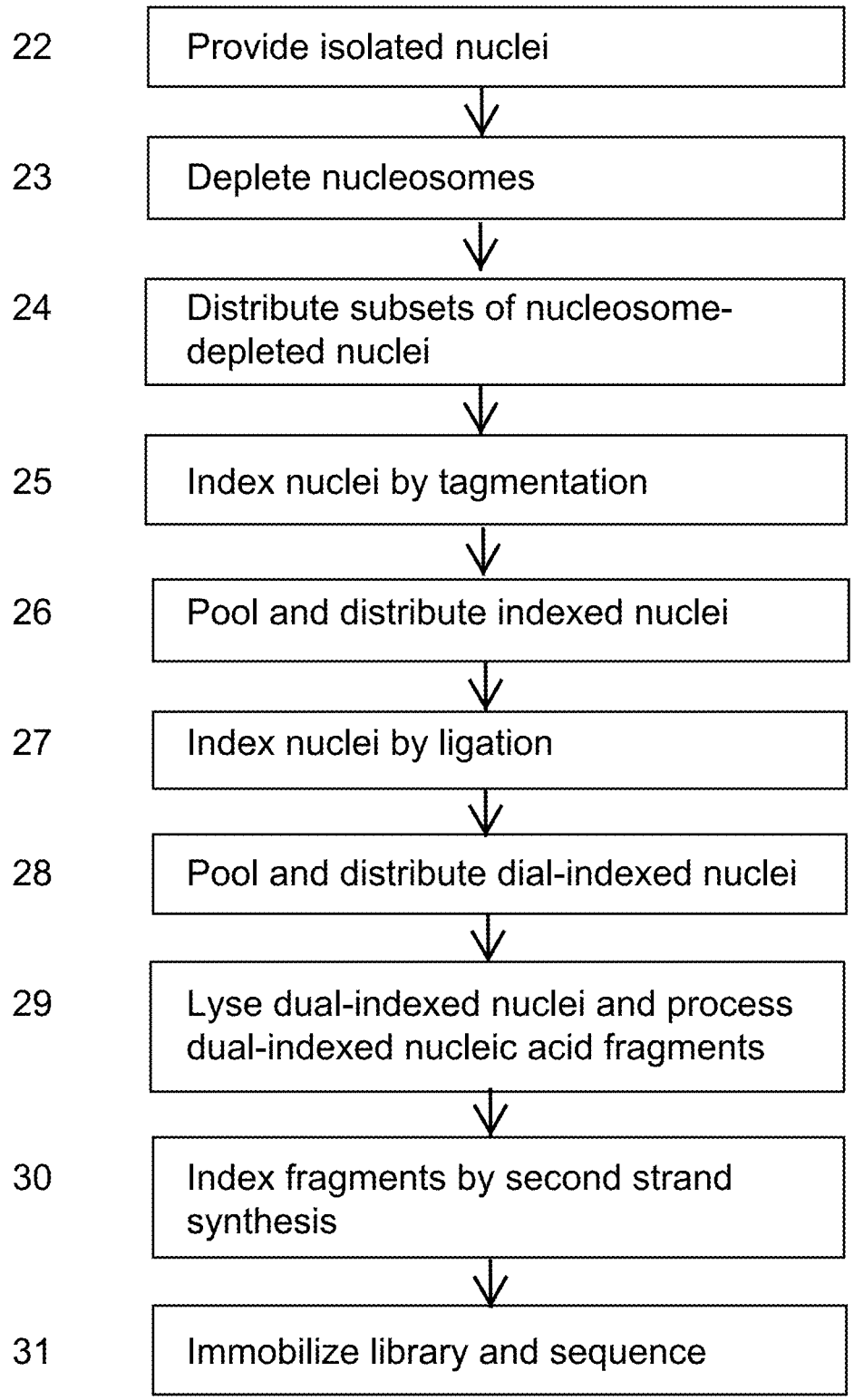
FIG. 2 shows a general block diagram of a general illustrative method for single-cell combinatorial indexing according to the present disclosure.

A non-limiting illustrative embodiment of the present disclosure is shown in FIG. 2 and described in Example 1. In this embodiment, the method includes providing isolated nuclei from a plurality of cells (FIG. 2, block 22). The isolated nuclei can be nucleosome-free, or can be subjected to conditions that deplete the nuclei of nucleosomes, generating nucleosome-depleted nuclei (FIG. 2, block 23).

In this embodiment, the method includes distributing subsets of the nucleosome-depleted nuclei into a first plurality of compartments (FIG. 2, block 24). The number of compartments in the first distribution step (FIG. 2, block 24) can depend on the format used. In one embodiment, the number of compartments is 24.

Figure 4:
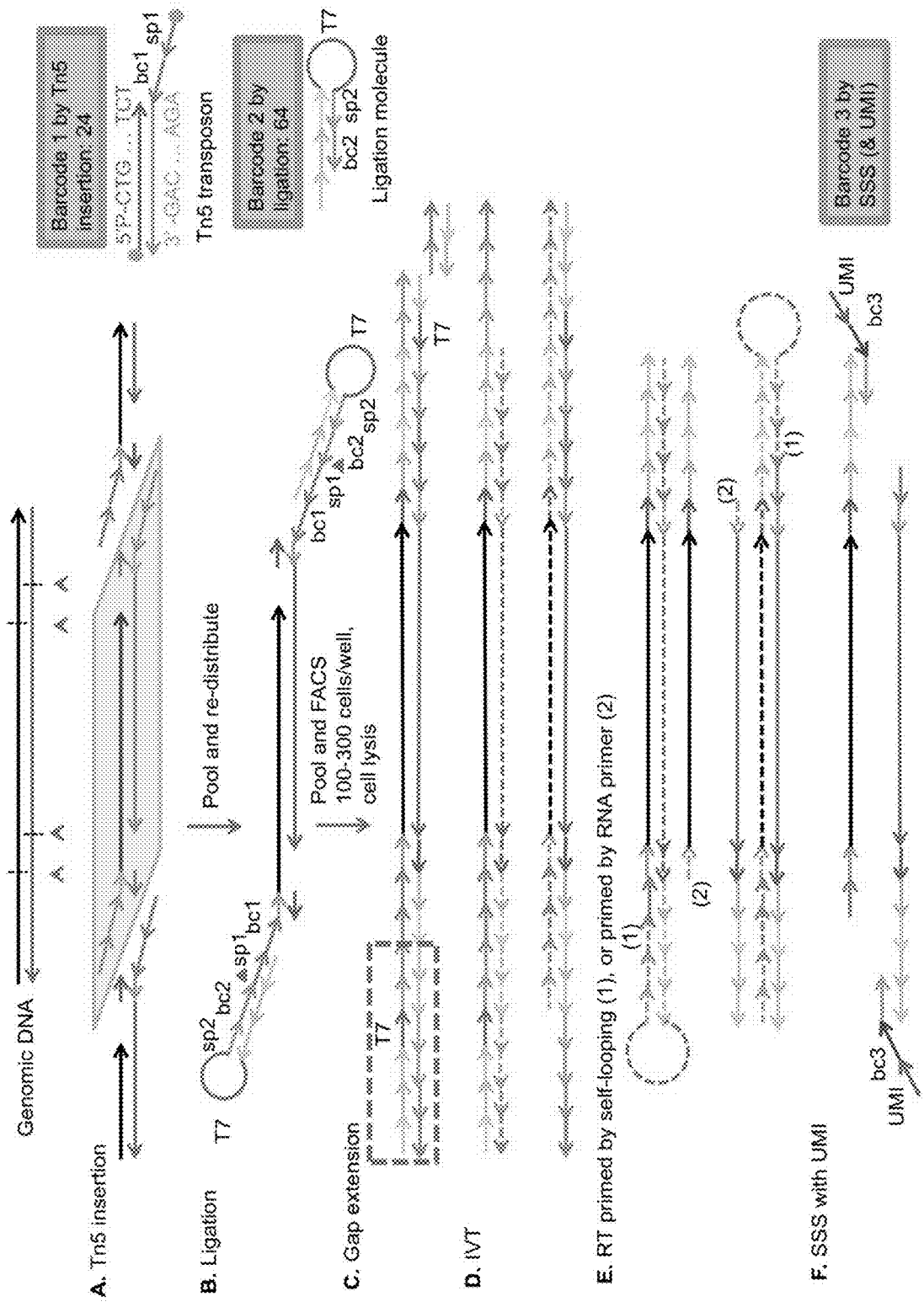
FIG. 4A-F shows molecular structures for sci-LIANTI at each step. Dashed line: RNA, solid line: DNA. (A) Tn5 adaptors have both 5' ends phosphorylated, one required for insertion and the other required for ligation. The overhang of the annealed transposon contains first round barcodes ("bc1") and a spacer ("sp1") for ligation. (B) The ligation molecule is pre-annealed as a hairpin loop, which reduces intermolecular ligation from three molecules to two molecules; the hairpin structure also helps improve RT efficiency in downstream steps. The hairpin contains 1) an overhang that anneals with "sp1" for ligation, 2) the second round barcodes ("bc2") and a spacer ("sp2") that serves as priming site in the stem for SSS in downstream steps, and 3) a T7 promoter in the loop for IVT. (C) Gap extension converts the looped T7 promoter to a duplex. Note that if ligation is successful on both ends, T7 promoters are present on both sides; however, if ligation is successful on one end, the boxed portion will be missing. Nevertheless, both can be reverse transcribed in downstream steps with different RT primers. (D) IVT generates single-stranded RNA amplicons downstream of the T7 promoter. (E) If ligation was successful on both ends, RT is preferably primed by self-looped RT primers, which are inherited from the looped ligation molecule; if ligation was successful on only one end, RT is primed by additional RNA RT primers added in excess. Excess RNA primers are then removed before SSS to avoid interfering with subsequent SSS reaction. (F) Double-stranded DNA molecules are produced by SSS which primes off "sp2" to simultaneously add the third rounds of barcodes and UMI tag each transcript. A more detailed explanation is provided in the Example 2, "Methods and molecular design of sci-L3-WGS and sci-L3-target-seq" section.

Each compartment includes a transposome complex. The transposome complex can be added to each compartment before, after, or at the same time a subset of the nuclei is added to the compartment. The transposome complex includes at least one index sequence and at least one universal sequence. A universal sequence present as part of a transposome complex can be referred to as a spacer sequence. The spacer sequence is present as part of the transposon sequence. In one embodiment, the spacer sequence can be present on a transferred strand, the strand of the transposase recognition site that is transferred into the target nucleic acid. A spacer sequence is useful as a site for annealing with a complementary sequence. For instance, a spacer sequence can be a universal primer, or the complement of a universal primer. The spacer sequence of a transposome complex can be the same for each compartment. In one embodiment, the index ("bet") and spacer ("sp 1") are present in an overhang, arranged in the orientation shown in FIG. 4A of Example 1.

The method also includes generating indexed nuclei (FIG. 2, block 25). In one embodiment, generating indexed nuclei includes processing nucleic acids present in the subsets of nucleosome-depleted nuclei (e.g., the nucleic acids present in each compartment) into a plurality of nucleic acid fragments. In one embodiment, after nucleic acids are fragmented the transposase remains attached to the nucleic acid fragments, such that nucleic acid fragments derived from the same genomic DNA molecule remain physically linked (Adey et al., 2014, Genome Res., 24:2041-2049). The result of the fragmenting is a population of indexed nuclei, where each nucleus contains indexed nucleic acid fragments. The index sequence of a transposome complex is different for each compartment, accordingly, the indexed nucleic acid fragments can, and typically do, include on at least one strand the index sequence indicative of the particular compartment. An example of an indexed nucleic acid fragment is shown in the boxed portion of FIG. 4A of Example 1.

The indexed nuclei from multiple compartments can be combined (FIG. 2, block 26). Subsets of these combined indexed nuclei are then distributed into a second plurality of compartments. The number of nuclei present in a subset, and therefor in each compartment, is based in part on the desire to reduce index collisions, which is the presence of two nuclei having the same transposase index ending up in the same compartment in this step of the method. In one embodiment, the number of nuclei present each subset is approximately equal.

Distribution of nuclei into subsets is followed by incorporating into the indexed nucleic acid fragments in each compartment a second index sequence to generate dual-index fragments. This results in the further indexing of the indexed nucleic acid fragments (FIG. 2, block 27). In those embodiments where cells are cross-linked by a cross-linking agent, the transposases attached to the indexed nucleic acid fragments can be dissociated from the indexed nucleic acid fragments. A detergent can be used to dissociate the transposases, and in one embodiment the detergent is sodium dodecyl sulfate (SDS).

In one embodiment, the incorporation of the second index sequence includes ligating a hairpin ligation duplex to the indexed nucleic acid fragments in each compartment. The ligation duplex can be ligated to one end or preferably both ends of the dual-indexed nucleic acid fragments. In one embodiment, the ligation duplex includes five elements: 1) reverse complement of the first spacer sequence (e.g., "sp 1" in FIG. 4B of Example 1), which serves as a "landing pad" in the ligation step described herein; 2) reverse complement of 2nd round barcode; 3) reverse complement of second-strand synthesis (SSS) primer; 4) T7 promoter, which is preferably the loop region of the hairpin; 5) second-strand synthesis (SSS) primer region starting with GGG for enhancing T7 transcription (the second spacer sequence, "sp2" in FIG. 4B of Example 1); and 6) 2nd round barcode the second index sequence, ("bc2" in FIG. 4B of Example 1). The second index sequences are unique for each compartment in which the distributed indexed nuclei were placed (FIG. 2, block 27) after the first index was added by tagmentation.

The indexed nuclei from multiple compartments can be combined (FIG. 2, block 28). Subsets of these combined indexed nuclei are then distributed into a third plurality of compartments. The number of nuclei present in a subset, and therefor in each compartment, is based in part on the desire to reduce index collisions, which is the presence of two nuclei having the same transposase index ending up in the same compartment in this step of the method. In one embodiment, 100 to 300 cells are distributed to each well. In one embodiment, up to 300 cells are distributed to each well. In one embodiment, the number of nuclei present each subset is approximately equal.

Distribution of dual-indexed nuclei into subsets is followed by lysis and further manipulation (FIG. 2, block 29). Methods for lysis of nuclei are known to the skilled person and routine. Further manipulation includes, but is not limited to, gap extension, in vitro transcription (IVT), and reverse transcription.

Gap extension converts the hairpin T7 promoter structure to a duplex (FIG. 4C of Example 1). A polymerase with strand displacement activity is typically used for gap extension. Polymerases having this activity, for instance Bst polymerase, are available.

IVT generates linear amplified single-stranded RNA molecules downstream of the T7 promoter (FIG. 4D of Example 1). Methods for IVT are known and routine.

Reverse transcription can occur by one of two routes (FIG. 4E of Example 1). The ligation reaction described herein results in two types of nucleic acid fragments: nucleic acid fragments having the ligation duplex at both ends and nucleic acid fragments having the ligation duplex at one end. If ligation was successful on both ends, reverse transcription can be primed by self-looped reverse transcription primers, which are inherited from the looped ligation duplex; if ligation was successful on only one end, reverse transcription is primed by additional RNA reverse transcription primers added in excess.

Lysis of the nuclei and processing of the nuclei acid fragments is followed by incorporating into the dual-indexed nucleic acid fragments in each compartment a third index sequence to generate triple-indexed fragments, where the third index sequence in each compartment is different from first and second index sequences in the other compartments, and the third index sequence in each compartment is different from the third index sequences in other compartments. This results in the further indexing of the indexed nucleic acid fragments (FIG. 2, block 30; FIG. 4F of Example 1) prior to immobilizing and sequencing. The third index can be incorporated by synthesis of the second DNA strand. In one embodiment, the second DNA strand is produced using a primer that include sequences complementary to nucleotides present at the ends of the dual-indexed nucleic acid fragments. For instance, the primer can include the second spacer sequence (sp2) which will anneal with the reverse complement of the second spacer sequence (FIG. 4F of Example 1). The primer further includes the third index ("bc3" in FIG. 4F of Example 1) and other unique molecular identifiers (UMI). The resulting double stranded DNA can be purified using routine methods.

The plurality of triple-indexed fragments can be prepared for sequencing. After the triple-indexed fragments are pooled they are enriched, typically by immobilization and/or amplification, prior to sequencing (FIG. 2, block 31).

Preparation of Immobilized Samples for Sequencing

The plurality of indexed fragments can be prepared for sequencing. For instance, in those embodiments where libraries of triple-indexed fragments are produced, the triple-indexed fragments are enriched, typically by immobilization and/or amplification, prior to sequencing (FIG. 2, block 21).

Methods for attaching indexed fragments from one or more sources to a substrate are known in the art. In one embodiment, indexed fragments are enriched using a plurality of capture oligonucleotides having specificity for the indexed fragments, and the capture oligonucleotides can be immobilized on a surface of a solid substrate. For instance, capture oligonucleotides can include a first member of a universal binding pair, and wherein a second member of the binding pair is immobilized on a surface of a solid substrate. Likewise, methods for amplifying immobilized dual-indexed fragments include, but are not limited to, bridge amplification and kinetic exclusion. Methods for immobilizing and amplifying prior to sequencing are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

A pooled sample can be immobilized in preparation for sequencing. Sequencing can be performed as an array of single molecules or can be amplified prior to sequencing. The amplification can be carried out using one or more immobilized primers. The immobilized primer(s) can be, for instance, a lawn on a planar surface, or on a pool of beads. The pool of beads can be isolated into an emulsion with a single bead in each "compartment" of the emulsion. At a concentration of only one template per "compartment," only a single template is amplified on each bead.

The term "solid-phase amplification" as used herein refers to any nucleic acid amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution.

In some embodiments, the solid support comprises a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S. Pat. Nos. 8,778,848, 8,778,849 and 9,079,148, and US Pub. No. 2014/0243224.

In some embodiments, the solid support includes an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, US Pub. No. 2013/184796, WO 2016/066586, and WO 2015/002813). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However, in many embodiments the gel need not be covalently linked to the wells. For example, in some conditions silane free acrylamide (SFA, see, for example, U.S. Pat. No. 8,563,477) which is not covalently attached to any part of the structured substrate, can be used as the gel material.

In particular embodiments, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of indexed fragments can then be contacted with the polished substrate such that individual indexed fragments will seed individual wells via interactions with primers attached to the gel material; however, the target nucleic acids will not occupy the interstitial regions due to absence or inactivity of the gel material. Amplification of the indexed fragments will be confined to the wells since absence or inactivity of gel in the interstitial regions prevents outward migration of the growing nucleic acid colony. The process can be conveniently manufactured, being scalable and utilizing conventional micro- or nanofabrication methods.

Although the disclosure encompasses "solid-phase" amplification methods in which only one amplification primer is immobilized (the other primer usually being present in free solution), in one embodiment it is preferred for the solid support to be provided with both the forward and the reverse primers immobilized. In practice, there will be a 'plurality' of identical forward primers and/or a 'plurality' of identical reverse primers immobilized on the solid support, since the amplification process requires an excess of primers to sustain amplification. References herein to forward and reverse primers are to be interpreted accordingly as encompassing a 'plurality' of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may include template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the disclosure. Other embodiments may use forward and reverse primers which contain identical template-specific sequences but which differ in some other structural features. For example, one type of primer may contain a non-nucleotide modification which is not present in the other.

In all embodiments of the disclosure, primers for solid-phase amplification are preferably immobilized by single point covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatization or functionalization applied to it. The primer itself may include a moiety, which may be a non-nucleotide chemical modification, to facilitate attachment. In a particular embodiment, the primer may include a sulphur-containing nucleophile, such as phosphorothioate or thiophosphate, at the 5' end. In the case of solid-supported polyacrylamide hydrogels, this nucleophile will bind to a bromoacetamide group present in the hydrogel. A more particular means of attaching primers and templates to a solid support is via 5' phosphorothioate attachment to a hydrogel comprised of polymerized acrylamide and N-(5-bromoacetamidylpentyl) acrylamide (BRAPA), as described in WO 05/065814.

Certain embodiments of the disclosure may make use of solid supports that include an inert substrate or matrix (e.g. glass slides, polymer beads, etc.) which has been "functionalized," for example by application of a layer or coating of an intermediate material including reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The pooled samples may be amplified on beads wherein each bead contains a forward and reverse amplification primer. In a particular embodiment, the library of indexed fragments is used to prepare clustered arrays of nucleic acid colonies, analogous to those described in U.S. Pub. No. 2005/0100900, U.S. Pat. No. 7,115,400, WO 00/18957 and WO 98/44151 by solid-phase amplification and more particularly solid phase isothermal amplification. The terms ' cluster' and ' colony' are used interchangeably herein to refer to a discrete site on a solid support including a plurality of identical immobilized nucleic acid strands and a plurality of identical immobilized complementary nucleic acid strands. The term "clustered array" refers to an array formed from such clusters or colonies. In this context, the term "array" is not to be understood as requiring an ordered arrangement of clusters.

The term "solid phase" or "surface" is used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in WO 98/44151, or a process whereby the temperature is maintained as a constant, and the cycles of extension and denaturing are performed using changes of reagents. Such isothermal amplification methods are described in patent application numbers WO 02/46456 and U.S. Pub. No. 2008/0009420. Due to the lower temperatures useful in the isothermal process, this is particularly preferred in some embodiments.

It will be appreciated that any of the amplification methodologies described herein or generally known in the art may be used with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354. The above amplification methods may be employed to amplify one or more nucleic acids of interest. For example, PCR, including multiplex PCR, SDA, TMA, NASBA and the like may be utilized to amplify immobilized DNA fragments. In some embodiments, primers directed specifically to the polynucleotide of interest are included in the amplification reaction.

Other suitable methods for amplification of polynucleotides may include oligonucleotide extension and ligation, rolling circle amplification (RCA) (Lizardi et al., Nat. Genet. 19:225-232 (1998)) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835) technologies. It will be appreciated that these amplification methodologies may be designed to amplify immobilized DNA fragments. For example, in some embodiments, the amplification method may include ligation probe amplification or oligonucleotide ligation assay (OLA) reactions that contain primers directed specifically to the nucleic acid of interest. In some embodiments, the amplification method may include a primer extension-ligation reaction that contains primers directed specifically to the nucleic acid of interest. As a non-limiting example of primer extension and ligation primers that may be specifically designed to amplify a nucleic acid of interest, the amplification may include primers used for the GoldenGate assay (Illumina, Inc., San Diego, CA) as exemplified by U.S. Pat. Nos. 7,582,420 and 7,611,869.

DNA nanoballs can also be used in combination with methods and compositions as described herein. Methods for creating and utilizing DNA nanoballs for genomic sequencing can be found at, for example, US patents and publications U.S. Pat. No. 7,910,354, 2009/0264299, 2009/0011943, 2009/0005252, 2009/0155781, 2009/0118488 and as described in, for example, Drmanac et al., 2010, Science 327(5961): 78-81. Briefly, following genomic library DNA fragmentation adaptors are ligated to the fragments, the adapter ligated fragments are circularized by ligation with a circle ligase and rolling circle amplification is carried out (as described in Lizardi et al., 1998. Nat. Genet. 19:225-232 and US 2007/0099208 A1). The extended concatameric structure of the amplicons promotes coiling thereby creating compact DNA nanoballs. The DNA nanoballs can be captured on substrates, preferably to create an ordered or patterned array such that distance between each nanoball is maintained thereby allowing sequencing of the separate DNA nanoballs. In some embodiments such as those used by Complete Genomics (Mountain View, Calif.), consecutive rounds of adapter ligation, amplification and digestion are carried out prior to circularization to produce head to tail constructs having several genomic DNA fragments separated by adapter sequences.

Exemplary isothermal amplification methods that may be used in a method of the present disclosure include, but are not limited to, Multiple Displacement Amplification (MDA) as exemplified by, for example Dean et al., Proc. Natl. Acad.

Sci. USA 99:5261-66 (2002) or isothermal strand displacement nucleic acid amplification exemplified by, for example U.S. Pat. No. 6,214,587. Other non-PCR-based methods that may be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyper-branched strand displacement amplification which is described in, for example Lage et al., Genome Res. 13:294-307 (2003). Isothermal amplification methods may be used with, for instance, the strand-displacing Phi 29 polymerase or Bst DNA polymerase large fragment, 5'→3' exo- for random primer amplification of genomic DNA. The use of these polymerases takes advantage of their high processivity and strand displacing activity. High processivity allows the polymerases to produce fragments that are 10-20 kb in length. As set forth above, smaller fragments may be produced under isothermal conditions using polymerases having low processivity and strand-displacing activity such as Klenow polymerase. Additional description of amplification reactions, conditions and components are set forth in detail in the disclosure of U.S. Pat. No. 7,670,810.

Another polynucleotide amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993). The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers may be removed and further replication may take place using primers complementary to the constant 5' region.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments, the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example, in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

In some embodiments, amplification sites in an array can be, but need not be, entirely clonal. Rather, for some applications, an individual amplification site can be predominantly populated with amplicons from a first indexed fragment and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with triple-indexed fragments from a solution and copies of the triple-indexed fragments are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of US Application Pub. No. 2013/0338042.

Kinetic exclusion can exploit a relatively slow rate for initiating amplification (e.g. a slow rate of making a first copy of an indexed fragment) vs. a relatively rapid rate for making subsequent copies of the triple-indexed fragment (or of the first copy of the indexed fragment). In the example of the previous paragraph, kinetic exclusion occurs due to the relatively slow rate of indexed fragment seeding (e.g. relatively slow diffusion or transport) vs. the relatively rapid rate at which amplification occurs to fill the site with copies of the indexed fragment seed. In another exemplary embodiment, kinetic exclusion can occur due to a delay in the formation of a first copy of an indexed fragment that has seeded a site (e.g. delayed or slow activation) vs. the relatively rapid rate at which subsequent copies are made to fill the site. In this example, an individual site may have been seeded with several different indexed fragments (e.g. several indexed fragments can be present at each site prior to amplification). However, first copy formation for any given indexed fragment can be activated randomly such that the average rate of first copy formation is relatively slow compared to the rate at which subsequent copies are generated. In this case, although an individual site may have been seeded with several different indexed fragments, kinetic exclusion will allow only one of those indexed fragments to be amplified. More specifically, once a first indexed fragment has been activated for amplification, the site will rapidly fill to capacity with its copies, thereby preventing copies of a second indexed fragment from being made at the site.

In one embodiment, the method is carried out to simultaneously (i) transport indexed fragments to amplification sites at an average transport rate, and (ii) amplify the indexed fragments that are at the amplification sites at an average amplification rate, wherein the average amplification rate exceeds the average transport rate (U.S. Pat. No. 9,169,513). Accordingly, kinetic exclusion can be achieved in such embodiments by using a relatively slow rate of transport. For example, a sufficiently low concentration of indexed fragments can be selected to achieve a desired average transport rate, lower concentrations resulting in slower average rates of transport. Alternatively or additionally, a high viscosity solution and/or presence of molecular crowding reagents in the solution can be used to reduce transport rates. Examples of useful molecular crowding reagents include, but are not limited to, polyethylene glycol (PEG), ficoll, dextran, or polyvinyl alcohol. Exemplary molecular crowding reagents and formulations are set forth in U.S. Pat. No. 7,399,590, which is incorporated herein by reference. Another factor that can be adjusted to achieve a desired transport rate is the average size of the target nucleic acids.

An amplification reagent can include further components that facilitate amplicon formation, and in some cases increase the rate of amplicon formation. An example is a recombinase. Recombinase can facilitate amplicon formation by allowing repeated invasion/extension. More specifically, recombinase can facilitate invasion of an indexed fragment by the polymerase and extension of a primer by the polymerase using the indexed fragment as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, MA). Further, examples of useful formulations that include a helicase protein are described in U.S. Pat. Nos. 7,399,590 and 7,829,284.

Yet another example of a component that can be included in an amplification reagent to facilitate amplicon formation and in some cases increase the rate of amplicon formation is an origin binding protein.

Use in Sequencing/Methods of Sequencing

Following attachment of indexed fragments to a surface, the sequence of the immobilized and amplified indexed fragments is determined. Sequencing can be carried out using any suitable sequencing technique, and methods for determining the sequence of immobilized and amplified indexed fragments, including strand re-synthesis, are known in the art and are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of an indexed fragment can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

In one embodiment, a nucleotide monomer includes locked nucleic acids (LNAs) or bridged nucleic acids (BNAs). The use of LNAs or BNAs in a nucleotide monomer increases hybridization strength between a nucleotide monomer and a sequencing primer sequence present on an immobilized indexed fragment.

SBS can use nucleotide monomers that have a terminator moiety or those that lack any terminator moieties. Methods using nucleotide monomers lacking terminators include, for example, pyrosequencing and sequencing using γ-phosphate-labeled nucleotides, as set forth in further detail herein. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can use nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments where two or more different nucleotides are present in a sequencing reagent, the different nucleotides can be distinguishable from each other, or alternatively the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320). In pyrosequencing, released PPi can be detected by being immediately converted to adenosine triphosphate (ATP) by ATP sulfurase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026. This approach is being commercialized by Solexa (now Illumina Inc.), and is also described in WO 91/06678 and WO 07/123,744. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In some reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments, each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth herein.

In particular embodiments some or all of the nucleotide monomers can include reversible terminators. In such embodiments, reversible terminators/cleavable fluorophores can include fluorophores linked to the ribose moiety via a 3' ester linkage (Metzker, Genome Res. 15:1767-1776 (2005)). Other approaches have separated the terminator chemistry from the cleavage of the fluorescence label (Ruparel et al., Proc Natl Acad Sci USA 102: 5932-7 (2005)). Ruparel et al. described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluorophore and effectively reverses the termination. Examples of modified nucleotides are also described in U.S. Pat. Nos. 7,427,673, and 7,057,026.

Additional exemplary SBS systems and methods which can be utilized with the methods and systems described herein are described in U.S. Pub. Nos. 2007/0166705, 2006/0188901, 2006/0240439, 2006/0281109, 2012/0270305, and 2013/0260372, U.S. Pat. No. 7,057,026, PCT Publication No. WO 05/065814, U.S. Patent Application Publication No. 2005/0100900, and PCT Publication Nos. WO 06/064199 and WO 07/010,251.

Some embodiments can use detection of four different nucleotides using fewer than four different labels. For example, SBS can be performed using methods and systems described in the incorporated materials of U.S. Pub. No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can use sequencing by ligation techniques. Such techniques use DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597.

Some embodiments can use nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis", Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003)). In such embodiments, the indexed fragment passes through a nanopore. The nanopore can be a synthetic pore or biological membrane protein, such as α-hemolysin. As the indexed fragment passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008)). Data obtained from nanopore sequencing can be stored, processed and analyzed as set forth herein. In particular, the data can be treated as an image in accordance with the exemplary treatment of optical images and other images that is set forth herein.

Some embodiments can use methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414, or nucleotide incorporations can be detected with zero-mode waveguides as described, for example, in U.S. Pat. No. 7,315,019, and using fluorescent nucleotide analogs and engineered polymerases as described, for example, in U.S. Pat. No. 7,405,281 and U.S. Pub. No. 2008/0108082. The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008)). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in U.S. Pub. Nos. 2009/0026082; 2009/0127589; 2010/0137143; and 2010/0282617. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different indexed fragments are manipulated simultaneously. In particular embodiments, different indexed fragments can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the indexed fragments can be in an array format. In an array format, the indexed fragments can be typically bound to a surface in a spatially distinguishable manner. The indexed fragments can be bound by direct covalent attachment, attachment to a bead or other particle or binding to a polymerase or other molecule that is attached to the surface. The array can include a single copy of an indexed fragment at each site (also referred to as a feature) or multiple copies having the same sequence can be present at each site or feature. Multiple copies can be produced by amplification methods such as, bridge amplification or emulsion PCR as described in further detail herein.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of cm$^2$, in parallel. Accordingly, the present disclosure provides integrated systems capable of preparing and detecting nucleic acids using techniques known in the art such as those exemplified herein. Thus, an integrated system of the present disclosure can include fluidic components capable of delivering amplification reagents and/or sequencing reagents to one or more immobilized indexed fragments, the system including components such as pumps, valves, reservoirs, fluidic lines and the like. A flow cell can be configured and/or used in an integrated system for detection of target nucleic acids. Exemplary flow cells are described, for example, in U.S. Pub. No. 2010/0111768 and U.S. Ser. No. 13/273,666. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. Ser. No. 13/273,666.

Also provided herein are compositions. During the practice of the methods described herein various compositions can result. For example, a composition including triple-indexed nucleic acid fragments, can result. Also provided is a multi-well plate, wherein a well of the multi-well plate includes triple-indexed nucleic acid fragments.

Also provided herein are kits. In one embodiment, a kit is for preparing a sequencing library. The kit includes a transposome and/or a linear amplification mediator described herein in a suitable packaging material in an amount sufficient for at least one assay or use. Optionally, other components can be included, such as one or more nucleic acids that include a primer, an index, a universal sequence, or a combination thereof. Other components that can be includes are reagents such as buffers and solutions. Instructions for use of the packaged components are also typically included. As used herein, the phrase "packaging material" refers to one or more physical structures used to house the contents of the kit. The packaging material is constructed by routine methods, generally to provide a sterile, contaminant-free environment. The packaging material may have a label which indicates that the components can be used producing a sequencing library. In addition, the packaging material contains instructions indicating how the materials within the kit are employed. As used herein, the term "package" refers to a container such as glass, plastic, paper, foil, and the like, capable of holding within fixed limits the components of the kit. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

EXEMPLARY EMBODIMENTS

Embodiment 1

A method for preparing a sequencing library comprising nucleic acids from a plurality of single nuclei or cells, the method comprising:
  providing a plurality of isolated nuclei or cells in a first plurality of compartments, wherein each compartment comprises a subset of isolated nuclei or cells, and wherein nuclei or cells comprise nucleic acid fragments;
  introducing a linear amplification mediator to the cells or nuclei;
  amplifying the nucleic acid fragments by linear amplification;
  processing each subset of nuclei or cells to generate indexed nuclei or cells, wherein the processing comprises adding to nucleic acid fragments present in the isolated nuclei or cells a first compartment specific index sequence to result in indexed nucleic acids present in isolated nuclei or cells, wherein the processing comprises ligation, primer extension, hybridization, amplification, or transposition; and
  combining the indexed nuclei or cells to generate pooled indexed nuclei or cells, thereby producing a sequencing library from the plurality of nuclei or cells.

Embodiment 2

The method of Embodiment 1 wherein the amplifying occurs before the processing.

Embodiment 3

The method of Embodiment 1 wherein the processing occurs before the amplifying.

Embodiment 4

A method for preparing a sequencing library comprising nucleic acids from a plurality of single nuclei or cells, the method comprising:
  providing a plurality of isolated nuclei or cells, wherein nuclei or cells comprise nucleic acid fragments;
  introducing a linear amplification mediator to the isolated nuclei or cells;
  distributing the isolated nuclei or cells into a first plurality of compartments, wherein each compartment comprises a subset of isolated nuclei or cells;
  amplifying the nucleic acid fragments by linear amplification;
  processing each subset of isolated nuclei or cells to generate indexed nuclei or cells, wherein the processing comprises adding to nucleic acid fragments present in the isolated nuclei or cells a first compartment specific index sequence to result in indexed nucleic acids present in isolated nuclei or cells, wherein the processing comprises ligation, primer extension, amplification, or transposition;

combining the indexed nuclei to generate pooled indexed nuclei or cells, thereby producing a sequencing library from the plurality of nuclei or cells.

Embodiment 5

A method for preparing a sequencing library comprising nucleic acids from a plurality of single nuclei or cells, the method comprising:

providing a plurality of isolated nuclei or cells in a first plurality of compartments, wherein each compartment comprises a subset of isolated nuclei or cells, and wherein nuclei or cells comprise nucleic acid fragments;

processing each subset of nuclei or cells to generate indexed nuclei or cells, wherein the processing comprises adding to nucleic acid fragments present in the isolated nuclei or cells (i) a first compartment specific index sequence to result in indexed nucleic acids present in isolated nuclei or cells and (ii) a nucleotide sequence recognized by a linear amplification mediator, wherein the processing comprises ligation, primer extension, hybridization, amplification, or transposition;

introducing a linear amplification mediator to the cells or nuclei;

amplifying the nucleic acid fragments by linear amplification; and combining the indexed nuclei or cells to generate pooled indexed nuclei or cells, thereby producing a sequencing library from the plurality of nuclei or cells.

Embodiment 6

The method of any one of Embodiments 1-5, wherein the linear amplification mediator comprises a phage RNA polymerase or a linear amplification primer.

Embodiment 7

The method of any one of Embodiments 1-6, wherein the nucleic acid fragments comprise a T7 promoter and the phage RNA polymerase comprises a T7 RNA polymerase.

Embodiment 8

The method of any one of Embodiments 1-7, wherein introducing the linear amplification mediator comprises adding to nucleic acid fragments present in the isolated nuclei or cells the linear amplification mediator.

Embodiment 9

The method of any one of Embodiments 1-8, further comprising exposing the plurality of isolated nuclei or cells of each compartment to a predetermined condition.

Embodiment 10

The method of any one of Embodiments 1-9, further comprising isolating nuclei from the plurality of cells after the exposing.

Embodiment 11

The method of any one of Embodiments 1-10, further comprising exposing the plurality of isolated nuclei or cells to a predetermined condition.

Embodiment 12

The method of any one of Embodiments 1-11, further comprising subjecting the isolated nuclei to conditions to generate nucleosome-depleted nuclei while maintaining integrity of the isolated nuclei.

Embodiment 13

The method of any one of Embodiments 1-12, wherein the processing comprises:

contacting each subset with a transposome complex, wherein the transposome complex in each compartment comprises the first index sequence that is different from first index sequences in the other compartments; and fragmenting nucleic acids in the subsets into a plurality of nucleic acids and incorporating the first index sequences into at least one strand of the nucleic acids to generate the indexed nuclei or cells comprising the indexed nucleic acids.

Embodiment 14

The method of any one of Embodiments 1-13, wherein the processing comprises:

contacting each subset with reverse transcriptase and a primer that anneals to RNA molecules in the isolated nuclei, wherein the primer in each compartment comprises the first index sequence that is different from first index sequences in the other compartments to generate the indexed nuclei or cells comprising the indexed nucleic acids.

Embodiment 15

The method of any one of Embodiments 1-14, wherein the contacting further comprises a target specific primer that anneals to a specific nucleotide sequence.

Embodiment 16

The method of any one of Embodiments 1-15, wherein the processing to add the first compartment specific index sequence comprises a two-step process of adding a nucleotide sequence comprising a universal sequence to the nucleic acid fragments and then adding the first compartment specific index sequence to the nucleic acid fragments.

Embodiment 17

The method of any one of Embodiments 1-16, wherein the adding comprises a transposome complex that comprises the universal sequence.

Embodiment 18

The method of any one of Embodiments 1-17, wherein the processing comprises adding a first index to DNA nucleic acids present in the isolated nuclei or cells, a first index to RNA nucleic acids present in the isolated nuclei or cells, or a combination thereof.

Embodiment 19

The method of any one of Embodiments 1-18, wherein the adding a first index sequence to RNA nucleic acids comprises:
contacting each subset with a reverse transcriptase and a primer that anneals to RNA molecules in the isolated nuclei or cells, wherein the primer in each compartment comprises the first compartment specific index sequence to generate the indexed nuclei or cells comprising the indexed nucleic acids.

Embodiment 20

The method of any one of Embodiments 1-19, wherein the adding a first index sequence to DNA nucleic acids comprises:
contacting each subset with a transposome complex, wherein the transposome complex in each compartment comprises the first compartment specific index sequence; and
fragmenting nucleic acids in the subsets into a plurality of nucleic acids and incorporating the first compartment specific index sequences into at least one strand of the nucleic acids to generate the indexed nuclei or cells comprising the indexed nucleic acids.

Embodiment 21

The method of any one of Embodiments 1-20, wherein the first index sequence added to DNA nucleic acids and the first index sequence added to RNA nucleic acids in each compartment are identical.

Embodiment 22

The method of any one of Embodiments 1-21, wherein the first index sequence added to DNA nucleic acids and the first index sequence added to RNA nucleic acids in each compartment are not identical.

Embodiment 23

The method of any one of Embodiments 1-22, further comprising an exponential amplification of the nucleic acid fragments, wherein the exponential amplification comprises a target specific primer that anneals to a specific nucleotide sequence.

Embodiment 24

The method of any one of Embodiments 1-23, further comprising after the combining:
distributing subsets of the pooled indexed nuclei or cells into a second plurality of compartments; and
introducing a second compartment specific index sequence to indexed nucleic acids to generate dual-indexed nuclei or cells comprising dual-indexed nucleic acids, wherein the introducing comprises ligation, primer extension, amplification, or transposition.

Embodiment 25

The method of any one of Embodiments 1-24, further comprising
combining the dual-indexed nuclei to generate pooled dual-indexed nuclei or cells,
distributing subsets of the pooled dual-indexed nuclei or cells into a third plurality of compartments; and
introducing a third compartment specific index sequence to indexed nucleic acids to generate triple-indexed nuclei or cells comprising triple-indexed nucleic acids, wherein the introducing comprises ligation, primer extension, amplification, or transposition.

Embodiment 26

The method of any one of Embodiments 1-25, further comprising treating the indexed nuclei or cells for methylation analysis to generate nucleic acid fragments suitable for methylation analysis.

Embodiment 27

The method of any one of Embodiments 1-26, further comprising subjecting the indexed nuclei or cells to proximity ligation to generate nucleic acid fragments suitable for analysis of chromatin conformation.

Embodiment 28

The method of any one of Embodiments 1-27, further comprising amplifying the nucleic acid fragments of the sequencing library to produce DNA nanoballs.

Embodiment 29

The method of any one of Embodiments 1-28, wherein the compartment comprises a well or a droplet.

Embodiment 30

The method of any one of Embodiments 1-29, wherein each compartment of the first plurality of compartments comprises from 50 to 100,000,000 nuclei or cells.

Embodiment 31

The method of any one of Embodiments 1-29, wherein each compartment of the second plurality of compartments comprises from 50 to 100,000,000 nuclei or cells.

Embodiment 32

The method of any one of Embodiments 1-31, further comprising:
providing a surface comprising a plurality of amplification sites, wherein the amplification sites comprise at least two populations of attached single stranded capture oligonucleotides having a free 3' end, and
contacting the surface comprising amplification sites with the indexed fragments under conditions suitable to produce a plurality of amplification sites that each comprise a clonal population of amplicons from an individual fragment comprising a plurality of indexes.

Embodiment 33

A method of preparing a sequencing library comprising nucleic acids from a plurality of single cells, the method comprising:
- (a) providing isolated nuclei from a plurality of cells;
- (b) subjecting the isolated nuclei to a chemical treatment to generate nucleosome-depleted nuclei, while maintaining integrity of the isolated nuclei;
- (c) distributing subsets of the nucleosome-depleted nuclei into a first plurality of compartments and contacting each subset with a transposome complex, wherein the transposome complex in each compartment comprises a transposase and a first index sequence that is different from first index sequences in the other compartments;
- (d) fragmenting nucleic acids in the subsets of nucleosome-depleted nuclei into a plurality of nucleic acid fragments and incorporating the first index sequences into at least one strand of the nucleic acid fragments to generate indexed nuclei comprising indexed nucleic acid fragments, wherein the indexed nucleic acid fragments remain attached to the transposases;
- (d) combining the indexed nuclei to generate pooled indexed nuclei;
- (e) distributing subsets of the pooled indexed nuclei into a second plurality of compartments and contacting each subset with a hairpin ligation duplex under conditions suitable for ligation of the hairpin ligation duplex to one or both ends of indexed nucleic acid fragments to result in dual-indexed nucleic acid fragments, wherein the hairpin ligation duplex comprises a second index sequence that is different from second index sequences in the other compartments;
- (f) combining the dual-indexed nuclei to generate pooled indexed nuclei;
- (g) distributing subsets of the pooled dual-indexed nuclei into a third plurality of compartments;
- (h) lysing the dual-indexed nuclei;
- (i) processing the dual-indexed nucleic fragments to include a third index sequence that is different from third index sequences in the other compartments; and
- (j) combining the triple-index fragments, thereby producing a sequencing library comprising whole genome nucleic acids from the plurality of single cells.

EXAMPLES

The present disclosure is illustrated by the following examples. It is to be understood that the particular examples, materials, amounts, and procedures are to be interpreted broadly in accordance with the scope and spirit of the disclosure as set forth herein.

Example 1

High-Throughput Single Cell Sequencing with Linear Amplification

Conventional methods for single cell genome sequencing are limited with respect to uniformity and throughput. Here we describe "sci-L3", a high-throughput, high-coverage single cell sequencing method that combines single cell combinatorial indexing ("sci") and linear ("L") amplification. The sci-L3 method adopts a unidirectional 3-level ("3") indexing scheme that minimizes amplification biases while enabling exponential gains in throughput. We demonstrate the generalizability of the sci-L3 framework through proof-of-concept demonstrations of single-cell whole genome sequencing ("sci-L3-WGS"), targeted genome sequencing ("sci-L3-target-seq"), and a co-assay of the genome and transcriptome ("sci-L3-RNA/DNA"). We apply sci-L3-WGS to profile the genomes of >10,000 sperm and sperm precursors from F1 hybrid male mice, mapping 86,786 crossovers and characterizing rare chromosome mis-segregation events in male meiosis, including instances of whole-genome equational chromosome segregation. We anticipate that sci-L3 assays can be applied to fully characterize recombination landscapes, to couple CRISPR perturbations and measurements of genome stability, and to other goals requiring high-throughput, high-coverage single cell genome sequencing.

Introduction

Contemporary single cell genome sequencing technologies have two major limitations. First, most methods require compartmentalizing individual cells, which limits throughput. Second, most amplification methods are PCR-based and thus suffer from exponential amplification biases. To resolve the first issue, we and colleagues developed single cell combinatorial indexing ('sci-'), wherein one performs several rounds of split-pool molecular barcoding to uniquely tag the nucleic acid contents of single cells, thereby enabling exponential gains in throughput with each successive round of indexing. Sci-methods have been successfully developed to profile chromatin accessibility (sci-ATAC-seq), transcriptomes (sci-RNA-seq), genomes (sci-DNA-seq), methylomes (sci-MET), chromosome conformation (sci-Hi-C) in large numbers of single cells (Cao et al., 2017; Cusanovich et al., 2015; Mulqueen et al., 2018; Ramani et al., 2017; Vitak et al., 2017). To resolve the second issue, linear amplification via T7-based transcription provides a potential solution that has previously been deployed in the context of single cell assays (Eberwine et al., 1992; Hashimshony et al., 2012; Sos et al., 2016). For example, recently, Chen et al. developed Linear Amplification via Transposon Insertion ("LIANTI"), which uses Tn5 transposon to fragment the genome and simultaneously insert a T7 RNA promoter for in vitro transcription (IVT). RNA copies generated from the DNA template cannot serve as template for further amplification; therefore, all copies derive directly from the original DNA template. By avoiding exponential amplification, LIANTI maintains uniformity and minimizes sequence errors. However, the method is low-throughput because it requires serial library preparation from each single cell (Chen et al., 2017).

To minimize amplification biases while at the same time enabling exponential gains in throughput, we developed sci-L3, which integrates single cell combinatorial indexing and linear amplification. With three rounds of molecular barcoding, sci-L3 improves the throughput of LIANTI to at least thousands and potentially millions of cells per experiment, while retaining the advantages of linear amplification. We demonstrate the generalizability of the sci-L3 framework through proof-of-concept demonstrations of single cell whole genome sequencing ("sci-L3-WGS"), targeted genome sequencing ("sci-L3-target-seq"), and a co-assay of the genome and transcriptome ("sci-L3-RNA/DNA"). As a further demonstration, we apply sci-L3-WGS to map an unprecedented number of meiotic crossover and rare chromosome mis-segregation events in premature and mature male germ cells from infertile, interspecific (B6×Spretus) F1 male mice, as well as fertile, intraspecific (B6×Cast) F1 male mice.

Design

A potential technical path to minimizing amplification biases while increasing throughput would be to simply combine the "sci" and "LIANTI" methods. However, the molecular structure of LIANTI, wherein the T7 promoter is inserted via Tn5 transposon, affords opportunities for only two rounds of cellular barcoding, which would limit throughput to thousands of single cells per experiment. It is furthermore restricted to profiling of genomic DNA (Chen et al., 2017; Sos et al., 2016). In developing sci-L3, we integrated single cell combinatorial indexing, linear amplification, and three rounds of cellular barcoding ("three-level") by introducing the T7 promoter by ligation (FIG. 3A). The sci-L3 approach has several major advantages over simply combining "sci" and "LIANTI". First, the potential throughput is exponentially increased by three-level indexing to over one million cells per experiment at a much reduced cost (Cao et al., 2019). Second, the unidirectional nature of single cell barcoding allows sci-L3 to be easily converted to targeted sequencing ("target-seq") in addition to whole-genome sequencing ("WGS"), which enables coupling CRISPR perturbations and resulting genome instability as well as other applications where it is desirable to sequence specific genomic loci across large numbers of single cells. Third, as a generalizable linear amplification and high-throughput cellular barcoding scheme, sci-L3 provides the flexibility for adapting to other single cell assays and co-assays with small modifications of the protocol, as demonstrated by our proof-of-concept here of a sci-L3-based single cell RNA/DNA co-assay.

Results

Proof-of-Concept of Sci-L3-WGS and Sci-L3-Target-Seq

The three-level combinatorial indexing and amplification schemes of sci-L3-WGS and sci-L3-target-seq are shown in FIG. 3A: (i) Cells are fixed with formaldehyde and nucleosomes are depleted by SDS (Vitak et al., 2017). The resulting nuclei are then evenly distributed to 24 wells. (ii) A first round of barcodes is added by indexed Tn5 insertion ("tagmentation") within each of the 24 wells. Unlike LIANTI, wherein the Tn5 transposon contains a T7 promoter without a barcode, a spacer sequence is included 5' to the barcodes, which serves as a "landing pad" for the subsequent ligation step (see FIG. 4 and Example 2, "Methods and molecular design of sci-L3-WGS and sci-L3-target-seq" section, for details of Tn5 transposon design). (iii) All of the nuclei are pooled and redistributed evenly into 64 new wells; a second round of barcodes is added by ligation, which includes a T7 promoter sequence positioned outside of both barcodes. (iv) All of the nuclei are once again pooled together and sorted by fluorescence-activated cell sorting (FACS) cytometry and distributed to a final round of wells at up to 300 cells per well. Note that nuclei of different ploidies can be gated and enriched by DAPI (4',6-diamidino-2-phenylindole) staining. Also, simple dilution is an alternative to FACS that can reduce the loss rate. (v) Sorted nuclei are lysed and subjected to in situ gap extension to form a duplex T7 promoter. This is followed by IVT, reverse transcription (RT), and second-strand synthesis (SSS) to amplify genomes in a linear fashion. A third round of barcodes is added during the SSS step, along with unique molecular identifiers (UMIs) to tag individual IVT transcripts. (vi) Duplex DNA molecules (FIG. 3B, top), each containing three barcodes that define their cell of origin, are compatible with conventional library construction methods if the goal is single cell WGS (e.g. appending sequence adaptors by ligation (FIG. 3B, middle) or tagmentation), or slightly modified methods if the goal is single cell targeted DNA-seq (e.g. adding a PCR step wherein one of the primers is target-specific (FIG. 3B, bottom)).

As an initial proof-of-concept, we mixed mouse and human cells and performed sci-L3-WGS. For over 95% of the resulting single cell genomes, the vast majority of reads mapped either to the mouse or human genome; occasional 'collisions' result from chance use of the same combination of barcodes by two or more cells (FIG. 3C). The performance of sci-L3-WGS is compared to LIANTI as well as our previous PCR-based sci-DNA-seq method in Table 1. We highlight several advantages of sci-L3-WGS: 1) We generally recover 90% of sorted cells as compared to 60% recovery with PCR-based sci-DNA-seq (Vitak et al., 2017); 2) With 40% fewer raw reads (329M by sci-L3-WGS vs. 549M by sci-DNA-seq), sci-L3-WGS produced sequence coverage at ~97,000 unique Tn5 insertions per cell, as compared to 30,000 unique insertions by sci-DNA-seq, a >3-fold improvement. Sequencing a smaller number of cells to a higher depth, we observed ~660,000 unique Tn5 insertions per cell while maintaining higher library complexity than sci-DNA-seq, suggesting a further improvement of >20-fold; 3) The rate of mappable reads is improved from 61% with LIANTI to 86% with sci-L3-WGS. This is likely because LIANTI is entirely in-tube and therefore it is hard to remove artifactual sequences (e.g. secondary to self-insertion of Tn5), whereas with sci-L3-WGS, nuclei are pelleted several times to remove excess free DNA; 4) Unlike PCR-based amplification where duplicate reads are not informative for SNP calling, sci-L3-WGS's 'duplicate' reads almost always result from independent IVT transcripts polymerized from the original template, and are therefore useful for de novo SNV discovery or for genotyping known SNPs.

TABLE 1

Performance comparison of sci-DNA-seq vs. sci-L3-WGS vs. LIANTI. sci-DNA-seq data from xSDS method of (Vitak et al., 2017). LIANTI from in-tube method of (Chen et al., 2017). For sci-L3-WGS, we show results for libraries yi140 and yi141 (at high depth of sequencing) and yi144 and yi145 (at low depth of sequencing). These four libraries use an optimized protocol where we used concentrated Tn5 transposome (0.2 µM) and an improved RT reaction with additional RNA primers (See FIG. 5 and Example 2, "Methods and molecular design of sci-L3-WGS and sci-L3-target-seq" section, for details).

|  | # raw reads (M) | # cells sorted | ideal # reads/sorted single cell (k) | single cell read cutoff | # cells recovered | % cells recovered | ideal # reads/ recovered single cell (k) |
|---|---|---|---|---|---|---|---|
| sci-DNA-seq | 549 | 6336 | 86.6 | 6051 | 3123 | 49% | 175.8 |
| sci-L3-WGS (low depth) | 329 | 2400 | 137 | 18945 | 2200 | 92% | 149.5 |

TABLE 1-continued

Performance comparison of sci-DNA-seq vs. sci-L3-WGS vs. LIANTI. sci-DNA-seq data from xSDS method of (Vitak et al., 2017). LIANTI from in-tube method of (Chen et al., 2017). For sci-L3-WGS, we show results for libraries yi140 and yi141 (at high depth of sequencing) and yi144 and yi145 (at low depth of sequencing). These four libraries use an optimized protocol where we used concentrated Tn5 transposome (0.2 μM) and an improved RT reaction with additional RNA primers (See FIG. 5 and Example 2, "Methods and molecular design of sci-L3-WGS and sci-L3-target-seq" section, for details).

| | | | | | | | |
|---|---|---|---|---|---|---|---|
| sci-L3-WGS (high depth) | 256 | 200 | 1280 | 159012 | 191 | 96% | 1340.3 |
| LIANTI | 3.84 | 3 | 1280 | 1280000 | 3 | 100% | 1280 |

| | mapping rate (of all raw reads) | median unique insertions/ single cell (k) | median Tn5 insertion complexity | median library complexity | # cells >5e4 reads | % cells >5e4 reads |
|---|---|---|---|---|---|---|
| sci-DNA-seq | 85% | 29.5 | 53% | 53% | 1056 | 17% |
| sci-L3-WGS (low depth) | 87% | 97.3 | 95% | 99% | 1828 | 83% |
| sci-L3-WGS (high depth) | 86% | 660.7 | 73% | 98% | 191 | 96% |
| LIANTI | 61% | 789.5 | 98% | 99% | 3 | 100% |

Same color indicates comparisons of interest.
Green: percentage of recovered single cells from sorting is improved by 1.9 fold with sci-L3-WGS compared to sci-DNA-seq;
pink: mapping rate of raw reads is improved by 1.4 fold with sci-L3-WGS compared to LIANTI;
yellow: unique insertion sites at varying sequencing depth;
rows 1 and 2 are compared at similar number of raw reads with 3.3-fold improvement with 40% fewer raw reads with sci-L3-WGS compared to sci-DNA-seq, and rows 1 and 3 are compared at similar library complexity with 22.4-fold improvement at 20% better Tn5 insertion complexity with sci-L3-WGS compared to LIANTI;
blue: median library complexity showing methods including both LIANTI and sci-L3-WGS have minimal PCR duplicates;
orange: number of cells with greater than 50k unique reads recovered are improved by 1.8-fold with sci-L3-WGS compared to LIANTI.

Figure 5:
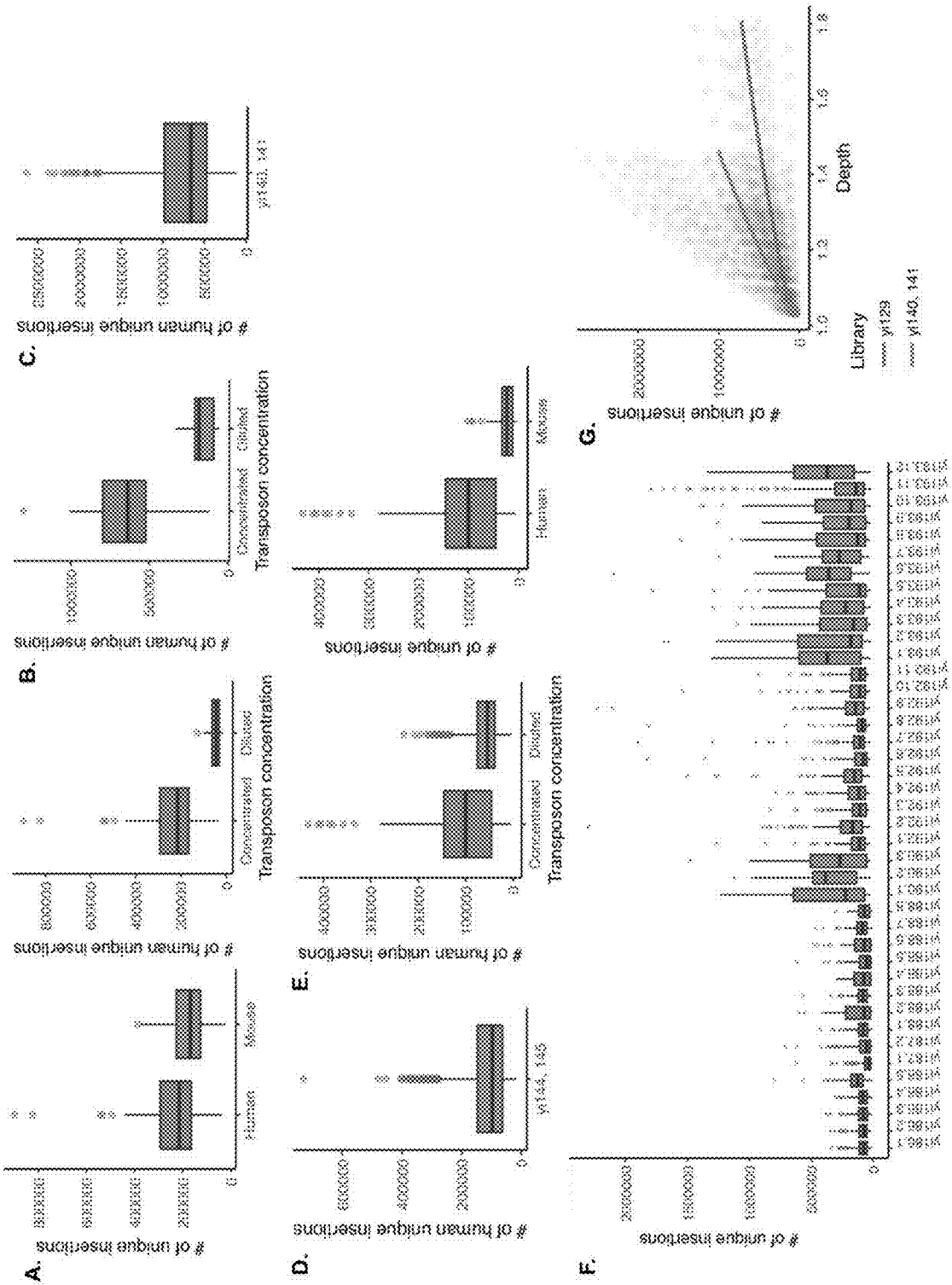
FIG. 5A-G shows read numbers in different sci-L3-WGS experiments and with different Tn5 transposome concentrations. Box plots showing the number of unique Tn5 insertion sites per cell at indicated depths. Depth is defined as the ratio between the number of unique IVT transcripts to the number of unique Tn5 insertion sites. Thick horizontal lines, medians; upper and lower box edges, first and third quartiles, respectively; whiskers, 1.5 times the interquartile range; circles, outliers). Concentrated Tn5 transposome: 0.2 µM, diluted Tn5 transposome: 0.1 µM. (A) yi128 (median depth: 1.19×) human vs. mouse unique reads (median human unique reads: 215 k, n=115 cells; median mouse unique reads: 169 k, n=44) with concentrated Tn5; human unique reads with concentrated Tn5 (median unique reads: 215 k) vs. diluted (median unique reads: 46 k) Tn5. (B) yi129 (median depth: 1.78×) human unique reads with concentrated Tn5 (median unique reads: 635 k) vs. diluted (median unique reads: 183 k) Tn5. Mouse unique reads presented in FIG. 3D. (C) yi140 and yi141 (median depth: 1.37×; median human unique reads: 660 k) with concentrated Tn5. See also Table 2 and Example 2. (D) yi144 and yi145 (median depth: 1.05×; median human unique reads: 97.3 k) with concentrated Tn5. See also Table 2. Note that yi140, yi141, yi144 and yi145 are libraries with the optimized protocol discussed in Example 2. (E) yi174 (median depth: 1.06×) human/mouse unique reads (median human unique reads: 100 k, n=103; median mouse unique reads: 23 k, n=35) with concentrated Tn5; human unique reads with concentrated Tn5 (median unique reads: 100 k) and diluted (median unique reads: 54 k) Tn5. (F) Libraries of mouse germ cells: yi186, yi187, yi188 are prepared with diluted Tn5; yi190, yi192, yi193 are prepared with concentrated Tn5. (G) Number of unique Tn5 insertion sites as a function of sequencing depth. Blue and red lines show sci-L3-WGS with vs. without RNA RT primers, respectively (Example 2). yi129 (as in panel B, median depth: 1.78×) human unique insertions with concentrated (median unique insertions: 635 k). When projected to 5× and 10× depth, the expected unique numbers of insertions are 1.9M and 2.6M, respectively. yi140 and yi141 combined have a median depth of 1.37× with median unique insertions of 660 k. When projected to 1.78×, 5× and 10× depth, the expected numbers of unique insertions are 1.5M, 4.2M and 6.0M, respectively.

With sci-L3-WGS, Tn5 inserts on average every 0.5-1.5 kb of the human genome, and IVT yields ~1,000 transcripts. This corresponds to 2 to 6 million unique Tn5 insertions, and therefore 2 to 6 billion unique genome-derived IVT transcripts, per single cell. It is obviously currently impractical to sequence the resulting libraries to saturation with respect to the number of unique IVT transcripts. Here we define the 'depth of sequencing' for each library as the ratio between the number of unique transcripts sequenced to the number of unique Tn5 insertions sites mapped. In this study, most of the libraries are sequenced at a depth of 1.1× to 2×, resulting in 0.5% to 5% coverage of the genome of each cell. The distribution of unique Tn5 insertion sites per cell in the human/mouse proof-of-concept experiment is shown in FIG. 3D, and for other experiments in FIG. 5. The estimated relative chromosomal copy numbers for representative single cells is shown in FIG. 3E, and their distributions across all cells in FIG. 3F. To extrapolate expected genome coverage per single cell at higher sequencing depth, we fit the number of unique insertion sites as a function of sequencing depth (FIG. 5G). We expect to observe 4.2M and 6.0M unique insertions per cell at a sequencing depth of 5× and 10×, respectively, which corresponds to 16% and 22% coverage of the genome of individual cells.

As noted above, the double-stranded amplicons generated by sci-L3 (FIG. 3B, top) are compatible not only with single cell WGS (sci-L3-WGS; FIG. 3B, middle), but also with single cell targeted DNA sequencing ("sci-L3-target-seq"). Specifically, for targeted sequencing, after second strand synthesis, one can add the sequencing adaptors by PCR with one primer bearing the third cellular barcode, but the other primer targeting a specific region of the genome (FIG. 3B, bottom). To quantify efficiency of recovery with sci-L3-target-seq, we integrated a lentiviral CRISPR library at a low MOI (see Example 2, "Methods and molecular design of sci-L3-WGS and sci-L3-target-seq" section for details) and recovered the DNA sequences corresponding to sgRNA spacers by sci-L3-target-seq. For 97 out of 1003 single cells, we are able to successfully recover a single integrated sgRNA. This 10% efficiency per haplotype is broadly consistent with genome coverage of 22% estimated above by projecting sequencing depth (FIG. 5G).

Note that at the molecular level, we have modified both the "sci" and "LIANTI" methods in several ways. To summarize, we: 1) changed design of the Tn5 transposon to be compatible with ligation and thus enabled more than two rounds of "sci", an approach that will potentially generalize to other single-cell assays, 2) added a loop structure of the T7 promoter to facilitate intramolecular ligation, and 3) changed the RT scheme such that we only require successful ligation at one of the two ends of the first-round barcoded molecules. Supposing that a single ligation event has 50% efficiency, this modification renders a 75% success rate at the ligation step instead of 25% (comparison shown in FIG. 5). We depict the structures of the molecules after each barcoding step in FIG. 4 and discuss rationales for these designs in Example 2, "Methods and molecular design of sci-L3-WGS and sci-L3-target-seq" section. Scalability and cost are also discussed in Example 2 and Table 2. For libraries of 100, 1000, 10,000 and 1 million single cells, we estimate the cost of sci-L3-WGS to be 14%, 1.5%, 0.26% and 0.014% of processing an equivalent number of cells with LIANTI. The use of three, rather than two, levels of combinatorial indexing can be leveraged either to increase throughput (e.g. the cost of constructing libraries for 1 million cells at a 5% collision rate with 3-level sci-L3-WGS is $8,000), or to reduce the collision rate (e.g. the cost of constructing libraries for 10,000 cells at a 1% collision rate with 3-level sci-L3-WGS is $1,500).

TABLE 2

Cost calculation of sci-L3-WGS. The current method involves three levels of indexing, which not only increases throughput and reduces barcode collisions, but also significantly reduces the cost per cell of library preparation. This is due to two reasons: 1) with 2-level indexing, one needs to start with more Tn5 transposome complexes to profile a similar number of cells, which adds to costs substantially; 2) with 2-level indexing, one is also limited to sorting a much smaller number of nuclei per well prior to IVT, RT and column purification, which also adds to costs substantially. For processing ~10k and ~1M cells, we estimate that 3-level sci-L3-WGS is nearly 400-fold and 7,000-fold less expensive per cell than LIANTI.

| | cell # | LIANTI | sci-LIANTI (2-level) | sci-L3-WGS |
|---|---|---|---|---|
| # of barcodes pre-sort (# cells sorted/well) | 100 | NA | 96 (25) | 24 × 64 (100) |
| tagmentation | 100 | 10 | 10 | 7 |
| ligation | 100 | NA | NA | 0.078 |
| gap filling | 100 | 0.21 | 0.0068 | 0.0017 |
| IVT | 100 | 5.40 | 0.22 | 0.054 |
| RT | 100 | 8.57 | 0.34 | 0.086 |
| SSS | 100 | 0.85 | 0.034 | 0.0085 |
| other (RNaseH, RNaseA, RCC-5, DCC-5) | 100 | 4.51 | 0.18 | 0.045 |
| library preparation | 100 | 24.60 | 0.25 | 0.25 |
| total cost per cell | 100 | $ 54.13 | $ 11.03 | $ 7.52 |
| total cost per library | 100 | $ 5,413 | $ 1,103 | $ 752 |
| # of barcodes pre-sort (# cells sorted/well) | 1,000 | NA | 96 (25) | 24 × 64 (300) |
| tagmentation | 1,000 | 10 | 1 | 0.7 |
| ligation | 1,000 | NA | NA | 0.0078 |
| gap filling | 1,000 | 0.21 | 0.0068 | 0.00057 |
| IVT | 1,000 | 5.40 | 0.22 | 0.018 |
| RT | 1,000 | 8.57 | 0.34 | 0.029 |
| SSS | 1,000 | 0.85 | 0.034 | 0.0028 |
| other (RNaseH, RNaseA, RCC-5, DCC-5) | 1,000 | 4.51 | 0.18 | 0.015 |
| library preparation | 1,000 | 24.60 | 0.025 | 0.025 |
| total cost per cell | 1,000 | $ 54.13 | $ 1.80 | $ 0.80 |
| total cost per library | 1,000 | $ 54,135 | $ 1,804 | $ 797 |
| # of barcodes pre-sort (# cells sorted/well) | 10,000 | NA | 96 (25) | 24 × 64 (300) |
| tagmentation | 10,000 | 10 | 0.10 | 0.07 |
| ligation | 10,000 | NA | NA | 0.00078 |
| gap filling | 10,000 | 0.21 | 0.0068 | 0.00057 |
| IVT | 10,000 | 5.40 | 0.22 | 0.018 |
| RT | 10,000 | 8.57 | 0.34 | 0.029 |
| SSS | 10,000 | 0.85 | 0.034 | 0.0028 |
| other (RNaseH, RNaseA, RCC-5, DCC-5) | 10,000 | 4.51 | 0.18 | 0.015 |
| library preparation | 10,000 | 24.60 | 0.0025 | 0.0025 |
| total cost per cell | 10,000 | $ 54.13 | $ 0.88 | $ 0.14 |
| total cost per library | 10,000 | $ 541,348 | $ 8,821 | $1,382 |
| # of barcodes pre-sort (# cells sorted/well) | 1,000,000 | NA | 96 (25) | 96 × 384 (4,000) |
| tagmentation | 1,000,000 | 10 | 0.001 | 0.0028 |
| ligation | 1,000,000 | NA | NA | 0.000047 |
| gap filling | 1,000,000 | 0.21 | 0.0068 | 0.000043 |
| IVT | 1,000,000 | 5.40 | 0.22 | 0.00135 |
| RT | 1,000,000 | 8.57 | 0.34 | 0.002 |
| SSS | 1,000,000 | 0.85 | 0.034 | 0.0002 |
| other (RNaseH, RNaseA, RCC-5, DCC-5) | 1,000,000 | 4.51 | 0.18 | 0.0011 |
| library preparation | 1,000,000 | 24.60 | 0.000025 | 0.000025 |
| total cost per cell | 1,000,000 | $ 54.13 | $ 0.78 | $ 0.0077 |
| total cost per library | 1,000,000 | $54,134,808 | $780,661 | $7,744 |

Leveraging Sci-L3-WGS for Single-Cell RNA/DNA Co-Assay

Figure 6:
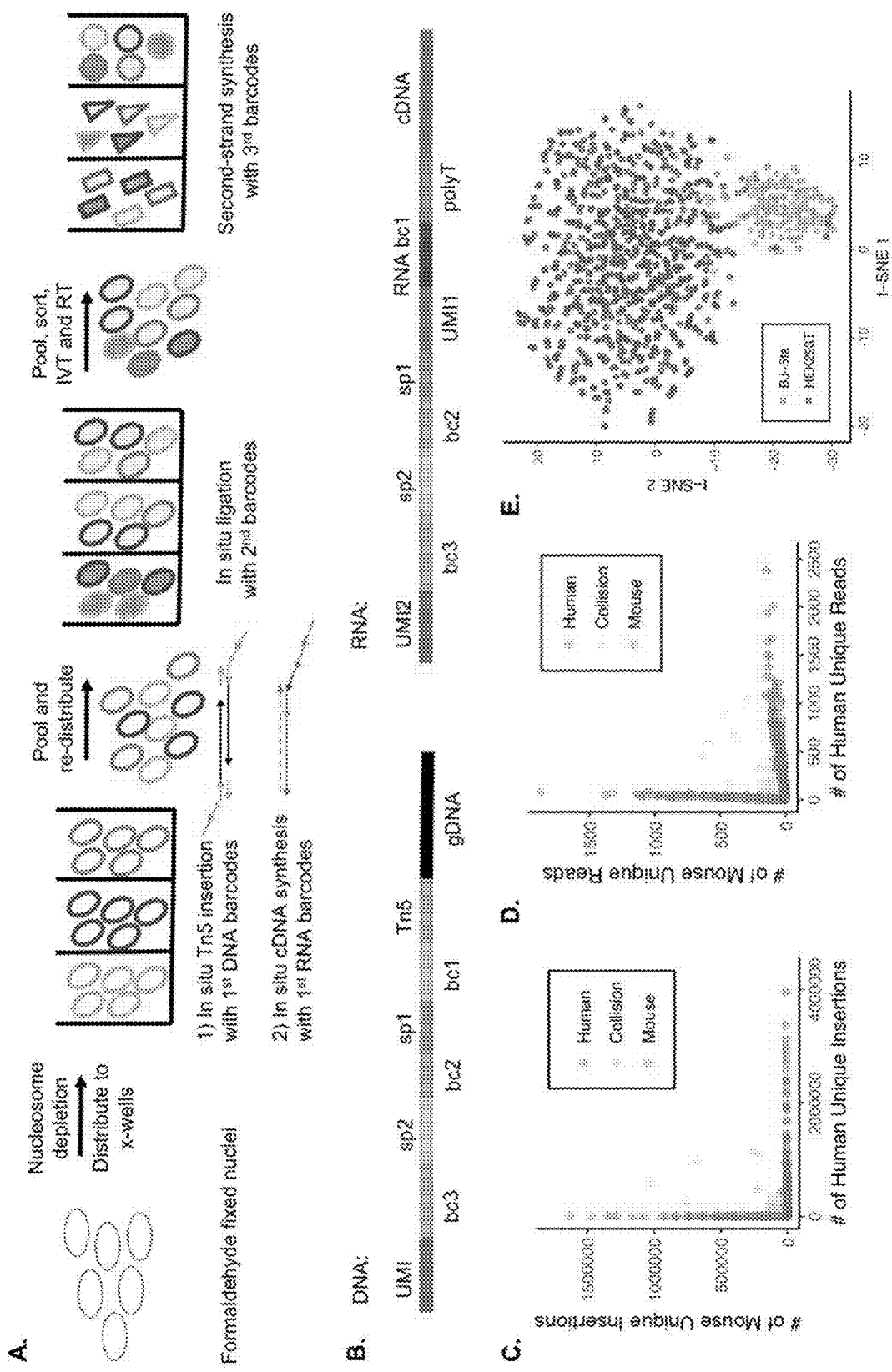
FIG. 6A-E shows Sci-L3-based RNA/DNA co-assay enables high-throughput and linear amplification jointly for genome and transcriptome from the same single cell. (A) Schematic of the sci-L3-RNA/DNA co-assay workflow with three levels of indexing. Note that both the Tn5 transposon and cDNA synthesis primer contain the same phosphorylated ligation landing pad (pink) at the 5' overhang outside of the first round barcodes. (B) Barcode structures of the resulting amplified duplexes corresponding to the genome and transcriptome (left and right respectively) that are compatible with various library preparation methods. bc, barcode; sp, spacer; gDNA, genomic DNA. (C) Scatter plot of numbers of unique Tn5 insertion sites from human and mouse cells at low and high sequencing depth plotted together, 24 bc1×64 bc2×6 bc3 sci-L3-RNA/DNA co-assay, 100 to 300 cells sorted per well. Blue, inferred mouse cells (percentage of mouse reads >95%, with median of 99.5%, n=2002); red, inferred human cells (percentage of human reads >95%, with median of 99.8%, n=2419); grey, inferred collisions (n=149, 6.6% with low and high depth combined; 5/270, 3.7% with high depth). (D) Same as in (C) for RNA. Blue, inferred mouse cells (median purity of mouse reads of 95.1%); red, inferred human cells (median purity of human reads of 91.5%); grey, inferred collisions (n=272, 12% with low and high depth combined; 7/270, 5.2% with high depth). (E) Seurat with RNA-seq signal shows distinct clusters corresponding to BJ-5ta human skin fibroblast (male) and HEK293T (female) cells. Based on presence or absence of the Y chromosome, 988/1024 cells (96.5%) are correctly assigned.

We realized that the sci-L3-WGS scheme could potentially be adapted to other aspects of molecular biology with small modifications to the protocol. To demonstrate this, we performed a proof-of-concept experiment of a sci-L3-RNA/DNA co-assay. In brief, the first round of DNA barcoding is performed by Tn5 insertion as in sci-L3-WGS, but concurrently perform a first round of RNA barcoding, tagging mRNAs via reverse transcription with a barcode and UMI-bearing polyT primer (FIG. 6A). Both the Tn5 insertion and the RT primer bear overhangs that can mediate ligation of the second round of barcodes as well as a T7 promoter, effectively enabling three-level indexing and subsequent IVT-based linear amplification in a manner largely identical to sci-L3-WGS (FIG. 6A-6B, Example 2, "Methods and molecular design of sci-L3-RNA/DNA co-assay" section). As a proof-of-concept, we mixed mouse cells together with cells from two human cell lines and performed the sci-L3-RNA/DNA co-assay. For the vast majority of cells, reads mapped either to the mouse or human genome, both for RNA (5.2% collision rate) and DNA (6.6% collision rate) (FIG. 6C-6D). Furthermore, consistent with a successful co-assay, 100% of cells were assigned the same species label by their RNA and DNA profiles. As a further check, we visualized in the human cells in t-SNE space based on their RNA profiles. As expected, they separated into two clusters. Labeling of individuals cells based on the presence or absence of a Y chromosome coherently identified the clusters as corresponding to BJ cells (male) or HEK293T cells (female) (FIG. 6E) with 96.5% accuracy.

Single Cell DNA Profiling of Mouse Germ Cells by Sci-L3-WGS

In normal mitotic cell divisions, diploid chromosomes undergo replication to generate four copies of DNA, and sister chromatids segregate apart into reciprocal daughter cells. Daughter cells receive one copy of each maternally and paternally inherited DNA sequence and almost always maintain heterozygosity at the centromere-proximal sequences (FIG. 7A). Rarely, chromosomes undergo mitotic crossover between chromosome homologs, which can sometimes result in diploid cells with loss-of-heterozygosity (LOH) at sequences centromere-distal to the crossover if the two recombined chromatids segregate into different daughter cells (FIG. 7B-C).

In meiosis, sister chromatids first co-segregate into the same daughter cell, and homologs segregate into reciprocal daughter cells in the Meiosis I ("MI") stage, also known as "reductional segregation", resulting in 2C cells (DNA content of an unreplicated diploid cell) with loss-of-heterozygosity (LOH) at the centromere-proximal sequences (FIG. 7D-E). For the successful reductional segregation of chromosomes in MI (FIG. 7D), crossovers initiated by Spo11-catalyzed double strand breaks (DSBs) (Baudat et al., 2000; Keeney et al., 1997; Romanienko and Camerini-Otero, 2000), provide the link and necessary tension (Hong et al., 2013) between chromosome homologs. Rarely, chromosomes will segregate in a meiotic fashion without any inter-homolog crossover, resulting in uniparental disomy (UPD). After MI, these 2C cells then undergo mitosis-like chromosome segregation in Meiosis II ("MII"), also termed "equational segregation", such that sister chromatids segregate apart to form 1C gametes (FIG. 7E). Below, as our study is primarily focused on MI, we refer to meiotic/reductional segregation during MI, where sister chromatids segregate together, as "reductional segregation", and mitosis-like/equational segregation during MI, where sister chromatids segregate apart, as "equational segregation".

To date, most work on the relationship between crossover position and chromosome segregation has been performed by imaging (Wang et al., 2017a, 2017b), which fails to fully characterize the underlying genomic sequences that are prone to meiotic crossover. Several assays enable detailed mapping of meiotic DSB hotspots (Lange et al., 2016; Smagulova et al., 2011, 2016), but these assays do not directly map meiotic crossovers. Assays that do dissect crossover vs. noncrossover at a fine scale are restricted to a few hotspots (Cole et al., 2014). Consequently, we know much less about the relationship between crossovers and chromosome-scale features such as replication domains than we do about meiotic DSB hotspots (Baudat et al., 2013; Choi and Henderson, 2015; Yamada et al., 2017). Genome-wide meiotic crossover maps have been generated by mapping tetrads in yeast (Mancera et al., 2008; Zhang et al., 2017), single human sperm and complete human female meioses (Hou et al., 2013; Lu et al., 2012; Ottolini et al., 2015; Wang et al., 2012). With the exception of the studies of human female meiosis, which altogether analyzed 87 complete meioses (Hou et al., 2013; Ottolini et al., 2015), most crossover maps are limited in at least three respects: 1) mature 1C gametes are analyzed where the cells have completed both rounds of meiotic division, which prevents direct observation of the more informative intermediate 2C cells to evaluate whether and how often chromosomes undergo reductional vs. equational segregation during MI (FIG. 7); 2) abnormal cells are selected against due to their failure to proceed to the mature gametic state; 3) analyses by single sperm or oocyte sequencing are limited in throughput and to a few hundred cells at the most, and as such could miss out on rare events. Even for fertile crosses, the number of offspring that can be reasonably generated and genotyped is quite limited (Liu et al., 2014).

To address all of these limitations at once, we applied sci-L3-WGS to the infertile offspring of an interspecific cross (female *Mus musculus domesticus* C57BL/6 ('B6')× male *Mus spretus* SPRET/Ei (subsequently 'Spret')) as well as the fertile offspring of an intraspecific hybrid (female B6×male *Mus musculus castaneous* CAST/Ei ('Cast')). By sequencing sperm with a highly scalable technology, we are able to map an unprecedented number of crossover events for a mammalian system, and in both infertile and fertile hybrids. Furthermore, by exploiting the throughput of sci-L3-WGS to recover profiles from rare 2C secondary spermatocytes, we can also assess crossover and chromosome mis-segregation simultaneously from the same single cells.

Figure 8:
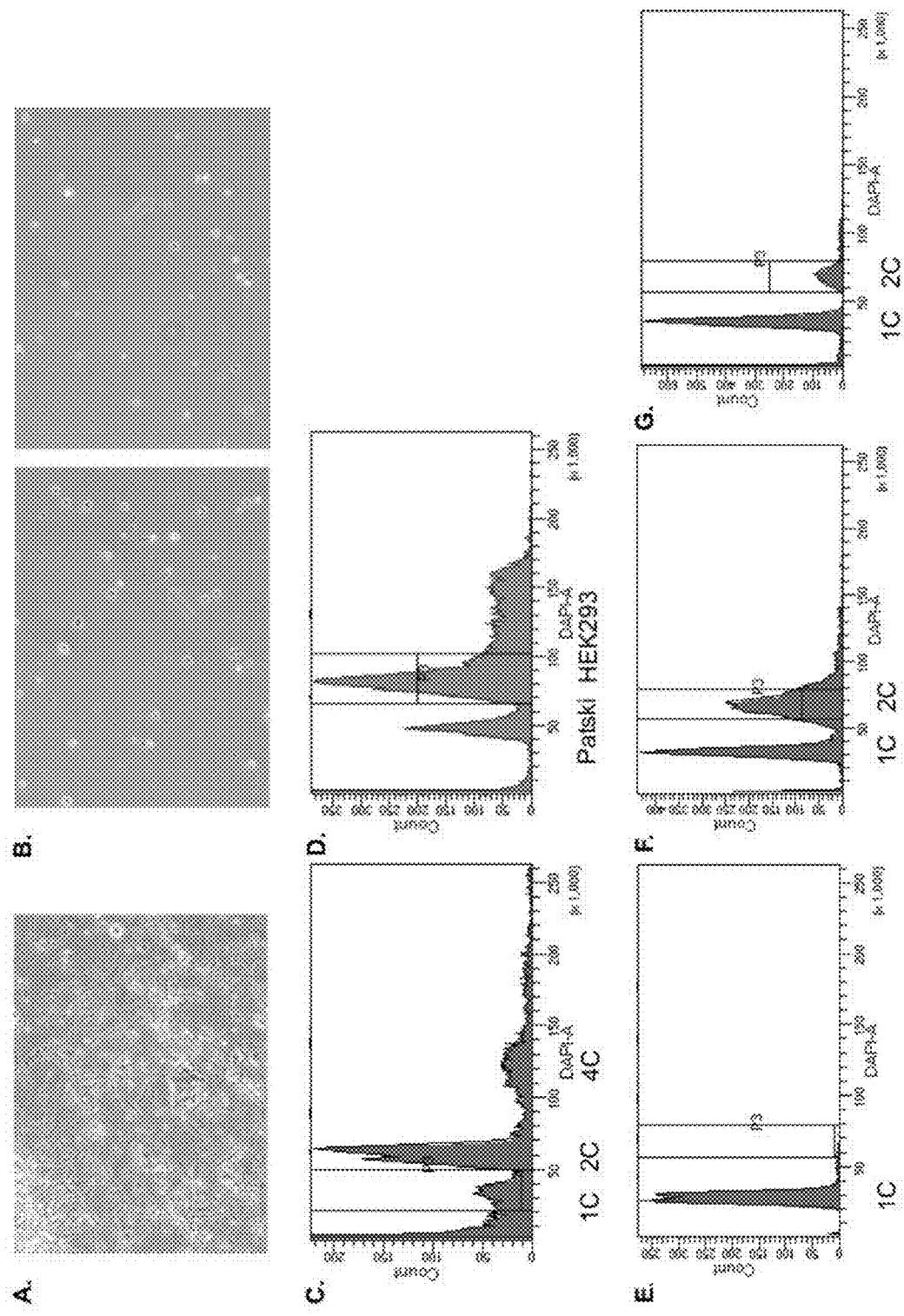
FIG. 8A-G shows sperm and sperm precursors and their ploidy by FACS. (A) Visualization of B6 sperm. (B) Visualization of (B6×Spret) F1 sperm. We observe low numbers of round germ cells of unknown ploidy, and extremely few morphologically mature sperm (arrows). (C) (B6×Spret) F1 sperm and sperm precursors, isolated from the epididymis, unexpectedly include a large proportion of 2C cells. DAPI voltage of 375. (D) HEK293/Patski mix, DAPI voltage of 350. The Patski peak (2C) is slightly shifted to the left relative to the 2C peak in (C) due to the lower DAPI voltage. (E) (B6×Cast) F1 sperm, isolated from the epididymis, consist almost entirely of 1C cells. DAPI voltage of 375. (F) (B6×Cast) F1 sperm precursors, pre-sorting for 2C cells from dissociated testes; large numbers of 1C cells are still present. DAPI voltage of 375. (G) (B6×Cast) F1 sperm and sperm precursors at the FACS step during sci-L3-WGS (after two rounds of barcoding), still consist mostly of 1C cells. Based on proportions of contaminated 1C nuclei in pre-sorted 2C nuclei from (F), we estimate the proportion of tagmented nuclei that are 2C to be 18%, a 7.2-fold enrichment over the 2.5% of 2C nuclei in homogenized testes. We sorted from the 2C population (~15.4% of all the cells, similar to the 18% estimated for the tagmentation step). DAPI voltage of 375.

Unlike inbred males as well as (B6×Cast) F1 males, whose epididymides store millions of mature sperm, the epididymides of (B6×Spret) F1 males (Berletch et al., 2015) contain extremely few morphologically mature sperm and limited numbers of round germ cells of unknown ploidy (FIG. 8A-B). Interestingly, we observed a much higher fraction of 2C cells during FACS (FIG. 8C-D) than would be expected for a 'normal' epididymis, which is dominated by 1C sperm. The number of cells recovered and their estimated ploidy are listed in Table 3. In contrast and as expected, the epididymides of (B6×Cast) F1 males contained almost entirely 1C sperm (FIG. 8E). For this cross, we therefore sorted 1C and 2C cells from dissociated testes (FIG. 8F).x

TABLE 3

Number of cells recovered and cell ploidy, (B6 × Spret) epididymides. Note that we did not make sequencing libraries for all the cells sorted; for example, 2C libraries in Exp1 only contain a subset of cells. We also gated widely for 1C cells (up to DAPI signal of 58 for certain wells), and due to the abundant 2C cells in this cross, we can only enrich for 1C cells to about 51-55%.

|  | Exp1 (yi186, yi187, yi188) | Exp2 (yi190, yi192, yi193) |
| --- | --- | --- |
| 1C (FACS) | 649 | 2060 |
| 1C (seq lib) | 649 (yi188) | 150 (yi190) |
|  |  | 1910 (yi193) |
| 2C (FACS) | 6650 | 600 |
| 2C (seq lib) | 900 (yi186) | 150 (yi190) |
|  | 450 (yi188) | 450 (yi193) |
| 4C (FACS) | 200 | NA |
| 4C (seq lib) | 200 (yi186) | NA |
| dilution | 3600 | 1837 |
| dilution (seq lib) | 720 (yi187) | 1837 (yi192) |
| total 1C recovered/ expected in seq lib | 439/793 | 1224/2417 |
| total 2C and 4C recovered/ expected in seq lib | 2250/2126 | 3015/2080 |

For cells from F1 males from both the (B6×Spret) and (B6×Cast) crosses, we proceeded with linear amplification, second strand synthesis to add the third-round barcode, library preparation, and sequencing (details in Example 2, "Setup of sci-L3-WGS experiment in (B6×Spret) cross and (B6×Cast) cross" section). An important point is that although 1C and 2C cells can be distinguished informatically, their relative abundance still impacts our analysis. Specifically, in the (B6×Spret) cross, 1C cells are rare such that any "doublets" (e.g. two 1C cells that are stuck together or that incidentally receive the same barcodes) do not substantially contribute to the 2C population. In contrast, in the (B6×Cast) cross, the majority of cells are 1C (~85%, FIG. 8G) despite enrichment, such that there may be many 1C doublets that mimic 2C cells. We discuss how to informatically distinguish 1C doublets from bonafide 2C cells in later sections.

M2 Cells Exhibit Clustered Reductional or Equational Chromosome Segregation

Chromosome Segregation in M2 Cells from the Infertile (B6×Spret) Cross

We first sought to analyze meiosis in cells from the epididymides of infertile (B6×Spretus) F1 males, obtained as described above. Across two sci-L3-WGS experiments, we profiled the genomes of 2,689 (92% of 2,919 sorted cells with >10 k raw reads) and 4,239 (94% of 4,497 sorted cells with >30 k raw reads) single cells. The number of uniquely mapping reads are shown in FIG. 5F. At a sequencing depth of 1.6× and 1.4× for the two libraries (details in FIG. 5), we obtained a median of ~70 k and ~144 k unique Tn5 sites per cell, corresponding to 0.7% and 1.4% median genome coverage, respectively.

Figure 9:
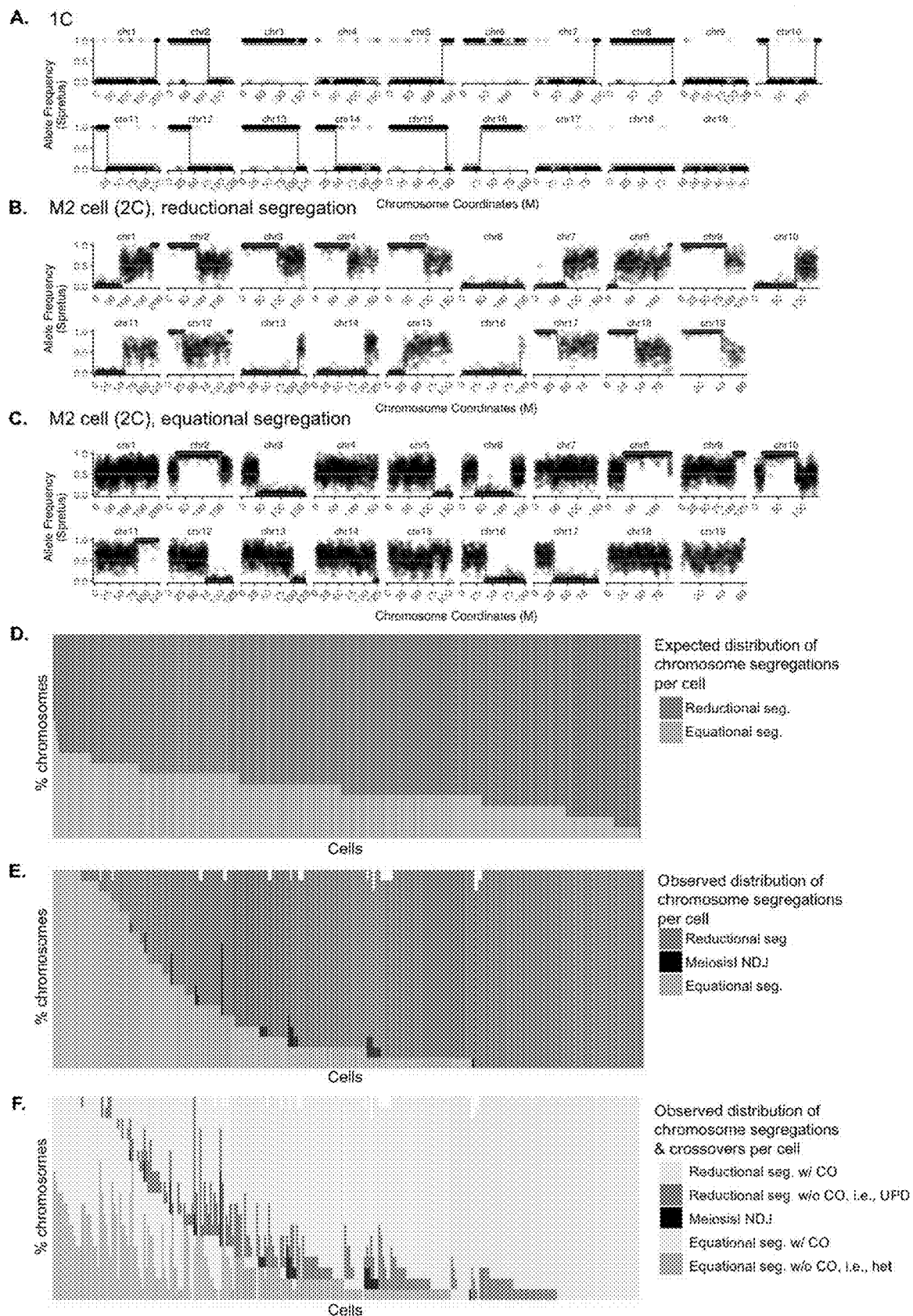
FIG. 9A-F shows sci-L3-WGS of the interspecific hybrid mouse male germline reveals numerous examples of non-independent equational segregation in MI. In (A), (B) and (C), red line depicts fitted crossover transition via HMM. Centromere is located at the leftmost for picture of each chromosome. (A) Example crossover plot for a 1C cell. Grey dot has a value of 1 for Spret allele and 0 for B6 allele. In (B) and (C), grey dot shows allele frequency of Spret averaging 40 SNP sites. (B) Example LOH plot for an M2 cell with reductional segregation (see also FIG. 7D). LOH is present at the centromere-proximal region of the crossover sites. (C) Example LOH plot for an M2 cell with equational segregation (see also FIG. 7B). LOH is present at the centromere-distal region of the crossover sites, unlike in (B). (D-F) Number of reductionally (red, pink, black) and equationally (blue, green) segregated chromosomes for each of the M2 cell. Each column represents one single M2 cell (19 chromosomes per cell, distributed as indicated by colors). (D) Expected distribution of reductional vs. equational segregation based on the binomial distribution and assuming the probability of reductional segregation p equals 0.76, the MLE from the observed data. (E) Observed data in M2 cells. In rare cases (27/5,548 chromosomes), we were not able to distinguish reductional vs. equational segregation due to sparse SNP coverage (white space at the top of the panel). Black bar depicts MI nondisjunction (NDJ, 40 chromosomes in total) where we observed 0 or 4 copies of the chromatids. Note that NDJ is considered as reductional segregation because the sister chromatids segregate together. (F) Same as (E) but further broken down by the number of chromosomes with or without crossovers (abbreviated as "CO"). Cells are sorted first by the number of equationally segregated chromosomes (light green and blue, in descending order) and then by the number of observed equationally segregated chromosomes without crossover (blue, in descending order).

To identify crossover breakpoints, we implemented a hidden Markov model (HMM) that relied on high-quality reads that could clearly be assigned to B6 vs. Spret (see Example 2, "Methods of bioinformatic and statistical analyses" section). We characterized crossovers in 1,663 1C cells, a representative example of which is shown in FIG. 9A. In addition, we searched ~5,200 2C cells for crossover events. Although most of these 5,200 could simply be somatic cells, to our surprise, we identified 292 2C cells with a significant number of crossovers, which we term "M2 cells" (FIGS. 9B and 9C). Even more surprisingly, a substantial proportion of these cells exhibited equational, rather than reductional, segregation.

After a crossover occurs between two chromosome homologs, if the chromosome segregates in a reductional fashion, the region between the centromere and the position of crossover will become homozygous, whereas heterozygosity will be maintained downstream of the crossover (FIG. 7D). However, if the chromosome segregates in an equational fashion, LOH is observed centromere-distal to the crossover if the recombined chromatids segregate apart (FIG. 7B). We show one example of an M2 cell whose chromosomes undergo the expected reductional segregation in FIG. 9B (note consistent homozygosity between centromere and point of crossover), and one example of an M2 cell whose chromosomes unexpectedly undergo equational segregation in FIG. 9C (note consistent heterozygosity between centromere and point of crossover). In total, across 292 M2 cells, we observed 4,162 examples of chromosomes undergoing reductional segregation, among which 3,740 harbor crossovers (90%), and 1,310 examples of chromosomes undergoing equational segregation, among which 636 harbor crossovers (49%). Of note, however, the number of crossover events in chromosomes that segregated equationally may be higher, as we cannot identify a subset of crossover outcomes (FIG. 7C); meanwhile, we can detect all crossovers for reductionally segregated chromosomes.

Although we observe many examples of cells where some chromosomes exhibit reductional segregation and other chromosomes exhibit equational segregation, the segregation pattern of individual chromosomes within M2 cells does not appear to be independent. If chromosomes in each cell chose reductional vs. equational segregation independently, we would expect a binomial distribution of reductionally and equationally segregated chromosomes, centered on the maximum likelihood estimate (MLE) of the probability, p, of reductional segregation (p=0.76 from the data, 4162/5472), with roughly three quarters of chromosomes segregating reductionally and one quarter segregating equationally (FIG. 9D). However, among the 292 M2 cells that we profiled, we observe 202 cells that have at least 15 chromosomes that segregated in a reductional fashion, and 38 cells that have at least 15 chromosomes that segregated in an equational fashion (FIG. 9E; this contrasts with 148 and 0 cells expected, respectively, under assumption of independence; p=4e-23, Fisher's exact test). That individual M2 cells are biased towards overwhelmingly undergoing reductional or equational segregation suggests the possibility of a cell-autonomous global sensing mechanism for deciding whether a cell proceeds with meiosis or returns to mitosis.

We can further classify cells by whether the chromosomes in M2 cells have a crossover (FIG. 9F). Reductionally segregated chromosomes appear to have more crossovers (pink in FIG. 9F) than equationally segregated chromosomes (green in FIG. 9F). However, unlike in reductionally segregated chromosomes where we can detect all the crossovers as centromeric LOH, equationally segregated chromosomes only have LOH if the two recombined chromatids segregate apart into reciprocal daughter cells (FIG. 7B). If instead recombined chromatids co-segregate, heterozygosity will be maintained throughout the chromosome despite the undetectable linkage switch (FIG. 7C). In FIG. 9F, the ratio of having (shown in green) vs. not having (shown in blue) an observable LOH in equationally segregated chromosomes is roughly 1:1. This could either mean that equationally segregated chromosomes have a 50% chance of segregating recombined chromatids together, if those completely heterozygous chromosomes (shown in blue) do have a linkage switch; or alternatively that equationally segregated chromosomes always segregate recombined chromatids apart, and the crossover frequency is reduced by half compared to reductionally segregated chromosomes.

Segmental or whole-chromosome LOH are known to be rare in mammalian mitotic cells. Nevertheless, to rule out a mitotic origin of such events, we examined such events in the Patski cell line, which is a spontaneously immortalized cell line derived from female (B6×Spret) F1 mouse We analyzed 1,107 single cells from Patski with sci-L3-WGS, among which we found an average of 0.36 UPD chromosomes and 0.098 segmental LOH events per cell, a much reduced rate compared to M2 cells. We also note that these events are not necessarily independent. For example, a UPD emerging early in the passage of the cell line can be shared in a large portion of descendant cells, such that the rate of independent LOH events is likely even lower. The distribution of these events (relatively uniform for Spretus-derived chromosomes and non-uniform for B6-derived chromosomes) is plotted in FIG. 10F.

Taken together, the contrast between the low rate of mitotic LOH (expected) and the relatively high rate of 2C cells exhibiting equational segregation (unexpected), both measured by the same technology, confirms that the latter are very unlikely to correspond to somatic cells. In the next section, by analyzing the fertile (B6×Cast) cross, we furthermore show: 1) that the whole genome equational segregation events observed here are not an artifact of doublets of two 1C cells, and 2) that such segregation events also occur in the fertile intraspecific hybrid, although of a reduced rate.

Chromosome Segregation in M2 Cells from the Fertile (B6×Cast) Cross

We wondered whether equational segregation also occurs during MI in the fertile progeny of intraspecific (B6×Cast) F1 males. As shown above, the epididymides from this cross almost entirely consist of 1C mature sperm; we therefore enriched for 2C secondary spermatocytes from whole testes. We then performed sci-L3-WGS on cells from both the epididymides and the testes.

In a first sci-L3-WGS experiment on this cross, primarily performed for quality control to assess recovery and barcode collision rates, we distributed 1C round spermatids evenly and only sorted for 1C cells after two rounds of barcoding. The doublets, identified by virtue of the fact that they are non-1C, allow us to quantify the rate of barcode collisions. Among 2,400 sorted cells (200/well), we recovered 2,127 (89%) with >7,000 reads per cell; 2,008 of these are 1Cs with meiotic crossovers, indicating a barcode collision rate of 5.5%. At a sequencing depth of 1.06×, we obtained a median of ~60 k unique Tn5 insertions per cell, corresponding to ~0.6% median genome coverage.

In a second sci-L3-WGS experiment on this cross, we tagmented 1C round spermatids from the testes ("barcode group 1"), 2C cells from the testes ("barcode group 2"; contaminated with large numbers of 1C spermatids as shown in FIG. 8F), and 1C mature sperm from the epididymis ("barcode group 3", Example 2, "Setup of sci-L3-WGS experiment in (B6×Spret) cross and (B6×Cast) cross" section), in separate wells during the first round of barcoding. As a further enrichment, during the FACS step of sci-L3-WGS, for a subset of wells, we specifically gated for 2C cells (15.5% of all cells, FIG. 8G). At a sequencing depth of 1.09×, we obtained a median of ~94 k unique Tn5 insertions per cell, corresponding to ~0.9% median genome coverage.

In total, we recovered 3,539 1C and 1,477 non-1C cells from this second sci-L3-WGS experiment. Interestingly, >97% of the 1C cells derive from barcode groups 1 (n=1, 853) and 2 (n=1,598) rather than group 3 (n=88), indicating that mature sperm from the epididymis are not well recovered by sci-L3-WGS. This suggests that the 1C cells recovered from (B6×Spret) cross above are likely also not from mature sperm but rather from round spermatids, consistent with the low number of sperm with mature morphology in FIG. 8B.

The 1,477 non-1C cells derived from both barcode group 1 (n=1,104; presumably doublets of 1C round spermatids) and barcode group 2 (n=373; presumably a mixture of bonafide M2 cells and 1C doublets). To identify a signature of 1C doublets, we examined the profiles of non-1C cells from barcode group 1 (which was specifically pre-sorted for 1C content, such that it is unlikely to contain bonafide M2 cells). The centromere-proximal SNPs of 1C cells that have completed both rounds of meiotic divisions should either be B6 or Cast-derived. For 1C doublets, these regions have an equal chance of appearing heterozygous or homozygous. Therefore, within any given 1C doublet, the number of chromosomes that appear to have segregated equationally, as well as the number that appear to have segregated reductionally, should follow a binomial distribution with n=19 and p=0.5. Indeed, this is what we observe for 1C doublets from barcode group 1 (p=0.53 for distribution of proportions of equationally segregated chromosomes deviating from a binomial (19, 0.5), Chi-squared test, FIG. 11A-B). In fact, there are only 11 1C doublet cells with at least 15 chromosomes that appear to segregate in a consistent fashion, whether equationally or reductionally.

In contrast, non-1C cells from barcode group 2 exhibit a very different distribution. Among 373 such cells, 258 are similar to the 1C doublets of barcode group 1 in that they have similar numbers of chromosomes with equational or reductional segregation patterns. The remaining 115 cells are biased, with at least 15 chromosomes segregating in a consistent fashion, whether equationally or reductionally (FIG. 11C-E; 115/373 for barcode group 2 vs. 11/1,104 for barcode group 1; p=3e-70, Chi-squared test), with many exhibiting completely equational (n=6) or completely reductional (n=91) patterns.

Finite Mixture Model for Fitting the Three Populations of Non-1C Cells

Figure 12:
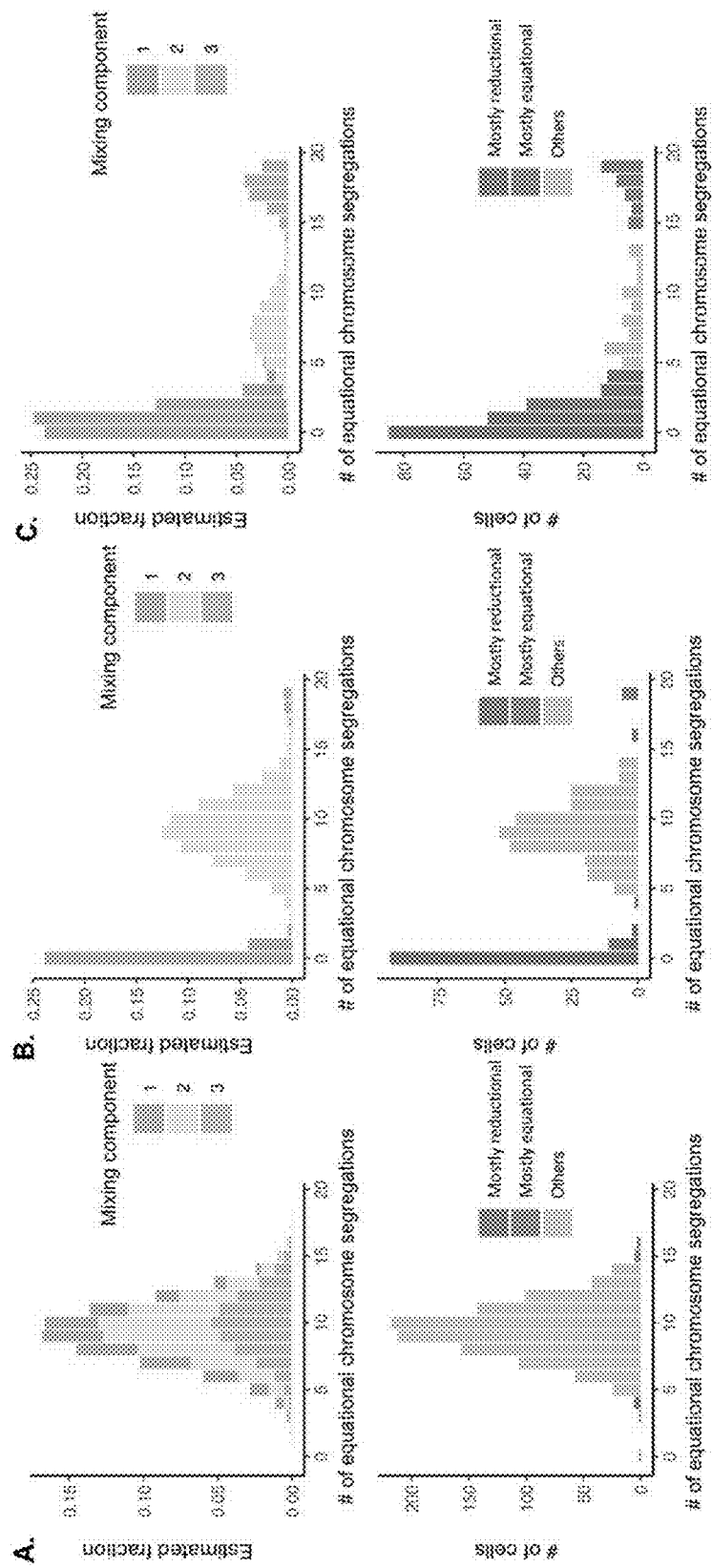

To consider this more formally, we fit the data from each experiments to a Bayesian finite mixture of three binomial distributions. Details are provided in Example 2, "Finite mixture model for fitting the three populations of non-1C cells" section and FIG. 12, with key conclusions summarized here. First, the non-1C cells from the testes of intraspecific (B6×Cast) F1 males (i.e. from barcode group 2) are estimated to include subsets of cells segregating reductionally (28%) vs. equationally (2%), as well as likely 1C doublets (69%) (FIG. 12B). The proportions differ for M2 cells from the interspecific (B6×Spret) F1 males, which are estimated to include subsets of cells segregating reductionally (66%) vs. equationally (14%), as well as likely 1C doublets (20%) (FIG. 12C). These analyses support the conclusion that the infertile (B6×Spret) cross has a much higher proportion of cells that are biased towards equational rather than reductional segregation.

Distribution of Meiotic Crossovers at the Chromosomal Level

We next sought to investigate the genomic correlates of crossover events. Altogether, we analyzed 1,663 1C cells harboring 19,601 crossover breakpoints and 240 M2 cells with 4,184 crossover breakpoints from the (B6×Spret) cross, and 5,547 1C cells harboring 60,755 crossover breakpoints and 115 M2 cells with 2,246 crossover breakpoints from the (B6×Cast) cross. To our knowledge, this is an unprecedented dataset with respect to the number of crossover events identified in association with mammalian meiosis.

The high-throughput nature of sci-L3-WGS allowed us to analyze large numbers of premature germ cells and identify the rare cell population that has completed MI but not MII, and thus observe meiotic crossover and chromosome mis-segregation events in the same cell. In comparing an infertile, interspecific (B6×Spret) hybrid with a fertile, intraspecific (B6×Cast) hybrid at a chromosomal level, we observe the following defects in MI: 1) the proportion of M2 cells that have at least one crossover on all 19 autosomes is reduced from ~2/3 in (B6×Cast) to ~1/2 in (B6×Spret); 2) the average number of crossovers per M2 cell is lower in (B6×Spret), but the average number of crossovers per 1C cell is higher; 3) crossover interference is weaker in (B6× Spret), where the median distance between adjacent crossovers is reduced from 97 Mb to 82 Mb; 4) in (B6×Spret) M2 cells, crossovers tend to occur in the middle half of each chromosome arm, in contrast with 1Cs of both crosses as well as (B6×Cast) M2 cells, where they favor the most centromere-distal quartile; 5) among M2 cells with biased equational or reductional chromosome segregation, (B6× Spret) exhibits a significantly higher proportion (38/240) of whole-genome equational segregation than (B6×Cast) (8/115); 6) among M2 cells whole-genome reductional segregation in MI, the average number of sporadic equational segregations (also termed reverse segregations (Ottolini et al., 2015)) is increased from 0.2 to 1.1. These findings suggest mechanisms that could contribute or reflect underlying factors that contribute to the infertility of (B6×Spret) F1 males, including defects in crossover formation and positioning, compromised mechanisms for ensuring at least one crossover per chromosome, and an increase in both sporadic and whole genome equational segregation. Details of these analyses are presented in FIG. 10, FIG. 13, and FIG. 14. and Example 2, "Distribution of meiotic crossovers at the chromosomal level" section.

Distribution of Meiotic Crossover Events in Relation to the Landscape of the Genome Genomic Features Regulating Crossover Hotness To evaluate the distribution of crossovers at a finer scale, we collapsed all crossover events to generate "hotness maps" along each murine chromosome. We first compared these maps with the single-stranded DNA sequencing (SSDS) map (Brick et al., 2018; Smagulova et al., 2011, 2016) and the Spo11 oligonucleotide-complex map (Lange et al., 2016), which identify meiotic DSB hotspots at the highest resolution (FIG. 15A). DSB maps in the B6 strain from these two mapping methods strongly correlate with each other along 100 kb windows (rho=0.87, p<2e-308). Although our 1C and M2 cell crossover pileups correlate with one another (rho=0.67 for (B6×Spret) cross and rho=0.55 for (B6×Cast) cross, p<2e-308 for both, FIG. 15B-C), both deviate from the DSB maps. Of relevance, the PRDM9 gene, a major player for hotspot specification, has evolved to bind different motifs between diverged mouse strains, even between subspecies of mice (Davies et al., 2016; Gregorova et al., 2018). We discuss its potential effect on differences between the two crosses in Example 2, "Effect of PRDM9 on crossover hotness" section.

Figure 16:
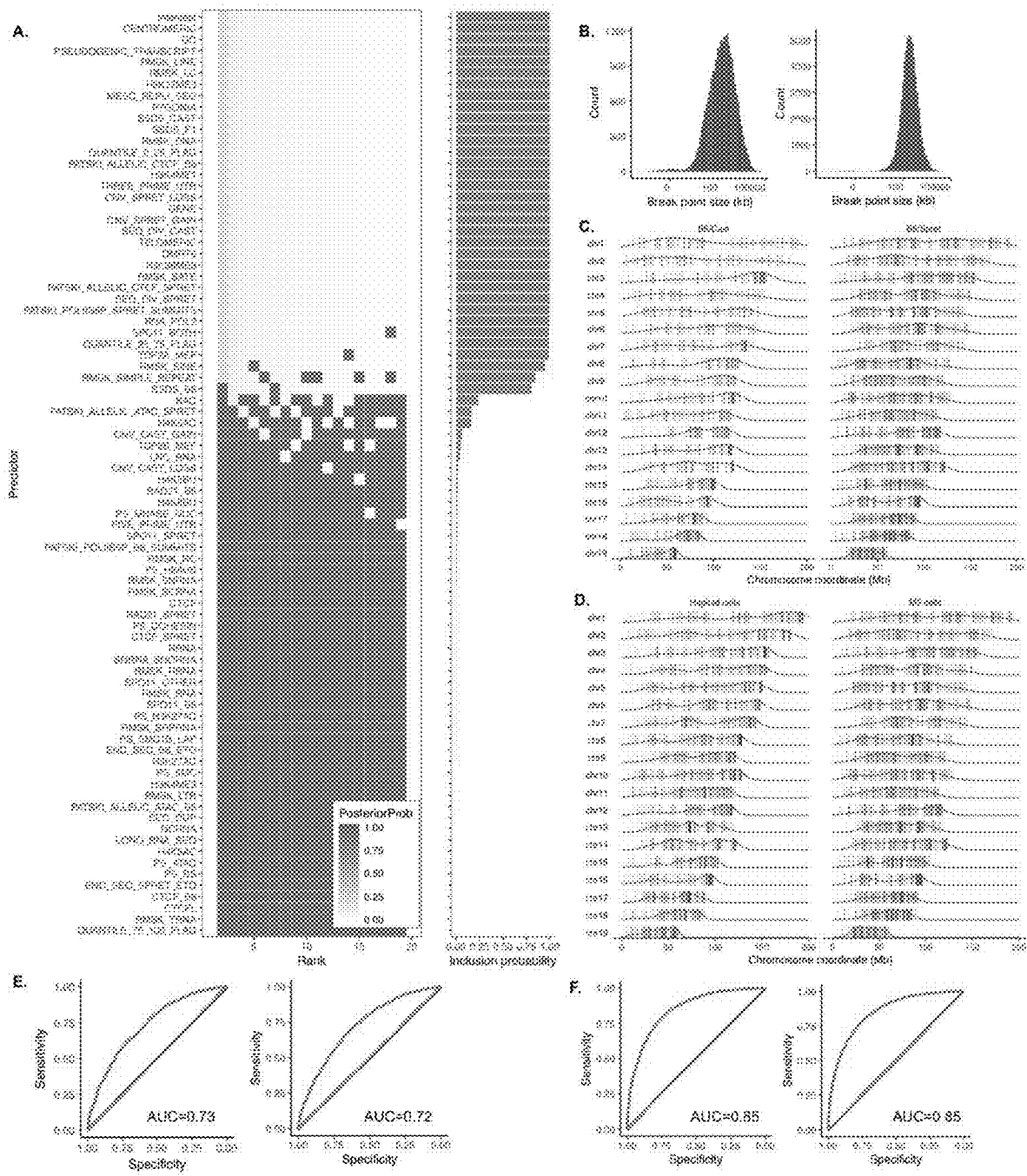

Only 10% of meiotic-specific DSBs are repaired as crossovers. We next looked at what factors beyond Spo11 breaks contribute to crossover formation by building a linear model with Bayesian Model Averaging (BMA) (Clyde et al., 2011). As applied here, BMA takes a weighted average of the more than 15,000 variable selection models explored and weights them by the posterior probability of each model, which accounts for uncertainty in model selection, unlike some other variable selection techniques like Lasso regression. We quantified a marginal inclusion probability (MIP) for ~80 potentially explanatory variables. Features that are known to be relevant to meiotic crossovers such as Spo11 break sites, GC content, etc. are included in almost all the models with high probabilities (FIG. 16A, FIG. 17); for example, regions with high GC content are hotter for crossover formation, We also found a few more features that have not previously been implicated in meiotic crossovers, such as specific families of repeats and chromatin marks, and particularly early replication domains. Correlation matrices between crossover hotness and all the features are plotted in FIGS. 18-19 for each crosses. Features used and summaries of the simple linear models and BMA are included in. The breakpoint resolution (median ~150 kb for (B6×Spret) and ~250 kb for (B6×Cast); FIG. 16B) is on par with previous efforts to map meiotic crossovers by single cell sequencing (150-500 kb) (Lu et al., 2012; Ottolini et al., 2015; Wang et al., 2012); however, the greater library complexity afforded by sci-L3-WGS enabled us to achieve this with a much lower sequencing depth.

Many of the features that correlate with crossover formation are consistent between the (B6×Spret) and (B6×Cast) crosses, but some are not. For example, the positional biases of crossover formation appear to be different. In 1C cells of both crosses, as well as in M2 cells in the (B6×Cast) cross, crossovers are underrepresented within 10 Mb from the centromere and rather tend to occur near the telomere in the rightmost positional 'quartile' (FIG. 18). However, in M2 cells in the (B6×Spret) cross, crossovers are underrepresented near the centromere as well as near the telomere, and rather tend to occur in the middle quartiles (FIG. 19). This trend holds in the linear models where we account for contributions from all other features.

Figure 20:
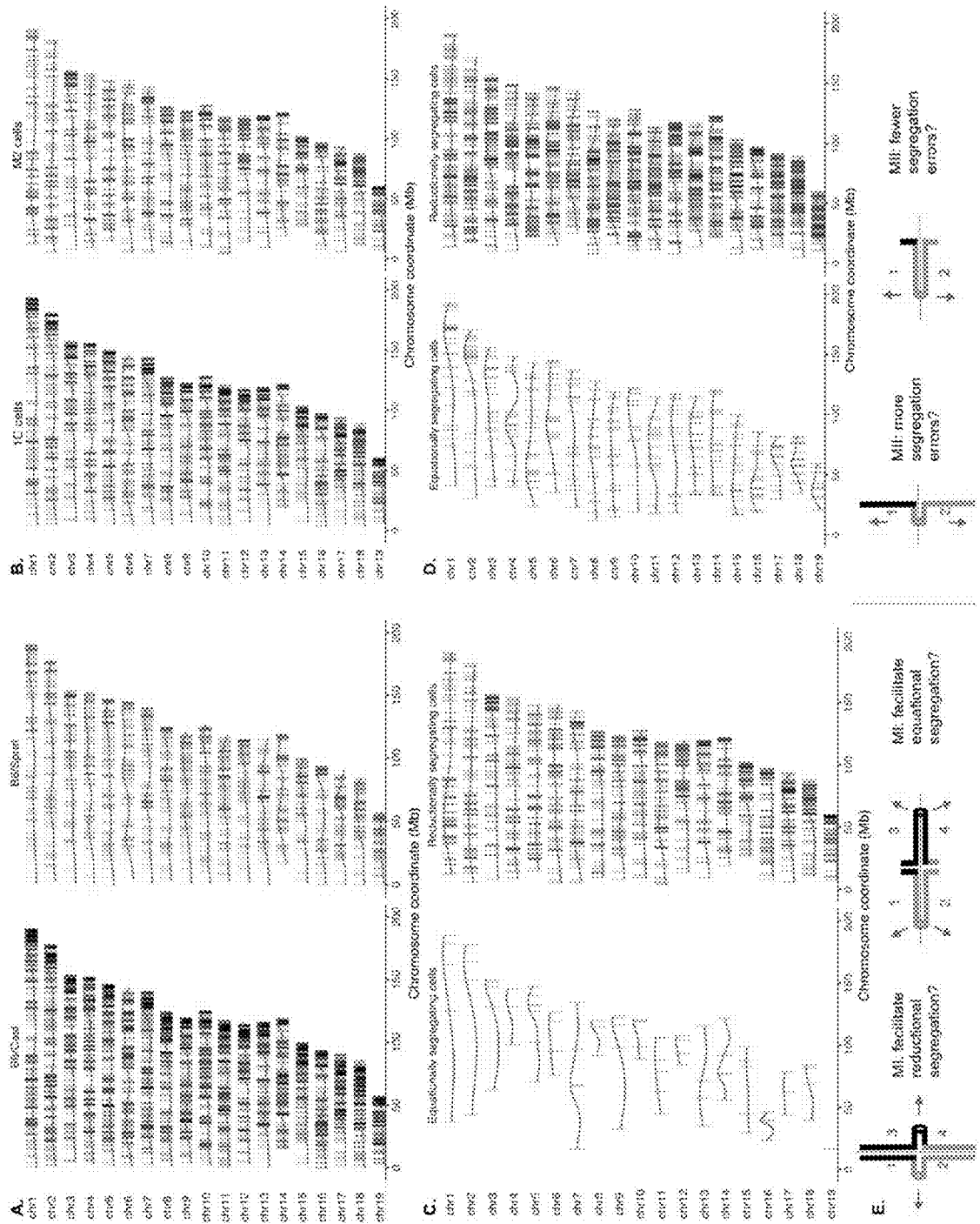

The position of a crossover can greatly affect the amount of tension enforced between chromosome homologs, which in turn facilitates proper chromosome segregation. We therefore explored this in more detail by taking only the rightmost crossover for each chromosome in each cell and examining its position along the chromosome arm in each cross (de Boer et al., 2015). Accounting for inter-chromosome variability with a linear mixed effect model, we estimate that the positions of the rightmost crossovers in the (B6×Spret) cross are on average 1.6 Mb more centromere-proximal than those in the (B6×Cast) cross in 1C cells (FIG. 20A, p=1e-13, F test), but are 5.5 Mb more centromere-proximal in the M2 cells (FIG. 16C, p=2.2e-15). Note that the rightmost crossovers in the M2 cells tend to be more centromere-proximal than those in the 1C cells in both crosses, but to a greater extent in the (B6×Spret) cross (FIG. 16D) than in the (B6×Cast) cross (FIG. 20B). These differences suggest that a subset of M2 cells in the (B6×Spret) cross whose crossovers occur too close to the centromere may fail to mature into 1C cells, possibly due to defects in MII segregation. Similarly, although of limited number of events, we have also compared the positions of crossovers in M2 cells that have biased chromosome segregation and found that in both crosses, crossovers in cells with biased equational segregation are more centromere-distal than those in cells with biased reductional segregation, with differences of 13.7 Mb in the (B6×Cast) cross (p=4e-15) and of 8.7 Mb in the (B6×Spret) cross (p=6e-14) (FIG. 20C-D). This suggests possible MI segregation defects in cells that have crossovers too close to the telomere. We propose a tentative model to explain this observation in FIG. 20E.

Cell Heterogeneity in Terms of Crossover Break Points

Although 1C and M2 cells appear broadly similar in the crossover pileups (FIG. 15), we wondered whether there was any structure to the features that influence crossover distributions in subsets of single cells. To explore this, we aggregated crossover-related information for each single cell for each of 78 features (Example 2, "Methods of bioinformatic and statistical analyses" section). We then used principal component analysis (PCA) on a matrix with each row as one single cell and each column as one summarized feature value. For the (B6×Spret) cross, the first two principal components (PCs) capture 26% of the variance, and for the (B6×Cast) cross, PC1 and PC3 capture 17% of the variance. In both crosses, the 1C and M2 cells are separated into two clusters by these PCs. In FIG. 21 and FIG. 22 we plot each feature projected on these PCs. The chromosomal distribution of crossovers, uniparental chromosomes and positions of crossovers in chromosome quartiles are the features that appear to drive the separation of 1C and M2 cells.

Predicting Crossover Tracts from Genomic Features

Finally, we sought to exploit the large number of events observed here to construct a predictive model of crossover locations. Specifically, we built a linear model of binary response with 1 being crossover tracts and 0 being a random tract sampled from the genome from the same tract length distribution (details in Example 2, "Methods of bioinformatic and statistical analyses" section). Using the same 76 features as in the BMA analyses, we can predict crossover tracts on held-out data with an average Receiver Operator Curve (ROC) Area Under Curve (AUC) of 0.73 for (B6× Spret) cross. With a subset of 25 variables of high inclusion probability (MIP>0.5) identified by BMA, we achieve a similar average AUC of 0.72 (FIG. 16E). Similarly, for the (B6×Cast) cross, we achieve an average AUC of 0.85 when all features or a subset of 25 features with MIP >0.5 are used (FIG. 16F).

Discussion

Here we describe sci-L3, a framework that combines 3-level single cell combinatorial indexing and linear amplification. We demonstrate that sci-L3 is applicable to single cell whole genome sequencing (sci-L3-WGS), single cell targeted DNA sequencing (sci-L3-target-seq) and a single cell co-assay of the genome and transcriptome (sci-L3-RNA/DNA). With sci-L3-WGS, at least tens-of-thousands, and potentially millions, of single cell genomes can be processed in a two day experiment, at a library construction cost of $0.14 per cell for 10 k cells and $0.008 per cell for 1M cells. The throughput of sci-L3-WGS is orders of magnitude higher than alternative single cell WGS methods based on linear amplification, such as 'in-tube' LIANTI (Chen et al., 2017). It furthermore improves on the number of unique molecules recovered from each single cell from the low thousands (Pellegrino et al., 2018) or low tens-of-thousands (Vitak et al., 2017) to the hundreds-of-thousands.

We applied sci-L3-WGS to study male mouse meiosis and identified an unexpected population of M2 cells. The single cell nature of the data also allowed us to simultaneously characterize meiotic crossover and chromosome mis-segregation. Reverse segregation events have previously been observed in complete analyses of human female meiosis (Ottolini et al., 2015), and we observe similar events here in the context of mouse male meiosis (i.e. equational segregation of one or several chromosomes). Among the 292 M2 cells we analyzed from the (B6×Spret) cross, individual cells were biased towards equational or reductional chromosome segregation, suggesting a global sensing mechanism for deciding whether a cell proceeds with meiosis or returns to mitotic segregation of its chromosomes. Also, to our knowledge for the first time in mammalian meiosis, we observed multiple instances of whole genome equational segregation during MI, suggesting a cell-autonomous rather than a chromosome autonomous mode of equational segregation. We identified such events in both crosses, albeit more rarely in the fertile (B6×Cast) cross.

The high incidence of whole-genome reverse segregation when compared to what would be expected for a chromosome-autonomous mechanism (a rate of $2^{-19}$), particularly in the interspecific (B6×Spret) cross, raises more questions than it answers. We depict the model and highlight several unresolved questions in FIG. 23. In normal MI, centromere cohesion is maintained in reductional segregation and sister chromatids centromere-proximal to the crossover do not split until MII (pattern 1 in FIG. 23D). Equational segregation in MI indicates premature centromeric cohesin separation (pattern 2 and/or 3 in FIG. 23D). Previous work has also shown that homolog pairing could be defective in these F1 cross due to erosions of PRDM9 binding sites (Davies et al., 2016; Gregorova et al., 2018; Smagulova et al., 2016) and the pairing problem is probably more severe in the interspecific cross. In Example 2, "Speculations on the causes and consequences of reverse segregation" section, we speculate on: 1) what might cause premature centromeric cohesin separation, 2) whether one crossover is sufficient for proper reductional segregation, and 3) what consequences equational segregation in MI may have.

The improved genome coverage enabled high-resolution mapping of crossover break points compared to other single-cell sequencing methods, and the throughput for mapping a total of ~87,000 crossovers allowed us to better characterize genomic and epigenomic features associated with crossover hotness with pileup data. We discuss how the continuum of crossover hotness is shaped by many factors in Example 2, "Crossover hotness and associated (epi)genomic factors" section.

One key difference from simply combining the high-throughput single-cell combinatorial indexing ("sci") scheme with linear amplification via transposon insertion (LIANTI) in the development of sci-L3 is that we introduced the T7 promoter by ligation, which not only enables more than two rounds of cell barcoding and further increase throughput at much reduced cost, but also provides the flexibility to generalize the method to other single cell assays with small tweaks of the protocol. As a first example, we demonstrate that sci-L3-WGS can be easily adapted to sci-L3-target-seq. Although single cell targeted sequencing has been reported with 10× Genomics platform, to our knowledge it is of RNA transcripts, rather than of DNA loci. Although the current 10% "recovery rate" per haplotype may not be ideal for targeted sequencing, it is mitigated by the large number of cells that can be analyzed. As a second example, we demonstrate that sci-L3-WGS can also be adapted to a sci-L3-RNA/DNA co-assay. We anticipate that it may be further possible to adapt sci-L3 to ATAC-seq, bisulfite-seq and Hi-C for single cell profiling of chromatin accessibility, the methylome and chromatin conformation, respectively, which may have advantages over published sci-methods (Cusanovich et al., 2015; Mulqueen et al., 2018; Ramani et al., 2017) for these goals in terms of throughput and amplification uniformity.

In summary, sci-L3-WGS, sci-L3-target-seq, and the sci-L3-RNA/DNA coassay expand the toolset for single cell sequencing. In this study, we furthermore show how sci-L3-WGS can provide a systematic and quantitative view of meiotic recombination, and uncover rare whole-genome chromosome mis-segregation event with unprecedented combination of throughput. We anticipate that sci-L3 methods will be highly useful in other contexts where single cell genome sequencing is proving transformative, e.g. for studying rare inter-homolog mitotic crossovers and for dissecting the genetic heterogeneity and evolution of cancers.

REFERENCES

Baudat, F., Manova, K., Yuen, J. P., Jasin, M., and Keeney, S. (2000). Chromosome synapsis defects and sexually dimorphic meiotic progression in mice lacking Spo11. Mol. Cell 6, 989-998.

Baudat, F., Imai, Y., and de Massy, B. (2013). Meiotic recombination in mammals: localization and regulation. Nat. Rev. Genet. 14, 794-806.

Berletch, J. B., Ma, W., Yang, F., Shendure, J., Noble, W. S., Disteche, C. M., and Deng, X. (2015). Escape from X inactivation varies in mouse tissues. PLoS Genet. 11, e1005079.

de Boer, E., Jasin, M., and Keeney, S. (2015). Local and sex-specific biases in crossover vs. noncrossover outcomes at meiotic recombination hot spots in mice. Genes Dev. 29, 1721-1733.

Brick, K., Pratto, F., Sun, C.-Y., Camerini-Otero, R. D., and Petukhova, G. (2018). Analysis of Meiotic Double-Strand Break Initiation in Mammals. Methods Enzymol. 601, 391-418.

Cao, J., Packer, J. S., Ramani, V., Cusanovich, D. A., Huynh, C., Daza, R., Qiu, X., Lee, C., Furlan, S. N., Steemers, F. J., et al. (2017). Comprehensive single-cell transcriptional profiling of a multicellular organism. Science 357, 661-667.

Cao, J., Spielmann, M., Qiu, X., Huang, X., Ibrahim, D. M., Hill, A. J., Zhang, F., Mundlos, S., Christiansen, L., Steemers, F. J., et al. (2019). The single-cell transcriptional landscape of mammalian organogenesis. Nature.

Chen, C., Xing, D., Tan, L., Li, H., Zhou, G., Huang, L., and Xie, X. S. (2017). Single-cell whole-genome analyses by Linear Amplification via Transposon Insertion (LIANTI). Science 356, 189-194.

Choi, K., and Henderson, I. R. (2015). Meiotic recombination hotspots—a comparative view. Plant J. 83, 52-61.

Clyde, M. A., Ghosh, J., and Littman, M. L. (2011). Bayesian Adaptive Sampling for Variable Selection and Model Averaging. J. Comput. Graph. Stat. 20, 80-101.

Cole, F., Baudat, F., Grey, C., Keeney, S., de Massy, B., and Jasin, M. (2014). Mouse tetrad analysis provides insights into recombination mechanisms and hotspot evolutionary dynamics. Nat. Genet. 46, 1072-1080.

Cusanovich, D. A., Daza, R., Adey, A., Pliner, H. A., Christiansen, L., Gunderson, K. L., Steemers, F. J., Trapnell, C., and Shendure, J. (2015). Multiplex single cell profiling of chromatin accessibility by combinatorial cellular indexing. Science 348, 910-914.

Davies, B., Hatton, E., Altemose, N., Hussin, J. G., Pratto, F., Zhang, G., Hinch, A. G., Moralli, D., Biggs, D., Diaz, R., et al. (2016). Re-engineering the zinc fingers of PRDM9 reverses hybrid sterility in mice. Nature 530, 171-176.

Eberwine, J., Yeh, H., Miyashiro, K., Cao, Y., Nair, S., Finnell, R., Zettel, M., and Coleman, P. (1992). Analysis of gene expression in single live neurons. Proceedings of the National Academy of Sciences 89, 3010-3014.

Gregorova, S., Gergelits, V., Chvatalova, I., Bhattacharyya, T., Valiskova, B., Fotopulosova, V., Jansa, P., Wiatrowska, D., and Forejt, J. (2018). Modulation of controlled meiotic chromosome asynapsis overrides hybrid sterility in mice. Elife 7.

Hashimshony, T., Wagner, F., Sher, N., and Yanai, I. (2012). CEL-Seq: single-cell RNA-Seq by multiplexed linear amplification. Cell Rep. 2, 666-673.

Hong, S., Sung, Y., Yu, M., Lee, M., Kleckner, N., and Kim, K. P. (2013). The logic and mechanism of homologous recombination partner choice. Mol. Cell 51, 440-453.

Hou, Y., Fan, W., Yan, L., Li, R., Lian, Y., Huang, J., Li, J., Xu, L., Tang, F., Xie, X. S., et al. (2013). Genome analyses of single human oocytes. Cell 155, 1492-1506.

Keeney, S., Giroux, C. N., and Kleckner, N. (1997). Meiosis-specific DNA double-strand breaks are catalyzed by Spo11, a member of a widely conserved protein family. Cell 88, 375-384.

Lange, J., Yamada, S., Tischfield, S. E., Pan, J., Kim, S., Zhu, X., Socci, N. D., Jasin, M., and Keeney, S. (2016). The Landscape of Mouse Meiotic Double-Strand Break Formation, Processing, and Repair. Cell 167, 695-708.e16.

Liu, E. Y., Morgan, A. P., Chesler, E. J., Wang, W., Churchill, G. A., and Pardo-Manuel de Villena, F. (2014). High-resolution sex-specific linkage maps of the mouse reveal polarized distribution of crossovers in male germline. Genetics 197, 91-106.

Lu, S., Zong, C., Fan, W., Yang, M., Li, J., Chapman, A. R., Zhu, P., Hu, X., Xu, L., Yan, L., et al. (2012). Probing meiotic recombination and aneuploidy of single sperm cells by whole-genome sequencing. Science 338, 1627-1630.

Mancera, E., Bourgon, R., Brozzi, A., Huber, W., and Steinmetz, L. M. (2008). High-resolution mapping of meiotic crossovers and non-crossovers in yeast. Nature 454, 479-485.

Mulqueen, R. M., Pokholok, D., Norberg, S. J., Torkenczy, K. A., Fields, A. J., Sun, D., Sinnamon, J. R., Shendure, J., Trapnell, C., O'Roak, B. J., et al. (2018). Highly scalable generation of DNA methylation profiles in single cells. Nat. Biotechnol. 36, 428-431.

Ottolini, C. S., Newnham, L., Capalbo, A., Natesan, S. A., Joshi, H. A., Cimadomo, D., Griffin, D. K., Sage, K., Summers, M. C., Thornhill, A. R., et al. (2015). Genome-wide maps of recombination and chromosome segregation in human oocytes and embryos show selection for maternal recombination rates. Nat. Genet. 47, 727-735.

Pellegrino, M., Sciambi, A., Treusch, S., Durruthy-Durruthy, R., Gokhale, K., Jacob, J., Chen, T. X., Geis, J. A., Oldham, W., Matthews, J., et al. (2018). High-throughput single-cell DNA sequencing of acute myeloid leukemia tumors with droplet microfluidics. Genome Res.

Ramani, V., Deng, X., Qiu, R., Gunderson, K. L., Steemers, F. J., Disteche, C. M., Noble, W. S., Duan, Z., and Shendure, J. (2017). Massively multiplex single-cell Hi-C. Nat. Methods 14, 263-266.

Romanienko, P. J., and Camerini-Otero, R. D. (2000). The mouse Spo11 gene is required for meiotic chromosome synapsis. Mol. Cell 6, 975-987.

Smagulova, F., Gregoretti, I. V., Brick, K., Khil, P., Camerini-Otero, R. D., and Petukhova, G. V. (2011). Genome-wide analysis reveals novel molecular features of mouse recombination hotspots. Nature 472, 375-378.

Smagulova, F., Brick, K., Pu, Y., Camerini-Otero, R. D., and Petukhova, G. V. (2016). The evolutionary turnover of recombination hot spots contributes to speciation in mice. Genes Dev. 30, 266-280.

Sos, B. C., Fung, H.-L., Gao, D. R., Osothprarop, T. F., Kia, A., He, M. M., and Zhang, K. (2016). Characterization of chromatin accessibility with a transposome hypersensitive sites sequencing (THS-seq) assay. Genome Biol. 17, 20.

Vitak, S. A., Torkenczy, K. A., Rosenkrantz, J. L., Fields, A. J., Christiansen, L., Wong, M. H., Carbone, L., Steemers, F. J., and Adey, A. (2017). Sequencing thousands of single-cell genomes with combinatorial indexing. Nat. Methods 14, 302-308.

Wang, J., Fan, H. C., Behr, B., and Quake, S. R. (2012). Genome-wide single-cell analysis of recombination activity and de novo mutation rates in human sperm. Cell 150, 402-412.

Wang, S., Kleckner, N., and Zhang, L. (2017a). Crossover maturation inefficiency and aneuploidy in human female meiosis. Cell Cycle 16, 1017-1019.

Wang, S., Hassold, T., Hunt, P., White, M. A., Zickler, D., Kleckner, N., and Zhang, L. (2017b). Inefficient Crossover Maturation Underlies Elevated Aneuploidy in Human Female Meiosis. Cell 168, 977-989.e17.

Yamada, S., Kim, S., Tischfield, S. E., Jasin, M., Lange, J., and Keeney, S. (2017). Genomic and chromatin features shaping meiotic double-strand break formation and repair in mice. Cell Cycle 16, 1870-1884.

Zhang, K., Wu, X.-C., Zheng, D.-Q., and Petes, T. D. (2017). Effects of Temperature on the Meiotic Recombination Landscape of the Yeast. MBio 8.

Example 2

Finite Mixture Model for Fitting the Three Populations of Non-1C Cells

The non-1C cells recovered from (B6×Cast) hybrid from barcode group 2 include 1C doublets, cells that appear biased towards equational segregation, and cells that appear biased towards reductional segregation. To quantify their relative proportions, we fit the data to a mixture of three binomial distributions, with probabilities of chromosomes segregating equationally of 0.01, 0.48 and 0.95, and mixing proportions of 0.28, 0.69 and 0.02 (FIG. 12A). In contrast, when we attempt to similarly fit non-1C cells from barcode group 1 to a mixture of three binomial distributions, we obtain probabilities of chromosomes segregating equationally of 0.46, 0.5 and 0.53 (all close to 0.5), and mixing proportions of 0.24, 0.44 and 0.31 (FIG. 12B).

Towards asking whether the proportion of M2 cells that are biased towards equational vs. reductional segregation differs between the fertile and infertile crosses, we can similarly fit the chromosomal data from the (B6×Spret) cross (FIG. 9E), which yields probabilities of chromosomes segregating equationally of 0.05, 0.39 and 0.91, and mixing proportions of 0.66, 0.2 and 0.14 (FIG. 12C). These proportions suggest that the infertile (B6×Spret) cross has higher proportion of cells that are biased towards equational rather than reductional segregation.

Distribution of Meiotic Crossovers at the Chromosomal Level

Basing on 1,663 1C cells harboring 19,601 crossover breakpoints and 240 M2 cells with 4,184 crossover breakpoints from the (B6×Spret) cross, and 5,547 1C cells harboring 60,755 crossover breakpoints and 115 M2 cells with 2,246 crossover breakpoints from the (B6×Cast) cross, we first considered the distribution of meiotic crossovers across chromosomes. Crossover density is defined here as the average number of crossovers per cell per division per Mb multiplied by 2 (in 1C cells) or 1 (in M2 cells). In the (B6×Spret) cross, we observed a strong negative correlation between chromosome size and crossover density in 1C cells (FIG. 13A, r=−0.66, p=0.002). Consistent with previous findings (Lange et al., 2016), this correlation is only partly explained by Spo11 oligonucleotide complex density (r=−0.46, p <0.05), suggesting that smaller chromosomes sustain more DSBs and those DSBs are more likely to give rise to crossovers. This negative correlation is even stronger in M2 cells (FIG. 13B, r=−0.83, p=1e-5). In FIG. 10A-B, we consider instances of multiple crossovers per chromosome per cell as a single event, which strengthens the negative correlation even further (r=−0.87, p=2e-6 for 1C cells; r=−0.91, p=8e-8 for M2 cells). These observations suggest that smaller chromosomes are hotter for crossovers, and particularly for having at least one crossover per cell division. The same trend is observed in the (B6×Cast) cross (FIG. 14A-D). 1C cells had an average of 0.62 and 0.58 crossovers per chromosome per cell for inter- and intra-specific crosses, respectively, while M2 cells had an average of 0.92 and 1.03 per chromosome per cell (FIGS. 13C-D, 10C-D). The crossover rate in interspecific M2 cells is only 9% lower than crossover counts measured by Mlh1 foci in 4C spermatocytes in B6 inbred mice (Froenicke et al., 2002), despite a sequence divergence of 2%. The crossover rate in 1C cells is 45% lower than observed in single human sperm sequencing (Lu et al., 2012; Wang et al., 2012). The latter difference could largely be due to the telocentric nature of mouse chromosomes. Although the interspecific (B6×Spret) cross has higher average number of crossovers detected in 1Cs compared to the (B6×Cast) cross (p=7e-26, Mann-Whitney test), the average number of crossovers in M2 cells are lower (p=2e-10). We note that the proportion of M2 cells that segregated all 19 autosomes reductionally that have a crossover on every chromosome is higher for the (B6×Cast) cross (60/91 of 66%) than the (B6×Spret) cross (41/80 or 51%) (p=0.06, Fisher's exact test), which could contribute to the infertility of the latter.

To examine crossover interference, we took chromosomes with at least two crossovers and plotted the distance between adjacent crossovers, and compared this distribution to expectation based on random simulation (FIG. 13E, FIG. 10E, FIG. 14E). The median observed distance between crossovers was 82 Mb for (B6×Spret) and 97 Mb for (B6×Cast); both are much larger than the expectation of 39 and 42 Mb (p=1e-267 and p<2e-308, respectively, Mann-Whitney test). This is consistent with the repulsion of crossovers in close proximity. Note that crossover interference is stronger in the (B6×Cast) than the (B6×Spret) cross, with longer distances between adjacent crossovers (p=5e-91).

We also analyzed the distribution of uniparental chromosomes (i.e. no observed crossovers) in each single cell (FIG. 13F) and for each chromosome (FIG. 13G) in (B6×Spret) cross (the same trends hold for the (B6×Cast) cross, as depicted in FIG. 14F-G). Although shorter chromosomes exhibit elevated crossover rates when normalized by length, the rate of uniparental chromosomes (collapsed across all classes of cells) still negatively correlated with chromosome size (FIG. 13G; r=−0.91, p=4.6e-8).

While we have shown that M2 cells are strongly biased towards either equational or reductional segregation of their chromosomes, we also observed hundreds of sporadic equational segregation events among cells that have at least 15 chromosomes with reductional segregation. This phenomenon has previously been observed and termed as "reverse segregation" (Ottolini et al., 2015). In FIG. 13H, we show chromosome distribution of these reverse segregation events. Note that although the rate of reverse segregation is significantly higher in the (B6×Spret) cross (mean=1.1) than the (B6×Cast) cross (mean=0.2, p=2e-14, Mann-Whitney test), chromosomes 7 and 11 have the highest rates of reverse segregation in both crosses.

We then examined the normalized proportion of reads per cell that map to the mitochondrial genome (FIG. 13I, FIG. 10G). The 1C cells exhibit a bimodal distribution in terms of the "copy number" of mitochondria DNA, an observation for which we lack a satisfactory explanation. We observed a modest negative correlation between the mitochondrial read proportion and the number of crossovers (rho=−0.11, p=3e-6). Interestingly, although of limited number, M2 cells that segregated at least 15 of their chromosomes either equationally vs. reductionally had very different distributions of mitochondrial read proportions (FIG. 10G). Consistent with this, the mitochondrial read proportion positively correlated with the number of reductionally segregated chromosomes in M2 cells (r=0.18, p=0.005). Note that we are not able to evaluate this in the (B6×Cast) cross because more than 90% of the single cells sequenced do not have any reads mapping to the mitochondrial genome. It is possible that the different methods used for nuclei isolation from the testes (B6×Cast)

vs. the epididymis (B6×Spret), coupled with pre-sorting of the nuclei from the testes, fractionated the mitochondria away from the bulk nuclei.

Effect of PRDM9 on Crossover Hotness

Basing on the crossover hotness map by piling up crossover breakpoints along the chromosomes throughout the genome (FIG. 15), we found that in the intraspecific (B6× Cast) cross, crossover hotness correlates better with DSB hot domains mapped in the Cast male than the B6 male (rho=0.28 and 0.12, p<2e-308 and p=1e-83, respectively), possibly as a result of Cast PRDM9 allele being semi-dominant in the F1 hybrid. The correlation is stronger with DSB hot domains mapped in (B6×Cast) F1 animals (rho=0.3, p<2e-308). For the (B6×Spret) cross, the erosion of PRDM9 consensus binding site results in four types of DSB hotspots defined by the Spo11 oligonucleotide-complex map: those that are conserved between B6 and Spret, termed as "symmetric" hotspots, those that are only present in B6 or Spret, termed as "asymmetric" hotspots, and those do not contain a PRDM9 binding site in either species. All four types of DSB hot domains correlate poorly with crossovers from the (B6×Spret) cross (rho=0.13, p=4e-87 for using all Spo11 hotspots mapped in B6; rho=0.11, p=3e-63 if we only use "symmetric hotspots"). One possibility is that the DSB sites in the (B6×Spret) cross are strongly dominated by the Spret PRDM9 allele, such that the DSB hotspots mapped in the B6 strain background do not predict sites of crossovers.

Speculations on the Causes and Consequences of Reverse Segregation

We have observed high incidence of reverse segregation, particularly in the interspecific (B6×Spret) cross. Below we speculate on: 1) what might cause premature centromeric cohesin separation, 2) whether one crossover is sufficient for proper reductional segregation, and 3) what consequences equational segregation in MI may have.

First, it is possible that due to insufficient homolog pairing between B6 and Spret chromosomes, DSBs that should have been normally repaired off the homolog during meiosis are instead frequently repaired using sister chromatids as template. This could cause disruption of cohesins (Storlazzi et al., 2008) and lead to premature centromere cohesin separation.

Second, the current model suggests that one inter-homolog crossover and proper sister chromatid cohesion are sufficient for forming chiasmata (FIG. 23) despite initial insufficient homolog pairing in the interspecific cross. Once a crossover is successfully formed, chromosome segregation should not be impaired. In our study, on the individual chromosome level, the large numbers of equationally segregated chromosomes observed do have normal crossovers as evidenced by centromere-distal LOH, which could indicate that defects in the initial homolog pairing impact the ultimate outcome. On the genome level, however, we cannot confidently assess whether those cells with biased equational segregation have similar numbers of crossovers as their reductionally biased counterparts, because we can detect all crossovers for chromosomes that segregate reductionally, but we can only detect crossovers in equationally segregated chromosomes when the two recombined chromatids segregate apart (FIG. 5B-C and FIG. 16D, patterns 2 and 3). Assuming recombined chromatids are equally likely to segregate together or apart, the number of crossovers is not smaller in those genome-level equational segregation cases, although we cannot exclude the possibility that segregation is biased away from 50/50 due to unresolved recombination intermediates (FIG. 23, pattern 3).

Third, what are the consequences of these equationally segregated chromosomes? Do they return to mitosis, bearing extensive LOH, or do they proceed to MII, and if so, contributing to forming 1C gametes? In yeast, a phenomenon called "return-to-growth" has been characterized wherein cells that initiate the meiosis program can revert to normal mitotic divisions in the presence of proper nutrients, resulting in large numbers of LOH events (Dayani et al., 2011). In human female meiosis, chromosomes with reverse segregation proceed to MII, leading to one euploid oocyte and one euploid polar body 2, consistent with normal MII segregation; the authors suggest that unresolved recombination intermediates may have both caused the reverse segregation in MI and facilitated proper MII segregation by linking the otherwise unrelated homolog chromatids (FIG. 23, pattern 3) (Ottolini et al., 2015). Mlh1 is important in both mismatch repair (MMR) and for resolving Holliday junction intermediates in meiosis. Given the 2% sequence divergence between B6 and Spret, it is possible that Mlh1 is limiting due to intensive MMR and there may not be enough Mlh1 for resolving recombination intermediates. However, we emphasize that if recombined homolog chromatids co-segregate, this would not lead to LOH (FIG. 5C). Therefore, M2 cells with LOH and equational segregation cannot be explained by co-segregation of unresolved intermediates.

Lastly, in FIG. 23, we also show possible contributions to forming gametes from chromosomes without any inter-homolog crossover, probably due to insufficient homolog pairing, because one of the patterns (pattern 4) is not distinguishable from cells that have a crossover but co-segregate recombined chromatids (pattern 3). However, if these cells without crossover contribute significantly to the 1C cells, we should observe a higher number of crossover-free chromosomes amongst the 1C cells. Of the 1C cells we observed in both crosses, the number of chromosomes with and without crossovers is roughly 50-50, indicating that they predominantly derive from some combination of patterns 1-3 in FIG. 23, and 2C cells without inter-homolog crossovers (patterns 4 and 5) do not substantially contribute to 1C cells that successfully complete MII.

Crossover Hotness and Associated (Epi)Genomic Factors

Crossover hotness is a continuum and shaped by many factors. Crossovers in the (B6×Cast) cross correlate more strongly with meiotic DSB hotspots mapped in the F1 cross than in individual maps for the two parental strains, which is expected based on the previous finding that novel meiotic hotspots can form in F1 hybrids (Smagulova et al., 2016). In the (B6×Spret) cross, crossovers are weakly but positively correlated with Spo11 breaks. Note that the Spo11 map only accounts for the PRDM9 sites bound by PRDM9 protein of the B6 allele, and it is likely that the Spret copy of PRDM9 binds different sites and creates new meiotic DSB hotspots, not accounted for in our analyses. Genomic features that we observe to be positively correlated with meiotic crossovers include GC-rich regions (also the case in yeast meiosis (Petes, 2001; Petes and Merker, 2002)), CNV gains between the strains (Lilue et al., 2018), gene bodies, pseudogenic transcripts, CTCF binding sites, replication domains (Marchal et al., 2018), DNA transposons, satellite DNA and a subset of histone modifications including H3K4me1, H3K27me3 and H3K36me3 (Mu et al., 2017). Intriguingly, the binding sites of Dmrt6, involved in regulating the switch from mitotic to meiotic divisions in male germ cells (Zhang et al., 2014) are strongly correlated with meiotic crossover hotness. Genomic features that are notably negatively correlated with meiotic crossovers include 3' UTRs, LINEs, and low complexity DNA. Unlike in yeast, where rDNA is extremely cold for meiotic crossovers (Petes and Botstein, 1977), mouse rDNA does not appear to suppress crossovers. With these genomic features, we are able to distinguish real meiotic crossover initiation sites from randomly sampled tracts in the mouse genome, with 0.73 and 0.85 accuracy in (B6×Spret) and (B6×Cast), respectively, and the 0.85 prediction accuracy in the (B6×Cast) cross holds with a subset of 25 genome features. We emphasize that although the various features behave largely consistently between modeling approaches, we cannot assign any causality without further experiments.

Methods

Methods and Molecular Design of Sci-L3-WGS and Sci-L3-Target-Seq

Single Cell Preparation and Nucleosome Depletion

Cell suspension is prepared by trypsinizing from a petri dish or homogenizing from tissues. Male F1 mice were euthanized by $CO_2$ followed by cervical dislocation according to University of Washington IACUC approved protocols. For isolation of male germ cells, we dissected the epididymis by slicing the tubes within and incubating the tissue in 1 ml of 1×PBS supplemented with 10% FBS at room temperature for 15 min. After incubation the cell suspension was collected by pipetting. Cells isolated from the epididymis were used for experiments of the (B6×Spret) cross and also as a source of mature sperm ("barcode group 3") in the (B6×Cast) cross. For isolation of nuclei from whole testis as an enrichment method for 2C cells for the (B6×Cast) cross, we first crosslinked testicular cells with 1% formaldehyde and extracted nuclei using hypotonic buffer. We then FACS-sorted 1C and 2C nuclei by DNA content primarily based on DAPI signal. Cultured human and mouse cells are pelleted at 550 g for 5 min at 4° C. and male germ cells are pelleted at 2400 g for 10 min at 4° C.

Nucleosome depletion largely follows xSDS methods in sci-DNA-seq (Vitak et al., 2017) except that the lysis buffer is modified to be compatible with downstream LIANTI protocol (Chen et al., 2017). Cells are crosslinked in 10 mL DMEM complete media with 406 37% formaldehyde (final conc. 1.5%) at r.t. for 10 min (gently inverting the tubes). We then add 800 μL 2.5 M Glycine and incubate on ice for 5 min. Cells are pelleted and washed with 1 mL lysis buffer (60 mM Tris-Ac pH 8.3, 2 mM EDTA pH 8.0, 15 mM DTT). The pellet is resuspended in 1 mL lysis buffer with 0.1% IGEPAL (18896, SIGMA) and incubated on ice for 20 min. Nuclei are then pelleted, washed with 1×NEBuffer2.1, and resuspended in 800 1×NEBuffer2.1 with 0.3% SDS for nucleosome depletion at 42° C. (vigorous shaking for 30 min, 500 rpm). We then add 180 uL 10% Triton-X and vigorous shaking for 30 min at 42° C. (500 rpm). Permeabilized nuclei are then washed in 1 mL lysis buffer twice and resuspended in lysis buffer at 20,000 nuclei per μL.

Transposome Design and Assembly

Transposon DNA oligo is synthesized with both 5' of the two strands phosphorylated, one required for Tn5 insertion (5'/Phos/CTGTCTCTTATACACATCT, IDT, PAGE purification (SEQ ID NO:1)) similar as in LIANTI and Nextera, the other required for ligation (5'/Phos/GTCTTG XXXXXXXX [$1^{st}$ round barcode] AGATGTGTATAAGA-GACAG, IDT, standard desalting (SEQ ID NO:2)). After annealing 1:1 with gradual cooling (95° C. 5 min, −0.1° C./cycle, 9 sec/cycle, 700 cycles to 25° C.) in annealing buffer (10 mM Tris-HCl pH 8.0, 50 mM NaCl, 1 mM EDTA, pH 8.0), Tn5 duplex with 5' overhang is diluted to 1.5 μM. We then add 7.2 μL storage buffer (1×TE with 50% Glycerol) to 12 μL ~1 μM Tn5 transposase (Lucigen, TNP92110) and incubate 0.79 μL diluted transposase with 0.4 μL 1.5 μM Tn5 duplex at r.t. for 30 min. The transposome dimerize to a final concentration of 0.2 μM. The transposome complex can be stably stored at −20° C. for up to one year. We set up 24 reactions for barcoding 24 wells in the first round but more wells could be desirable depending the application. For each new biological application, we first further dilute the transposome to 0.1 μM for a test experiment. The number of unique reads and library complexity is less optimal (FIG. 5) but usable for mapping at low resolution.

Figure 7:
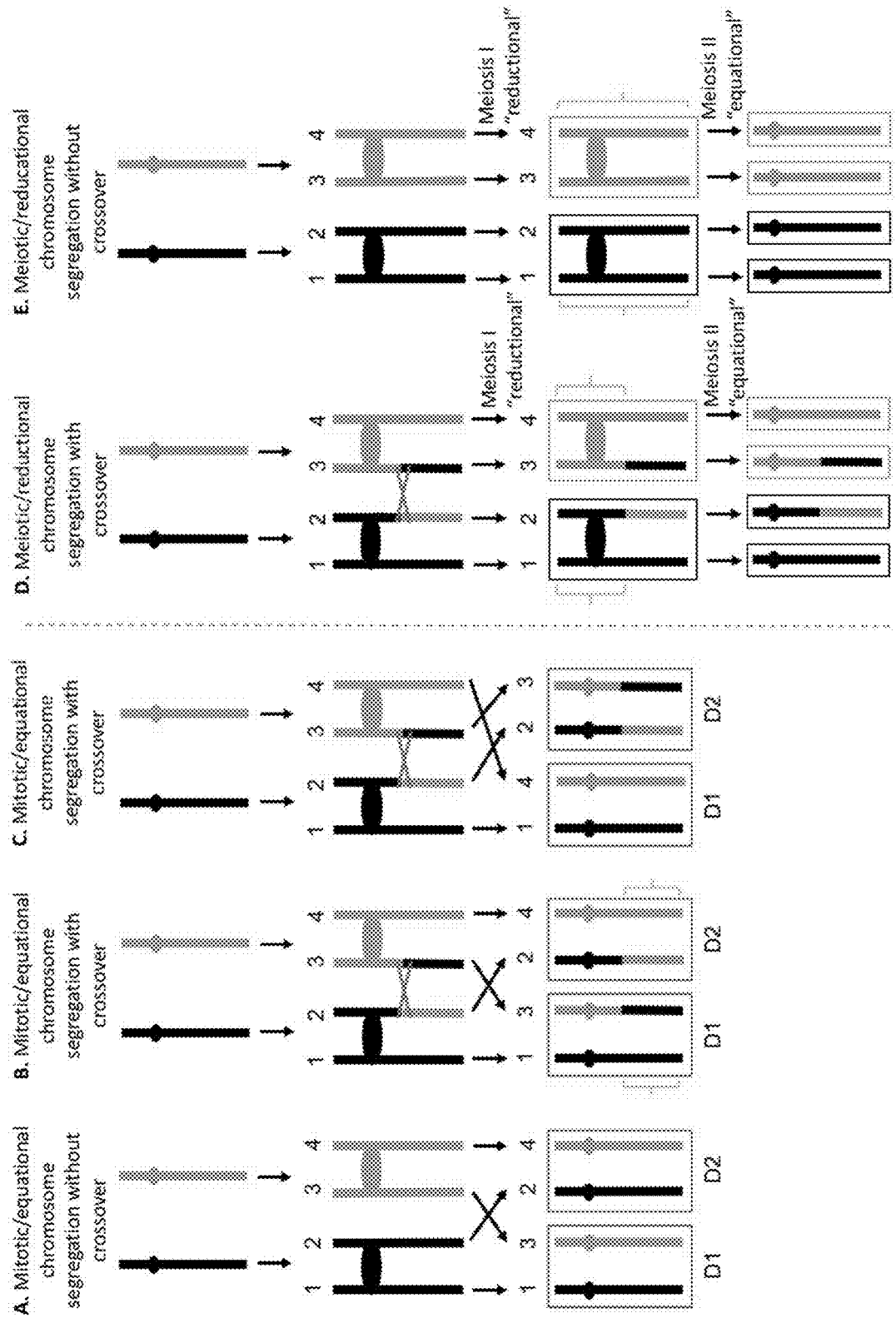
FIG. 7A-E shows mitotic/equational and meiotic/reductional chromosome segregation with and without crossovers. Each vertical segment represents one chromatid (DNA strands not shown). Black and blue represent homologs. Ovals represent centromeres. Note that mouse chromosomes are telocentric. Grey crosses depict sites of crossover after DNA replication at the 4C stage. Red boxes indicate daughter cells of mitosis that are heterozygous, and black and blue boxes indicate daughter cells of Meiosis I (MI) that are homozygous for respective strain background at the centromere-proximal regions. LOH regions in daughter cells are marked by curly brackets. (A) Mitotic/equational segregation without crossover. Both daughter cells retain heterozygosity. (B) Mitotic/equational segregation with crossover between homologs. Recombined chromatids segregate apart, resulting in LOH centromere-distal to the crossover. (C) Mitotic/equational segregation with crossover between homologs. Recombined chromatids segregate together, such that both daughter cells retain heterozygosity but one daughter cell has a linkage switch. (D) Meiotic/reductional segregation with crossover, resulting in LOH centromere-proximal to the crossover, unlike in (B). (E) Meiotic/reductional segregation without crossover, resulting in reciprocal uniparental disomy (UPD) in daughter cells. Note that MI with equational chromosome segregation resembles (B) and (C). In the text, as our study is primarily focused on MI, we refer to the expected meiotic/reductional segregation during MI, where sister chromatids segregate together, as "reductional segregation", and unexpected mitosis-like/equational segregation during MI, where sister chromatids segregate apart, as "equational segregation".

In FIG. 7, we show molecular structures of sci-L3-WGS at each step. In commercial Nextera library preparation, one loses at least half of the sequenceable DNA material due to: 1) Tn5 insertion introduces symmetric transposon sequence at the two ends of fragmented genomic DNA, which can result in formation of hairpin loop when denatured and prevent PCR amplification; and 2) if the two ends are tagmented with both i5 or i7 with 50% chance, the molecule cannot be sequenced. One key advantage of LIANTI over Nextera-based library preparation, is that the looped Tn5 design breaks the symmetry introduced by transposome dimer and facilitates reverse transcription (RT) by using an intramolecular RT primer, also characteristic of the looped transposon. However, looped transposon is not compatible with more than two rounds of barcoding, which limits throughput and significantly increase library cost (see Table 2 for comparison). In the changes we made for sci-L3-WGS, we maintain advantages brought by looped Tn5 during the ligation step.

Tagmentation (First-Round Barcodes) and Ligation (Second-Round Barcodes)

We then distribute 1.5 μL of nuclei at 20,000/4, concentration into each well in a lo-bind 96-well plate, add 6.5 μL $H_2O$ and 0.7 μL 50 mM MgCl2 (final conc. of 3.24 mM accounting for the EDTA in the lysis buffer). The 1.2 μL transposome prepared above is added into each well and the plate is then incubated at 55° C. for 20 min (thermomixer is recommended but not required). We then add 5 μL of stop solution (40 mM EDTA and 1 mM spermidine) and pool nuclei in a trough. An additional 1 mL of lysis buffer is added to the nuclei suspension before pelleting. After carefully removing the supernatant, we resuspend the nuclei in 312 μL resuspension buffer (24 μL 10 mM dNTP, 48 μL 10× tagmentation buffer [50 mM $MgCl_2$, 100 mM Tris-HCl pH 8.0], 96 μL $H_2O$, 144 μL lysis buffer), and distribute 4.7 μL nuclei mix into each well of a new lo-bind 96-well plate. Hairpin ligation duplex (1. CAAGAC 2. Y'Y'Y'Y'Y'Y' [reverse complement of $2^{nd}$ round barcode] 3. CAG-GAGCGAGCTGCATCCC 4. AATTTAATACGACTCAC-TATA 5. GGGATGCAGCTCGCTCCTG 6. YYYYYYY [$2^{nd}$ round barcode] (SEQ ID NO:3)) is pre-annealed similarly as the Tn5 transposon duplex and diluted to 1.5 μM. Note that the ligation duplex contains five elements: 1) reverse complement of ligation adaptor on Tn5; 2) reverse complement of $2^{nd}$ round barcode; 3) reverse complement of second-strand synthesis (SSS) primer; 4) T7 promoter, note that this is the loop region of the hairpin; 5) second-strand synthesis (SSS) primer region starting with GGG for enhancing T7 transcription ("sp2" in FIG. 4B); 6) $2^{nd}$ round barcode ("bc2" in FIG. 4B). We add 0.8 μL of these duplex to each of the 64 wells with nuclei suspension and add 1.18 μL ligation mix (0.6 μL 10×NEB T4 ligase buffer, 0.48 μL PEG-4000, 0.1 uL T4 DNA ligase [Thermo EL0011]) into each well and incubate at 20° C. for 30 min. Note that after ligation, the looped structure mimics that of LIANTI and facilitates efficiency at the RT step (discussed below), and that both rounds of barcodes are present at the 3' of the T7 promoter and thus will be included in the amplified molecule. Ligation reaction is stopped by adding 4 μL stop solution. Cells are then pooled in a new trough (~630 μL), stained with DAPI at a final conc. of 5 μg/mL and sorted 100-300 into each new well with 3 μL lysis buffer added prior to cell sorting. Note that each sorting event with FACS is associated with ~3-5 nL FACS buffer depending on the size of the nozzle, we recommend keeping the total volume of liquid added into each well <1 μL to keep the salt concentration low.

Cell Lysis, Gap Extension and Linear Amplification by In Vitro Transcription

We then proceed with a total of 3.5-4 μL sorted nuclei in each well for cell lysis by incubating at 75° C. for 45 min, cooling to 4° C. and treating with freshly diluted Qiagen Protease (final conc. 2 mg/mL) at 55C for 8 hrs. Protease is then heat-inactivated by incubating at 75° C. for 30 min. Cell lysate can be stored at −80° C. We recommend processing no more than 32 wells of samples (~9600 single cells) for each experiment because subsequent amplification step involves RNA and is time-sensitive. For gap extension (FIG. 4C), polymerase with strand displacement activity is used by adding a mixture of 2 μL $H_2O$, 0.7 μL 10× tagmentation buffer, 0.35 μL 10 mM dNTP and 0.35 μL Bst WarmStart 2.0 polymerase with strand displacement activity, and incubate at 68° C. for 5 min. Note that if ligation is successful on both ends, the duplex is symmetric with T7 promoter on both sides, but if ligation is only successful on one end, the region in the dashed box is missing on one side. Inter-molecular ligation is generally inefficient. Although we have included pre-annealed hairpin loop to minimize the necessity of inter-molecular ligation, two molecules (instead of three without the hairpin loop) still need to find each other. If the ligation efficiency is 50%, having ligation on both ends has 25% rate, but having ligation on either end has 75% rate. Later in the RT step, we show that successful ligation is required for only one end. After gap extension, a 20 μL T7 in vitro transcription system is assembled by adding 2 μL $H_2O$, 2 μL T7 Pol mix and 10 μL rNMP mix (NEB, Hi Scribe™ T7 Quick High Yield RNA Synthesis Kit). The mixture is incubated at 37° C. for 10-16 hrs.

RNA Purification, RT and SSS (or Targeted Sequencing)

Transcription is terminated by adding 2.2 μL 0.5M EDTA. Amplified RNA molecules are then purified with RCC-5 (Zymo Research, R1016) and eluted with 18 μL 0.1× TE. A 30 μL RT system is assembled by first adding 0.6 μL RNA RT primer (rArGrArUrGrUrGrUrArUrArArGrArGrAr-CrArG, IDT(SEQ ID NO:4)), 2 μL 10 mM dNTP and 0.5 μL SUPERase.In™ RNase Inhibitor (20 U/μL, Thermo Fisher AM2696). We then incubate at 70° C. for 1 min and 90° C. for 20 sec for denaturing and removing secondary structures and sudden cool on ice. SuperScript™ IV Reverse Transcriptase (SSIV, Thermo Fisher 18090050) is used for RT with 6 μL 5× RT buffer, 1.5 μL 0.1M DTT, 1 SUPERase.In™ and 1 μL SSIV. The RT reaction is incubated at 55° C. for 15 min, 60° C. for 10 min, 65° C. for 12 min, 70° C. for 8 min, 75° C. for 5 min, and 80° C. for 10 min. The reaction is cooled to r.t. before adding 0.5 μL RNaseH (NEB) and 0.3 μL RNaseA (Life Technologies, AM2270) and incubating at 37° C. for 30 min. Note that FIG. 4E depicts two scenarios during the RT step: 1) if both ends have successful ligation, RT is likely primed by fold-back loop as in LIANTI; 2) if only one end has successful ligation, RT is likely primed by the RNA RT primer added before the denaturing step. Excessive RNA primers and RNA transcripts are degraded after cDNA synthesis. Lastly, we synthesize the second strand with Q5 DNA polymerase by adding 27 μL $H_2O$, 20 μL 5× Q5 buffer, 20 μL Q5 GC enhancer, 1 μL Q5 polymerase and 1 μL SSS primer (NNNN [UMI] ZZZZZZ [$3^{rd}$ round barcode] GGGATGCAGCTCGCTCCTG, IDT, standard desalting (SEQ ID NO:5)). Resulting double stranded DNA can be purified with DCC-5 (Zymo Research, D4014) and proceed with library preparation kit such as NEBNext Ultra II with the minimal 3 cycles of PCR for adding the sequencing adaptor.

It is worth noting that the SSS step can be easily modified to enable targeted sequencing by using a single cell barcode primer with P5 end (AATGATACGGCGAC-CACCGAGATCTACACTCTTTCCCTACACGAC GCTCTTCCGATCT NNNNNNN ZZZZZZ [$3^{rd}$ round barcode] GGGATGCAGCTCGCTCCTG (SEQ ID NO:6)) together with a targeting primer for one region in the genome (FIG. 3B). For example, in applications where one integrates lentivirus-based CRISPR library (Shalem et al., 2014), the guide RNA sequence in each single cell could be read off using P7 end with lentivirus-integrated CRISPR library primer, CAAGCAGAAGACGGCATACGAGAT TCGCCTTG [index 1] GTGACTGGAGTTCA-GACGTGTGCTCTT CCGATCTCCGACTCGGTGC-CACTTTTTCAA (SEQ ID NO:7)), thus bypassing the need to sequence the whole genome and enrich for a specific region of interest. In this case, the library preparation step can be omitted and replaced by gel or bead purification to remove primer dimers.

Methods and Molecular Design of Sci-L3-RNA/DNA Co-Assay

Single Cell Preparation and Nucleosome Depletion

Cell suspensions are prepared with the same protocol as in sci-L3-WGS other than differences indicated below. HEK293T, BJ-5ta and 3T3 cells were trypsinized from a petri dish and fixed with 2% PFA in 1×PBS at room temperature for 10 min at 1M/mL cell concentration. Subsequent quenching (with Glycine), washing, nuclei isolation (with 0.1% IGEPAL), nucleosome depletion (xSDS method) steps are identical with sci-L3-WGS except that we add 1% Superase-In to all the lysis buffer and 1×NEBuffer2.1. Nuclei are resuspended in lysis buffer with 1% Superase-In at 20,000 nuclei per μL.

Transposome and Reverse Transcription (RT) Primer Design,

For the single cell genome amplification component, transposome design and assembly are identical to sci-L3-WGS.

For single cell transcriptome profiling component, reverse transcription primers share similar structure with sci-RNA-seq in (Cao et al., 2017; Cusanovich et al., 2015; Mulqueen et al., 2018; Ramani et al., 2017; Vitak et al., 2017) for the reverse transcription aspect, i.e., polyT priming part of the oligo, but contain a different barcode structure and landing pad for the subsequent ligation step (/5Phos/GTCTTG [same landing pad sequence as in sci-L3-WGS] NNNNNN [UMI1 for tagging unique transcripts] X'X'X'X'X'X'X'X' [$1^{st}$ round barcode for transcriptome, which are different sequences from Tn5 transposon barcodes] TTTTTTTTTTTTTTTTTTTTTT TTTTTTTTVN, IDT, standard desalting (SEQ ID NO:8)).

RT and Tagmentation (First-Round Barcodes), Ligation (Second-Round Barcodes), FACS and Cell Lysis We then distribute 1.5 μL of nuclei at 20,000/4, concentration into each well in a lo-bind 96-well plate, add 0.2 μL $H_2O$, 0.3 μL 50 mM MgCl2 (to neutralize EDTA in the lysis buffer), 0.25 μL 10 mM dNTP and 1 μL 25 μM RT primer described above to prepare for the RT step. The nuclei mixture is then incubated at 55° C. for 5 min to remove secondary structures and quickly quench on ice. We then add 1 μL 5× RT buffer, 0.03 μL 100 mM DTT (note that there is DTT from lysis buffer, final conc. 5 mM), 0.25 μL SSIV, 0.25 μL RNaseOUT (Thermo Fisher Cat. No. 10777019), incubate for RT reaction at 25° C. 1 min, 37° C. 1 min, 42° C. 1 min, 50° C. 1 min, 55° C. 15 min. Then add 0.4 μL MgCl2 and 3.52 μL H₂O and the 1.2 μL transposome prepared above into each well. All subsequent steps until after cell lysis are identical to sci-L3-WGS.

Gap Extension and Linear Amplification by In Vitro Transcription

We use random heptamer for gap extension with partial NEBNext Read 1 primer as the 5' overhang (CACGACGCTCTTCCGATCT (SEQ ID NO:9)). We add 1 μL of 20 μM oligo, incubate at 95° C. for 3 min to denature the DNA, and gradually cool to r.t. (~5 min) for the oligos to anneal. We then add 2 μL H₂O, 0.8 μL 10×NEBuffer2, 0.4 μL 10 mM dNTP, 0.4 μL Klenow Fragment (3'→5' exo-, NEB M0212S) and incubate at 30° C. for 8 min and 75° C. for 10 min. After gap extension, a 20 μL T7 in vitro transcription system is assembled by the same sci-L3-WGS protocol.

RNA Purification, RT and SSS

All the steps are identical to sci-L3-WGS except for different oligo sequences. At the RT step after IVT, instead using 0.6 μL RNA RT primer, we use 0.6 μL NEBNext Read 1 primer (AATGATACGGCGACCACCG AGATCTA-CACTCTTTCCCTACACGACGCTCTTCCGATCT, P5 end of Illumina sequencing, IDT (SEQ ID NO:10)). For SSS primer, we use AAGCAGAAGACGGCATACGAGAT [P7 end] NNNN [UMI2] Z'Z'Z'Z'Z' [3$^{rd}$ round barcode] CGTCTCTAC GGGATGCAGCTCGCTCCTG (SEQ ID NO:11) to add the sequencing adaptor. Note that the resulting double stranded DNA now contains both the P5 and P7 end for Illumina sequencing and can be purified with 1.1× AmpureXP beads and proceed with sequencing. The library preparation step and the minimal 3 cycles of PCR in sci-L3-WGS for adding the sequencing adaptor are unessaccery for the co-assay.

Setup of Sci-L3-WGS Experiment in (B6×Spret) Cross and (B6×Cast) Cross (B6×Spret) Cross We pooled cells isolated from 6 and 3 epididymides from (B6×Spret) F1 males aged 70 days and 88 days, respectively, in two separate experiments, and fixed with 1% formaldehyde. For each experiment, after nucleosome depletion, we distributed 30,000 cells per well and performed in situ indexed Tn5 insertion across 24 wells to add the first-round barcodes. We then pooled all cells and redistributed these to 64 wells to add the second-round barcodes and T7 promoter by ligation. After again pooling all cells, we split the cell mixture 1:6, FACS-sorted the majority of cells (6/7), and diluted the rest (1/7). The resulting wells contained 100 to 360 cells per well with an estimated collision rate of 4-11%.

(B6×Cast) Cross

From 6 testes, we recovered ~12M 1C round spermatids and ~0.5M 2C cells. However, due to the >20-fold higher number of 1C cells, we still found many 1C cells in the population sorted for 2C cells (FIG. 8F). In one of the sci-L3-WGS experiments where we tried to enrich for 2C cells, we estimate that we tagmented ~160 k sperm from the epididymis, ~160 k 1C round spermatids and ~70 k 2C cells, and further enriched for 2C cells during the FACS step of sci-L3-WGS (FIG. 8G). However, despite two rounds of enrichment, 1C cells still dominated.

TABLE 4

Oligos for sci-L3.

| oligo name | oligo modification and sequence | note |
|---|---|---|
| yy_Tn5rc19nt_5P | /5Phos/CTGTCTCTTATACACATCT (SEQ ID NO: 12) | Tn5 forward |
| lianti_v2_bc1_1 | /5Phos/GTCTTG TGATATTG AGATGTGTATAAGAGACAG (SEQ ID NO: 13) | 1st round barcode: Tn5 reverse |
| lianti_v2_bc1_2 | /5Phos/GTCTTG GATCCCGT AGATGTGTATAAGAGACAG (SEQ ID NO: 14) | 1st round barcode: Tn5 reverse |
| lianti_v2_bc1_3 | /5Phos/GTCTTG CTCGATTA AGATGTGTATAAGAGACAG (SEQ ID NO: 15) | 1st round barcode: Tn5 reverse |
| lianti_v2_bc1_4 | /5Phos/GTCTTG CATCAAGG AGATGTGTATAAGAGACAG (SEQ ID NO: 16) | 1st round barcode: Tn5 reverse |
| lianti_v2_bc1_5 | /5Phos/GTCTTG TCCTTGTG AGATGTGTATAAGAGACAG (SEQ ID NO: 17) | 1st round barcode: Tn5 reverse |
| lianti_v2_bc1_6 | /5Phos/GTCTTG GGTCATAT AGATGTGTATAAGAGACAG (SEQ ID NO: 18) | 1st round barcode: Tn5 reverse |
| lianti_v2_bc1_7 | /5Phos/GTCTTG ATCGCGTT AGATGTGTATAAGAGACAG (SEQ ID NO: 19) | 1st round barcode: Tn5 reverse |
| lianti_v2_bc1_8 | /5Phos/GTCTTG CATGCCCC AGATGTGTATAAGAGACAG (SEQ ID NO: 20) | 1st round barcode: Tn5 reverse |
| lianti_v2_bc1_9 | /5Phos/GTCTTG GTTACGCG AGATGTGTATAAGAGACAG (SEQ ID NO: 21) | 1st round barcode: Tn5 reverse |
| lianti_v2_bc1_10 | /5Phos/GTCTTG CCGCGCTT AGATGTGTATAAGAGACAG (SEQ ID NO: 22) | 1st round barcode: Tn5 reverse |

TABLE 4-continued

Oligos for sci-L3.

| oligo name | oligo modification and sequence | note |
| --- | --- | --- |
| lianti_v2_bc1_11 | /5Phos/GTCTTG TCTTAGTG AGATGTGTATAAGAGACAG (SEQ ID NO: 23) | 1st round barcode: Tn5 reverse |
| lianti_v2_bc1_12 | /5Phos/GTCTTG TCGGCCTA AGATGTGTATAAGAGACAG (SEQ ID NO: 24) | 1st round barcode: Tn5 reverse |
| lianti_v2_bc1_13 | /5Phos/GTCTTG CTTTCTCT AGATGTGTATAAGAGACAG (SEQ ID NO: 25) | 1st round barcode: Tn5 reverse |
| lianti_v2_bc1_14 | /5Phos/GTCTTG TCGCGTTT AGATGTGTATAAGAGACAG (SEQ ID NO: 26) | 1st round barcode: Tn5 reverse |
| lianti_v2_bc1_15 | /5Phos/GTCTTG GTCAGTAG AGATGTGTATAAGAGACAG (SEQ ID NO: 27) | 1st round barcode: Tn5 reverse |
| lianti_v2_bc1_16 | /5Phos/GTCTTG CCATGGAA AGATGTGTATAAGAGACAG (SEQ ID NO: 28) | 1st round barcode: Tn5 reverse |
| lianti_v2_bc1_17 | /5Phos/GTCTTG ATGCTGCG AGATGTGTATAAGAGACAG (SEQ ID NO: 29) | 1st round barcode: Tn5 reverse |
| lianti_v2_bc1_18 | /5Phos/GTCTTG GAGTCTTT AGATGTGTATAAGAGACAG (SEQ ID NO: 30) | 1st round barcode: Tn5 reverse |
| lianti_v2_bc1_19 | /5Phos/GTCTTG TACGATAT AGATGTGTATAAGAGACAG (SEQ ID NO: 31) | 1st round barcode: Tn5 reverse |
| lianti_v2_bc1_20 | /5Phos/GTCTTG ACCATTTA AGATGTGTATAAGAGACAG (SEQ ID NO: 32) | 1st round barcode: Tn5 reverse |
| lianti_v2_bc1_21 | /5Phos/GTCTTG ATCGGGAC AGATGTGTATAAGAGACAG (SEQ ID NO: 33) | 1st round barcode: Tn5 reverse |
| lianti_v2_bc1_22 | /5Phos/GTCTTG GACGTCGG AGATGTGTATAAGAGACAG (SEQ ID NO: 34) | 1st round barcode: Tn5 reverse |
| lianti_v2_bc1_23 | /5Phos/GTCTTG CATTGTGT AGATGTGTATAAGAGACAG (SEQ ID NO: 35) | 1st round barcode: Tn5 reverse |
| lianti_v2_bc1_24 | /5Phos/GTCTTG TTTGACTC AGATGTGTATAAGAGACAG (SEQ ID NO: 36) | 1st round barcode: Tn5 reverse |
| lianti_v2_bc2_1 | CAAGAC AGGTGGCCAGGAGCGAGCTGCATCCC AATTTAATACGACTCACTATA GGGATGCAGCTCGCTCCTG GCCACCT (SEQ ID NO: 37) | 2nd round barcode: ligation |
| lianti_v2_bc2_2 | CAAGAC TAATAGCCAGGAGCGAGCTGCATCCC AATTTAATACGACTCACTATA GGGATGCAGCTCGCTCCTG GCTATTA (SEQ D NO: 38) | 2nd round barcode: ligation |
| lianti_v2_bc2_3 | CAAGAC CAACATACAGGAGCGAGCTGCATCCC AATTTAATACGACTCACTATA GGGATGCAGCTCGCTCCTG TATGTTG (SEQ ID NO: 39) | 2nd round barcode: ligation |
| lianti_v2_bc2_4 | CAAGAC CGGTTAACAGGAGCGAGCTGCATCCC AATTTAATACGACTCACTATA GGGATGCAGCTCGCTCCTG TTAACCG (SEQ ID NO: 40) | 2nd round barcode: ligation |
| lianti_v2_bc2_5 | CAAGAC TGTACCCCAGGAGCGAGCTGCATCCC AATTTAATACGACTCACTATA GGGATGCAGCTCGCTCCTG GGGTACA (SEQ ID NO: 41) | 2nd round barcode: ligation |
| lianti_v2_bc2_6 | CAAGAC AATAGAACAGGAGCGAGCTGCATCCC AATTTAATACGACTCACTATA GGGATGCAGCTCGCTCCTG TTCTATT (SEQ ID NO: 42) | 2nd round barcode: ligation |
| lianti_v2_bc2_7 | CAAGAC ATCAAGCCAGGAGCGAGCTGCATCCC AATTTAATACGACTCACTATA GGGATGCAGCTCGCTCCTG GCTTGAT (SEQ ID NO: 43) | 2nd round barcode: ligation |
| lianti_v2_bc2_8 | CAAGAC ACTTGGACAGGAGCGAGCTGCATCCC AATTTAATACGACTCACTATA GGGATGCAGCTCGCTCCTG TCCAAGT (SEQ ID NO: 44) | 2nd round barcode: ligation |

TABLE 4-continued

Oligos for sci-L3.

| oligo name | oligo modification and sequence | note |
|---|---|---|
| lianti_v2_bc2_9 | CAAGAC TAGTTCTCAGGAGCGAGCTGCATCCC AATTTAATACGACTCACTATA GGGATGCAGCTCGCTCCTG AGAACTA (SEQ ID NO: 45) | 2nd round barcode: ligation |
| lianti_v2_bc2_10 | CAAGAC AAACCGACAGGAGCGAGCTGCATCCC AATTTAATACGACTCACTATA GGGATGCAGCTCGCTCCTG TCGGTTT (SEQ ID NO: 46) | 2nd round barcode: ligation |
| lianti_v2_bc2_11 | CAAGAC AGTCTCTCAGGAGCGAGCTGCATCCC AATTTAATACGACTCACTATA GGGATGCAGCTCGCTCCTG AGAGACT (SEQ ID NO: 47) | 2nd round barcode: ligation |
| lianti_v2_bc2_12 | CAAGAC TTAACAGCAGGAGCGAGCTGCATCCC AATTTAATACGACTCACTATA GGGATGCAGCTCGCTCCTG CTGTTAA (SEQ ID NO: 48) | 2nd round barcode: ligation |
| lianti_v2_bc2_13 | CAAGAC ACTACCTCAGGAGCGAGCTGCATCCC AATTTAATACGACTCACTATA GGGATGCAGCTCGCTCCTG AGGTAGT (SEQ ID NO: 49) | 2nd round barcode: ligation |
| lianti_v2_bc2_14 | CAAGAC CCAAGCCCAGGAGCGAGCTGCATCCC AATTTAATACGACTCACTATA GGGATGCAGCTCGCTCCTG GGCTTGG (SEQ ID NO: 50) | 2nd round barcode: ligation |
| lianti_v2_bc2_15 | CAAGAC AACAGTGCAGGAGCGAGCTGCATCCC AATTTAATACGACTCACTATA GGGATGCAGCTCGCTCCTG CACTGTT (SEQ ID NO: 51) | 2nd round barcode: ligation |
| lianti_v2_bc2_16 | CAAGAC ACGACGTCAGGAGCGAGCTGCATCCC AATTTAATACGACTCACTATA GGGATGCAGCTCGCTCCTG ACGTCGT (SEQ ID NO: 52) | 2nd round barcode: ligation |
| lianti_v2_bc2_17 | CAAGAC TTAAGCACAGGAGCGAGCTGCATCCC AATTTAATACGACTCACTATA GGGATGCAGCTCGCTCCTG TGCTTAA (SEQ ID NO: 53) | 2nd round barcode: ligation |
| lianti_v2_bc2_18 | CAAGAC CTATGGACAGGAGCGAGCTGCATCCC AATTTAATACGACTCACTATA GGGATGCAGCTCGCTCCTG TCCATAG (SEQ ID NO: 54) | 2nd round barcode: ligation |
| lianti_v2_bc2_19 | CAAGAC GCGGCACCAGGAGCGAGCTGCATCCC AATTTAATACGACTCACTATA GGGATGCAGCTCGCTCCTG GTGCCGC (SEQ ID NO: 55) | 2nd round barcode: ligation |
| lianti_v2_bc2_20 | CAAGAC GACCTGCCAGGAGCGAGCTGCATCCC AATTTAATACGACTCACTATA GGGATGCAGCTCGCTCCTG GCAGGTC (SEQ ID NO: 56) | 2nd round barcode: ligation |
| lianti_v2_bc2_21 | CAAGAC CGGTGCACAGGAGCGAGCTGCATCCC AATTTAATACGACTCACTATA GGGATGCAGCTCGCTCCTG TGCACCG (SEQ ID NO: 57) | 2nd round barcode: ligation |
| lianti_v2_bc2_22 | CAAGAC AGTCTCTCAGGAGCGAGCTGCATCCC AATTTAATACGACTCACTATA GGGATGCAGCTCGCTCCTG AGAGACT (SEQ ID NO: 58) | 2nd round barcode: ligation |
| lianti_v2_bc2_23 | CAAGAC CTTTTATCAGGAGCGAGCTGCATCCC AATTTAATACGACTCACTATA GGGATGCAGCTCGCTCCTG ATAAAAG (SEQ ID NO: 59) | 2nd round barcode: ligation |
| lianti_v2_bc2_24 | CAAGAC TGGGACCCAGGAGCGAGCTGCATCCC AATTTAATACGACTCACTATA GGGATGCAGCTCGCTCCTG GGTCCCA (SEQ ID NO: 60) | 2nd round barcode: ligation |
| lianti_v2_bc2_25 | CAAGAC GTGCGAC CAGGAGCGAGCTGCATCCC AATTTAATACGACTCACTATA GGGATGCAGCTCGCTCCTG GTCGCAC (SEQ ID NO: 61) | 2nd round barcode: ligation |
| lianti_v2_bc2_26 | CAAGAC CCTTTAC CAGGAGCGAGCTGCATCCC AATTTAATACGACTCACTATA GGGATGCAGCTCGCTCCTG GTAAAGG (SEQ ID NO: 62) | 2nd round barcode: ligation |
| lianti_v2_bc2_27 | CAAGAC CAAGTCG CAGGAGCGAGCTGCATCCC AATTTAATACGACTCACTATA GGGATGCAGCTCGCTCCTG CGACTTG (SEQ ID NO: 63) | 2nd round barcode: ligation |

TABLE 4-continued

Oligos for sci-L3.

| oligo name | oligo modification and sequence | note |
|---|---|---|
| lianti_v2_bc2_28 | CAAGAC TAAGCGG CAGGAGCGAGCTGCATCCC AATTTAATACGACTCACTATA GGGATGCAGCTCGCTCCTG CCGCTTA (SEQ ID NO: 64) | 2nd round barcode: ligation |
| lianti_v2_bc2_29 | CAAGAC TGACCAT CAGGAGCGAGCTGCATCCC AATTTAATACGACTCACTATA GGGATGCAGCTCGCTCCTG ATGGTCA (SEQ ID NO: 65) | 2nd round barcode: ligation |
| lianti_v2_bc2_30 | CAAGAC TGGATGG CAGGAGCGAGCTGCATCCC AATTTAATACGACTCACTATA GGGATGCAGCTCGCTCCTG CCATCCA (SEQ ID NO: 66) | 2nd round barcode: ligation |
| lianti_v2_bc2_31 | CAAGAC CTCGCCC CAGGAGCGAGCTGCATCCC AATTTAATACGACTCACTATA GGGATGCAGCTCGCTCCTG GGGCGAG (SEQ ID NO: 67) | 2nd round barcode: ligation |
| lianti_v2_bc2_32 | CAAGAC CATGCAG CAGGAGCGAGCTGCATCCC AATTTAATACGACTCACTATA GGGATGCAGCTCGCTCCTG CTGCATG (SEQ ID NO: 68) | 2nd round barcode: ligation |
| lianti_v2_bc2_33 | CAAGAC CTGTAGG CAGGAGCGAGCTGCATCCC AATTTAATACGACTCACTATA GGGATGCAGCTCGCTCCTG CCTACAG (SEQ ID NO: 69) | 2nd round barcode: ligation |
| lianti_v2_bc2_34 | CAAGAC ACCTCTG CAGGAGCGAGCTGCATCCC AATTTAATACGACTCACTATA GGGATGCAGCTCGCTCCTG CAGAGGT (SEQ ID NO: 70) | 2nd round barcode: ligation |
| lianti_v2_bc2_35 | CAAGAC CGTTTTG CAGGAGCGAGCTGCATCCC AATTTAATACGACTCACTATA GGGATGCAGCTCGCTCCTG CAAAACG (SEQ ID NO: 71) | 2nd round barcode: ligation |
| lianti_v2_bc2_36 | CAAGAC GAAGGTC CAGGAGCGAGCTGCATCCC AATTTAATACGACTCACTATA GGGATGCAGCTCGCTCCTG GACCTTC (SEQ ID NO: 72) | 2nd round barcode: ligation |
| lianti_v2_bc2_37 | CAAGAC GGCTACT CAGGAGCGAGCTGCATCCC AATTTAATACGACTCACTATA GGGATGCAGCTCGCTCCTG AGTAGCC (SEQ ID NO: 73) | 2nd round barcode: ligation |
| lianti_v2_bc2_38 | CAAGAC CCGGCTA CAGGAGCGAGCTGCATCCC AATTTAATACGACTCACTATA GGGATGCAGCTCGCTCCTG TAGCCGG (SEQ ID NO: 74) | 2nd round barcode: ligation |
| lianti_v2_bc2_39 | CAAGAC TAGACTA CAGGAGCGAGCTGCATCCC AATTTAATACGACTCACTATA GGGATGCAGCTCGCTCCTG TAGTCTA (SEQ ID NO: 75) | 2nd round barcode: ligation |
| lianti_v2_bc2_40 | CAAGAC AAATTAC CAGGAGCGAGCTGCATCCC AATTTAATACGACTCACTATA GGGATGCAGCTCGCTCCTG GTAATTT (SEQ ID NO: 76) | 2nd round barcode: ligation |
| lianti_v2_bc2_41 | CAAGAC TACTCGA CAGGAGCGAGCTGCATCCC AATTTAATACGACTCACTATA GGGATGCAGCTCGCTCCTG TCGAGTA (SEQ ID NO: 77) | 2nd round barcode: ligation |
| lianti_v2_bc2_42 | CAAGAC TCCTACC CAGGAGCGAGCTGCATCCC AATTTAATACGACTCACTATA GGGATGCAGCTCGCTCCTG GGTAGGA (SEQ ID NO: 78) | 2nd round barcode: ligation |
| lianti_v2_bc2_43 | CAAGAC CCCCGTC CAGGAGCGAGCTGCATCCC AATTTAATACGACTCACTATA GGGATGCAGCTCGCTCCTG GACGGGG (SEQ ID NO: 79) | 2nd round barcode: ligation |
| lianti_v2_bc2_44 | CAAGAC GATACGA CAGGAGCGAGCTGCATCCC AATTTAATACGACTCACTATA GGGATGCAGCTCGCTCCTG TCGTATC (SEQ ID NO: 80) | 2nd round barcode: ligation |
| lianti_v2_bc2_45 | CAAGAC GCTGTGA CAGGAGCGAGCTGCATCCC AATTTAATACGACTCACTATA GGGATGCAGCTCGCTCCTG TCACAGC (SEQ ID NO: 81) | 2nd round barcode: ligation |

TABLE 4-continued

Oligos for sci-L3.

| oligo name | oligo modification and sequence | note |
|---|---|---|
| lianti_v2_bc2_46 | CAAGAC TATAGGC CAGGAGCGAGCTGCATCCC AATTTAATACGACTCACTATA GGGATGCAGCTCGCTCCTG GCCTATA (SEQ ID NO: 82) | 2nd round barcode: ligation |
| lianti_v2_bc2_47 | CAAGAC CGACGCA CAGGAGCGAGCTGCATCCC AATTTAATACGACTCACTATA GGGATGCAGCTCGCTCCTG TGCGTCG (SEQ ID NO: 83) | 2nd round barcode: ligation |
| lianti_v2_bc2_48 | CAAGAC TCCATTT CAGGAGCGAGCTGCATCCC AATTTAATACGACTCACTATA GGGATGCAGCTCGCTCCTG AAATGGA (SEQ ID NO: 84) | 2nd round barcode: ligation |
| lianti_v2_bc2_49 | CAAGAC AAGACCG CAGGAGCGAGCTGCATCCC AATTTAATACGACTCACTATA GGGATGCAGCTCGCTCCTG CGGTCTT (SEQ ID NO: 85) | 2nd round barcode: ligation |
| lianti_v2_bc2_50 | CAAGAC TAAGTAA CAGGAGCGAGCTGCATCCC AATTTAATACGACTCACTATA GGGATGCAGCTCGCTCCTG TTACTTA (SEQ ID NO: 86) | 2nd round barcode: ligation |
| lianti_v2_bc2_51 | CAAGAC CTACTGC CAGGAGCGAGCTGCATCCC AATTTAATACGACTCACTATA GGGATGCAGCTCGCTCCTG GCAGTAG (SEQ ID NO: 87) | 2nd round barcode: ligation |
| lianti_v2_bc2_52 | CAAGAC TCTTATA CAGGAGCGAGCTGCATCCC AATTTAATACGACTCACTATA GGGATGCAGCTCGCTCCTG TATAAGA (SEQ ID NO: 88) | 2nd round barcode: ligation |
| lianti_v2_bc2_53 | CAAGAC AACCCAC CAGGAGCGAGCTGCATCCC AATTTAATACGACTCACTATA GGGATGCAGCTCGCTCCTG GTGGGTT (SEQ ID NO: 89) | 2nd round barcode: ligation |
| lianti_v2_bc2_54 | CAAGAC TACGGAT CAGGAGCGAGCTGCATCCC AATTTAATACGACTCACTATA GGGATGCAGCTCGCTCCTG ATCCGTA (SEQ ID NO: 90) | 2nd round barcode: ligation |
| lianti_v2_bc2_55 | CAAGAC AATTCCA CAGGAGCGAGCTGCATCCC AATTTAATACGACTCACTATA GGGATGCAGCTCGCTCCTG TGGAATT (SEQ ID NO: 91) | 2nd round barcode: ligation |
| lianti_v2_bc2_56 | CAAGAC GTCTCCG CAGGAGCGAGCTGCATCCC AATTTAATACGACTCACTATA GGGATGCAGCTCGCTCCTG CGGAGAC (SEQ ID NO: 92) | 2nd round barcode: ligation |
| lianti_v2_bc2_57 | CAAGAC ATGCAGT CAGGAGCGAGCTGCATCCC AATTTAATACGACTCACTATA GGGATGCAGCTCGCTCCTG ACTGCAT (SEQ ID NO: 93) | 2nd round barcode: ligation |
| lianti_v2_bc2_58 | CAAGAC GAGCTTG CAGGAGCGAGCTGCATCCC AATTTAATACGACTCACTATA GGGATGCAGCTCGCTCCTG CAAGCTC (SEQ ID NO: 94) | 2nd round barcode: ligation |
| lianti_v2_bc2_59 | CAAGAC GAGAAAC CAGGAGCGAGCTGCATCCC AATTTAATACGACTCACTATA GGGATGCAGCTCGCTCCTG GTTTCTC (SEQ ID NO: 95) | 2nd round barcode: ligation |
| lianti_v2_bc2_60 | CAAGAC TTTGGCC CAGGAGCGAGCTGCATCCC AATTTAATACGACTCACTATA GGGATGCAGCTCGCTCCTG GGCCAAA (SEQ ID NO: 96) | 2nd round barcode: ligation |
| lianti_v2_bc2_61 | CAAGAC TGCGAGT CAGGAGCGAGCTGCATCCC AATTTAATACGACTCACTATA GGGATGCAGCTCGCTCCTG ACTCGCA (SEQ ID NO: 97) | 2nd round barcode: ligation |
| lianti_v2_bc2_62 | CAAGAC TGCATCA CAGGAGCGAGCTGCATCCC AATTTAATACGACTCACTATA GGGATGCAGCTCGCTCCTG TGATGCA (SEQ ID NO: 98) | 2nd round barcode: ligation |
| lianti_v2_bc2_63 | CAAGAC GGGATAT CAGGAGCGAGCTGCATCCC AATTTAATACGACTCACTATA GGGATGCAGCTCGCTCCTG ATATCCC (SEQ ID NO: 99) | 2nd round barcode: ligation |
| lianti_v2_bc2_64 | CAAGAC TCGCCTC CAGGAGCGAGCTGCATCCC AATTTAATACGACTCACTATA GGGATGCAGCTCGCTCCTG GAGGCGA (SEQ ID NO: 100) | 2nd round barcode: ligation |

TABLE 4-continued

Oligos for sci-L3.

| oligo name | oligo modification and sequence | note |
|---|---|---|
| yy_lianti_v2_RT_RNAprimer | rArGrArUrGrUrGrUrArUrArArGrArGrArCrArG (SEQ ID NO: 101) | RNA RT primer |
| liantSSS_bc1 | NNNN ACGCGA GGGATGCAGCTCGCTCCTG (SEQ ID NO: 102) | 3rd round barcode: SSS |
| liantSSS_bc2 | NNNN CGCTTG GGGATGCAGCTCGCTCCTG (SEQ ID NO: 103) | 3rd round barcode: SSS |
| liantSSS_bc3 | NNNN GTCCTA GGGATGCAGCTCGCTCCTG (SEQ ID NO: 104) | 3rd round barcode: SSS |
| liantSSS_bc4 | NNNN AGGATG GGGATGCAGCTCGCTCCTG (SEQ ID NO: 105) | 3rd round barcode: SSS |
| liantSSS_bc5 | NNNN TTCTCC GGGATGCAGCTCGCTCCTG (SEQ ID NO: 106) | 3rd round barcode: SSS |
| liantSSS_bc6 | NNNN ACCACT GGGATGCAGCTCGCTCCTG (SEQ ID NO: 107) | 3rd round barcode: SSS |
| liantSSS_bc7 | NNNN TTTCGC GGGATGCAGCTCGCTCCTG (SEQ ID NO: 108) | 3rd round barcode: SSS |
| liantSSS_bc8 | NNNN CGGTGG GGGATGCAGCTCGCTCCTG (SEQ ID NO: 109) | 3rd round barcode: SSS |
| liantSSS_bc9 | NNNN TATTCT GGGATGCAGCTCGCTCCTG (SEQ ID NO: 110) | 3rd round barcode: SSS |
| liantSSS_bc10 | NNNN ACTTAA GGGATGCAGCTCGCTCCTG (SEQ ID NO: 111) | 3rd round barcode: SSS |
| liantSSS_bc11 | NNNN TAAAGA GGGATGCAGCTCGCTCCTG (SEQ ID NO: 112) | 3rd round barcode: SSS |
| liantSSS_bc12 | NNNN GAGTTT GGGATGCAGCTCGCTCCTG (SEQ ID NO: 113) | 3rd round barcode: SSS |
| liantSSS_bc13 | NNNN GGGTGC GGGATGCAGCTCGCTCCTG (SEQ ID NO: 114) | 3rd round barcode: SSS |
| liantSSS_bc14 | NNNN GGGCCG GGGATGCAGCTCGCTCCTG (SEQ ID NO: 115) | 3rd round barcode: SSS |
| liantSSS_bc15 | NNNN AATTGA GGGATGCAGCTCGCTCCTG (SEQ ID NO: 116) | 3rd round barcode: SSS |
| liantSSS_bc16 | NNNN TAAGCG GGGATGCAGCTCGCTCCTG (SEQ ID NO: 117) | 3rd round barcode: SSS |
| liantSSS_bc17 | NNNN TAATGC GGGATGCAGCTCGCTCCTG (SEQ ID NO: 118) | 3rd round barcode: SSS |
| liantSSS_bc18 | NNNN GTCTAT GGGATGCAGCTCGCTCCTG (SEQ ID NO: 119) | 3rd round barcode: SSS |
| yy_dna_rna_bc1_1 | /5Phos/GTCTTG NNNNNN ACCCGACA TTTTTTTTTTTTTTTTTTTTTTTTTTTTTVN (SEQ ID NO: 120) | 1st round barcode: RT |
| yy_dna_rna_bc1_2 | /5Phos/GTCTTG NNNNNN AGGCTCTC TTTTTTTTTTTTTTTTTTTTTTTTTTTTTVN (SEQ ID NO: 121) | 1st round barcode: RT |
| yy_dna_rna_bc1_3 | /5Phos/GTCTTG NNNNNN TCTAAACT TTTTTTTTTTTTTTTTTTTTTTTTTTTTTVN (SEQ ID NO: 122) | 1st round barcode: RT |
| yy_dna_rna_bc1_4 | /5Phos/GTCTTG NNNNNN TACCCTCG TTTTTTTTTTTTTTTTTTTTTTTTTTTTTVN (SEQ ID NO: 123) | 1st round barcode: RT |
| yy_dna_rna_bc1_5 | /5Phos/GTCTTG NNNNNN CTGGTCAT TTTTTTTTTTTTTTTTTTTTTTTTTTTTTVN (SEQ ID NO: 124) | 1st round barcode: RT |
| yy_dna_rna_bc1_6 | /5Phos/GTCTTG NNNNNN TTATAAGC TTTTTTTTTTTTTTTTTTTTTTTTTTTTTVN (SEQ ID NO: 125) | 1st round barcode: RT |

TABLE 4-continued

Oligos for sci-L3.

| oligo name | oligo modification and sequence | note |
| --- | --- | --- |
| yy_dna_rna_bc1_7 | /5Phos/GTCTTG NNNNNN AATGTAGA TTTTTTTTTTTTTTTTTTTTTTTTTTTTTTVN (SEQ ID NO: 126) | 1st round barcode: RT |
| yy_dna_rna_bc1_8 | /5Phos/GTCTTG NNNNNN CGCAGACC TTTTTTTTTTTTTTTTTTTTTTTTTTTTTTVN (SEQ ID NO: 127) | 1st round barcode: RT |
| yy_dna_rna_bc1_9 | /5Phos/GTCTTG NNNNNN CGAATCAA TTTTTTTTTTTTTTTTTTTTTTTTTTTTTTVN (SEQ ID NO: 128) | 1st round barcode: RT |
| yy_dna_rna_bc1_10 | /5Phos/GTCTTG NNNNNN CCGGAAAG TTTTTTTTTTTTTTTTTTTTTTTTTTTTTTVN (SEQ ID NO: 129) | 1st round barcode: RT |
| yy_dna_rna_bc1_11 | /5Phos/GTCTTG NNNNNN GTTTAAAG TTTTTTTTTTTTTTTTTTTTTTTTTTTTTTVN (SEQ ID NO: 130) | 1st round barcode: RT |
| yy_dna_rna_bc1_12 | /5Phos/GTCTTG NNNNNN AAAGTTGA TTTTTTTTTTTTTTTTTTTTTTTTTTTTTTVN (SEQ ID NO: 131) | 1st round barcode: RT |
| yy_dna_rna_bc1_13 | /5Phos/GTCTTG NNNNNN CGGAAACT TTTTTTTTTTTTTTTTTTTTTTTTTTTTTTVN (SEQ ID NO: 132) | 1st round barcode: RT |
| yy_dna_rna_bc1_14 | /5Phos/GTCTTG NNNNNN TGAGTACC TTTTTTTTTTTTTTTTTTTTTTTTTTTTTTVN (SEQ ID NO: 133) | 1st round barcode: RT |
| yy_dna_rna_bc1_15 | /5Phos/GTCTTG NNNNNN CGTAGAAT TTTTTTTTTTTTTTTTTTTTTTTTTTTTTTVN (SEQ ID NO: 134) | 1st round barcode: RT |
| yy_dna_rna_bc1_16 | /5Phos/GTCTTG NNNNNN CGACACCC TTTTTTTTTTTTTTTTTTTTTTTTTTTTTTVN (SEQ ID NO: 135) | 1st round barcode: RT |
| yy_dna_rna_bc1_17 | /5Phos/GTCTTGNNNNNNN GTACTGAA TTTTTTTTTTTTTTTTTTTTTTTTTTTTTTVN (SEQ ID NO: 136) | 1st round barcode: RT |
| yy_dna_rna_bc1_18 | /5Phos/GTCTTGNNNNNNN CGGAAAGA TTTTTTTTTTTTTTTTTTTTTTTTTTTTTTVN (SEQ ID NO: 137) | 1st round barcode: RT |
| yy_dna_rna_bc1_19 | /5Phos/GTCTTGNNNNNNN ATATCAAT TTTTTTTTTTTTTTTTTTTTTTTTTTTTTTVN (SEQ ID NO: 138) | 1st round barcode: RT |
| yy_dna_rna_bc1_20 | /5Phos/GTCTTGNNNNNNN TACCCGGC TTTTTTTTTTTTTTTTTTTTTTTTTTTTTTVN (SEQ ID NO: 139) | 1st round barcode: RT |
| yy_dna_rna_bc1_21 | /5Phos/GTCTTGNNNNNNN GCCATCCC TTTTTTTTTTTTTTTTTTTTTTTTTTTTTTVN (SEQ ID NO: 140) | 1st round barcode: RT |
| yy_dna_rna_bc1_22 | /5Phos/GTCTTGNNNNNNN ACCAACGC TTTTTTTTTTTTTTTTTTTTTTTTTTTTTTVN (SEQ ID NO: 141) | 1st round barcode: RT |
| yy_dna_rna_bc1_23 | /5Phos/GTCTTGNNNNNNN TGCAAGCT TTTTTTTTTTTTTTTTTTTTTTTTTTTTTTVN (SEQ ID NO: 142) | 1st round barcode: RT |
| yy_dna_rna_bc1_24 | /5Phos/GTCTTGNNNNNNN GCAACCGG TTTTTTTTTTTTTTTTTTTTTTTTTTTTTTVN (SEQ ID NO: 143) | 1st round barcode: RT |
| yy_dna_rna_gf | CACGACGCTCTTCCGATCT NNNNNNN (SEQ ID NO: 144) | gap filling oligo for co-assay |
| yy_dna_rna_bc3_27 | CAAGCAGAAGACGGCATACGAGAT NNNN GATCCG CGTCTCTAC GGGATGCAGCTCGCTCCTG (SEQ ID NO: 145) | 3rd round barcode: SSS, co-assay |
| yy_dna_rna_bc3_28 | CAAGCAGAAGACGGCATACGAGAT NNNN GGGTAT CGTCTCTAC GGGATGCAGCTCGCTCCTG (SEQ ID NO: 146) | 3rd round barcode: SSS, co-assay |
| yy_dna_rna_bc3_29 | CAAGCAGAAGACGGCATACGAGAT NNNN CATGGA CGTCTCTAC GGGATGCAGCTCGCTCCTG (SEQ ID NO: 147) | 3rd round barcode: SSS, co-assay |
| yy_dna_rna_bc3_30 | CAAGCAGAAGACGGCATACGAGAT NNNN TTGAAG CGTCTCTAC GGGATGCAGCTCGCTCCTG (SEQ ID NO: 148) | 3rd round barcode: SSS, co-assay |
| yy_dna_rna_bc3_31 | CAAGCAGAAGACGGCATACGAGAT NNNN CTGGGT CGTCTCTAC GGGATGCAGCTCGCTCCTG (SEQ ID NO: 149) | 3rd round barcode: SSS, co-assay |
| yy_dna_rna_bc3_32 | CAAGCAGAAGACGGCATACGAGAT NNNN CACTAC CGTCTCTAC GGGATGCAGCTCGCTCCTG (SEQ ID NO: 150) | 3rd round barcode: SSS, co-assay |

TABLE 4-continued

Oligos for sci-L3.

| oligo name | oligo modification and sequence | note |
| --- | --- | --- |
| yy_dna_rna_bc3_33 | CAAGCAGAAGACGGCATACGAGAT NNNN CTTATA CGTCTCTAC GGGATGCAGCTCGCTCCTG (SEQ ID NO: 151) | 3rd round barcode: SSS, co-assay |
| yy_dna_rna_bc3_34 | CAAGCAGAAGACGGCATACGAGAT NNNN GTTGGA CGTCTCTAC GGGATGCAGCTCGCTCCTG (SEQ ID NO: 152) | 3rd round barcode: SSS, co-assay |
| yy_dna_rna_bc3_35 | CAAGCAGAAGACGGCATACGAGAT NNNN AGCGGT CGTCTCTAC GGGATGCAGCTCGCTCCTG (SEQ ID NO: 153) | 3rd round barcode: SSS, co-assay |
| yy_dna_rna_bc3_36 | CAAGCAGAAGACGGCATACGAGAT NNNN CCGTTC CGTCTCTAC GGGATGCAGCTCGCTCCTG (SEQ ID NO: 154) | 3rd round barcode: SSS, co-assay |
| yy_dna_rna_bc3_37 | CAAGCAGAAGACGGCATACGAGAT NNNN ACGTTA CGTCTCTAC GGGATGCAGCTCGCTCCTG (SEQ ID NO: 155) | 3rd round barcode: SSS, co-assay |
| yy_dna_rna_bc3_38 | CAAGCAGAAGACGGCATACGAGAT NNNN AACATA CGTCTCTAC GGGATGCAGCTCGCTCCTG (SEQ ID NO: 156) | 3rd round barcode: SSS, co-assay |
| yy_dna_rna_bc3_39 | CAAGCAGAAGACGGCATACGAGAT NNNN GCAGAC CGTCTCTAC GGGATGCAGCTCGCTCCTG (SEQ ID NO: 157) | 3rd round barcode: SSS, co-assay |
| yy_dna_rna_bc3_40 | CAAGCAGAAGACGGCATACGAGAT NNNN ATTCGT CGTCTCTAC GGGATGCAGCTCGCTCCTG (SEQ ID NO: 158) | 3rd round barcode: SSS, co-assay |
| yy_dna_rna_bc3_41 | CAAGCAGAAGACGGCATACGAGAT NNNN TGGGGT CGTCTCTAC GGGATGCAGCTCGCTCCTG (SEQ ID NO: 159) | 3rd round barcode: SSS, co-assay |
| yy_dna_rna_bc3_42 | CAAGCAGAAGACGGCATACGAGAT NNNN CTTCCC CGTCTCTAC GGGATGCAGCTCGCTCCTG (SEQ ID NO: 160) | 3rd round barcode: SSS, co-assay |
| yy_dna_rna_bc3_43 | CAAGCAGAAGACGGCATACGAGAT NNNN TCCGTG CGTCTCTAC GGGATGCAGCTCGCTCCTG (SEQ ID NO: 161) | 3rd round barcode: SSS, co-assay |
| yy_dna_rna_bc3_44 | CAAGCAGAAGACGGCATACGAGAT NNNN TTTGTA CGTCTCTAC GGGATGCAGCTCGCTCCTG (SEQ ID NO: 162) | 3rd round barcode: SSS, co-assay |
| yy_dna_rna_bc3_45 | CAAGCAGAAGACGGCATACGAGAT NNNN GAGATG CGTCTCTAC GGGATGCAGCTCGCTCCTG (SEQ ID NO: 163) | 3rd round barcode: SSS, co-assay |
| yy_dna_rna_bc3_46 | CAAGCAGAAGACGGCATACGAGAT NNNN GGACCA CGTCTCTAC GGGATGCAGCTCGCTCCTG (SEQ ID NO: 164) | 3rd round barcode: SSS, co-assay |
| yy_dna_rna_bc3_47 | CAAGCAGAAGACGGCATACGAGAT NNNN TATGTT CGTCTCTAC GGGATGCAGCTCGCTCCTG (SEQ ID NO: 165) | 3rd round barcode: SSS, co-assay |
| yy_dna_rna_bc3_48 | CAAGCAGAAGACGGCATACGAGAT NNNN CGACGC CGTCTCTAC GGGATGCAGCTCGCTCCTG (SEQ ID NO: 166) | 3rd round barcode: SSS, co-assay |
| yy_dna_rna_bc3_49 | CAAGCAGAAGACGGCATACGAGAT NNNN GCTATT CGTCTCTAC GGGATGCAGCTCGCTCCTG (SEQ ID NO: 167) | 3rd round barcode: SSS, co-assay |
| yy_dna_rna_bc3_50 | CAAGCAGAAGACGGCATACGAGAT NNNN CGGCTG CGTCTCTAC GGGATGCAGCTCGCTCCTG (SEQ ID NO: 168) | 3rd round barcode: SSS, co-assay |
| yy_dna_rna_bc3_51 | CAAGCAGAAGACGGCATACGAGAT NNNN CATCTG CGTCTCTAC GGGATGCAGCTCGCTCCTG (SEQ ID NO: 169) | 3rd round barcode: SSS, co-assay |
| yy_dna_rna_bc3_52 | CAAGCAGAAGACGGCATACGAGAT NNNN AAGTTC CGTCTCTAC GGGATGCAGCTCGCTCCTG (SEQ ID NO: 170) | 3rd round barcode: SSS, co-assay |
| yy_dna_rna_bc3_53 | CAAGCAGAAGACGGCATACGAGAT NNNN TTGTTA CGTCTCTAC GGGATGCAGCTCGCTCCTG (SEQ ID NO: 171) | 3rd round barcode: SSS, co-assay |
| yy_dna_rna_bc3_54 | CAAGCAGAAGACGGCATACGAGAT NNNN CAGGCA CGTCTCTAC GGGATGCAGCTCGCTCCTG (SEQ ID NO: 172) | 3rd round barcode: SSS, co-assay |
| yy_dna_rna_bc3_55 | CAAGCAGAAGACGGCATACGAGAT NNNN GGTGAG CGTCTCTAC GGGATGCAGCTCGCTCCTG (SEQ ID NO: 173) | 3rd round barcode: SSS, co-assay |
| yy_dna_rna_bc3_56 | CAAGCAGAAGACGGCATACGAGAT NNNN CAAAAG CGTCTCTAC GGGATGCAGCTCGCTCCTG (SEQ ID NO: 174) | 3rd round barcode: SSS, co-assay |
| yy_dna_rna_bc3_57 | CAAGCAGAAGACGGCATACGAGAT NNNN ACTCCT CGTCTCTAC GGGATGCAGCTCGCTCCTG (SEQ ID NO: 175) | 3rd round barcode: SSS, co-assay |

TABLE 4-continued

Oligos for sci-L3.

| oligo name | oligo modification and sequence | note |
|---|---|---|
| yy_dna_rna_bc3_58 | CAAGCAGAAGACGGCATACGAGAT NNNN TGCGGG CGTCTCTAC GGGATGCAGCTCGCTCCTG (SEQ ID NO: 176) | 3rd round barcode: SSS, co-assay |

Methods of Bioinformatic and Statistical Analyses
Read Processing, Alignment and SNV Calling Base calls were converted to fastq file by bcl2fastq with 1 mismatch allowed for errors in the index. We then used customized shell script "sci_lianti_v2.sh" for de-multiplexing (python scripts and the R Markdown file are uploaded separately as "sci_lianti_inst.tar.gz"; the R package containing intermediate data files for generating all the main and supplemental figures can be downloaded and installed via the following link: https://drive.google.com/file/d/19NFubouHrahZ8Wob1L-tcDrrTIIZEpJh/view?usp=sharing), which calls python scripts or NGS tools for the following steps: 1) order read pairs such that all single-cell combinatorial barcodes are in read 1 (R1); 2) de-multiplex $3^{rd}$ round (SSS, Ent, no error allowed) barcodes and attach both the barcodes and UMI for transcripts to the read names, and split library by $3^{rd}$ round barcodes. Note that all subsequent steps are done in parallel for individual libraries split up by $3^{rd}$ round barcodes, which contain 100-300 single cells; 3) using cutadapt to split $1^{st}$ (Tn5, 8 nt, 1 error allowed) and $2^{nd}$ rounds (ligation, Int, 1 error allowed) of barcodes in R1, errors being calculated by Levenshtein distance, and attach both rounds of barcodes to the read names. This step is done in paired-end mode, i.e., if R1 does not have the correct barcode and spacer structure, the paired read 2 (R2) is discarded; 4) using cutadapt to clean up R2; 5) align in paired-end mode to hg19 or mm10 genome with bwa mem (Li and Durbin, 2009). For experiments where we assess barcode collision, we use concatenated reference of hg19 and mm10 and use uniquely aligned reads to determine relative mapping rate to human or mouse genomes; 6) split bam files into single cell bam files using $1^{st}$ and $2^{nd}$ rounds of barcodes attached in the read name; 7) convert bam file to bed files with bedtools (Quinlan and Hall, 2010), and determine unique insertion sites if either R1 or R2 shares the same end points. Unique Tn5 insertion site is defined as fragments where both ends of the read pair need to be different; 8) using the "pileup" function in the "lianti" package (https://github.com/lh3/lianti/blob/master/pileup.c) (Chen et al., 2017) to call variants in a allele-aware mode. Note that we include the combined bulk bam file (generated by samtools merge (Chen et al., 2017; Li and Durbin, 2009) of all the 6900 single cells, more than 30×) with each single cell bam file at this step such that the threshold of depth at each SNP location only needs to be exceeded in the bulk file for a SNP call to be included in the final vcf file, therefore raw counts of the REF and ALT alleles are included in the single cell column as long as the variant is present as a heterozygous SNP in the bulk file. This circumvents the problem of high false negative rate due to low-depth sequencing in single cells by converting the de novo SNP calling question to a genotyping question; 9) annotate SNV called in terms of SNP quality in each single cell by the reference SNP vcf file for Spret (SPRET_EiJ.mgp.v5.snps.dbSNP142.vcf.gz downloaded from the Mouse Genome Project). The annotated SNP file is then used as input for subsequent crossover break point analyses.

HMM for Calling Breakpoints

The genotype at a given SNP site is determined by comparing the number of reads supporting reference and alternative alleles. For 1C cells, the crossover position is determined by fitting a hidden Markov model with three states: reference, alternative and heterozygous.

The transition matrix is specified in Table 5.

TABLE 5

Transition matrix.

| From | To | | |
|---|---|---|---|
| | reference | alternative | heterozygous |
| reference | 1 − transprob | transprob * 0.3 | transprob * 0.7 |
| alternative | transprob * 0.3 | 1 − transprob | transprob * 0.7 |
| heterozygous | transprob * 0.5 | transprob * 0.5 | 1 − transprob |

We selected the parameters manually based on visual assessment of how well the HMM captures the apparent structure in the data and that the results do not change appreciably when we vary the primary parameter by two orders of magnitude. The transprob takes a very small number [1e-10/(total number of SNPs on the given chromosome) in this case] to reflect the belief that state transitioning at any individual SNP site should be a very rare event. The further breakdown of transprob by fractions of 0.3 and 0.7 aims to suppress rapid successive transitions of the form reference-alternative-reference or alternative-reference-alternative.

The emission matrix is specified in Table 6.

TABLE 6

Emission matrix.

| State | Emission | |
|---|---|---|
| | reference | alternative |
| reference | 0.9 | 0.1 |
| alternative | 0.1 | 0.9 |
| heterozygous | 0.5 | 0.5 |

After hidden states are called for each individual SNP, continuous long state blocks are called by removing state blocks shorter than 50 kb. The crossover position is then determined by where the long state block switches to a different state, where the break point tract start position is the last SNP position of the previous state block and the tract end position is the first SNP position of the following state block.

For M2 cells, an average allele frequency is first obtained by averaging over alleles within a window of 40 SNPs. The binned allele frequencies are then used to infer underlying chromosome states from a hidden Markov model with single Gaussian probability distributions.

The transition matrix is specified in Table 7.

TABLE 7

Transition matrix.

| From | To | | |
| --- | --- | --- | --- |
| | reference | alternative | heterozygous |
| reference | 1 − transprob | 0 | transprob |
| alternative | 0 | 1 − transprob | transprob |
| heterozygous | transprob * 0.5 | transprob * 0.5 | 1 − transprob |

The emission matrix is specified in Table 8

TABLE 8

Emission matrix.

| State | Emission |
| --- | --- |
| reference | Normal(0.05, 0.1) |
| alternative | Normal(0.5, 0.1) |
| heterozygous | Normal(0.95, 0.1) |

Continuous long state blocks are called by removing state blocks shorter than 50 kb, then approximate break point position is determined by where the long state blocks switches to a different state. The approximate break point position is then refined by a likelihood ratio test aiming to find the likely break point within the upstream 20 and downstream 20 SNPs around the approximate break point. For each SNP, the probability of observing the observed genotype is specified in Table 9.

TABLE 9

Probability of observing the observed genotype.

| State | Observed | |
| --- | --- | --- |
| | reference | alternative |
| reference | 1 − error_prob | error_prob |
| alternative | error_prob | 1 − error_prob |
| heterozygous | 0.5 | 0.5 |

The error_prob is specified as 1e-3 which reflects the probability that a SNP is called incorrectly. For each SNP around the approximate break point, the likelihood of it being the actual break point is calculated by the above distribution. All SNPs with likelihood greater than 0.01*maximum likelihood are considered to be within the break point range. The start of the break tract is determined as the left-most SNP within these SNPs, while the end of the break tract as the right-most SNP. As in the 1C case, all M2 cell breakpoint tracts are further manually examined to remove artifacts, e.g. where two immediately adjacent switches are present within 50 kb. We also performed the same breakpoint calling in mitotically dividing Patski cells. For M2 cells and Patski cells, we also manually examined breakpoint tracts by comparing bin sizes of 10 and 40 SNPs for cells with sparse genome coverage.

This step generate crossover break points. We postprocess to add the chromosome segregation information based on whether the centromeric region, i.e., the starting region of each chromosome, is heterozygous ("mt", mitotic segregation) or homozygous ("me", meiotic segregation).

Analyses of Uniparental Chromosomes

This step takes the rds file from the HMM output and generates uniparental chromosome calls.

Figure 10:
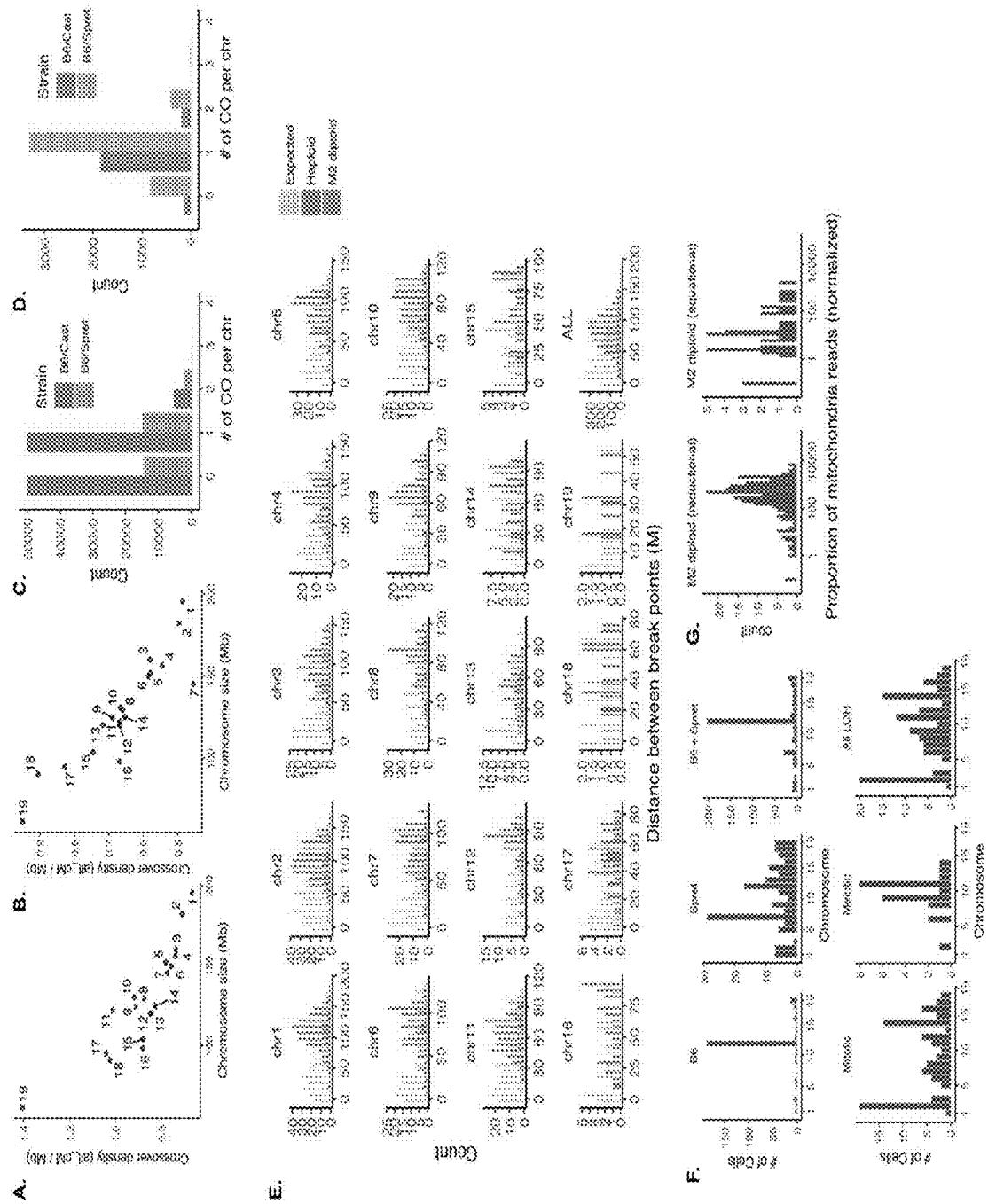
Figure 11:
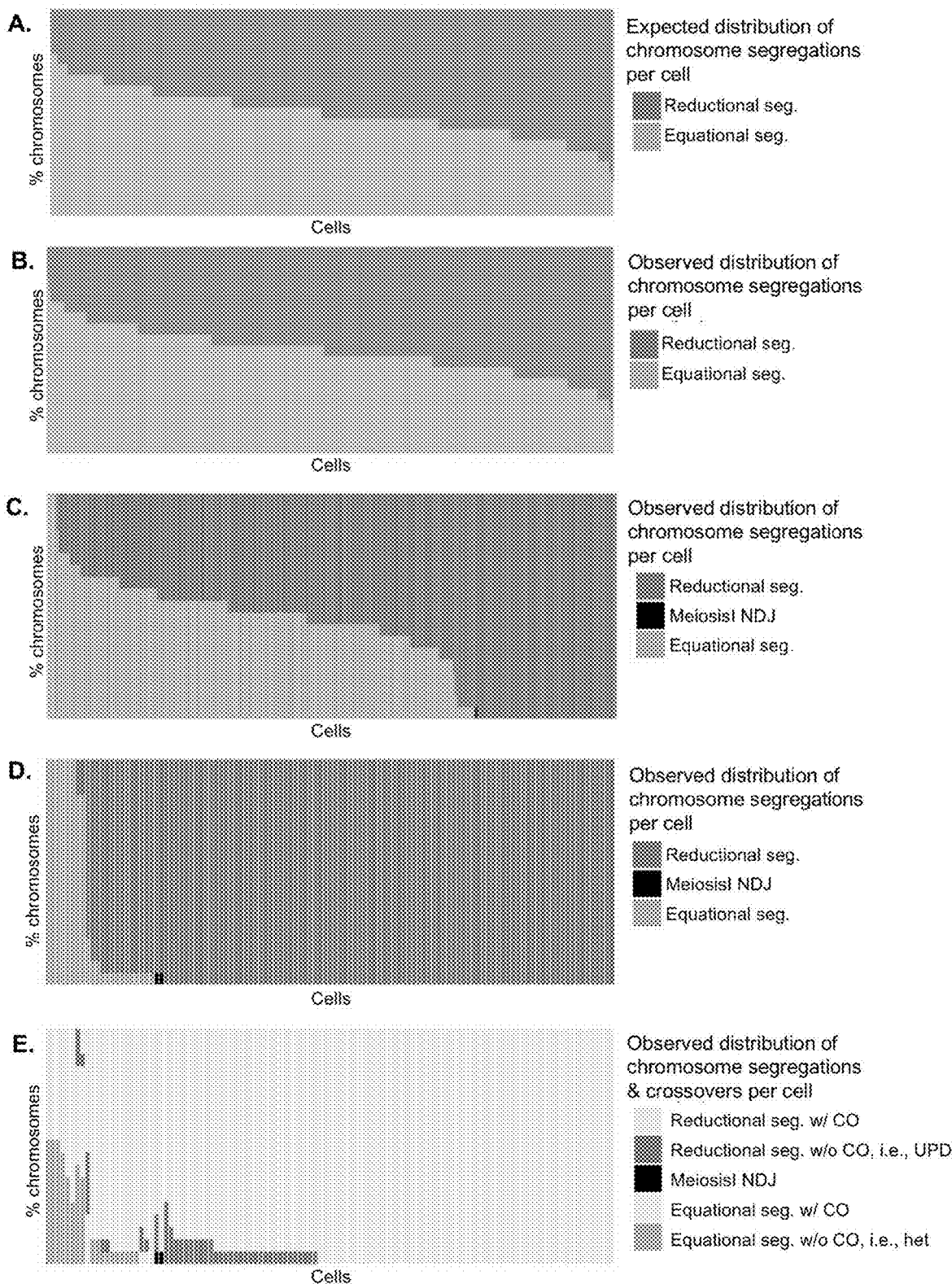
Figure 13:
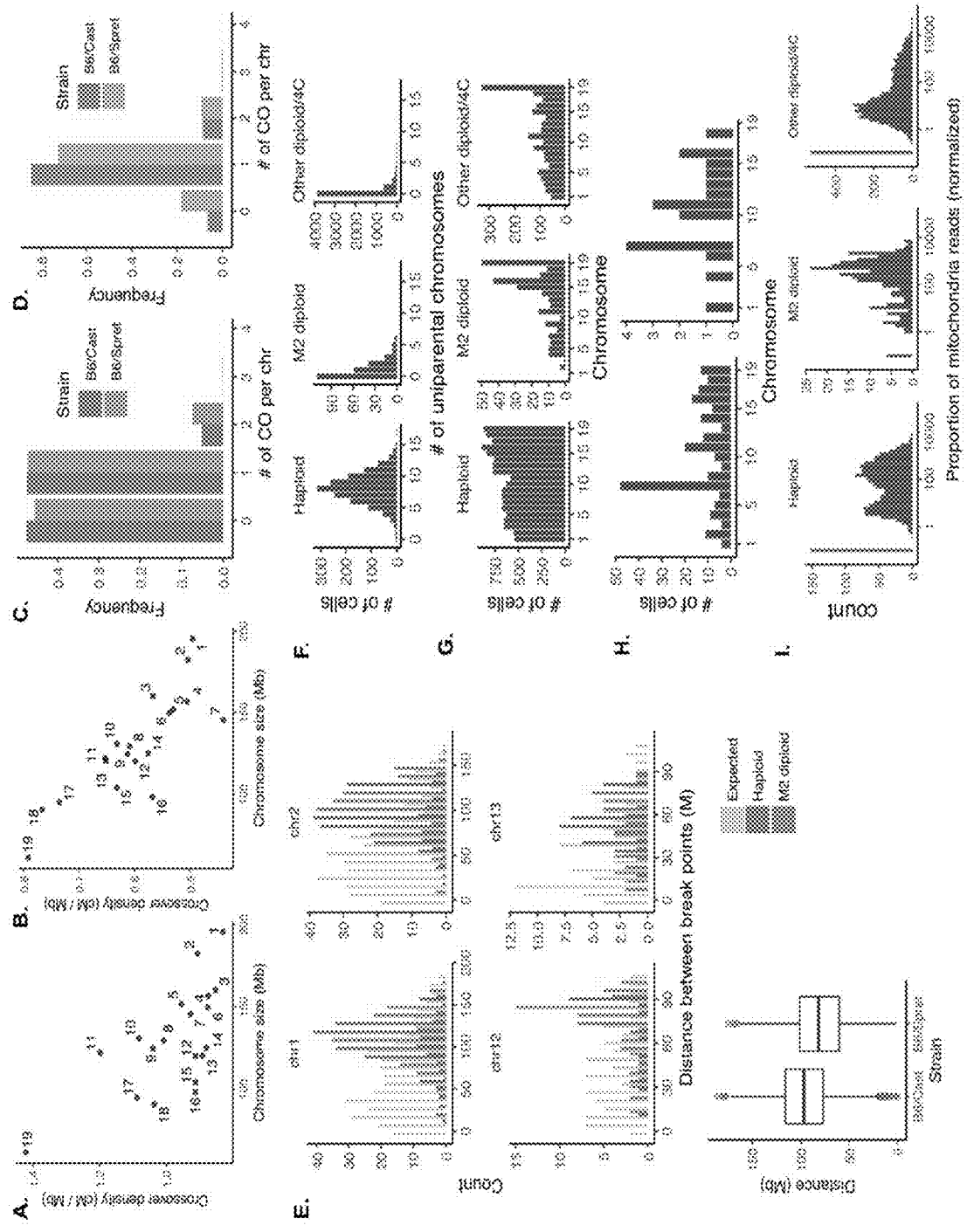
Figure 14:
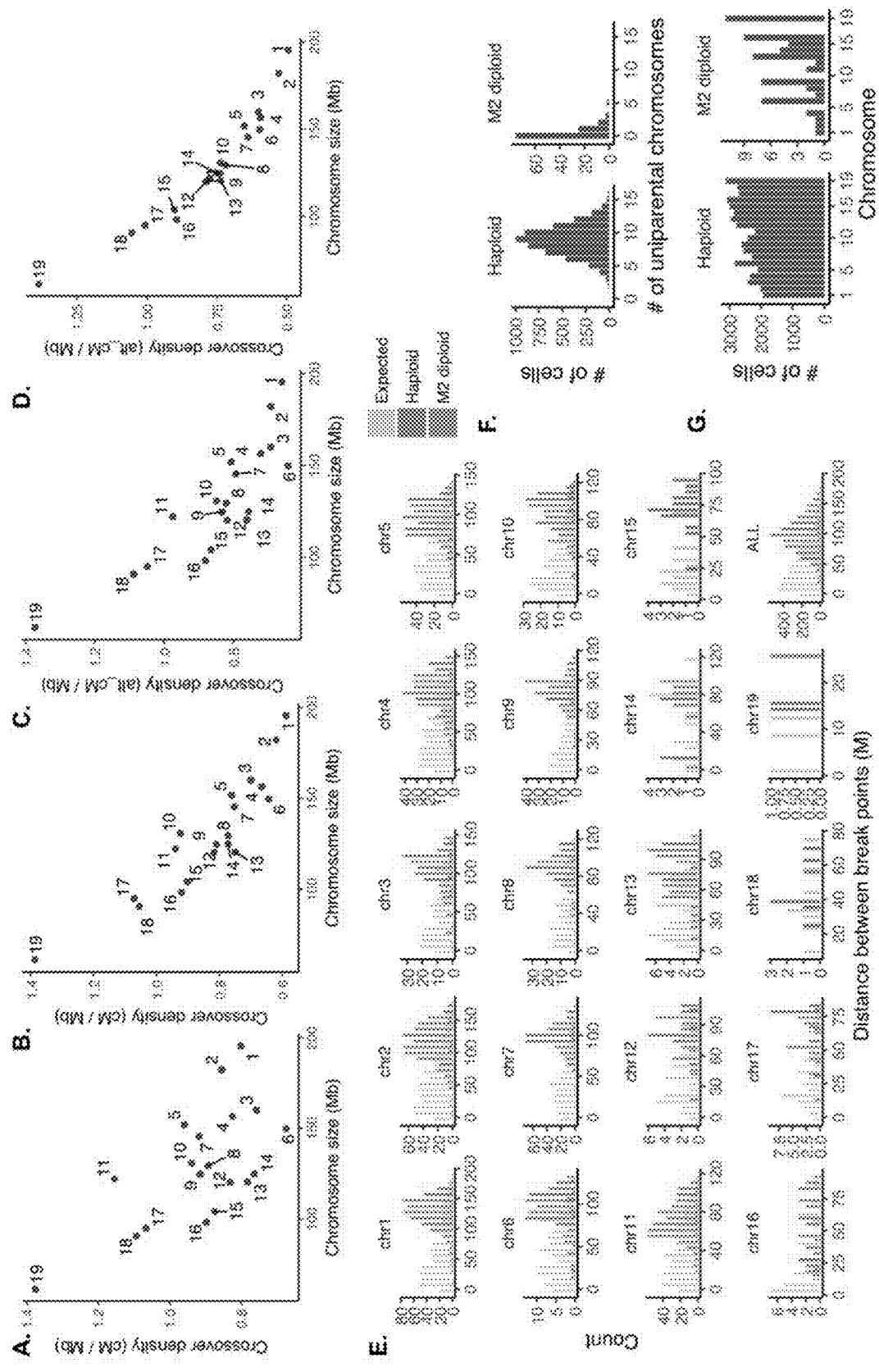

Analyses of Meiotic Crossover and Chromosome Segregation at the Chromosomal Level This step generates chromosomal level characteristics of meiotic crossovers shown in FIGS. 10, 13, and 14.

Fitting a Finite Mixture Model to the 2C Cells in Barcode Group 2 in the (B6×Cast) Cross We fit the data to a mixture of three binomial distributions parameterized by $p_1$, $p_2$, $p_3$, respectively, denoting their probabilities of chromosomes segregating equationally. The relative contribution of these three binomial distributions are denoted by a length 3 vector theta. We estimate $p_1$, $p_2$, $p_3$ as well as θ by drawing samples from their posterior distributions using the R package rstan (http://mc-stan.org/users/interfaces/rstan) with uniform Dirichlet prior for θ: θ~Dir (K=3, α=1), and beta prior for p: p ~Beta(a=5, b=5). For further details on the model specification, see the Stan file mt_mixture_model.stan.

Preprocessing of datasets from other genomic studies for building linear models of crossover hotness and cell clustering.

We processed datasets from previous genomic studies and from downloaded mouse annotation file in gff3 format and RepeatMasker from UCSC Genome Browser (https://genome.ucsc.edu/cgi-bin/hgTables) in terms of various genome elements. Datasets based on mm9 are first lifted over to mm10. These datasets roughly fall into two categories: count data in bed format or signal of various genetic or epigenetic marks in bedGraph format. For cell clustering and predictive modeling, crossover tracts have different lengths. We normalize count data by dividing the total amount of sequences summed up from all the crossover in each single cell for the cell clustering analyses and we normalize by dividing tract lengths plus 1 kb for each crossover tracts or randomly sampled tracts such that extremely short tracts will not be overly weighted. Note that the median tract length is 150 kb such that adding the 1 kb do not include much extra sequence. For dataset with continuous signal of various marks, we take the average signal of marks that intersect with crossover or random tracts. For the crossover pileup dataset, since we used evenly-sized 100 kb windows, we did not normalize for tract lengths when using count data.

In addition to datasets mentioned in the Discussion section, where features have statistically significant association with crossover occurrence, we also used the following datasets: 1) sequence divergence (Lilue et al., 2018); 2) ATAC-seq and H3K27ac mapped from purified pachytene spermatocytes (Maezawa et al., 2018); 3) bisulfite sequencing from spermatogonia (Inoue et al., 2017); 4) MNase-based nucleosome positioning in spermatocytes (Barral et al., 2017); 5) H4K5 and H4K8 butyrylation and acetylation in spermatocytes (Goudarzi et al., 2016); 6) H2A ubiquitination in spermatocytes (Hasegawa et al., 2015); 7). binding sites of CTCFL, the testis-specific paralogue of CTCF binding sites (Sleutels et al., 2012); 8) 5-hmC map in pachytene spermatocytes (Gan et al., 2013); 9) End-seq after etoposide treatment and CTCF and RAD21 ChIP-seq in activated B cells, TOP2A and TOP2B ChIP-seq in MEFs (Canela et al., 2017); 10) Patski allelic ATAC-seq data (Bonora et al., 2018).

PCA for Cell Clustering, BMA for Linear Models of Crossover Hotness and Random Forest for Predictive Models of Crossover and Random Tracts Principal component analysis is used to visualize in 2D the separation of 1C and M2 cells based on their break point features. We aggregated crossover-related information for each single cell a total of 78 features corresponding to three types. As a first type, we simply calculated the number of crossover or whole-chromosome LOH events for each chromosome in each cell. As a second type, for features such as GC content, sequence divergence, intensity of chromatin marks, etc., we calculated median values for the crossover breakpoints in each cell. As a third type, we calculated normalized counts of genomic elements such as genes bodies, long terminal repeats (LTR), LINE elements that overlapped with crossover breakpoints in each cell.

Bayesian model averaging using the "bas" package (Clyde et al., 2011) is used to construct linear models predicting crossover hotness (function bas.lm sampling $2^{14}$ models with default settings), and variables important for predicting hotness are identified based on their marginal inclusion probabilities. Random forests are trained to distinguish true crossover tracts from tracts randomly sampled from the genome resembling the "null" distribution. Model accuracy is determined by full nested 5-fold cross validation, with 5 external folds and 5 folds within each training set (see section called "Models" in sci-L3-WGS-figures.Rmd for R code and annotations).

To estimate the strain (or cell type) effect on the positioning of the rightmost crossovers along chromosomes, we use a linear mixed effect model with fixed effect for strain (or cell type) and random intercept for chromosome to account for inter-chromosome variability (see section called "Karyotype Plots" in sci-L3-WGS-figures.Rmd for R code and annotations).

REFERENCES

Barral, S., Morozumi, Y., Tanaka, H., Montellier, E., Govin, J., de Dieuleveult, M., Charbonnier, G., Couté, Y., Puthier, D., Buchou, T., et al. (2017). Histone Variant H2A.L.2 Guides Transition Protein-Dependent Protamine Assembly in Male Germ Cells. Mol. Cell 66, 89-101.e8.

Bonora, G., Deng, X., Fang, H., Ramani, V., Qiu, R., Berletch, J. B., Filippova, G. N., Duan, Z., Shendure, J., Noble, W. S., et al. (2018). Orientation-dependent Dxz4 contacts shape the 3D structure of the inactive X chromosome. Nat. Commun. 9, 1445.

Canela, A., Maman, Y., Jung, S., Wong, N., Callen, E., Day, A., Kieffer-Kwon, K.-R., Pekowska, A., Zhang, H., Rao, S. S. P., et al. (2017). Genome Organization Drives Chromosome Fragility. Cell 170, 507-521.e18.

Cao, J., Packer, J. S., Ramani, V., Cusanovich, D. A., Huynh, C., Daza, R., Qiu, X., Lee, C., Furlan, S. N., Steemers, F. J., et al. (2017). Comprehensive single-cell transcriptional profiling of a multicellular organism. Science 357, 661-667.

Chen, C., Xing, D., Tan, L., Li, H., Zhou, G., Huang, L., and Xie, X. S. (2017). Single-cell whole-genome analyses by Linear Amplification via Transposon Insertion (LIANTI). Science 356, 189-194.

Clyde, M. A., Ghosh, J., and Littman, M. L. (2011). Bayesian Adaptive Sampling for Variable Selection and Model Averaging. J. Comput. Graph. Stat. 20, 80-101.

Cusanovich, D. A., Daza, R., Adey, A., Pliner, H. A., Christiansen, L., Gunderson, K. L., Steemers, F. J., Trapnell, C., and Shendure, J. (2015). Multiplex single cell profiling of chromatin accessibility by combinatorial cellular indexing. Science 348, 910-914.

Dayani, Y., Simchen, G., and Lichten, M. (2011). Meiotic recombination intermediates are resolved with minimal crossover formation during return-to-growth, an analogue of the mitotic cell cycle. PLoS Genet. 7, e1002083.

Froenicke, L., Anderson, L. K., Wienberg, J., and Ashley, T. (2002). Male mouse recombination maps for each autosome identified by chromosome painting. Am. J. Hum. Genet. 71, 1353-1368.

Gan, H., Wen, L., Liao, S., Lin, X., Ma, T., Liu, J., Song, C.-X., Wang, M., He, C., Han, C., et al. (2013). Dynamics of 5-hydroxymethylcytosine during mouse spermatogenesis. Nat. Commun. 4, 1995.

Goudarzi, A., Zhang, D., Huang, H., Barral, S., Kwon, O. K., Qi, S., Tang, Z., Buchou, T., Vitte, A.-L., He, T., et al. (2016). Dynamic Competing Histone H4 K5K8 Acetylation and Butyrylation Are Hallmarks of Highly Active Gene Promoters. Mol. Cell 62, 169-180.

Hasegawa, K., Sin, H.-S., Maezawa, S., Broering, T. J., Kartashov, A. V., Alavattam, K. G., Ichijima, Y., Zhang, F., Bacon, W. C., Greis, K. D., et al. (2015). SCML2 establishes the male germline epigenome through regulation of histone H2A ubiquitination. Dev. Cell 32, 574-588.

Inoue, K., Ichiyanagi, K., Fukuda, K., Glinka, M., and Sasaki, H. (2017). Switching of dominant retrotransposon silencing strategies from posttranscriptional to transcriptional mechanisms during male germ-cell development in mice. PLoS Genet. 13, e1006926.

Lange, J., Yamada, S., Tischfield, S. E., Pan, J., Kim, S., Zhu, X., Socci, N. D., Jasin, M., and Keeney, S. (2016). The Landscape of Mouse Meiotic Double-Strand Break Formation, Processing, and Repair. Cell 167, 695-708.e16.

Li, H., and Durbin, R. (2009). Fast and accurate short read alignment with Burrows-Wheeler transform. Bioinformatics 25, 1754-1760.

Lilue, J., Doran, A. G., Fiddes, I. T., Abrudan, M., Armstrong, J., Bennett, R., Chow, W., Collins, J., Czechanski, A., Danecek, P., et al. (2018). Multiple laboratory mouse reference genomes define strain specific haplotypes and novel functional loci.

Lu, S., Zong, C., Fan, W., Yang, M., Li, J., Chapman, A. R., Zhu, P., Hu, X., Xu, L., Yan, L., et al. (2012). Probing meiotic recombination and aneuploidy of single sperm cells by whole-genome sequencing. Science 338, 1627-1630.

Maezawa, S., Yukawa, M., Alavattam, K. G., Barski, A., and Namekawa, S. H. (2018). Dynamic reorganization of open chromatin underlies diverse transcriptomes during spermatogenesis. Nucleic Acids Res. 46, 593-608.

Marchal, C., Sasaki, T., Vera, D., Wilson, K., Sima, J., Rivera-Mulia, J. C., Trevilla-Garcia, C., Nogues, C., Nafie, E., and Gilbert, D. M. (2018). Genome-wide analysis of replication timing by next-generation sequencing with E/L Repli-seq. Nat. Protoc. 13, 819-839.

Mu, W., Starmer, J., Shibata, Y., Yee, D., and Magnuson, T. (2017). EZH1 in germ cells safeguards the function of PRC2 during spermatogenesis. Dev. Biol. 424, 198-207.

Mulqueen, R. M., Pokholok, D., Norberg, S. J., Torkenczy, K. A., Fields, A. J., Sun, D., Sinnamon, J. R., Shendure, J., Trapnell, C., O'Roak, B. J., et al. (2018). Highly scalable generation of DNA methylation profiles in single cells. Nat. Biotechnol. 36, 428-431.

Ottolini, C. S., Newnham, L., Capalbo, A., Natesan, S. A., Joshi, H. A., Cimadomo, D., Griffin, D. K., Sage, K., Summers, M. C., Thornhill, A. R., et al. (2015). Genome-wide maps of recombination and chromosome segregation in human oocytes and embryos show selection for maternal recombination rates. Nat. Genet. 47, 727-735.

Petes, T. D. (2001). Meiotic recombination hot spots and cold spots. Nat. Rev. Genet. 2, 360-369.

Petes, T. D., and Botstein, D. (1977). Simple Mendelian inheritance of the reiterated ribosomal DNA of yeast. Proc. Natl. Acad. Sci. U.S.A 74, 5091-5095.

Petes, T. D., and Merker, J. D. (2002). Context dependence of meiotic recombination hotspots in yeast: the relationship between recombination activity of a reporter construct and base composition. Genetics 162, 2049-2052.

Quinlan, A. R., and Hall, I. M. (2010). BEDTools: a flexible suite of utilities for comparing genomic features. Bioinformatics 26, 841-842.

Ramani, V., Deng, X., Qiu, R., Gunderson, K. L., Steemers, F. J., Disteche, C. M., Noble, W. S., Duan, Z., and Shendure, J. (2017). Massively multiplex single-cell Hi-C. Nat. Methods 14, 263-266.

Shalem, O., Sanjana, N. E., Hartenian, E., Shi, X., Scott, D. A., Mikkelson, T., Heckl, D., Ebert, B. L., Root, D. E., Doench, J. G., et al. (2014). Genome-scale CRISPR-Cas9 knockout screening in human cells. Science 343, 84-87.

Sleutels, F., Soochit, W., Bartkuhn, M., Heath, H., Dienstbach, S., Bergmaier, P., Franke, V., Rosa-Garrido, M., van de Nobelen, S., Caesar, L., et al. (2012). The male germ cell gene regulator CTCFL is functionally different from CTCF and binds CTCF-like consensus sites in a nucleosome composition-dependent manner. Epigenetics Chromatin 5, 8.

Smagulova, F., Brick, K., Pu, Y., Camerini-Otero, R. D., and Petukhova, G. V. (2016). The evolutionary turnover of recombination hot spots contributes to speciation in mice. Genes Dev. 30, 266-280.

Storlazzi, A., Tesse, S., Ruprich-Robert, G., Gargano, S., Poggeler, S., Kleckner, N., and Zickler, D. (2008). Coupling meiotic chromosome axis integrity to recombination. Genes Dev. 22, 796-809.

Vitak, S. A., Torkenczy, K. A., Rosenkrantz, J. L., Fields, A. J., Christiansen, L., Wong, M. H., Carbone, L., Steemers, F. J., and Adey, A. (2017). Sequencing thousands of single-cell genomes with combinatorial indexing. Nat. Methods 14, 302-308.

Wang, J., Fan, H. C., Behr, B., and Quake, S. R. (2012). Genome-wide single-cell analysis of recombination activity and de novo mutation rates in human sperm. Cell 150, 402-412.

Zhang, T., Murphy, M. W., Gearhart, M. D., Bardwell, V. J., and Zarkower, D. (2014). The mammalian Doublesex homolog DMRT6 coordinates the transition between mitotic and meiotic developmental programs during spermatogenesis. Development 141, 3662-3671.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for preparing a sequencing library comprising nucleic acids from a plurality of single nuclei or cells, the method comprising:
(a) providing a plurality of isolated single nuclei or cells, wherein the isolated single nuclei or cells comprise DNA molecules and RNA molecules;
(b) distributing the isolated nuclei or cells into a first plurality of compartments,
wherein each compartment comprises a subset of more than one isolated nuclei or cells;
(c) processing each subset of isolated nuclei or cells to generate indexed nuclei or cells comprising indexed RNA nucleic acids and indexed DNA nucleic acids,
wherein the processing comprises adding to the RNA molecules a first compartment specific index sequence by reverse transcription to result in the indexed RNA nucleic acids,
wherein the adding to the RNA molecules comprises:
contacting each subset with a reverse transcriptase and a first primer that anneals to RNA molecules in the isolated nuclei or cells,
wherein the first primer in each compartment comprises the first compartment specific index sequence to generate the indexed nuclei or cells comprising the indexed RNA nucleic acids,
wherein the processing further comprises adding to the DNA molecules a first compartment specific index sequence by transposition to result in the indexed DNA nucleic acids,
wherein the adding to the DNA molecules comprises:
contacting each subset with a transposome complex,
wherein the transposome complex in each compartment comprises the first compartment specific index sequence; and
wherein the first index sequence added to the DNA molecules and the first index sequence added to the RNA molecules in each compartment are either identical or not identical;
(d) combining the indexed nuclei or cells to generate pooled indexed nuclei or cells;
(e) distributing the pooled indexed nuclei or cells into a second plurality of compartments,
wherein each compartment comprises a subset of more than one indexed nuclei or cells;
(f) processing each subset of indexed nuclei or cells to generate dual-indexed nuclei or cells comprising dual-indexed nuclei acids,
wherein the processing comprises adding to the indexed RNA nucleic acids and the indexed DNA nucleic acids a second compartment specific index sequence by ligation of a ligation molecule,
wherein the ligation molecule comprises the second compartment specific index sequence;
(g) combining the dual-indexed nuclei or cells to generate pooled dual-indexed nuclei or cells;
(h) distributing the pooled dual-indexed nuclei or cells into a third plurality of compartments,
wherein each compartment comprises a subset of more than one dual-indexed nuclei or cells;
(i) processing each subset of dual-indexed nuclei or cells to generate triple-indexed nucleic acids,
wherein the processing comprises producing amplified dual-indexed nucleic acids by linear amplification and adding a third compartment specific index to the amplified dual-indexed nucleic acids,
wherein the third compartment specific index is added to the amplified dual-indexed nucleic acids by ligation, primer extension, amplification, or transposition; and (j) combining the triple-indexed nuclei acids to generate pooled triple-indexed nucleic acids, thereby producing a sequencing library from the plurality of nuclei or cells.

2. The method of claim 1, wherein the ligation molecule further comprises a phage promoter, and wherein the linear amplification comprises in vitro transcription of the dual-indexed nucleic acids with a phage RNA polymerase followed by reverse transcription with a reverse transcriptase to produce the amplified dual-indexed nucleic acids.

3. The method of claim 2, wherein the phage promoter comprises a T7 promoter and the phage RNA polymerase comprises a T7 RNA polymerase.

4. The method of claim 2, wherein the processing of step (i) further comprises lysing the pooled dual-indexed nuclei or cells and gap extension of the dual-indexed nucleic acids prior to linear amplification.

5. The method of claim 1, further comprising exposing the plurality of isolated nuclei or cells to an agent or perturbation.

6. The method of claim 1, further comprising subjecting the isolated nuclei to conditions to generate nucleosome-depleted nuclei while maintaining integrity of the isolated nuclei.

7. The method of claim 1, wherein the first primer in each compartment comprises a first compartment specific index sequence that is different from first compartment specific index sequences in the other compartments.

8. The method of claim 1, wherein the contacting each subset with a reverse transcriptase and a first primer further comprises a target specific primer that anneals to a specific nucleotide sequence of the RNA molecules.

9. The method of claim 1, further comprising an exponential amplification of the triple-indexed nucleic acids, wherein the exponential amplification comprises a target specific primer that anneals to a specific nucleotide sequence.

10. The method of claim 1, further comprising treating the indexed RNA nucleic acids and the indexed DNA nucleic acids for methylation analysis to generate nucleic acid fragments suitable for methylation analysis.

11. The method of claim 1, further comprising subjecting the indexed RNA nucleic acids and the indexed DNA nucleic acids to proximity ligation to generate nucleic acid fragments suitable for analysis of chromatin conformation.

12. The method of claim 1, further comprising amplifying the triple-indexed nucleic acids of the sequencing library to produce DNA nanoballs.

13. The method of claim 1, wherein each compartment of the first plurality of compartments comprises a well or a droplet.

14. The method of claim 1, wherein each compartment of the first plurality of compartments comprises from 50 to 100,000,000 nuclei or cells.

15. The method of claim 1, wherein each compartment of the second plurality of compartments comprises from 50 to 100,000,000 nuclei or cells.

16. The method of claim 1, further comprising:
providing a surface comprising a plurality of amplification sites,
wherein the amplification sites comprise at least two populations of attached single stranded capture oligonucleotides having a free 3' end, and
contacting the surface comprising amplification sites with the triple-indexed nucleic acids under conditions suitable to produce a plurality of amplification sites that each comprise a clonal population of amplicons from an individual triple-indexed nucleic acid.

17. The method of claim 1, wherein the DNA molecules comprise genomic DNA.

18. The method of claim 1, wherein the transposition comprises a transposome complex, wherein the transposome complex in each compartment comprises a first compartment specific index sequence that is different from first compartment specific index sequences in the other compartments.

19. The method of claim 1, wherein the third compartment specific index is added to the amplified dual-indexed nucleic acids during the linear amplification.

20. The method of claim 1, wherein the ligation molecule further comprises a nucleotide sequence for linear amplification by a linear amplification primer.

21. The method of claim 20, wherein the linear amplification primer comprises the third compartment specific index, and wherein the third compartment specific index is added to the amplified dual-indexed nucleic acids during the linear amplification.

22. The method of claim 1, wherein the ligation molecule further comprises a nucleotide sequence recognized by a strand-displacing polymerase, wherein the nucleotide sequence recognized by the strand-displacing polymerase comprises a nicking site, and wherein the linear amplification is linear strand-displacement amplification (SDA).

23. The method of claim 4, wherein the third compartment specific index is added to the amplified dual-indexed nucleic acids by second strand synthesis (SSS) using a DNA polymerase and an SSS primer comprising the third compartment specific index.

24. The method of claim 1, wherein the third compartment specific index sequence is different from third compartment specific index sequences in the other compartments.

* * * * *

SEQUENCE LISTING

```
<160> NUMBER OF SEQ ID NOS: 176

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctgtctctta tacacatct                                                   19

<210> SEQ ID NO 2
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(14)
<223> OTHER INFORMATION: a, c, t, or g
<220> FEATURE:
<221> NAME/KEY: misc_feature
<222> LOCATION: (7)..(14)
<223> OTHER INFORMATION: n is a, c, g, or t

<400> SEQUENCE: 2
gtcttgnnnn nnnnagatgt gtataagaga cag                                33

<210> SEQ ID NO 3
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(13)
<223> OTHER INFORMATION: a, c, t, or g
<220> FEATURE:
<221> NAME/KEY: misc_feature
<222> LOCATION: (7)..(13)
<223> OTHER INFORMATION: n is a, c, g, or t
<220> FEATURE:
<221> NAME/KEY: modified_base
<222> LOCATION: (73)..(79)
<223> OTHER INFORMATION: a, c, t, or g
<220> FEATURE:
<221> NAME/KEY: misc_feature
<222> LOCATION: (73)..(79)
<223> OTHER INFORMATION: n is a, c, g, or t

<400> SEQUENCE: 3
caagacnnnn nnncaggagc gagctgcatc ccaatttaat acgactcact atagggatgc   60
agctcgctcc tgnnnnnnn                                                79

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
agauguguau aagagacag                                                19

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(10)
<223> OTHER INFORMATION: n is a, c, g, or t
```

```
<220> FEATURE:
<221> NAME/KEY: modified_base
<222> LOCATION: (5)..(10)
<223> OTHER INFORMATION: a, c, t, or g

<400> SEQUENCE: 5
nnnnnnnnnn gggatgcagc tcgctcctg                                              29

<210> SEQ ID NO 6
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (59)..(65)
<223> OTHER INFORMATION: a, c, t, g, unknown or other
<220> FEATURE:
<221> NAME/KEY: misc_feature
<222> LOCATION: (59)..(71)
<223> OTHER INFORMATION: n is a, c, g, or t
<220> FEATURE:
<221> NAME/KEY: modified_base
<222> LOCATION: (66)..(71)
<223> OTHER INFORMATION: a, c, t, or g

<400> SEQUENCE: 6
aatgatacgg cgaccaccga gatctacact ctttccctac acgacgctct tccgatctnn           60
nnnnnnnnnn ngggatgcag ctcgctcctg                                            90

<210> SEQ ID NO 7
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
caagcagaag acggcatacg agattcgcct tggtgactgg agttcagacg tgtgctcttc           60
cgatctccga ctcggtgcca ctttttcaa                                             89

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(20)
<223> OTHER INFORMATION: n is a, c, g, or t
<220> FEATURE:
<221> NAME/KEY: modified_base
<222> LOCATION: (13)..(20)
<223> OTHER INFORMATION: a, c, t, or g
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t
```

<400> SEQUENCE: 8
gtcttgnnnn nnnnnnnnnn tttttttttt tttttttttt tttttttttt vn          52

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(26)
<223> OTHER INFORMATION: a, c, t, g, unknown or other
<220> FEATURE:
<221> NAME/KEY: misc_feature
<222> LOCATION: (20)..(26)
<223> OTHER INFORMATION: n is a, c, g, or t

<400> SEQUENCE: 9
cacgacgctc ttccgatctn nnnnnn                                        26

<210> SEQ ID NO 10
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aatgatacgg cgaccaccga gatctacact ctttccctac acgacgctct tccgatct     58

<210> SEQ ID NO 11
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(27)
<223> OTHER INFORMATION: a, c, t, g, unknown or other
<220> FEATURE:
<221> NAME/KEY: misc_feature
<222> LOCATION: (24)..(33)
<223> OTHER INFORMATION: n is a, c, g, or t
<220> FEATURE:
<221> NAME/KEY: modified_base
<222> LOCATION: (28)..(33)
<223> OTHER INFORMATION: a, c, t, or g

<400> SEQUENCE: 11
aagcagaaga cggcatacga gatnnnnnnn nnncgtctct acgggatgca gctcgctcct   60
g                                                                   61

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctgtctctta tacacatct                                                19

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtcttgtgat attgagatgt gtataagaga cag                                33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtcttggatc ccgtagatgt gtataagaga cag                                33

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtcttgctcg attaagatgt gtataagaga cag                                33

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtcttgcatc aaggagatgt gtataagaga cag                                33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtcttgtcct tgtgagatgt gtataagaga cag                                33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtcttgggtc atatagatgt gtataagaga cag                                33

-continued

```
<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtcttgatcg cgttagatgt gtataagaga cag                               33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtcttgcatg ccccagatgt gtataagaga cag                               33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtcttggtta cgcgagatgt gtataagaga cag                               33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtcttgccgc gcttagatgt gtataagaga cag                               33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtcttgtctt agtgagatgt gtataagaga cag                               33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gtcttgtcgg cctaagatgt gtataagaga cag                               33

<210> SEQ ID NO 25
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtcttgcttt ctctagatgt gtataagaga cag                                33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtcttgtcgc gtttagatgt gtataagaga cag                                33

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtcttggtca gtagagatgt gtataagaga cag                                33

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtcttgccat ggaaagatgt gtataagaga cag                                33

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gtcttgatgc tgcgagatgt gtataagaga cag                                33

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtcttggagt ctttagatgt gtataagaga cag                                33

<210> SEQ ID NO 31
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtcttgtacg atatagatgt gtataagaga cag                               33

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtcttgacca tttaagatgt gtataagaga cag                               33

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gtcttgatcg ggacagatgt gtataagaga cag                               33

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtcttggacg tcggagatgt gtataagaga cag                               33

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gtcttgcatt gtgtagatgt gtataagaga cag                               33

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gtcttgtttg actcagatgt gtataagaga cag                               33

<210> SEQ ID NO 37
<211> LENGTH: 79
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 37
caagacaggt ggccaggagc gagctgcatc ccaatttaat acgactcact atagggatgc    60
agctcgctcc tggccacct                                                 79

<210> SEQ ID NO 38
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
caagactaat agccaggagc gagctgcatc ccaatttaat acgactcact atagggatgc    60
agctcgctcc tggctatta                                                 79

<210> SEQ ID NO 39
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
caagaccaac atacaggagc gagctgcatc ccaatttaat acgactcact atagggatgc    60
agctcgctcc tgtatgttg                                                 79

<210> SEQ ID NO 40
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
caagaccggt taacaggagc gagctgcatc ccaatttaat acgactcact atagggatgc    60
agctcgctcc tgttaaccg                                                 79

<210> SEQ ID NO 41
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
caagactgta ccccaggagc gagctgcatc ccaatttaat acgactcact atagggatgc    60
agctcgctcc tggggtaca                                                 79

<210> SEQ ID NO 42
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 42
caagacaata gaacaggagc gagctgcatc ccaatttaat acgactcact atagggatgc    60
agctcgctcc tgttctatt                                                79

<210> SEQ ID NO 43
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
caagacatca agccaggagc gagctgcatc ccaatttaat acgactcact atagggatgc    60
agctcgctcc tggcttgat                                                79

<210> SEQ ID NO 44
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
caagacactt ggacaggagc gagctgcatc ccaatttaat acgactcact atagggatgc    60
agctcgctcc tgtccaagt                                                79

<210> SEQ ID NO 45
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
caagactagt tctcaggagc gagctgcatc ccaatttaat acgactcact atagggatgc    60
agctcgctcc tgagaacta                                                79

<210> SEQ ID NO 46
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
caagacaaac cgacaggagc gagctgcatc ccaatttaat acgactcact atagggatgc    60
agctcgctcc tgtcggttt                                                79

<210> SEQ ID NO 47
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
caagacagtc tctcaggagc gagctgcatc ccaatttaat acgactcact atagggatgc    60
agctcgctcc tgagagact                                                79

<210> SEQ ID NO 48
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
caagacttaa cagcaggagc gagctgcatc ccaatttaat acgactcact atagggatgc    60
agctcgctcc tgctgttaa                                                79

<210> SEQ ID NO 49
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
caagacacta cctcaggagc gagctgcatc ccaatttaat acgactcact atagggatgc    60
agctcgctcc tgaggtagt                                                79

<210> SEQ ID NO 50
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
caagacccaa gcccaggagc gagctgcatc ccaatttaat acgactcact atagggatgc    60
agctcgctcc tgggcttgg                                                79

<210> SEQ ID NO 51
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
caagacaaca gtgcaggagc gagctgcatc ccaatttaat acgactcact atagggatgc    60
agctcgctcc tgcactgtt                                                79

<210> SEQ ID NO 52
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
caagacacga cgtcaggagc gagctgcatc ccaatttaat acgactcact atagggatgc    60
agctcgctcc tgacgtcgt                                                79

<210> SEQ ID NO 53
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
caagacttaa gcacaggagc gagctgcatc ccaatttaat acgactcact atagggatgc    60
agctcgctcc tgtgcttaa                                                 79

<210> SEQ ID NO 54
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
caagacctat ggacaggagc gagctgcatc ccaatttaat acgactcact atagggatgc    60
agctcgctcc tgtccatag                                                 79

<210> SEQ ID NO 55
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
caagacgcgg caccaggagc gagctgcatc ccaatttaat acgactcact atagggatgc    60
agctcgctcc tggtgccgc                                                 79

<210> SEQ ID NO 56
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
caagacgacc tgccaggagc gagctgcatc ccaatttaat acgactcact atagggatgc    60
agctcgctcc tggcaggtc                                                 79

<210> SEQ ID NO 57
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
caagaccggt gcacaggagc gagctgcatc ccaatttaat acgactcact atagggatgc    60
agctcgctcc tgtgcaccg                                                 79

<210> SEQ ID NO 58
<211> LENGTH: 79
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 58
caagacagtc tctcaggagc gagctgcatc ccaatttaat acgactcact atagggatgc      60
agctcgctcc tgagagact                                                  79

<210> SEQ ID NO 59
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
caagaccttt tatcaggagc gagctgcatc ccaatttaat acgactcact atagggatgc      60
agctcgctcc tgataaaag                                                  79

<210> SEQ ID NO 60
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
caagactggg acccaggagc gagctgcatc ccaatttaat acgactcact atagggatgc      60
agctcgctcc tgggtccca                                                  79

<210> SEQ ID NO 61
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
caagacgtgc gaccaggagc gagctgcatc ccaatttaat acgactcact atagggatgc      60
agctcgctcc tggtcgcac                                                  79

<210> SEQ ID NO 62
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
caagaccctt taccaggagc gagctgcatc ccaatttaat acgactcact atagggatgc      60
agctcgctcc tggtaaagg                                                  79

<210> SEQ ID NO 63
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 63
caagaccaag tcgcaggagc gagctgcatc ccaatttaat acgactcact atagggatgc    60
agctcgctcc tgcgacttg                                                 79

<210> SEQ ID NO 64
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
caagactaag cggcaggagc gagctgcatc ccaatttaat acgactcact atagggatgc    60
agctcgctcc tgccgctta                                                 79

<210> SEQ ID NO 65
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
caagactgac catcaggagc gagctgcatc ccaatttaat acgactcact atagggatgc    60
agctcgctcc tgatggtca                                                 79

<210> SEQ ID NO 66
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
caagactgga tggcaggagc gagctgcatc ccaatttaat acgactcact atagggatgc    60
agctcgctcc tgccatcca                                                 79

<210> SEQ ID NO 67
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
caagacctcg ccccaggagc gagctgcatc ccaatttaat acgactcact atagggatgc    60
agctcgctcc tggggcgag                                                 79

<210> SEQ ID NO 68
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
caagaccatg cagcaggagc gagctgcatc ccaatttaat acgactcact atagggatgc    60
```
agctcgctcc tgctgcatg					79

<210> SEQ ID NO 69
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
caagacctgt aggcaggagc gagctgcatc ccaatttaat acgactcact atagggatgc		60 agctcgctcc tgcctacag					79

<210> SEQ ID NO 70
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
caagacacct ctgcaggagc gagctgcatc ccaatttaat acgactcact atagggatgc		60 agctcgctcc tgcagaggt					79

<210> SEQ ID NO 71
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
caagaccgtt ttgcaggagc gagctgcatc ccaatttaat acgactcact atagggatgc		60 agctcgctcc tgcaaaacg					79

<210> SEQ ID NO 72
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
caagacgaag gtccaggagc gagctgcatc ccaatttaat acgactcact atagggatgc		60 agctcgctcc tggaccttc					79

<210> SEQ ID NO 73
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
caagacggct actcaggagc gagctgcatc ccaatttaat acgactcact atagggatgc		60 agctcgctcc tgagtagcc					79

<210> SEQ ID NO 74

```
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
caagacccgg ctacaggagc gagctgcatc ccaatttaat acgactcact atagggatgc   60
agctcgctcc tgtagccgg                                                79

<210> SEQ ID NO 75
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
caagactaga ctacaggagc gagctgcatc ccaatttaat acgactcact atagggatgc   60
agctcgctcc tgtagtcta                                                79

<210> SEQ ID NO 76
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
caagacaaat taccaggagc gagctgcatc ccaatttaat acgactcact atagggatgc   60
agctcgctcc tggtaattt                                                79

<210> SEQ ID NO 77
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
caagactact cgacaggagc gagctgcatc ccaatttaat acgactcact atagggatgc   60
agctcgctcc tgtcgagta                                                79

<210> SEQ ID NO 78
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
caagactcct acccaggagc gagctgcatc ccaatttaat acgactcact atagggatgc   60
agctcgctcc tgggtagga                                                79

<210> SEQ ID NO 79
<211> LENGTH: 79
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 79
caagaccccc gtccaggagc gagctgcatc ccaatttaat acgactcact atagggatgc    60
agctcgctcc tggacggggg                                                79

<210> SEQ ID NO 80
<211> LENGTH: 79
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 80
caagacgata cgacaggagc gagctgcatc ccaatttaat acgactcact atagggatgc    60
agctcgctcc tgtcgtatc                                                 79

<210> SEQ ID NO 81
<211> LENGTH: 79
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 81
caagacgctg tgacaggagc gagctgcatc ccaatttaat acgactcact atagggatgc    60
agctcgctcc tgtcacagc                                                 79

<210> SEQ ID NO 82
<211> LENGTH: 79
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 82
caagactata ggccaggagc gagctgcatc ccaatttaat acgactcact atagggatgc    60
agctcgctcc tggcctata                                                 79

<210> SEQ ID NO 83
<211> LENGTH: 79
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 83
caagaccgac gcacaggagc gagctgcatc ccaatttaat acgactcact atagggatgc    60
agctcgctcc tgtgcgtcg                                                 79

<210> SEQ ID NO 84
<211> LENGTH: 79
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 84
caagactcca tttcaggagc gagctgcatc ccaatttaat acgactcact atagggatgc    60
agctcgctcc tgaaatgga                                                79

<210> SEQ ID NO 85
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
caagacaaga ccgcaggagc gagctgcatc ccaatttaat acgactcact atagggatgc    60
agctcgctcc tgcggtctt                                                79

<210> SEQ ID NO 86
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
caagactaag taacaggagc gagctgcatc ccaatttaat acgactcact atagggatgc    60
agctcgctcc tgttactta                                                79

<210> SEQ ID NO 87
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
caagacctac tgccaggagc gagctgcatc ccaatttaat acgactcact atagggatgc    60
agctcgctcc tggcagtag                                                79

<210> SEQ ID NO 88
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
caagactctt atacaggagc gagctgcatc ccaatttaat acgactcact atagggatgc    60
agctcgctcc tgtataaga                                                79

<210> SEQ ID NO 89
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
caagacaacc caccaggagc gagctgcatc ccaatttaat acgactcact atagggatgc    60
agctcgctcc tggtgggtt                                                79

<210> SEQ ID NO 90
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
caagactacg gatcaggagc gagctgcatc ccaatttaat acgactcact atagggatgc     60
agctcgctcc tgatccgta                                                 79

<210> SEQ ID NO 91
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
caagacaatt ccacaggagc gagctgcatc ccaatttaat acgactcact atagggatgc     60
agctcgctcc tgtggaatt                                                 79

<210> SEQ ID NO 92
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
caagacgtct ccgcaggagc gagctgcatc ccaatttaat acgactcact atagggatgc     60
agctcgctcc tgcggagac                                                 79

<210> SEQ ID NO 93
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
caagacatgc agtcaggagc gagctgcatc ccaatttaat acgactcact atagggatgc     60
agctcgctcc tgactgcat                                                 79

<210> SEQ ID NO 94
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
caagacgagc ttgcaggagc gagctgcatc ccaatttaat acgactcact atagggatgc     60
agctcgctcc tgcaagctc                                                 79

<210> SEQ ID NO 95
<211> LENGTH: 79

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
caagacgaga aaccaggagc gagctgcatc ccaatttaat acgactcact atagggatgc    60
agctcgctcc tggtttctc                                                 79

<210> SEQ ID NO 96
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
caagactttg gcccaggagc gagctgcatc ccaatttaat acgactcact atagggatgc    60
agctcgctcc tgggccaaa                                                 79

<210> SEQ ID NO 97
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
caagactgcg agtcaggagc gagctgcatc ccaatttaat acgactcact atagggatgc    60
agctcgctcc tgactcgca                                                 79

<210> SEQ ID NO 98
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
caagactgca tcacaggagc gagctgcatc ccaatttaat acgactcact atagggatgc    60
agctcgctcc tgtgatgca                                                 79

<210> SEQ ID NO 99
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
caagacggga tatcaggagc gagctgcatc ccaatttaat acgactcact atagggatgc    60
agctcgctcc tgatatccc                                                 79

<210> SEQ ID NO 100
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 100
caagactcgc ctccaggagc gagctgcatc ccaatttaat acgactcact atagggatgc    60
agctcgctcc tggaggcga                                                 79

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
agauguguau aagagacag                                                 19

<210> SEQ ID NO 102
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 102
nnnnacgcga gggatgcagc tcgctcctg                                      29

<210> SEQ ID NO 103
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 103
nnnncgcttg gggatgcagc tcgctcctg                                      29

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 104
nnnngtccta gggatgcagc tcgctcctg                                29

<210> SEQ ID NO 105
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 105
nnnnaggatg gggatgcagc tcgctcctg                                29

<210> SEQ ID NO 106
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 106
nnnnttctcc gggatgcagc tcgctcctg                                29

<210> SEQ ID NO 107
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 107
nnnnaccact gggatgcagc tcgctcctg                                29

<210> SEQ ID NO 108
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)

<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 108
nnnntttcgc gggatgcagc tcgctcctg                                          29

<210> SEQ ID NO 109
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 109
nnnncggtgg gggatgcagc tcgctcctg                                          29

<210> SEQ ID NO 110
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 110
nnnntattct gggatgcagc tcgctcctg                                          29

<210> SEQ ID NO 111
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 111
nnnnacttaa gggatgcagc tcgctcctg                                          29

<210> SEQ ID NO 112
<211> LENGTH: 29
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 112
nnnntaaaga gggatgcagc tcgctcctg                                   29

<210> SEQ ID NO 113
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 113
nnnngagttt gggatgcagc tcgctcctg                                   29

<210> SEQ ID NO 114
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 114
nnnngggtgc gggatgcagc tcgctcctg                                   29

<210> SEQ ID NO 115
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 115
nnnngggccg gggatgcagc tcgctcctg                                   29
```

```
<210> SEQ ID NO 116
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 116
nnnnaattga gggatgcagc tcgctcctg                                29

<210> SEQ ID NO 117
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 117
nnnntaagcg gggatgcagc tcgctcctg                                29

<210> SEQ ID NO 118
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 118
nnnntaatgc gggatgcagc tcgctcctg                                29

<210> SEQ ID NO 119
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t
```

<400> SEQUENCE: 119
nnnngtctat gggatgcagc tcgctcctg                                              29

<210> SEQ ID NO 120
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 120
gtcttgnnnn nnacccgaca tttttttttt tttttttttt tttttttttt vn                    52

<210> SEQ ID NO 121
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 121
gtcttgnnnn nnaggctctc tttttttttt tttttttttt tttttttttt vn                    52

<210> SEQ ID NO 122
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:

```
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 122
gtcttgnnnn nntctaaact tttttttttt tttttttttt tttttttttt vn            52

<210> SEQ ID NO 123
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 123
gtcttgnnnn nntaccctcg tttttttttt tttttttttt tttttttttt vn            52

<210> SEQ ID NO 124
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 124
gtcttgnnnn nnctggtcat tttttttttt tttttttttt tttttttttt vn            52

<210> SEQ ID NO 125
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 125
gtcttgnnnn nnttataagc tttttttttt tttttttttt tttttttttt vn        52

<210> SEQ ID NO 126
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 126
gtcttgnnnn nnaatgtaga tttttttttt tttttttttt tttttttttt vn        52

<210> SEQ ID NO 127
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 127
gtcttgnnnn nncgcagacc tttttttttt tttttttttt tttttttttt vn        52
```

```
<210> SEQ ID NO 128
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 128
gtcttgnnnn nncgaatcaa tttttttttt tttttttttt tttttttttt vn         52

<210> SEQ ID NO 129
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 129
gtcttgnnnn nnccggaaag tttttttttt tttttttttt tttttttttt vn         52

<210> SEQ ID NO 130
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
```

```
<222> LOCATION: (52)..(52)
<223> OTHER INFORMATION: n is a, c, g, or t

<400> SEQUENCE: 130
gtcttgnnnn nngtttaaag tttttttttt tttttttttt tttttttttt vn          52

<210> SEQ ID NO 131
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 131
gtcttgnnnn nnaaagttga tttttttttt tttttttttt tttttttttt vn          52

<210> SEQ ID NO 132
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 132
gtcttgnnnn nncggaaact tttttttttt tttttttttt tttttttttt vn          52

<210> SEQ ID NO 133
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
```

<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 133
gtcttgnnnn nntgagtacc tttttttttt tttttttttt tttttttttt vn          52

<210> SEQ ID NO 134
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 134
gtcttgnnnn nncgtagaat tttttttttt tttttttttt tttttttttt vn          52

<210> SEQ ID NO 135
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 135
gtcttgnnnn nncgacaccc tttttttttt tttttttttt tttttttttt vn          52

<210> SEQ ID NO 136
<211> LENGTH: 52
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 136
gtcttgnnnn nngtactgaa tttttttttt tttttttttt tttttttttt vn          52

<210> SEQ ID NO 137
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 137
gtcttgnnnn nncggaaaga tttttttttt tttttttttt tttttttttt vn          52

<210> SEQ ID NO 138
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 138
```

```
gtcttgnnnn nnatatcaat tttttttttt tttttttttt tttttttttt vn            52
```

<210> SEQ ID NO 139
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 139

```
gtcttgnnnn nntacccggc tttttttttt tttttttttt tttttttttt vn            52
```

<210> SEQ ID NO 140
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 140

```
gtcttgnnnn nngccatccc tttttttttt tttttttttt tttttttttt vn            52
```

<210> SEQ ID NO 141
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)

```
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 141
gtcttgnnnn nnaccaacgc tttttttttt tttttttttt tttttttttt vn          52

<210> SEQ ID NO 142
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 142
gtcttgnnnn nntgcaagct tttttttttt tttttttttt tttttttttt vn          52

<210> SEQ ID NO 143
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, t, g, unknown or other
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: misc_feature
<222> LOCATION: (52)..(52)
<223> OTHER INFORMATION: n is a, c, g, or t

<400> SEQUENCE: 143
gtcttgnnnn nngcaaccgg tttttttttt tttttttttt tttttttttt vn          52

<210> SEQ ID NO 144
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(26)
```

```
<223> OTHER INFORMATION: a, c, t, g, unknown or other
<220> FEATURE:
<221> NAME/KEY: misc_feature
<222> LOCATION: (20)..(26)
<223> OTHER INFORMATION: n is a, c, g, or t

<400> SEQUENCE: 144
cacgacgctc ttccgatctn nnnnnn                                         26

<210> SEQ ID NO 145
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 145
caagcagaag acggcatacg agatnnnnga tccgcgtctc tacgggatgc agctcgctcc    60
tg                                                                  62

<210> SEQ ID NO 146
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 146
caagcagaag acggcatacg agatnnnngg gtatcgtctc tacgggatgc agctcgctcc    60
tg                                                                  62

<210> SEQ ID NO 147
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 147
caagcagaag acggcatacg agatnnnnca tggacgtctc tacgggatgc agctcgctcc    60
tg                                                                  62
```

<210> SEQ ID NO 148
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 148
caagcagaag acggcatacg agatnnnntt gaagcgtctc tacgggatgc agctcgctcc    60
tg                                                                  62

<210> SEQ ID NO 149
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 149
caagcagaag acggcatacg agatnnnnct gggtcgtctc tacgggatgc agctcgctcc    60
tg                                                                  62

<210> SEQ ID NO 150
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 150
caagcagaag acggcatacg agatnnnnca ctaccgtctc tacgggatgc agctcgctcc    60
tg                                                                  62

<210> SEQ ID NO 151
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 151
caagcagaag acggcatacg agatnnnnct tatacgtctc tacgggatgc agctcgctcc      60
tg                                                                    62

<210> SEQ ID NO 152
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 152
caagcagaag acggcatacg agatnnnngt tggacgtctc tacgggatgc agctcgctcc      60
tg                                                                    62

<210> SEQ ID NO 153
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 153
caagcagaag acggcatacg agatnnnnag cggtcgtctc tacgggatgc agctcgctcc      60
tg                                                                    62

<210> SEQ ID NO 154
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 154
caagcagaag acggcatacg agatnnnncc gttccgtctc tacgggatgc agctcgctcc      60
``` tg                                                             62

<210> SEQ ID NO 155
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 155
caagcagaag acggcatacg agatnnnnac gttacgtctc tacgggatgc agctcgctcc    60
tg                                                             62

<210> SEQ ID NO 156
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 156
caagcagaag acggcatacg agatnnnnaa catacgtctc tacgggatgc agctcgctcc    60
tg                                                             62

<210> SEQ ID NO 157
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 157
caagcagaag acggcatacg agatnnnngc agaccgtctc tacgggatgc agctcgctcc    60
tg                                                             62

<210> SEQ ID NO 158
<211> LENGTH: 62
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 158
caagcagaag acggcatacg agatnnnnat tcgtcgtctc tacgggatgc agctcgctcc      60
tg                                                                    62

<210> SEQ ID NO 159
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 159
caagcagaag acggcatacg agatnnnntg gggtcgtctc tacgggatgc agctcgctcc      60
tg                                                                    62

<210> SEQ ID NO 160
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 160
caagcagaag acggcatacg agatnnnnct tccccgtctc tacgggatgc agctcgctcc      60
tg                                                                    62

<210> SEQ ID NO 161
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t
```

<400> SEQUENCE: 161
caagcagaag acggcatacg agatnnnntc cgtgcgtctc tacgggatgc agctcgctcc    60
tg    62

<210> SEQ ID NO 162
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 162
caagcagaag acggcatacg agatnnnntt tgtacgtctc tacgggatgc agctcgctcc    60
tg    62

<210> SEQ ID NO 163
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 163
caagcagaag acggcatacg agatnnnnga gatgcgtctc tacgggatgc agctcgctcc    60
tg    62

<210> SEQ ID NO 164
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 164
caagcagaag acggcatacg agatnnnngg accacgtctc tacgggatgc agctcgctcc    60
tg    62

<210> SEQ ID NO 165
<211> LENGTH: 62
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 165
caagcagaag acggcatacg agatnnnnta tgttcgtctc tacgggatgc agctcgctcc      60
tg                                                                    62

<210> SEQ ID NO 166
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 166
caagcagaag acggcatacg agatnnnncg acgccgtctc tacgggatgc agctcgctcc      60
tg                                                                    62

<210> SEQ ID NO 167
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 167
caagcagaag acggcatacg agatnnnngc tattcgtctc tacgggatgc agctcgctcc      60
tg                                                                    62

<210> SEQ ID NO 168
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
```

```
<222> LOCATION: (25)..(28)
<223> OTHER INFORMATION: n is a, c, g, or t

<400> SEQUENCE: 168
caagcagaag acggcatacg agatnnnncg gctgcgtctc tacgggatgc agctcgctcc    60
tg                                                                  62

<210> SEQ ID NO 169
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 169
caagcagaag acggcatacg agatnnnnca tctgcgtctc tacgggatgc agctcgctcc    60
tg                                                                  62

<210> SEQ ID NO 170
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 170
caagcagaag acggcatacg agatnnnnaa gttccgtctc tacgggatgc agctcgctcc    60
tg                                                                  62

<210> SEQ ID NO 171
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 171
caagcagaag acggcatacg agatnnnntt gttacgtctc tacgggatgc agctcgctcc    60
tg                                                                  62
```

```
<210> SEQ ID NO 172
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 172
caagcagaag acggcatacg agatnnnnca ggcacgtctc tacgggatgc agctcgctcc    60
tg                                                                  62

<210> SEQ ID NO 173
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 173
caagcagaag acggcatacg agatnnnngg tgagcgtctc tacgggatgc agctcgctcc    60
tg                                                                  62

<210> SEQ ID NO 174
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 174
caagcagaag acggcatacg agatnnnnca aaagcgtctc tacgggatgc agctcgctcc    60
tg                                                                  62

<210> SEQ ID NO 175
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
```

```
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 175
caagcagaag acggcatacg agatnnnnac tcctcgtctc tacgggatgc agctcgctcc     60
tg                                                                   62

<210> SEQ ID NO 176
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(28)
<223> OTHER INFORMATION: a, c, t, g, unknown or other
<220> FEATURE:
<221> NAME/KEY: misc_feature
<222> LOCATION: (25)..(28)
<223> OTHER INFORMATION: n is a, c, g, or t

<400> SEQUENCE: 176
caagcagaag acggcatacg agatnnnntg cgggcgtctc tacgggatgc agctcgctcc     60
tg                                                                   62
```